US012473564B2

(12) United States Patent
Cargill et al.

(10) Patent No.: US 12,473,564 B2
(45) Date of Patent: Nov. 18, 2025

(54) METHODS AND COMPOSITIONS FOR GENERATING DOMINANT ALLELES USING GENOME EDITING

(71) Applicant: MONSANTO TECHNOLOGY LLC, St. Louis, MO (US)

(72) Inventors: Edward James Cargill, Chesterfield, MO (US); Douglas Michael Eudy, Maxwell, IA (US); Andrei Y. Kouranov, Chesterfield, MO (US); Richard Joseph Lawrence, Kirkwood, MO (US); Thomas L. Slewinski, Chesterfield, MO (US); Randy Shultz, Davis, CA (US); PokChun Jennifer To, Durham, NC (US); Samuel Sukhwan Yang, Ballwin, MO (US); Yuanji Zhang, Chesterfield, MO (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

(21) Appl. No.: 16/886,683

(22) Filed: May 28, 2020

(65) Prior Publication Data

US 2020/0377900 A1 Dec. 3, 2020

Related U.S. Application Data

(60) Provisional application No. 62/854,142, filed on May 29, 2019, provisional application No. 62/886,726, filed on Aug. 14, 2019, provisional application No. 62/886,732, filed on Aug. 14, 2019.

(51) Int. Cl.
*C12N 15/82* (2006.01)

(52) U.S. Cl.
CPC ...... *C12N 15/8218* (2013.01); *C12N 2310/11* (2013.01); *C12N 2310/127* (2013.01); *C12N 2310/141* (2013.01)

(58) Field of Classification Search
CPC .................................................. C12N 15/8218
See application file for complete search history.

(56) References Cited

U.S. PATENT DOCUMENTS

| | | | |
|---|---|---|---|
| 5,939,539 A | 8/1999 | Lange | |
| 10,724,047 B2 | 7/2020 | Allen et al. | |
| 2003/0159160 A1 | 8/2003 | Chambon et al. | |
| 2004/0060080 A1 | 3/2004 | Tanaka et al. | |
| 2007/0209085 A1 | 9/2007 | Wu et al. | |
| 2010/0293665 A1 | 11/2010 | Puzio et al. | |
| 2015/0052634 A1 | 2/2015 | Park et al. | |
| 2015/0128300 A1 | 5/2015 | Warming et al. | |
| 2018/0051295 A1* | 2/2018 | Allen | C12N 15/8218 |
| 2018/0105824 A1* | 4/2018 | Simmons | C12N 15/8273 |
| 2020/0029538 A1 | 1/2020 | Mashimo et al. | |

FOREIGN PATENT DOCUMENTS

| | | | |
|---|---|---|---|
| CN | 104540382 | A | 4/2015 |
| CN | 113473845 | A | 10/2021 |
| EP | 0335451 | A2 | 10/1989 |
| EP | 1281765 | A1 | 2/2003 |
| EP | 3546575 | A1 | 10/2019 |
| JP | H0216985 | A | 1/1990 |
| JP | 2001511007 | A | 8/2001 |
| JP | 2001321174 | A | 11/2001 |
| JP | 2004166577 | A | 6/2004 |
| WO | 199428141 | A1 | 12/1994 |
| WO | 9835051 | A1 | 8/1998 |
| WO | 2006013072 | A2 | 2/2006 |
| WO | 2015117041 | A1 | 8/2015 |
| WO | 2017143061 | A1 | 8/2017 |
| WO | 2018035354 | A1 | 2/2018 |
| WO | 2018080389 | A1 | 5/2018 |
| WO | 2018097257 | A1 | 5/2018 |
| WO | 2018119225 | A1 | 6/2018 |
| WO | 2019036599 | A1 | 2/2019 |
| WO | 2019089884 | A2 | 5/2019 |
| WO | 2019161146 | A1 | 8/2019 |
| WO | 2020117553 | A1 | 6/2020 |

OTHER PUBLICATIONS

Lyanuagh et al Translocation and duplication from CRISPR-Cas9 editing in *Arabidopsis thaliana* bioRxiv 1-34 (Year: 2018).*

GenBank. (2014) GenBank Accession No. AC209074, "*Zea mays* Cultivar B73 Chromosome 8 Clone CH201-426A6," 40 pages.

International Search Report and Written Opinion, dated Nov. 2, 2020, for PCT Application No. PCT/US2020/034993, filed May 28, 2020, 14 pages.

International Search Report and Written Opinion, dated Oct. 19, 2020, for PCT Application No. PCT/US2020/034996, filed May 28, 2020, 19 pages.

International Search Report and Written Opinion, dated Oct. 23, 2020, for PCT Application No. PCT/US2020/035001, filed May 28, 2020, 25 pages.

Kraft, K. et al. (2015) "Deletions, Inversions, Duplications: Engineering of Structural Variants using CRISPR/Cas in Mice," Cell Reports 10:833-839.

Nakamura, T. et al. (Jul. 2012, e-pub May 9, 2012). "Mechanistic Insight Into Pentatricopeptide Repeat Proteins as Sequence-Specific RNA-Binding Proteins for Organellar RNAs in Plants," Plant and Cell Physiology 53(7): 1171-1179.

Nicholson, S. J. (2009) "Transgene Constructs Lacking Transcription Termination Signal Induce Efficient Silencing Of Endogenous Targets In *Arabidopsis*," Mol. Genet. Genomics, 282:319-328.

(Continued)

*Primary Examiner* — Brent T Page
(74) *Attorney, Agent, or Firm* — Morrison & Foerster LLP

(57) ABSTRACT

The present disclosure provides methods and compositions for generating dominant alleles using targeted editing techniques. Also provided are modified chromosomes, cells, tissues, and plants comprising modified dominant allele.

6 Claims, 40 Drawing Sheets

Specification includes a Sequence Listing.

(56) References Cited

OTHER PUBLICATIONS

Soininen, R. et al. (1988) "The Structural Genes for a 1 and a2 Chains of Human Type IV Collagen Are Divergently Encoded on Opposite DNA Strands and Have an Overlapping Promoter Region," The Journal of Biological Chemistry, 263(33): 17217-17220.
Yan, H. et al. (Aug. 2006) "New Construct Approaches for Efficient Gene Silencing in Plants," Plant Physiology, 141:1508-1518.
Hahn, F. et al. (Jul. 5, 2017). "Generation of Targeted Knockout Mutants in *Arabidopsis thaliana* Using CRISPR/Cas9," Bio Protoc. 7(13): e2384, 20 pages.
Kasim, V. et al. (2004, e-pub Apr. 23, 2004). "Control of siRNA Expression Using the Cre-loxP Recombination System," Nucleic Acids Res. 32(7):e66, 8 pages.
Qi, Y. et al. (Oct. 2013, e-pub Oct. 1, 2013). "Targeted Deletion and Inversion of Tandemly Arrayed Genes in *Arabidopsis thaliana* Using Zinc Finger Nucleases," G3 (Bethesda) 3(10):1707-1715.
Kollner, T. G. et al. (Aug. 2010, e-pub. Jun. 2, 2010). "Herbivore-induced SABATH Methyltransferases of Maize that Methylate Anthranilic Acid Using S-Adenosyl-L-Methionine," Plant Physiol. 153(4):1795-1807.
Wang, Y. et al. (Aug. 2017, e-pub. Jun. 5, 2017). "Deletion of a Target Gene in Indica Rice Via CRISPR/Cas9," Plant Cell Rep 36(8):1333-1343.
Li, J. et al. (Aug. 2015, e-pub. Mar. 10, 2015). "Efficient Inversions and Duplications of Mammalian Regulatory DNA Elements and Gene Clusters by CRISPR/Cas9," Journal of Molecular Cell Biology 7(4):284-298.
Wang, Y et al. (2006). "The Development of Dwarf Mutants Related Gibberellin," Chinese Journal of Biotechnology 8:22-27. English Abstract only.

* cited by examiner

Panel A Panel B Panel C Panel D Panel E

METHODS AND COMPOSITIONS FOR GENERATING DOMINANT ALLELES USING GENOME EDITING

CROSS-REFERENCE TO RELATED APPLICATIONS

This application claims the benefit of U.S. Provisional Application No. 62/854,142, filed May 29, 2019, U.S. Provisional Application No. 62/886,726, filed Aug. 14, 2019, and U.S. Provisional Application No. 62/886,732, filed Aug. 14, 2019, all of which are incorporated by reference in their entireties herein.

FIELD

The present disclosure relates to methods and compositions for generating dominant alleles via targeted editing of genomes.

INCORPORATION OF SEQUENCE LISTING

A sequence listing contained in the file named "P34497US01_SL.TXT" which is 172,842 bytes (measured in MS-Windows®) and created on May 28, 2020, is filed electronically herewith and incorporated by reference in its entirety.

BACKGROUND

Dominant alleles are alleles that mask the contribution of a second allele at the same locus. A dominant allele can be a dominant negative allele or a dominant positive allele. Dominant negative alleles, or antimorphs, are alleles that act in opposition to normal allelic function. For example, a dominant negative allele often abrogates the normal function of an allele in a heterozygous or homozygous state. Dominant positive alleles can increase normal gene function (e.g., a hypermorph) and/or provide broadened or new functions for a gene (e.g., a neomorph).

Naturally occurring and random mutagenesis techniques (e.g., ethyl methyl sulfonate and T-DNA insertions) have been used to generate mutations in a variety of cell types. However, dominant mutations occur at low frequencies and are difficult to obtain in a given gene of interest. Therefore, methods and compositions to selectively edit a genome to create a dominant negative allele or a dominant positive allele would be beneficial.

SUMMARY

In one aspect, this disclosure provides a method of generating a dominant negative allele of a gene in a cell comprising inverting a portion of the gene using a targeted editing technique, generating an antisense RNA transcript capable of triggering suppression of an unmodified allele.

In one aspect, this disclosure provides a method of generating a dominant negative allele of a gene in a cell comprising deleting a portion of a chromosome between a first gene region and a second gene region using a targeted editing technique, where an antisense mRNA transcript of the first gene region is generated following the deletion of the portion of the chromosome.

In one aspect, this disclosure provides a method of generating a dominant negative allele of a gene in one or more cells comprising: (a) inducing a first double-stranded break and a second double-stranded break flanking a targeted region of the gene; (b) identifying one or more cells comprising an inversion of the targeted region of the gene, where the inversion results in the production of an antisense RNA transcript from the targeted region; and (c) selecting one or more cells comprising the inversion of the targeted region of the gene.

In one aspect, this disclosure provides a method of reducing the expression of a protein in a cell comprising: (a) inducing a first double-stranded break and a second double-stranded break flanking a targeted region of a chromosome; and (b) identifying one or more cells comprising an inversion in the targeted region of the chromosome, where expression of the protein is reduced as compared to a control cell that does not comprise the inversion in the targeted region.

In one aspect, this disclosure provides a method comprising: (a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; (b) inducing a first double-stranded break and a second double-stranded break flanking a targeted region; (c) identifying one or more cells comprising a deletion of the targeted region of the chromosome; and (d) selecting one or more cells comprising the deletion of the targeted region of the chromosome.

In one aspect, this disclosure provides a method of reducing the expression of a gene in at least one cell comprising: (a) inducing a double-stranded break using a targeted editing technique at a target site of the gene; (b) inserting a donor sequence at the double-stranded break, where the donor sequence comprises a tissue-specific or tissue-preferred promoter, and where the donor sequence is inserted into the target site such that the tissue-specific or tissue-preferred promoter is in reverse orientation as compared to the gene; and (b) identifying at least one cell comprising the insertion of the donor sequence in reverse orientation, where expression of the gene is reduced as compared to a control cell that does not comprise the insertion of the donor sequence.

In one aspect, this disclosure provides a method of modifying gene expression comprising: (a) inducing a double-stranded break using a targeted editing technique at a target site; (b) inserting a donor sequence at the double-stranded break, where the donor sequence comprises an endogenous (e.g., promoter, enhancer or promoter/enhancer fragment) or designed element capable of inducing increased or ectopic expression of the gene; and (c) identifying at least one cell comprising the donor sequence, where expression of the target gene is increased in at least one tissue as compared to a control cell that does not comprise the donor sequence.

In one aspect, this disclosure provides a method of enhancing gene expression comprising: (a) inducing a double-stranded break using a targeted editing technique at a target site; (b) inserting a donor sequence at the double-stranded break, where the donor sequence comprises an endogenous (e.g., promoter, enhancer or promoter/enhancer fragment) or designed element capable of inducing increased or ectopic expression of the gene; and (c) identifying at least one cell comprising the donor sequence, where expression of the target gene is increased in at least one tissue as compared to a control cell that does not comprise the donor sequence.

In one aspect, this disclosure provides a method generating a dominant positive allele comprising: (a) inducing a double-stranded break using a targeted editing technique at a target site; (b) inserting a donor sequence at the double-stranded break, where the donor sequence comprises a sequence of an endogenous gene; and (c) identifying at least one cell comprising the donor sequence, where expression of the gene is increased in at least one tissue as compared to a control cell that does not comprise the donor sequence.

In one aspect, this disclosure provides a method of reducing expression of a gene in a cell comprising: (a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; (b) inducing a first double-stranded break and a second double-stranded break flanking a targeted region using a targeted editing technique, where the targeted region comprises the second coding region and the intervening region; and (c) identifying one or more cells comprising a deletion of the targeted region, where the second promoter generates at least one antisense RNA of the first coding region, and where expression of the first coding region is reduced as compared to a control cell that does not comprise the deletion of the targeted region.

In one aspect, this disclosure provides a method of reducing expression of a protein of interest in a cell comprising: (a) identifying a chromosomal region comprising a gene region encoding the protein of interest comprising a first promoter and a coding region for the protein, and a second chromosomal region comprising a second promoter and a intervening region, where the coding region for the protein of interest and the second promoter are separated by an the intervening region, and where the first promoter and the second promoter are positioned in opposite orientations; (b) inducing a first double-stranded break and a second double-stranded break flanking a the intervening region using a targeted editing technique; and (c) identifying one or more cells comprising a deletion of the intervening region, and where expression of the protein of interest is reduced as compared to a control cell that does not comprise the deletion of the intervening region.

In one aspect, this disclosure provides a method of generating an inversion in a targeted region of a gene comprising: (a) providing to one or more cells at least one RNA-guided nuclease or one or more vectors encoding at least one RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a first target site and a second target site flanking the targeted region of the gene, where the first target site and the second target site are linked, where the at least one RNA-guided nuclease creates double-stranded breaks in the gene at the first target site and the second target site; (b) identifying one or more cells comprising an inversion in the targeted region of the gene, where the inversion results in the production of an antisense RNA transcript from the targeted region; and (c) selecting one or more cells comprising the inversion in the targeted region of the gene.

A method comprising: (a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; (b) providing to one or more cells at least one RNA-guided nuclease or one or more vectors encoding at least one RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a first target site and a second target site flanking a targeted region of a chromosome, where the targeted region comprises the second encoding region and the intervening region, where the RNA-guided nuclease creates double-stranded breaks in the chromosome at the first target site and the second target site; (c) identifying one or more cells comprising a deletion of the targeted region; and (d) selecting one or more cells comprising the deletion of the targeted region.

In one aspect, this disclosure provides a method comprising: (a) providing to one or more cells at least one RNA-guided nuclease and at least one donor molecule, or one or more vectors encoding at least one RNA-guided nuclease and at least one donor molecule, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the donor molecule comprises a designed element, where the RNA-guided nuclease creates a double-stranded break at the target site, and where the designed element is inserted at the double-stranded break; (b) identifying one or more cells comprising an insertion of the designed element at the target site; and (c) selecting one or more cells comprising the insertion of the designed element at the target site.

In one aspect, this disclosure provides a method comprising: (a) providing to one or more cells at least one RNA-guided nuclease and at least one donor molecule, or one or more vectors encoding at least one RNA-guided nuclease and at least one donor molecule, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the donor molecule comprises a sequence encoding a tissue-specific or tissue-preferred promoter, where the RNA-guided nuclease creates a double-stranded break at the target site, and where the sequence encoding the tissue-specific or tissue-preferred promoter is inserted at the double-stranded break; (b) identifying one or more cells comprising the insertion of the sequence encoding the tissue-specific or tissue-preferred promoter at the target site such that the sequence encoding the tissue-specific or tissue-preferred promoter is in reverse orientation as compared to the gene; and (c) selecting one or more cells comprising the insertion of the sequence encoding the tissue-specific or tissue-preferred promoter at the target site.

In one aspect, this disclosure provides a method comprising: (a) providing to one or more cells one or more RNA-guided nucleases or one or more vectors encoding one or more RNA nucleases, where the one or more RNA-guided nucleases are capable of binding to at least 18, at least 19, at least 20, at least 21, at least 22, at least 23, at least 24, at least 25, or at least 26 consecutive nucleotides of a target site, where the one or more RNA-guided nucleases create a double-stranded break at the target site; (b) identifying at least one cell comprising an insertion or a deletion at the target site, where the insertion or deletion at the target site results in the generation of a dominant negative allele of the at least one gene; and (c) selecting one or more cells comprising the dominant negative allele of the at least one gene.

In one aspect, this disclosure provides a method comprising: (a) providing to one or more cells one or more RNA-guided nucleases or one or more vectors encoding one or more RNA nucleases, where the one or more RNA-guided nucleases are capable of binding to at least 18, at least 19, at least 20, at least 21, at least 22, at least 23, at least 24, at least 25, or at least 26 consecutive nucleotides of a target site, where the one or more RNA-guided nucleases create a double-stranded break at the target site; (b) identifying at least one cell comprising an insertion or a deletion at the target site, where the insertion or deletion at the target site results in the generation of a dominant positive allele of the at least one gene; and (c) selecting one or more cells comprising the dominant positive allele of the at least one gene.

In one aspect, this disclosure provides a method comprising: (a) generating a first double-stranded break (DSB) and a second DSB in a first allele of a gene in a cell using a targeted editing technique; (b) generating a third DSB in a second allele of the gene in the cell using a targeted editing technique; and (c) identifying a cell comprising an insertion of a region of the first allele in inverted orientation at the third DSB site in the second allele, thereby generating a modified second allele.

In one aspect, this disclosure provides a method of generating a dominant negative allele of a gene comprising using a targeted editing technique to introduce at least one non-coding RNA target site into the gene.

In one aspect, this disclosure provides a method of generating a dominant allele of a gene comprising using a targeted editing technique to introduce a nonsense mutation in the gene to create a truncated protein or protein with altered amino acid composition downstream of the mutation. This technique can also be paired with a second targeted editing mutation to restore the frame of normal amino acid sequence down stream of the initial mutation to create a nonsense region inside the polypeptide.

In one aspect, this disclosure provides a method comprising: (a) providing to a cell an engineered pentatricopeptide repeat (PPR) protein or a vector encoding the engineered PPR protein operably linked to a promoter, where the engineered PPR protein is capable of binding to an RNA transcript of a target gene; (b) selecting one or more cells from step (a) expressing the engineered PPR protein; and (c) identifying one or more cells selected in step (b) comprising altered expression of the target gene.

In one aspect, this disclosure provides a method of generating a dominant negative allele of a gene in a cell comprising inserting an inverted copy of the gene, or a portion thereof, adjacent to a native copy of the gene using a targeted editing technique to generate an inverted repeat sequence capable of producing an antisense RNA transcript of the gene, or a portion thereof.

In one aspect, this disclosure provides a method of generating a dominant negative or dominant positive allele of a gene in a cell comprising deleting a portion of a gene using a targeted editing technique, where a microprotein is generated following the deletion of the portion of the gene.

In one aspect, this disclosure provides a method of generating a dominant negative or dominant positive allele of a gene in a cell comprising deleting a portion of an intergenic region using a targeted editing technique such that the deletion renders the gene under the control of an upstream promoter. In some embodiments, the upstream promoter drives increased expression of the gene. In some embodiments, the upstream promoter drives reduced expression of the gene. In some embodiments, the upstream promoter drives altered temporal expression of the gene. In some embodiments, the upstream promoter drives altered tissue specific expression of the gene.

In one aspect, this disclosure provides a method of generating a dominant negative allele of at least one gene in at least one cell comprising: (a) introducing to the at least one cell a genome editing system comprising: (i) a site-specific nuclease, or a molecule encoding a site-specific nuclease, (ii) a single guide RNA (sgRNA), or a molecule encoding a sgRNA and (iii) at least a first tether guided oligo (tgOligo) and a second tgOligo, or one or more molecules encoding a first and a second tgOligo, operably linked to at least one promoter; (b) generating a first double-stranded break (DSB) and a second DSB in the at least one gene, where the first tgOligo and the second tgOligo hybridize to the 3' free ends of opposing strands at the first DSB and second DSB, where at least 1, at least 2, at least 3, at least 4, at least 5, at least 10, at least 25, at least 50, at least 100, at least 250, at least 500, at least 750, at least 1000, at least 2500, or at least 5000 nucleotides of the at least one gene are deleted, thereby generating a dominant negative allele of the gene that encodes a truncated protein; and (c) identifying and selecting at least one cell comprising the truncated protein.

In one aspect, this disclosure provides a method of generating a dominant negative allele of at least one gene in at least one cell comprising: (a) introducing to the at least one cell one or more vectors encoding: (i) at least one site-specific nuclease, (ii) at least one single guide RNA (sgRNA), and (iii) at least a first tether guided oligo (tgOligo) and a second tgOligo operably linked to at least one promoter; (b) generating a first double-stranded break (DSB) and a second DSB in the gene, where the first tgOligo and the second tgOligo hybridize to the 3' free ends of opposing strands at the first DSB and second DSB, where the region of the at least one gene between the first DSB and second DSB is inverted in orientation, thereby generating a dominant negative allele of the at least one gene that encodes an antisense RNA transcript of the gene; and (c) identifying and selecting at least one cell comprising the antisense RNA transcript of the at least one gene.

In one aspect, this disclosure provides a modified plant cell comprising a non-transposon mediated genome deletion or inversion of a gene, or a portion thereof, at the endogenous locus of the gene, where the deletion or inversion results in the production of an RNA transcript comprising a sequence complementary to a native transcript sequence of the gene, or portion thereof.

In one aspect, this disclosure provides a modified chromosome comprising a non-transposon mediated deletion or inversion of a gene or, a portion thereof, at the endogenous locus of the gene, where the deletion or inversion results in the production of an RNA transcript comprising a sequence complementary to a native transcript sequence of the gene, or portion thereof.

In one aspect, this disclosure provides a modified plant, or part thereof, comprising a non-transposon mediated genome deletion or inversion of a gene, or a portion thereof, at the endogenous locus of the gene, where the deletion or inversion results in the production of an RNA transcript comprising a sequence complementary to a native transcript sequence of the gene, or portion thereof.

In one aspect, this disclosure provides a modified cell comprising (a) a non-transposon mediated genome deletion of at least one gene, or a portion thereof, at the endogenous locus of the at least one gene, or (b) a non-transposon mediated and non-T-DNA mediated insertion of a polynucleotide sequence into the at least one gene, where the deletion or insertion creates a dominant positive allele of the at least one gene.

In one aspect, this disclosure provides a modified cell comprising a non-transposon mediated genome deletion or inversion of a gene, or a portion thereof, at the endogenous locus of the at least one gene, where the deletion or inversion results in the production of an RNA transcript comprising a sequence complementary to a native transcript sequence of the gene.

In one aspect, this disclosure provides a modified cell comprising a targeted edit of at least one gene or a portion thereof, where the targeted edit generates an RNA transcript that is complementary to a native transcript sequence of the gene.

In one aspect, this disclosure provides a modified cell comprising at least one dominant negative allele of at least one gene generated by a targeted editing technique, where the allele generates an RNA transcript capable of forming a hairpin loop secondary structure when the at least one dominant negative allele is transcribed.

In one aspect, this disclosure provides a modified cell comprising a non-transgenic dominant negative allele of a gene, said dominant negative allele comprising a heterologous non-coding RNA target site in the endogenous locus of the gene.

In one aspect, this disclosure provides a modified cell comprising a non-transgenic dominant positive allele of a gene, said dominant positive allele comprising a heterologous non-coding RNA target site in the endogenous locus of the gene.

In one aspect, this disclosure provides a modified cell comprising at least one insertion or deletion at the endogenous locus of the at least one gene generated by a targeted editing technique, where the insertion or deletion results in expression of a truncated protein.

In one aspect, this disclosure provides a modified cell comprising a dominant negative allele of at least one gene comprising an inverted copy of the gene adjacent to a native copy of the gene at the endogenous locus of the gene.

DETAILED DESCRIPTION

Figure 1:
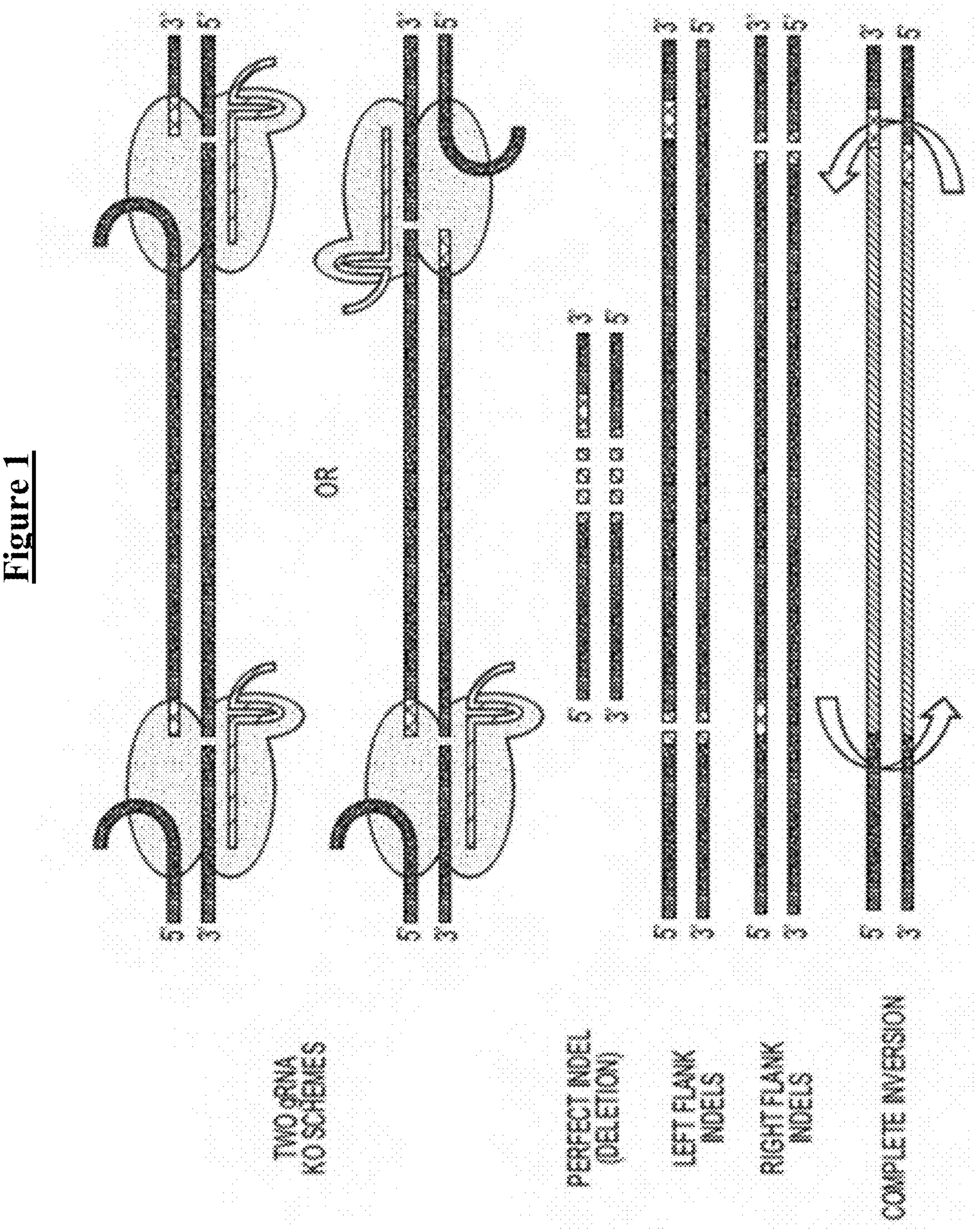
FIG. 1 comprises Panel A and Panel B. Panel A shows that two sRNAs coupled to two RNA-guided nucleases can hybridize target DNA on the same or different strands to isolate a region of DNA from the rest of the DNA strand(s) by generating two double-stranded breaks (DSBs). Panel B shows different outcomes that are possible after two RNA-guided nucleases generate two DSBs in DNA. Native cellular machinery can repair the two DSBs by deleting the entire region between the DSBs, by deleting a small portion of the region from the 5' or 3' end, or by inverting the region between the DSBs.

Unless defined otherwise, technical and scientific terms used herein have the same meaning as commonly understood by one of ordinary skill in the art. One skilled in the art will recognize many methods can be used in the practice of the present disclosure. Indeed, the present disclosure is in no way limited to the methods and materials described. For purposes of the present disclosure, the following terms are defined below.

The present specification provides methods and compositions for generating dominant alleles using targeted editing techniques in a wide range of organisms including plants, animals, fungi, and protozoa. Dominant alleles are alleles that mask the contribution of a second allele at the same locus. A dominant allele can be a "dominant negative allele" or a "dominant positive allele." Dominant negative alleles, or antimorphs, are alleles that act in opposition to normal allelic function. A dominant negative allele typically does not function normally and either directly inhibits the activity of a wild-type protein (e.g., through dimerization) or inhibits the activity of a second protein that is required for the normal function of the wild-type protein (e.g., an activator or a downstream component of a pathway). For example, a dominant negative allele abrogates or reduces the normal function of an allele in a heterozygous or homozygous state. Dominant positive alleles can increase or expand normal gene function (e.g., a hypermorph) or provide new functions for a gene (e.g., a neomorph). A semi-dominant allele occurs when penetrance of a linked phenotype in individuals heterozygous for the allele is less than that which is observed in individuals homozygous for the allele.

The practice of the present disclosure employs, unless otherwise indicated, conventional techniques of biochemistry, chemistry, molecular biology, microbiology, cell biology, genomics and biotechnology, which are within the skill of the art. See Green and Sambrook, *Molecular Cloning: A Laboratory Manual,* 4th Edition (2012); *Current Protocols In Molecular Biology* (F. M. Ausubel, et al. eds., (1987)); the series *Methods In Enzymology* (Academic Press, Inc.): *PCR 2: A Practical Approach* (M. J. MacPherson, B. D. Hames and G. R. Taylor eds. (1995)); Harlow and Lane, eds. (1988) *Antibodies, A Laboratory Manual; Animal Cell Culture* (R. I. Freshney, ed. (1987)); *Recombinant Protein Purification: Principles And Methods,* 18-1142-75, GE Healthcare Life Sciences; C. N. Stewart, A. Touraev, V. Citovsky, T. Tzfira eds. (2011) *Plant Transformation Technologies* (Wiley-Blackwell); and R. H. Smith (2013) *Plant Tissue Culture. Techniques And Experiments* (Academic Press, Inc.).

Any references cited herein, including, e.g., all patents, published patent applications, and non-patent publications, are incorporated by reference in their entirety.

As used herein, the singular form "a," "an," and "the" include plural references unless the context clearly dictates otherwise. For example, the term "a compound" or "at least one compound" can include a plurality of compounds, including mixtures thereof.

The term "and/or" when used in a list of two or more items, means that any one of the listed items can be employed by itself or in combination with any one or more of the listed items. For example, the expression "A and/or B" is intended to mean either or both of A and B—i.e., A alone, B alone, or A and B in combination. The expression "A, B and/or C" is intended to mean A alone, B alone, C alone, A and B in combination, A and C in combination, B and C in combination, or A, B, and C in combination.

Nucleic acid molecules provided herein include deoxyribonucleic acids (DNA) and ribonucleic acids (RNA) and functional analogues thereof, such as complementary DNA (cDNA). Nucleic acid molecules provided herein can be single stranded or double stranded. Nucleic acid molecules comprise the nucleotide bases adenine (A), guanine (G), thymine (T), cytosine (C). Uracil (U) replaces thymine in RNA molecules. The symbol "N" can be used to represent any nucleotide base (e.g., A, G, C, T, or U). As used herein, "encoding" refers to a polynucleotide encoding for the amino acids of a polypeptide. A series of three nucleotide bases encodes one amino acid. As used herein, "expressed," "expression," or "expressing" refers to transcription of RNA from a DNA molecule. As used herein, terms "polypeptide", "peptide" and "protein" are used interchangeably to refer to a polymer of amino acid residues. The term also applies to amino acid polymers in which one or more amino acids are chemical analogues or modified derivatives of a corresponding naturally-occurring amino acids. A "messenger RNA" or "mRNA" refers to an RNA transcript that is transcribed from a polynucleotide, where the RNA transcript is capable of being translated into a protein. Typically, DNA encodes an mRNA, which encodes a protein. When DNA is transcribed by an RNA polymerase to ultimately generate a protein, a sense mRNA strand is typically produced by the RNA polymerase from the antisense DNA strand. A sense strand of DNA or RNA runs from 5' to 3', while the antisense strand runs from 3' to 5'. Sense and antisense strands of the same polynucleotide are complementary to each other.

In one aspect, a nucleic acid molecule provided herein comprises a protein coding nucleic acid molecule that is codon optimized for a eukaryotic cell. In another aspect, a protein-coding nucleic acid molecule is codon optimized for a plant cell. In another aspect, a protein-coding nucleic acid molecule is codon optimized for a monocot species. In a further aspect, a protein-coding nucleic acid molecule is codon optimized for a corn or soybean cell.

The terms "percent identity" or "percent identical" as used herein in reference to two or more nucleotide or protein sequences is calculated by (i) comparing two optimally aligned sequences (nucleotide or protein) over a window of comparison, (ii) determining the number of positions at which the identical nucleic acid base (for nucleotide sequences) or amino acid residue (for proteins) occurs in both sequences to yield the number of matched positions, (iii) dividing the number of matched positions by the total number of positions in the window of comparison, and then (iv) multiplying this quotient by 100% to yield the percent identity. If the "percent identity" is being calculated in relation to a reference sequence without a particular comparison window being specified, then the percent identity is determined by dividing the number of matched positions over the region of alignment by the total length of the reference sequence. Accordingly, for purposes of the present application, when two sequences (query and subject) are optimally aligned (with allowance for gaps in their alignment), the "percent identity" for the query sequence is equal to the number of identical positions between the two sequences divided by the total number of positions in the query sequence over its length (or a comparison window), which is then multiplied by 100%. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity can be adjusted upwards to correct for the conservative nature of the substitution. Sequences that differ by such conservative substitutions are said to have "sequence similarity" or "similarity."

For optimal alignment of sequences to calculate their percent identity, various pair-wise or multiple sequence alignment algorithms and programs are known in the art, such as ClustalW or Basic Local Alignment Search Tool® (BLAST), etc., that can be used to compare the sequence identity or similarity between two or more nucleotide or protein sequences. Although other alignment and comparison methods are known in the art, the alignment and percent identity between two sequences (including the percent identity ranges described above) can be as determined by the ClustalW algorithm, see, e.g., Chenna R. et al., "Multiple sequence alignment with the Clustal series of programs," *Nucleic Acids Research* 31: 3497-3500 (2003); Thompson J D et al., "Clustal W: Improving the sensitivity of progressive multiple sequence alignment through sequence weighting, position-specific gap penalties and weight matrix choice," *Nucleic Acids Research* 22: 4673-4680 (1994); Larkin M A et al., "Clustal W and Clustal X version 2.0," *Bioinformatics* 23: 2947-48 (2007); and Altschul, S. F., Gish, W., Miller, W., Myers, E.W. & Lipman, D. J. (1990) "Basic local alignment search tool." *J. Mol. Biol.* 215:403-410 (1990), the entire contents and disclosures of which are incorporated herein by reference.

The terms "percent complementarity" or "percent complementary" as used herein in reference to two nucleotide sequences is similar to the concept of percent identity but refers to the percentage of nucleotides of a query sequence that optimally base-pair or hybridize to nucleotides a subject sequence when the query and subject sequences are linearly arranged and optimally base paired without secondary folding structures, such as loops, stems or hairpins. Such a percent complementarity can be between two DNA strands, two RNA strands, or a DNA strand and a RNA strand. The "percent complementarity" can be calculated by (i) optimally base-pairing or hybridizing the two nucleotide sequences in a linear and fully extended arrangement (i.e., without folding or secondary structures) over a window of comparison, (ii) determining the number of positions that base-pair between the two sequences over the window of comparison to yield the number of complementary positions, (iii) dividing the number of complementary positions by the total number of positions in the window of comparison, and (iv) multiplying this quotient by 100% to yield the percent complementarity of the two sequences. Optimal base pairing of two sequences can be determined based on the known pairings of nucleotide bases, such as G-C, A-T, and A-U, through hydrogen binding. If the "percent complementarity" is being calculated in relation to a reference sequence without specifying a particular comparison window, then the percent identity is determined by dividing the number of complementary positions between the two linear sequences by the total length of the reference sequence. Thus, for purposes of the present application, when two sequences (query and subject) are optimally base-paired (with allowance for mismatches or non-base-paired nucleotides), the "percent complementarity" for the query sequence is equal to the number of base-paired positions between the two sequences divided by the total number of positions in the query sequence over its length, which is then multiplied by 100%.

The term "operably linked" refers to a functional linkage between a promoter or other regulatory element and an associated transcribable DNA sequence or coding sequence of a gene (or transgene), such that the promoter, etc., operates to initiate, assist, affect, cause, and/or promote the transcription and expression of the associated transcribable DNA sequence or coding sequence, at least in certain tissue(s), developmental stage(s) and/or condition(s). In addition to promoters, regulatory elements include, without being limiting, an enhancer, a leader, a transcription start site (TSS), a linker, 5' and 3' untranslated regions (UTRs), an intron, a polyadenylation signal, and a termination region or sequence, etc., that are suitable, necessary or preferred for regulating or allowing expression of the gene or transcribable DNA sequence in a cell. Such additional regulatory element(s) can be optional and used to enhance or optimize expression of the gene or transcribable DNA sequence. For purposes of the present application, an "enhancer" can be distinguished from a "promoter" in that an enhancer typically lacks a transcription start site, TATA box, or equivalent sequence and is thus insufficient alone to drive transcription. As used herein, a "leader" can be defined generally as the DNA sequence of the 5'-UTR of a gene (or transgene) between the transcription start site (TSS) and 5' end of the transcribable DNA sequence or protein coding sequence start site of the gene.

As commonly understood in the art, the term "promoter" refers to a DNA sequence that contains an RNA polymerase binding site, transcription start site, and/or TATA box and assists or promotes the transcription and expression of an associated transcribable polynucleotide sequence and/or gene (or transgene). A promoter can be synthetically produced, varied or derived from a known or naturally occurring promoter sequence or other promoter sequence. A promoter can also include a chimeric promoter comprising a combination of two or more heterologous sequences. A promoter of the present application can thus include variants of promoter sequences that are similar in composition, but not identical to, other promoter sequence(s) known or provided herein. A promoter can be classified according to a variety of criteria relating to the pattern of expression of an associated coding or transcribable sequence or gene (including a transgene) operably linked to the promoter, such as constitutive, developmental, tissue-specific, inducible, etc. Promoters that drive expression in all or most tissues of the plant are referred to as "constitutive" promoters. Promoters that drive expression during certain periods or stages of development are referred to as "developmental" promoters. Promoters that drive enhanced expression in certain tissues of the plant relative to other plant tissues are referred to as "tissue-enhanced" or "tissue-preferred" promoters. Thus, a "tissue-preferred" promoter causes relatively higher or preferential expression in a specific tissue(s) of the plant, but with lower levels of expression in other tissue(s) of the plant. Promoters that express within a specific tissue(s) of the plant, with little or no expression in other plant tissues, are referred to as "tissue-specific" promoters. An "inducible" promoter is a promoter that initiates transcription in response to an environmental stimulus such as cold, drought or light, or other stimuli, such as wounding or chemical application. A promoter can also be classified in terms of its origin, such as being heterologous, homologous, chimeric, synthetic, etc. A "heterologous" promoter is a promoter sequence having a different origin relative to its associated transcribable sequence, coding sequence, or gene (or transgene), and/or not naturally occurring in the plant species to be transformed.

Examples describing a promoter that can be used herein include without limitation U.S. Pat. No. 6,437,217 (maize RS81 promoter), U.S. Pat. No. 5,641,876 (rice actin promoter), U.S. Pat. No. 6,426,446 (maize RS324 promoter), U.S. Pat. No. 6,429,362 (maize PR-1 promoter), U.S. Pat. No. 6,232,526 (maize A3 promoter), U.S. Pat. No. 6,177,611 (constitutive maize promoters), U.S. Pat. Nos. 5,322,938, 5,352,605, 5,359,142 and 5,530,196 (35S promoter), U.S. Pat. No. 6,433,252 (maize L3 oleosin promoter), U.S. Pat. No. 6,429,357 (rice actin 2 promoter as well as a rice actin 2 intron), U.S. Pat. No. 5,837,848 (root specific promoter), U.S. Pat. No. 6,294,714 (light inducible promoters), U.S. Pat. No. 6,140,078 (salt inducible promoters), U.S. Pat. No. 6,252,138 (pathogen inducible promoters), U.S. Pat. No. 6,175,060 (phosphorus deficiency inducible promoters), U.S. Pat. No. 6,635,806 (gamma-coixin promoter), and U.S. patent application Ser. No. 09/757,089 (maize chloroplast aldolase promoter). Additional promoters that can find use are a nopaline synthase (NOS) promoter (Ebert et al., 1987), the octopine synthase (OCS) promoter (which is carried on tumor-inducing plasmids of *Agrobacterium tumefaciens*), the caulimovirus promoters such as the cauliflower mosaic virus (CaMV) 19S promoter (Lawton et al., *Plant Molecular Biology* (1987) 9: 315-324), the CaMV 35S promoter (Odell et al., *Nature* (1985) 313: 810-812), the figwort mosaic virus 35S-promoter (U.S. Pat. Nos. 6,051,753; 5,378,619), the sucrose synthase promoter (Yang and Russell, *Proceedings of the National Academy of Sciences, USA* (1990) 87: 4144-4148), the R gene complex promoter (Chandler et al., *Plant Cell* (1989) 1: 1175-1183), and the chlorophyll a/b binding protein gene promoter, PC1SV (U.S. Pat. No. 5,850, 019), and AGRtu.nos (GenBank Accession V00087; Depicker et al., *Journal of Molecular and Applied Genetics* (1982) 1: 561-573; Bevan et al., 1983) promoters.

Promoter hybrids can also be used and constructed to enhance transcriptional activity (see U.S. Pat. No. 5,106, 739), or to combine desired transcriptional activity, inducibility and tissue specificity or developmental specificity. Promoters that function in plants include but are not limited to promoters that are inducible, viral, synthetic, constitutive, temporally regulated, spatially regulated, and spatio-temporally regulated. Other promoters that are tissue-enhanced, tissue-specific, or developmentally regulated are also known in the art and envisioned to have utility in the practice of this disclosure.

As used herein, the term "heterologous" in reference to a promoter is a promoter sequence having a different origin relative to its associated transcribable DNA sequence, coding sequence or gene (or transgene), and/or not naturally occurring in the plant species to be transformed. The term "heterologous" can refer more broadly to a combination of two or more DNA molecules or sequences, such as a promoter and an associated transcribable DNA sequence, coding sequence or gene, when such a combination is man-made and not normally found in nature.

In addition, the term "recombinant" in reference to a polynucleotide (DNA or RNA) molecule, protein, construct, vector, etc., refers to a polynucleotide or protein molecule or sequence that is man-made and not normally found in nature, and/or is present in a context in which it is not normally found in nature, including a polynucleotide (DNA or RNA) molecule, protein, construct, etc., comprising a combination of polynucleotide or protein sequences that would not naturally occur contiguously or in close proximity together without human intervention, and/or a polynucleotide molecule, protein, construct, etc., comprising at least two polynucleotide or protein sequences that are heterologous with respect to each other. A recombinant polynucleotide or protein molecule, construct, etc., can comprise polynucleotide or protein sequence(s) that is/are (i) separated from other polynucleotide or protein sequence(s) that exist in proximity to each other in nature, and/or (ii) adjacent to (or contiguous with) other polynucleotide or protein sequence(s) that are not naturally in proximity with each other. Such a recombinant polynucleotide molecule, protein, construct, etc., can also refer to a polynucleotide or protein molecule or sequence that has been genetically engineered and/or constructed outside of a cell. For example, a recombinant DNA molecule can comprise any suitable plasmid, vector, etc., and can include a linear or circular DNA molecule. Such plasmids, vectors, etc., can contain various maintenance elements including a prokaryotic origin of replication and selectable marker, as well as one or more transgenes or expression cassettes perhaps in addition to a plant selectable marker gene, etc.

As used herein, "adjacent" refers to a nucleic acid sequence that is in close proximity, or next to another nucleic acid sequence. In one aspect, adjacent nucleic acid sequences are physically linked. In another aspect, adjacent nucleic acid sequences or genes are immediately next to each other such that there are no intervening nucleotides between the end of a first nucleic acid sequence and the start of a second nucleic acid sequence. In an aspect, a first gene and a second gene are adjacent to each other if they are separated by less than 50,000, less than 25,000, less than 10,000, less than 9000, less than 8000, less than 7000, less than 6000, less than 5000, less than 4000, less than 3000, less than 2500, less than 2000, less than 1750, less than 1500, less than 1250, less than 1000, less than 900, less than 800, less than 700, less than 600, less than 500, less than 400, less than 300, less than 200, less than 100, less than 75, less than 50, less than 25, less than 20, less than 10, less than 5, less than 4, less than 3, less than 2, or less than 1 nucleotides.

In one aspect, methods and compositions provided herein comprise a vector. As used herein, the terms "vector" or "plasmid" are used interchangeably and refer to a circular, double-stranded DNA molecule that is physically separate from chromosomal DNA. In one aspect, a plasmid or vector used herein is capable of replication in vivo. A "transformation vector," as used herein, is a plasmid that is capable of transforming a plant cell. In an aspect, a plasmid provided herein is a bacterial plasmid. In another aspect, a plasmid provided herein is an *Agrobacterium* Ti plasmid or derived from an *Agrobacterium* Ti plasmid.

In one aspect, a plasmid or vector provided herein is a recombinant vector. As used herein, the term "recombinant vector" refers to a vector formed by laboratory methods of genetic recombination, such as molecular cloning. In another aspect, a plasmid provided herein is a synthetic plasmid. As used herein, a "synthetic plasmid" is an artificially created plasmid that is capable of the same functions (e.g., replication) as a natural plasmid (e.g., Ti plasmid). Without being limited, one skilled in the art can create a synthetic plasmid de novo via synthesizing a plasmid by individual nucleotides, or by splicing together nucleic acid molecules from different pre-existing plasmids.

As used herein, "modified", in the context of plants, seeds, plant components, plant cells, and plant genomes, refers to a state containing changes or variations from their natural or native state. For instance, a "native transcript" of a gene refers to an RNA transcript that is generated from an unmodified gene. Typically, a native transcript is a sense transcript. Modified plants or seeds contain molecular changes in their genetic materials, including either genetic or epigenetic modifications. Typically, modified plants or seeds, or a parental or progenitor line thereof, have been subjected to mutagenesis, genome editing (e.g., without being limiting, via methods using site-specific nucleases), genetic transformation (e.g., without being limiting, via methods of *Agrobacterium* transformation or microprojectile bombardment), or a combination thereof. In one aspect, a modified plant provided herein comprises no non-plant genetic material or sequences. In yet another aspect, a modified plant provided herein comprises no interspecies genetic material or sequences. In one aspect, this disclosure provides methods and compositions related to modified plants, seeds, plant components, plant cells, and products made from modified plants, seeds, plant parts, and plant cells. In one aspect, a modified seed provided herein gives rise to a modified plant provided herein. In one aspect, a modified plant, seed, plant component, plant cell, or plant genome provided herein comprises a recombinant DNA construct or vector provided herein. In another aspect, a product provided herein comprises modified a plant, plant component, plant cell, or plant chromosome or genome provided herein. The present disclosure provides modified plants with desirable or enhanced properties, e.g., without being limiting, disease, insect, or pest tolerance (for example, virus tolerance, bacteria tolerance, fungus tolerance, nematode tolerance, arthropod tolerance, gastropod tolerance); herbicide tolerance; environmental stress resistance; quality improvements such as yield, nutritional enhancements, environmental or stress tolerances; any desirable changes in plant physiology, growth, development, morphology or plant product(s) including starch production, modified oils production, high oil production, modified fatty acid content, high protein production, fruit ripening, enhanced animal and human nutrition, biopolymer production, pharmaceutical peptides and secretable peptides production; improved processing traits; improved digestibility; low raffinose; industrial enzyme production; improved flavor; nitrogen fixation; hybrid seed production; and fiber production.

As used herein, "genome editing" or editing refers to targeted mutagenesis, insertion, deletion, inversion, substitution, or translocation of a nucleotide sequence of interest in a genome using a targeted editing technique. A nucleotide sequence of interest can be of any length, e.g., at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 75, at least 100, at least 250, at least 500, at least 1000, at least 2500, at least 5000, at least 10,000, or at least 25,000 nucleotides. As used herein, a "targeted editing technique" refers to any method, protocol, or technique that allows the precise and/or targeted editing of a specific location in a genome (e.g., the editing is not random). Without being limiting, use of a site-specific nuclease is one example of a targeted editing technique. Another non-limiting example of a targeted editing technique is the use of one or more tether guide Oligos (tgOligos). As used herein, a "targeted edit" refers to a targeted mutagenesis, insertion, deletion, inversion, or substitution caused by a targeted editing technique. A nucleotide sequence of interest can be an endogenous genomic sequence or a transgenic sequence.

In one aspect, a "targeted editing technique" refers to any method, protocol, or technique that allows the precise and/or targeted editing of a specific location in a genome (e.g., the editing is not random). Without being limiting, use of a site-specific nuclease is one example of a targeted editing technique.

In one aspect, a targeted editing technique is used to edit an endogenous locus or an endogenous gene. In another aspect, a targeted editing technique is used to edit a transgene. As used herein, an "endogenous gene" or a "native copy" of a gene refers to a gene that originates from within a given organism, cell, tissue, genome, or chromosome. An "endogenous gene" or a "native copy" of a gene is a gene that was not previously modified by human action.

As used herein, a "locus" refers to a specific position on a chromosome or other nucleic acid molecule. Without being limiting, a locus can comprise a polynucleotide that encodes a protein or an RNA. A locus can also comprise a non-coding RNA. A locus can comprise a gene. A locus can comprise a promoter, a 5'-untranslated region (UTR), an exon, an intron, a 3'-UTR, or any combination thereof. A locus can comprise a coding region.

As used herein, "physically linked" refers to two or more loci that are positioned on the same nucleic acid molecule.

As used herein, a "coding region," a "gene region," or a "gene" refers to a polynucleotide that can produce a functional unit (e.g., without being limiting, for example, a protein, or a non-coding RNA molecule). A "coding region," "gene," or "gene region" can comprise a promoter, an enhancer sequence, a leader sequence, a transcriptional start site, a transcriptional stop site, a polyadenylation site, one or more exons, one or more introns, a 5'-UTR, a 3'-UTR, or any combination thereof. A "coding region sequence," a "gene sequence," or a "gene region sequence" can comprise a polynucleotide sequence encoding a promoter, an enhancer sequence, a leader sequence, a transcriptional start site, a transcriptional stop site, a polyadenylation site, one or more exons, one or more introns, a 5'-UTR, a 3'-UTR, or any combination thereof. In one aspect, a "gene" encodes a non-coding RNA molecule or a precursor thereof. In another aspect, a "gene" encodes a protein.

Non-limiting examples of a non-coding RNA molecule include a microRNA (miRNA), a miRNA precursor (pre-miRNA), a small interfering RNA (siRNA), a small RNA (18-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), a naturally occurring antisense siRNA (nat-siRNA), a CRISPR RNA (crRNA), a tracer RNA (tracrRNA), a guide RNA (gRNA), and a single-guide RNA (sgRNA). In one aspect, a non-coding RNA provided herein is selected from the group consisting of a microRNA, a small interfering RNA, a secondary small interfering RNA, a transfer RNA, a ribosomal RNA, a trans-acting small interfering RNA, a naturally occurring antisense small interfering RNA, a heterochromatic small interfering RNA, and precursors thereof. In another aspect, a non-coding RNA provided herein is selected from the group consisting of a miRNA, a pre-miRNA, a siRNA, a hc-siRNA, a piRNA, a hairpin dsRNA, a ta-siRNA, a nat-siRNA, a crRNA, a tracrRNA, a gRNA, and a sgRNA. Non-coding RNAs are often 100% complementary, or at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99%, at least 99.5% complementary, to a non-coding RNA target site. A non-coding RNA target site can be present in a DNA molecule or an RNA molecule. Non-coding RNA target sites can be hybridized (or bound) by a non-coding RNA to effect various outcomes. For instance, some non-coding RNAs (without being limiting, e.g., miRNA, siRNA, ta-siRNA) assist in the cleavage of mRNA transcripts comprising a complementary non-coding RNA target site. Alternatively, a non-coding RNA (without being limiting, e.g., miRNA, siRNA, ta-siRNA) can assist with the inhibition of protein translation of an mRNA transcript by binding to a non-coding RNA target site in the mRNA. Some non-coding RNAs (without being limiting, e.g., hc-siRNA) assist with inducing epigenetic changes to DNA. In one aspect, a non-coding RNA target site is a miRNA target site or an siRNA target site. In another aspect, a gene provided herein comprises at least one, at least two, at least three, at least four, at least five, at least six, at least seven, at least eight, at least nine, or at least ten non-coding RNA target sites. In another aspect, a gene provided herein comprises at least one, at least two, at least three, at least four, at least five, at least six, at least seven, at least eight, at least nine, or at least ten heterologous non-coding RNA target sites. In another aspect, a dominant negative allele provided herein comprises at least one, at least two, at least three, at least four, at least five, at least six, at least seven, at least eight, at least nine, or at least ten non-coding RNA target sites. In another aspect, a dominant negative allele provided herein comprises at least one, at least two, at least three, at least four, at least five, at least six, at least seven, at least eight, at least nine, or at least ten heterologous non-coding RNA target sites. In an aspect, an endogenous gene provided herein is modified to comprise at least one, at least two, at least three, at least four, at least five, at least six, at least seven, at least eight, at least nine, or at least ten heterologous non-coding RNA target sites.

As used herein, an "allele" refers to a variant of a given locus or gene in a genome. If the same allele is present on both chromosomes of a chromosome pair in a cell the cell is considered homozygous at the given locus. If each member of the chromosome pair comprises a different allele for the given locus the cell is heterozygous for the locus. A minimum of one allele is possible for a given locus, although typically multiple alleles are possible for any given locus in a genome.

As used herein, the terms "suppress," "inhibit," "inhibition," "inhibiting", and "downregulation" are defined as any method known in the art or described herein that decreases the expression or function of a gene product (e.g., an mRNA, a protein, a non-coding RNA). "Inhibition" can be in the context of a comparison between two cells, for example, a modified cell versus a control cell. Inhibition of expression or function of a gene product can also be in the context of a comparison between plant cells, organelles, organs, tissues, or plant components within the same plant or between different plants, and includes comparisons between developmental or temporal stages within the same plant or plant component or between plants or plant components. "Inhibition" includes any relative decrement of function or production of a gene product of interest, up to and including complete elimination of function or production of that gene product. The term "inhibition" encompasses any method or composition that down-regulates translation and/or transcription of the target gene product or functional activity of the target gene product. "Inhibition" need not comprise complete elimination of expression of a gene product. In an aspect, a gene product in a modified cell provided herein comprises expression that is at least 1%, at least 2%, at least 3%, at least 4%, at least 5%, at least 10%, at least 20%, at least 25%, at least 30%, at least 40%, at least 50%, at least 60%, at least 70%, at least 80%, at least 90%, at least 95%, or 100% lower than the expression of the gene product in a control cell. In another aspect, a gene product in a modified cell provided herein comprises expression that is between 1% and 100%, between 1% and 95%, between 1% and 90%, between 1% and 80%, between 1% and 70%, between 1% and 60%, between 1% and 50%, between 1% and 40%, between 1% and 30%, between 1% and 25%, between 1% and 20%, between 1% and 15%, between 1% and 10%, between 1% and 5%, between 5% and 25%, between 5% and 50%, between 5% and 75%, between 5% and 100%, between 10% and 25%, between 10% and 50%, between 10% and 75%, between 10% and 100%, between 25% and 50%, between 25% and 75%, between 25% and 100%, or between 50% and 100% lower than the expression of the gene product in a control cell.

As used herein, a "target site" refers to a location of a polynucleotide sequence that is bound to and cleaved by a site-specific nuclease introducing a double stranded break into the nucleic acid backbone. In another aspect a target site comprises at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 29, or at least 30 consecutive nucleotides. In another aspect, a target site provided herein is at least 10, at least 20, at least 30, at least 40, at least 50, at least 75, at least 100, at least 125, at least 150, at least 200, at least 250, at least 300, at least 400, or at least 500 nucleotides. In one aspect a site-specific nuclease binds to a target site. In another aspect a site-specific nuclease binds to a target site via a guiding non-coding RNA (i.e., such as, without being limiting, a CRISPR RNA or single-guide RNA (both described in detail below)). In one aspect, a non-coding RNA provided herein is complementary to a target site. It will be appreciated that perfect complementarity is not required for a non-coding RNA to bind to a target site; at least 1, at least 2, at least 3, at least 4, or at least 5, at least 6, at least 7 or at least 8 mismatches between a target site and a non-coding RNA can be tolerated. As used herein, a "target region" or a "targeted region" refers to a polynucleotide sequence that desired to be modified. In one aspect, a "target region," "targeted region", or a "target gene" is flanked by two or more, three or more, four or more, five or more, six or more, seven or more, eight or more, nine or more, or ten or more target sites. A "target gene" refers to a polynucleotide sequence encoding a gene that is desired to be modified. In one aspect, a polynucleotide sequence comprising a target gene further comprises one or more target sites. In another aspect, a target region comprises one or more, two or more, three or more, four or more, five or more, six or more, seven or more, eight or more, nine or more, or ten or more target genes. Without being limiting, in one aspect a target region can be subject to deletion or inversion. As used herein, "flanked" when used to describe a target region, refers to two or more target sites physically surrounding the target region, with one target site on each side of the target region.

A target site can be positioned in a polynucleotide sequence encoding a leader, an enhancer, a transcriptional start site, a promoter, a 5'-UTR, an exon, an intron, a 3'-UTR, a polyadenylation site, or a termination sequence. It will be appreciated that a target site can be also be positioned upstream or downstream of a sequence encoding a leader, an enhancer, a transcriptional start site, a promoter, a 5'-UTR, an exon, an intron, a 3'-UTR, a polyadenylation site, or a termination sequence. In one aspect, a target site is positioned within 10, within 20, within 30, within 40, within 50, within 75, within 100, within 125, within 150, within 200, within 250, within 300, within 400, within 500, within 600, within 700, within 800, within 900, within 1000, within 1250, within 1500, within 2000, within 2500, within 5000, within 10,000, or within 25,000 nucleotides of a polynucleotide encoding a leader, an enhancer, a transcriptional start site, a promoter, a 5'-UTR, an exon, an intron, a 3'-UTR, a polyadenylation site, a gene, or a termination sequence.

As used herein, "upstream" refers to a nucleic acid sequence that is positioned before the 5' end of a linked nucleic acid sequence. As used herein, "downstream" refers to a nucleic acid sequence is positioned after the 3' end of a linked nucleic acid sequence. As used herein, "5'" refers to the start of a coding DNA sequence or the beginning of an RNA molecule. As used herein, "3'" refers to the end of a coding DNA sequence or the end of an RNA molecule. It will be appreciated that an "inversion" refers to reversing the orientation of a given polynucleotide sequence. For example, if the sample sequence 5'-ATGATC-3' is inverted it will read 5'-CTAGTA-3' in reverse orientation. Additionally, the sample sequence 5'-ATGATC-3' is considered to be in "opposite orientation" to the sample sequence 5'-CTAGTA-3'.

As used herein a "donor molecule" is defined as a nucleic acid sequence that has been selected for site directed, targeted insertion into a genome. In an aspect, a donor molecule comprises a "donor sequence." In one aspect, a targeted editing technique provided herein comprises the use of one or more, two or more, three or more, four or more, or five or more donor molecules or donor sequences. A donor molecule or donor sequence provided herein can be of any length. For example, a donor molecule or donor sequence provided herein is between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000 or between 20 and 10,000 nucleotides in length. A donor molecule or donor sequence can comprise one or more genes that encode actively transcribed and/or translated gene sequences. Such transcribed sequences can encode a protein or a non-coding RNA. In one embodiment, the donor molecule or donor sequence can comprise a polynucleotide sequence which does not comprise a functional gene or an entire gene (i.e., the donor molecule can simply comprise regulatory sequences such as a promoter), or does not contain any identifiable gene expression elements or any actively transcribed gene sequence. Further, the donor molecule or donor sequence can be can be linear or circular, and can be single-stranded or double-stranded. It can be delivered to the cell as naked nucleic acid, as a complex with one or more delivery agents (e.g., liposomes, poloxamers, T-strand encapsulated with proteins, etc.) or contained in a bacterial or viral delivery vehicle, such as, for example, *Agrobacterium tumefaciens* or a geminivirus, respectively. In another aspect, a donor molecule or donor sequence provided herein is operably linked to a promoter. In a still further aspect, a donor molecule or donor sequence provided herein is transcribed into RNA. In another aspect, a donor molecule or donor sequence provided herein is not operably linked to a promoter.

In an aspect, a donor molecule or donor sequence provided herein can comprise at least one, at least two, at least three, at least four, at least five, at least six, at least seven, at least eight, at least nine, or at least ten genes. In an aspect, a donor molecule or donor sequence provided herein comprises no genes. Without being limiting, a gene provided herein can include an insecticidal resistance gene, an herbicide tolerance gene, a nitrogen use efficiency gene, a water use efficiency gene, a nutritional quality gene, a DNA binding gene, a selectable marker gene, an RNAi construct, a site-specific genome modification enzyme gene, a single guide RNA of a CRISPR/Cas9 system, a geminivirus based expression cassette, or a plant viral expression vector system. In one aspect, a donor molecule or donor sequence comprises a polynucleotide that encodes a promoter. In another aspect, a donor molecule or donor sequence provided herein comprises a polynucleotide that encodes a tissue-specific or tissue-preferred promoter. In still another aspect, a donor molecule or donor sequence provided herein comprises a polynucleotide that encodes a constitutive promoter. In another aspect, a donor molecule or donor sequence provided herein comprises a polynucleotide that encodes an inducible promoter. In another aspect, a donor molecule or donor sequence comprises a polynucleotide that encodes a structure selected from the group consisting of a leader, an enhancer, a transcriptional start site, a 5'-UTR, an exon, an intron, a 3'-UTR, a polyadenylation site, a transcriptional termination site, a promoter, a full-length gene, a partial gene, a gene, or a non-coding RNA. In one aspect, a donor molecule or donor sequence provided herein comprises one or more, two or more, three or more, four or more, or five or more designed elements.

As used herein, a "donor template", which may be a recombinant DNA donor template, is defined as a nucleic acid molecule having a nucleic acid template or insertion sequence for site-directed, targeted insertion or recombination into the genome of a plant cell via repair of a nick or double-stranded DNA break in the genome of a plant cell. For example, a "donor template" may be used for site-directed integration of a DNA segment encoding an antisense sequence of interest, or as a template to introduce a mutation, such as an insertion, deletion, etc., into a target site within the genome of a plant. A targeted genome editing technique provided herein may comprise the use of one or more, two or more, three or more, four or more, or five or more donor templates. A "donor template" may be a single-stranded or double-stranded DNA or RNA molecule or plasmid. An "insertion sequence" of a donor template is a sequence designed for targeted insertion into the genome of a plant cell, which may be of any suitable length. For example, the insertion sequence of a donor template may be between 2 and 50,000, between 2 and 10,000, between 2 and 5000, between 2 and 1000, between 2 and 500, between 2 and 250, between 2 and 100, between 2 and 50, between 2 and 30, between 15 and 50, between 15 and 100, between 15 and 500, between 15 and 1000, between 15 and 5000, between 18 and 30, between 18 and 26, between 20 and 26, between 20 and 50, between 20 and 100, between 20 and 250, between 20 and 500, between 20 and 1000, between 20 and 5000, between 20 and 10,000, between 50 and 250, between 50 and 500, between 50 and 1000, between 50 and 5000, between 50 and 10,000, between 100 and 250, between 100 and 500, between 100 and 1000, between 100 and 5000, between 100 and 10,000, between 250 and 500, between 250 and 1000, between 250 and 5000, or between 250 and 10,000 nucleotides or base pairs in length. A donor template may also have at least one homology sequence or homology arm, such as two homology arms, to direct the integration of a mutation or insertion sequence into a target site within the genome of a plant via homologous recombination, wherein the homology sequence or homology arm(s) are identical or complementary, or have a percent identity or percent complementarity, to a sequence at or near the target site within the genome of the plant. When a donor template comprises homology arm(s) and an insertion sequence, the homology arm(s) will flank or surround the insertion sequence of the donor template.

A donor template may be linear or circular and may be single-stranded or double-stranded. A donor template may be delivered to the cell as a naked nucleic acid (e.g., via particle bombardment), as a complex with one or more delivery agents (e.g., liposomes, proteins, poloxamers, T-strand encapsulated with proteins, etc.), or contained in a bacterial or viral delivery vehicle, such as, for example, *Agrobacterium tumefaciens* or a geminivirus, respectively. An insertion sequence of a donor template or insertion sequence provided herein may comprise a transcribable DNA sequence or segment that may be transcribed into all or a portion of an RNA molecule, such as an antisense sequence or portion of a RNA molecule.

As used herein, a "designed element" refers to a polynucleotide capable of inducing a desired expression pattern of an operably linked polynucleotide. In one aspect, a designed element comprises at least 10, at least 11, at least 12, at least 13, at least 14, at least 15, at least 16, at least 17, at least 18, at least 19, at least 20, at least 25, at least 30, at least 35, at least 40, at least 45, at least 50, at least 60, at least 70, at least 80, at least 90, at least 100, at least 200, at least 300, at least 400, at least 500, at least 600, at least 700, at least 800, at least 900, at least 1000, at least 1500, at least 2000, at least 2500, at least 3000, at least 4000, or at least 5000 nucleotides. In another aspect, a designed element comprises 20-50 nucleotides. In still another aspect, a designed element comprises between 10 and 5000, between 10 and 2500, between 10 and 1000, between 10 and 500, between 10 and 100, between 20 and 50, between 20 and 100, between 20 and 500, between 20 and 1000, between 20 and 2000, between 20 and 5000, between 50 and 100, between 50 and 500, between 50 and 1000, or between 50 and 5000 nucleotides. In one aspect, a designed element comprises a constitutive promoter. In another aspect, a designed element comprises an inducible promoter. In another aspect, a designed element comprises a tissue-specific or tissue-preferred promoter. In another aspect, a designed element comprises a native promoter. In another aspect, a designed element comprises a non-native promoter. In another aspect, a designed element comprises a tissue-specific or tissue-preferred promoter element. In another aspect, a designed element comprises a transcriptional enhancer element. In another aspect, a designed element comprises a transcriptional repressor element.

One aspect of the present application relates to methods of screening and selecting cells for targeted edits and methods of selecting cells comprising targeted edits. Nucleic acids can be isolated using various techniques. For example, nucleic acids can be isolated using any method including, without limitation, recombinant nucleic acid technology, and/or the polymerase chain reaction (PCR). General PCR techniques are described, for example in PCR Primer: A Laboratory Manual, Dieffenbach & Dveksler, Eds., Cold Spring Harbor Laboratory Press, 1995. Recombinant nucleic acid techniques include, for example, restriction enzyme digestion and ligation, which can be used to isolate a nucleic acid. Isolated nucleic acids also can be chemically synthesized, either as a single nucleic acid molecule or as a series of oligonucleotides. Polypeptides can be purified from natural sources (e.g., a biological sample) by known methods such as DEAE ion exchange, gel filtration, and hydroxyapatite chromatography. A polypeptide also can be purified, for example, by expressing a nucleic acid in an expression vector. In addition, a purified polypeptide can be obtained by chemical synthesis. The extent of purity of a polypeptide can be measured using any appropriate method, e.g., column chromatography, polyacrylamide gel electrophoresis, or HPLC analysis.

In one aspect, this disclosure provides methods of detecting recombinant nucleic acids and polypeptides in modified and unmodified plant cells. Without being limiting, nucleic acids also can be detected using hybridization. Hybridization between nucleic acids is discussed in detail in Sambrook et al. (1989, Molecular Cloning: A Laboratory Manual, 2nd Ed., Cold Spring Harbor Laboratory Press, Cold Spring Harbor, NY).

Polypeptides can be detected using antibodies. Techniques for detecting polypeptides using antibodies include enzyme linked immunosorbent assays (ELISAs), Western blots, immunoprecipitations and immunofluorescence. An antibody provided herein can be a polyclonal antibody or a monoclonal antibody. An antibody having specific binding affinity for a polypeptide provided herein can be generated using methods well known in the art. An antibody provided herein can be attached to a solid support such as a microtiter plate using methods known in the art.

Detection (e.g., of an amplification product, of a hybridization complex, of a polypeptide) can be accomplished using detectable labels. The term "label" is intended to encompass the use of direct labels as well as indirect labels. Detectable labels include enzymes, prosthetic groups, fluorescent materials, luminescent materials, bioluminescent materials, and radioactive materials.

The screening and selection of modified, engineered, or transgenic plants or plant cells can be through any methodologies known to those having ordinary skill in the art. Examples of screening and selection methodologies include, but are not limited to, Southern analysis, PCR amplification for detection of a polynucleotide, Northern blots, RNase protection, primer-extension, RT-PCR amplification for detecting RNA transcripts, Sanger sequencing, Next Generation sequencing technologies (e.g., Illumina, PacBio, Ion Torrent, 454) enzymatic assays for detecting enzyme or ribozyme activity of polypeptides and polynucleotides, and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known.

Genome editing or targeted editing can be effected via the use of one or more site-specific nucleases. Site-specific nucleases can induce a double-stranded break (DSB) at a target site of a genome sequence that is then repaired by the natural processes of either homologous recombination (HR) or non-homologous end-joining (NHEJ). Sequence modifications, such as insertions, deletions, can occur at the DSB locations via NHEJ repair. If two DSBs flanking one target region are created, the breaks can be repaired via NHEJ by reversing the orientation of the targeted DNA (also referred to as an "inversion"). HR can be used to integrate a donor nucleic acid sequence into a target site. Without being limited by any theory, in order to integrate a donor nucleic acid sequence (or donor molecule) into a DSB, the donor molecule comprises a polynucleotide of interest flanked by a first and second homologous region, where the first and second homologous regions are homologous to each side of the DSB at the target site. Homologous recombination machinery in the cell then repairs the DSB by integrating the donor molecule into the target site. In one aspect, a double-stranded break provided herein is repaired by NHEJ. In another aspect, a double-stranded break provided herein is repaired by HR.

Although a double-stranded break only occurs between two nucleotides on each strand, a double-stranded break site can comprise at least 2, at least 3, at least 4, at least 5, at least 6, at least 7, at least 8, at least 9, at least 10, at least 15, at least 20, at least 25, at least 30, at least 40, at least 50, at least 60, at least 70, at least 75, at least 80, at least 90, or at least 100 nucleotides. As used herein, a "double-stranded break site" refers to a polynucleotide sequence that is recognized and bound by a site-specific nuclease or guide RNA.

In an aspect, a vector or construct provided herein comprises polynucleotides encoding at least 1, at least 2, at least 3, at least 4, at least 5, at least 6, at least 7, at least 8, at least 9, or at least 10 site-specific nuclease. In another aspect, a cell provided herein already comprises a site-specific nuclease. In an aspect, a polynucleotide encoding a site-specific nuclease provided herein is stably transformed into a cell. In another aspect, a polynucleotide encoding a site-specific nuclease provided herein is transiently transformed into a cell. In another aspect, a polynucleotide encoding a site-specific nuclease is under the control of a regulatable promoter, a constitutive promoter, a tissue specific promoter, or any promoter useful for expression of the site-specific nuclease.

In one aspect, a vector comprises in cis a cassette encoding a site-specific nuclease and a donor molecule such that when contacted with the genome of a cell, the site-specific nuclease enables site-specific integration of the donor molecule. In one aspect, a first vector comprises a cassette encoding a site-specific nuclease and a second vector comprises a donor molecule such that when contacted with the genome of a cell, the site-specific nuclease provided in trans enables site-specific integration of the donor molecule.

Site-specific nucleases provided herein can be used as part of a targeted editing technique. Non-limiting examples of site-specific nucleases used in methods and/or compositions provided herein include meganucleases, zinc finger nucleases (ZFNs), transcription activator-like effector nucleases (TALENs), RNA-guided nucleases (e.g., Cas9 and Cpf1), a recombinase (without being limiting, for example, a serine recombinase attached to a DNA recognition motif, a tyrosine recombinase attached to a DNA recognition motif), a transposase (without being limiting, for example, a DNA transposase attached to a DNA binding domain), or any combination thereof. In one aspect, a method provided herein comprises the use of one or more, two or more, three or more, four or more, or five or more site-specific nucleases to induce one, two, three, four, five, or more than five DSBs at one, two, three, four, five, or more than five target sites.

In one aspect, a site-specific nuclease protein is provided to a cell. In another aspect, a nucleic acid sequence (e.g., a vector) encoding a site-specific nuclease protein is provided to a cell. In another aspect, a site-specific nuclease protein and a guide RNA are provided to a cell separately. In another aspect, a site-specific nuclease protein and a guide RNA are provided to a cell as a complex. In an aspect, a site-specific nuclease protein and a guide RNA are assembled into a complex in vitro, in vivo, or ex vivo.

In one aspect, a genome editing system provided herein (e.g., a meganuclease, a ZFN, a TALEN, a CRISPR/Cas9 system, a CRISPR/Cpf1 system, a recombinase, a transposase), or a combination of genome editing systems provided herein, is used in a method to introduce one or more insertions, deletions, substitutions, or inversions to a locus in a cell to generate a dominant negative allele or a dominant positive allele.

Site-specific nucleases, such as meganucleases, ZFNs, TALENs, Argonaute proteins (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, or modified versions thereof), Cas9 nucleases (non-limiting examples of RNA-guided nucleases include Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof), induce a double-strand DNA break at the target site of a genomic sequence that is then repaired by the natural processes of HR or NHEJ. Sequence modifications then occur at the cleaved sites, which can include inversions, deletions, or insertions that result in gene disruption in the case of NHEJ, or integration of nucleic acid sequences by HR.

In an aspect, a site-specific nuclease provided herein is selected from the group consisting of a zinc-finger nuclease, a meganuclease, an RNA-guided nuclease, a TALE-nuclease, a recombinase, a transposase, or any combination thereof. In another aspect, a site-specific nuclease provided herein is selected from the group consisting of a Cas9 or a Cpf1. In another aspect a site-specific nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a CasX, a CasY, a homolog thereof, or a modified version thereof. In another aspect, an RNA-guided nuclease provided herein is selected from the group consisting of a Cas9 or a Cpf1. In another aspect an RNA guided nuclease provided herein is selected from the group consisting of a Cas1, a Cas1B, a Cas2, a Cas3, a Cas4, a Cas5, a Cas6, a Cas7, a Cas8, a Cas9, a Cas10, a Csy1, a Csy2, a Csy3, a Cse1, a Cse2, a Csc1, a Csc2, a Csa5, a Csn2, a Csm2, a Csm3, a Csm4, a Csm5, a Csm6, a Cmr1, a Cmr3, a Cmr4, a Cmr5, a Cmr6, a Csb1, a Csb2, a Csb3, a Csx17, a Csx14, a Csx10, a Csx16, a CsaX, a Csx3, a Csx1, a Csx15, a Csf1, a Csf2, a Csf3, a Csf4, a Cpf1, a CasX, a CasY, a homolog thereof, or a modified version thereof. In another aspect, an RNA-guided nuclease is a Cas9 nuclease or a homolog or modified version thereof. In one aspect, an RNA-guided nuclease is a Cas9 protein, or a modified version thereof, from *Streptococcus pyogenes, Streptococcus thermophilius, Staphylococcus aureus, Neisseria meningitides*, or *Treponema denticola*. In another aspect, an RNA-guided nuclease is Cpf1 or a homolog or modified version thereof.

In another aspect, a method and/or a composition provided herein comprises at least one, at least two, at least three, at least four, at least five, at least six, at least seven, at least eight, at least nine, or at least ten site-specific nucleases. In yet another aspect, a method and/or a composition provided herein comprises at least one, at least two, at least three, at least four, at least five, at least six, at least seven, at least eight, at least nine, or at least ten polynucleotides encoding at least one, at least two, at least three, at least four, at least five, at least six, at least seven, at least eight, at least nine, or at least ten site-specific nucleases.

In one aspect, a targeted editing technique described herein comprises the use of a recombinase. In an aspect, a tyrosine recombinase attached to a DNA recognition motif provided herein is selected from the group consisting of a Cre recombinase, a Gin recombinase a Flp recombinase, and a Tnp1 recombinase. In an aspect, a Cre recombinase or a Gin recombinase provided herein is tethered to a zinc-finger DNA binding domain. The Flp-FRT site-directed recombination system comes from the 2μ plasmid from the baker's yeast *Saccharomyces cerevisiae*. In this system, Flp recombinase (flippase) recombines sequences between flippase recognition target (FRT) sites. FRT sites comprise 34 nucleotides. Flp binds to the "arms" of the FRT sites (one arm is in reverse orientation) and cleaves the FRT site at either end of an intervening nucleic acid sequence. After cleavage, Flp recombines nucleic acid sequences between two FRT sites. Cre-lox is a site-directed recombination system derived from the bacteriophage P1 that is similar to the Flp-FRT recombination system. Cre-lox can be used to invert a nucleic acid sequence, delete a nucleic acid sequence, or translocate a nucleic acid sequence. In this system, Cre recombinase recombines a pair of lox nucleic acid sequences. Lox sites comprise 34 nucleotides, with the first and last 13 nucleotides (arms) being palindromic. During recombination, Cre recombinase protein binds to two lox sites on different nucleic acids and cleaves at the lox sites. The cleaved nucleic acids are spliced together (reciprocally translocated) and recombination is complete. In another aspect, a lox site provided herein is a loxP, lox 2272, loxN, lox 511, lox 5171, lox71, lox66, M2, M3, M7, or M11 site.

In another aspect, a serine recombinase attached to a DNA recognition motif provided herein is selected from the group consisting of a PhiC31 integrase, an R4 integrase, and a TP-901 integrase. In another aspect, a DNA transposase attached to a DNA binding domain provided herein is selected from the group consisting of a TALE-piggyBac and TALE-Mutator.

In one aspect, a targeted editing technique described herein comprises the use of a zinc-finger nuclease (ZFN). ZFNs are synthetic proteins consisting of an engineered zinc finger DNA-binding domain fused to the cleavage domain of the FokI restriction nuclease. ZFNs can be designed to cleave almost any long stretch of double-stranded DNA for modification of the zinc finger DNA-binding domain. ZFNs form dimers from monomers composed of a non-specific DNA cleavage domain of FokI nuclease fused to a zinc finger array engineered to bind a target DNA sequence.

The DNA-binding domain of a ZFN is typically composed of 3-4 zinc-finger arrays. The amino acids at positions −1, +2, +3, and +6 relative to the start of the zinc finger ∞-helix, which contribute to site-specific binding to the target DNA, can be changed and customized to fit specific target sequences. The other amino acids form the consensus backbone to generate ZFNs with different sequence specificities. Rules for selecting target sequences for ZFNs are known in the art.

The FokI nuclease domain requires dimerization to cleave DNA and therefore two ZFNs with their C-terminal regions are needed to bind opposite DNA strands of the cleavage site (separated by 5-7 nt). The ZFN monomer can cute the target site if the two-ZF-binding sites are palindromic. The term ZFN, as used herein, is broad and includes a monomeric ZFN that can cleave double stranded DNA without assistance from another ZFN. The term ZFN is also used to refer to one or both members of a pair of ZFNs that are engineered to work together to cleave DNA at the same site.

Without being limited by any scientific theory, because the DNA-binding specificities of zinc finger domains can in principle be re-engineered using one of various methods, customized ZFNs can theoretically be constructed to target nearly any gene sequence. Publicly available methods for engineering zinc finger domains include Context-dependent Assembly (CoDA), Oligomerized Pool Engineering (OPEN), and Modular Assembly.

In one aspect, a method and/or composition provided herein comprises one or more, two or more, three or more, four or more, or five or more ZFNs. In another aspect, a ZFN provided herein is capable of generating a targeted DSB. In one aspect, vectors comprising polynucleotides encoding one or more, two or more, three or more, four or more, or five or more ZFNs are provided to a cell by transformation methods known in the art (e.g., without being limiting, viral transfection, particle bombardment, PEG-mediated protoplast transfection or *Agrobacterium*-mediated transformation).

In one aspect, a targeted editing technique described herein comprises the use of a meganuclease. Meganucleases, which are commonly identified in microbes, are unique enzymes with high activity and long recognition sequences (>14 nt) resulting in site-specific digestion of target DNA. Engineered versions of naturally occurring meganucleases typically have extended DNA recognition sequences (for example, 14 to 40 nt). The engineering of meganucleases can be more challenging than that of ZFNs and TALENs because the DNA recognition and cleavage functions of meganucleases are intertwined in a single domain. Specialized methods of mutagenesis and high-throughput screening have been used to create novel meganuclease variants that recognize unique sequences and possess improved nuclease activity.

In one aspect, a method and/or composition provided herein comprises one or more, two or more, three or more, four or more, or five or more meganucleases. In another aspect, a meganuclease provided herein is capable of generating a targeted DSB. In one aspect, vectors comprising polynucleotides encoding one or more, two or more, three or more, four or more, or five or more meganucleases are provided to a cell by transformation methods known in the art (e.g., without being limiting, viral transfection, particle bombardment, PEG-mediated protoplast transfection or *Agrobacterium*-mediated transformation).

In one aspect, a targeted editing technique described herein comprises the use of a transcription activator-like effector nuclease (TALEN). TALENs are artificial restriction enzymes generated by fusing the transcription activator-like effector (TALE) DNA binding domain to a FokI nuclease domain. When each member of a TALEN pair binds to the DNA sites flanking a target site, the FokI monomers dimerize and cause a double-stranded DNA break at the target site. Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity.

TALENs are artificial restriction enzymes generated by fusing the transcription activator-like effector (TALE) DNA binding domain to a nuclease domain. In one aspect, the nuclease is selected from a group consisting of PvuII, MutH, TevI and FokI, AZwI, MlyI, SbfI, SdaI, StsI, CleDORF, Clo051, Pept071. When each member of a TALEN pair binds to the DNA sites flanking a target site, the FokI monomers dimerize and cause a double-stranded DNA break at the target site.

The term TALEN, as used herein, is broad and includes a monomeric TALEN that can cleave double stranded DNA without assistance from another TALEN. The term TALEN is also used to refer to one or both members of a pair of TALENs that work together to cleave DNA at the same site.

Transcription activator-like effectors (TALEs) can be engineered to bind practically any DNA sequence. TALE proteins are DNA-binding domains derived from various plant bacterial pathogens of the genus *Xanthomonas*. The X pathogens secrete TALEs into the host plant cell during infection. The TALE moves to the nucleus, where it recognizes and binds to a specific DNA sequence in the promoter region of a specific DNA sequence in the promoter region of a specific gene in the host genome. TALE has a central DNA-binding domain composed of 13-28 repeat monomers of 33-34 amino acids. The amino acids of each monomer are highly conserved, except for hypervariable amino acid residues at positions 12 and 13. The two variable amino acids are called repeat-variable diresidues (RVDs). The amino acid pairs NI, NG, HD, and NN of RVDs preferentially recognize adenine, thymine, cytosine, and guanine/adenine, respectively, and modulation of RVDs can recognize consecutive DNA bases. This simple relationship between amino acid sequence and DNA recognition has allowed for the engineering of specific DNA binding domains by selecting a combination of repeat segments containing the appropriate RVDs.

Besides the wild-type FokI cleavage domain, variants of the FokI cleavage domain with mutations have been designed to improve cleavage specificity and cleavage activity. The FokI domain functions as a dimer, requiring two constructs with unique DNA binding domains for sites in the target genome with proper orientation and spacing. Both the number of amino acid residues between the TALEN DNA binding domain and the FokI cleavage domain and the number of bases between the two individual TALEN binding sites are parameters for achieving high levels of activity. PvuII, MutH, and TevI cleavage domains are useful alternatives to FokI and FokI variants for use with TALEs. PvuII functions as a highly specific cleavage domain when coupled to a TALE (see Yank et al. 2013. *PLoS One*. 8: e82539). MutH is capable of introducing strand-specific nicks in DNA (see Gabsalilow et al. 2013. *Nucleic Acids Research*. 41: e83). TevI introduces double-stranded breaks in DNA at targeted sites (see Beurdeley et al., 2013. *Nature Communications*. 4: 1762).

The relationship between amino acid sequence and DNA recognition of the TALE binding domain allows for designable proteins. Software programs such as DNA Works can be used to design TALE constructs. Other methods of designing TALE constructs are known to those of skill in the art. See Doyle et al., *Nucleic Acids Research* (2012) 40: W117-122; Cermak et al., *Nucleic Acids Research* (2011). 39:e82; and tale-nt.cac.cornell.edu/about.

In one aspect, a method and/or composition provided herein comprises one or more, two or more, three or more, four or more, or five or more TALENs. In another aspect, a TALEN provided herein is capable of generating a targeted DSB. In one aspect, vectors comprising polynucleotides encoding one or more, two or more, three or more, four or more, or five or more TALENs are provided to a cell by transformation methods known in the art (e.g., without being limiting, viral transfection, particle bombardment, PEG-mediated protoplast transfection or *Agrobacterium*-mediated transformation).

In one aspect, a targeted editing technique described herein comprises the use of a RNA-guided nuclease. A CRISPR/Cas9 system or a CRISPR/Cpf1 system are alternatives to the FokI-based methods ZFN and TALEN. The CRISPR systems are based on RNA-guided engineered nucleases that use complementary base pairing to recognize DNA sequences at target sites.

In an aspect, a vector provided herein can comprise any combination of a nucleic acid sequence encoding a RNA-guided nuclease (non-limiting examples of RNA-guided nucleases include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof); and, optionally, a guide RNA necessary for targeting the respective nucleases. As used herein, the term "guide RNA" or gRNA generally refers to an RNA molecule (or a group of RNA molecules collectively) that can bind to an RNA-guided endonuclease and aid in targeting the nuclease to a specific location within a target polynucleotide (e.g., a DNA).

While not being limited by any particular scientific theory, CRISPR/Cas nucleases are part of the adaptive immune system of bacteria and archaea, protecting them against invading nucleic acids such as viruses by cleaving target DNA in a sequence-dependent manner. The immunity is acquired by the integration of short fragments of the invading DNA, known as spacers, between ~20 nucleotide long CRISPR repeats at the proximal end of a CRISPR locus (a CRISPR array). A well described Cas protein is the Cas9 nuclease (also known as Csn1), which is part of the Class 2, type II CRISPR/Cas system in *Streptococcus pyogenes*. See Makarova et al. *Nature Reviews Microbiology* (2015) doi: 10.1038/nrmicro3569. Cas9 comprises an RuvC-like nuclease domain at its amino terminus and an HNH-like nuclease domain positioned in the middle of the protein. Cas9 proteins also contain a PAM-interacting (PI) domain, a recognition lobe (REC), and a BH domain. The Cpf1 nuclease, another type II system, acts in a similar manner to Cas9, but Cpf1 does not require a tracrRNA. See Cong et al. *Science* (2013) 339: 819-823; Zetsche et al., *Cell* (2015) doi: 10.1016/j.cell.2015.09.038; U.S. Patent Publication No. 2014/0068797; U.S. Patent Publication No. 2014/0273235; U.S. Patent Publication No. 2015/0067922; U.S. Pat. Nos. 8,697,359; 8,771,945; 8,795,965; 8,865,406; 8,871,445; 8,889,356; 8,889,418; 8,895,308; and 8,906,616, each of which is herein incorporated by reference in its entirety.

When Cas9 or Cpf1 cleaves targeted DNA, endogenous double stranded break (DSB) repair mechanisms are activated. DSBs can be repaired via non-homologous end joining, which can incorporate insertions or deletions (indels) into the targeted locus. If two DSBs flanking one target region are created, the breaks can be repaired by reversing the orientation of the targeted DNA. Alternatively, if a donor polynucleotide with homology to the target DNA sequence is provided, the DSB can be repaired via homology-directed repair. This repair mechanism allows for the precise integration of a donor polynucleotide into the targeted DNA sequence.

While not being limited by any particular scientific theory, in Class 2, type II CRISPR/Cas systems, CRISPR arrays, including spacers, are transcribed during encounters with recognized invasive DNA and are processed into small interfering CRISPR RNAs (crRNAs), which are approximately 40 nucleotides in length. The crRNAs hybridize with trans-activating crRNAs (tracrRNAs) to activate and guide the Cas9 nuclease to a target site. Nucleic acid molecules provided herein can combine a crRNA and a tracrRNA into one nucleic acid molecule in what is herein referred to as a "single-chain guide RNA (sgRNA)." A prerequisite for cleavage of the target site by Cas9 is the presence of a conserved protospacer-adjacent motif (PAM) downstream of the target DNA, which usually has the sequence 5-NGG-3 but less frequently NAG. Specificity is provided by the so-called "seed sequence" approximately 12 bases upstream of the PAM, which must match between the RNA and target DNA. Cpf1 acts in a similar manner to Cas9, but Cpf1 does not require a tracrRNA. Therefore, in an aspect utilizing Cpf1 a sgRNA can be replaced by a crRNA. The PAM motif of Cpf1 is upstream of the target site. Additionally, for Cpf1 orthologs LbCpf1 and AsCpf1, the PAM sequence is 5-TTTV-3 where V can be A, C, or G. In an aspect, when two or more sgRNAs are provided herein, the first sgRNA and the second sgRNA are complementary to different strands of a double-stranded DNA molecule. In another aspect, when two or more sgRNAs are provided herein, the first sgRNA and the second sgRNA are complementary to the same strand of a double-stranded DNA molecule. As used herein, a "protospacer adjacent motif" (PAM) refers to a 2-6 base pair DNA sequence immediately upstream or downstream of a target sequence of a CRISPR complex. In another aspect, a first and a second gRNA target different PAM sequences. In another aspect, a first and a second gRNA target the same PAM sequences.

In one aspect, a method and/or composition provided herein comprises one or more, two or more, three or more, four or more, or five or more Cas9 nucleases. In one aspect, a method and/or composition provided herein comprises one or more polynucleotides encoding one or more, two or more, three or more, four or more, or five or more Cas9 nucleases. In another aspect, a Cas9 nuclease provided herein is capable of generating a targeted DSB. In one aspect, a method and/or composition provided herein comprises one or more, two or more, three or more, four or more, or five or more Cpf1 nucleases. In one aspect, a method and/or composition provided herein comprises one or more polynucleotides encoding one or more, two or more, three or more, four or more, or five or more Cpf1 nucleases. In another aspect, a Cpf1 nuclease provided herein is capable of generating a targeted DSB.

When a Cas9 nuclease hybridizes to a target site via an sgRNA, Cas9 produces two blunt-end cuts in the double-stranded DNA. The "target strand" of the double-stranded DNA is complementary to the sgRNA, while the "non-target strand" comprises the PAM motif adjacent to, and on the 3' end of, the cut site on the non-target strand. Cas9 holds the target stand and the PAM motif, but the 3' cut end of the non-target strand is free and is referred to as the "3' flap." In one aspect, the 3' flap comprises at least 10, at least 15, at least 20, at least 25, at least 26, at least 27, at least 28, at least 29, at least 30, at least 31, at least 32, at least 33, at least 34, at least 35, at least 36, at least 37, at least 38, at least 39, or at least 40 nucleotides.

In one aspect, vectors comprising polynucleotides encoding a site-specific nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation). In one aspect, vectors comprising polynucleotides encoding a Cas9 nuclease, and optionally one or more, two or more, three or more, or four or more sgRNAs are provided to a plant cell by transformation methods known in the art (e.g., without being limiting, particle bombardment, PEG-mediated protoplast transfection or *Agrobacterium*-mediated transformation),In another aspect, vectors comprising polynucleotides encoding a Cpf1 and, optionally one or more, two or more, three or more, or four or more crRNAs are provided to a cell by transformation methods known in the art (e.g., without being limiting, viral transfection, particle bombardment, PEG-mediated protoplast transfection or *Agrobacterium*-mediated transformation).

In one aspect, an RNA-guided nuclease provided herein is selected from the group consisting of Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof, an Argonaute (non-limiting examples of Argonaute proteins include *Thermus thermophilus* Argonaute (TtAgo), *Pyrococcus furiosus* Argonaute (PfAgo), *Natronobacterium gregoryi* Argonaute (NgAgo), homologs thereof, modified versions thereof), a DNA guide for an Argonaute protein, and any combination thereof. In another aspect, an RNA-guided nuclease provided herein is selected from the group consisting of Cas9 and Cpf1. an RNA-guided nuclease provided herein comprises Cas9. In one aspect, an RNA-guided nuclease provided herein is selected from the group consisting of Cas1, Cas1B, Cas2, Cas3, Cas4, Cas5, Cas6, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, homologs thereof, or modified versions thereof. In one aspect a site-specific nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, TtAgo, PfAgo, and NgAgo. In another aspect, an RNA-guided nuclease is selected from the group consisting of Cas1, Cas1B, Cas2, Cas3, Cas4, Cas5, Cas6, Cas7, Cas8, Cas9, Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, Cpf1, CasX, CasY, TtAgo, PfAgo, and NgAgo.

Figure 11:
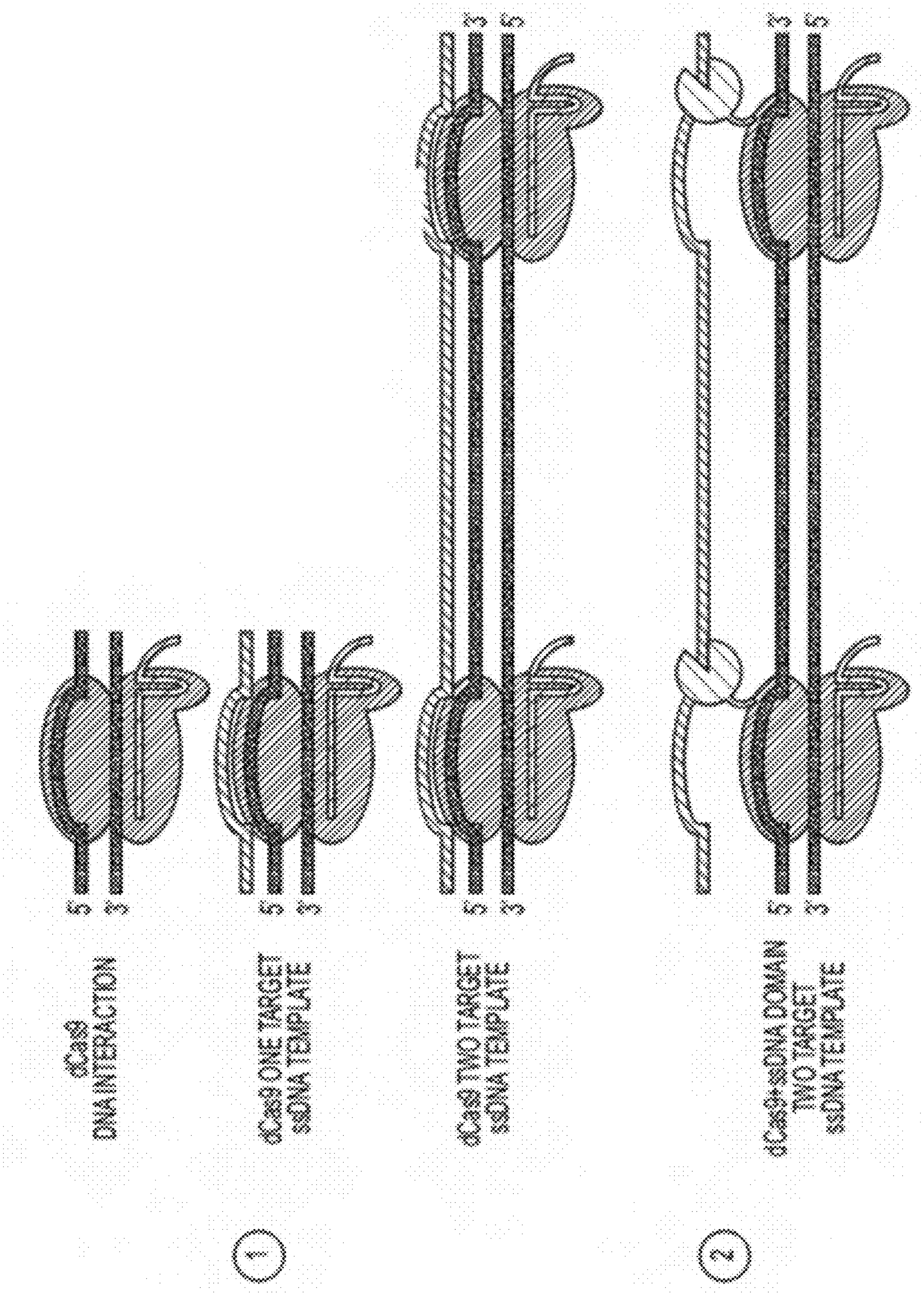
FIG. 11 depicts use of catalytically deactivated Cas9 (dCas9) to increase genome editing efficiency. Panel 1 illustrates that dCas9 binds to DNA at a target site specified by the gRNA and creates a loop structure accessible for template-based editing. Panel 2 illustrates a modified scheme for further facilitating template-based editing via a dCas9 conjugated with a ssDNA-binding domain. The editing efficiency with this modified scheme is expected to be higher compared to those in Panel 1, because a ssDNA template is bound to dCas9 complex and would be brought into proximity of the gRNA target.

Nucleases, such as Cas9, can also be engineered to form a catalytically deactivated from, such catalytically deactivated Cas9 (dCas9). dCas9 binds to DNA at a target site specified by a gRNA and creates a loop structure accessible for template-based editing (FIG. 11, Panel 1). dCas9 can be further modified to form a fusion with a ssDNA binding domain for further facilitating template-based editing (FIG. 11, Panel 2). The editing efficiency with this modified dCas9-ssDNA binding scheme is expected to be higher compared to a dCas9-alone approach, because a ssDNA template is bound to dCas9 complex and would be brought into proximity of the gRNA target. As used herein, a "deactivated Cas nuclease" (dCas) refers to an enzymatically inactive form of a Cas nuclease protein which can bind DNA, but cannot cleave DNA. In one aspect, a nuclease provided herein is a dCas. In another aspect, a site-specific nuclease provided herein is a dCas.

In one aspect, methods and compositions provided herein can be used to edit a locus in a eukaryotic cell. In one aspect, a eukaryotic cell provided herein is part of a multicellular eukaryotic organism. In another aspect, a eukaryotic cell provided herein is a unicellular organism. In another aspect, a eukaryotic cell provided herein is selected from the group consisting of an animal cell, a plant cell, a fungus cell, and a protozoan cell. In one aspect, an animal cell provided herein is selected from the group consisting of an insect cell, an arachnid cell, an arthropod cell, a crustacean cell, a rotifer cell, a cnidarian cell, a Platyhelminthes cell, a mollusk cell, a gastropod cell, a nematode cell, an annelid cell, a vertebrate cell, a mammal cell, an avian cell, a fish cell, a reptile cell, and an amphibian cell. In another aspect a plant cell provided herein is a monocot cell or a dicot cell. In still another aspect a plant cell provided herein is an algae cell. In yet another aspect, a plant cell provided herein is selected from the group consisting of a corn cell, a wheat cell, a sorghum cell, a canola cell, a soybean cell, an alfalfa cell, a cotton cell, and a rice cell. In still another aspect, a plant cell provided herein is selected from the group consisting of an Acacia cell, an alfalfa cell, an aneth cell, an apple cell, an apricot cell, an artichoke cell, an arugula cell, an asparagus cell, an avocado cell, a banana cell, a barley cell, a bean cell, a beet cell, a blackberry cell, a blueberry cell, a broccoli cell, a Brussels sprout cell, a cabbage cell, a canola cell, a cantaloupe cell, a carrot cell, a cassava cell, a cauliflower cell, a celery cell, a Chinese cabbage cell, a cherry cell, a cilantro cell, a citrus cell, a clementine cell, a coffee cell, a corn cell, a cotton cell, a cucumber cell, a Douglas fir cell, an eggplant cell, an endive cell, an escarole cell, an *eucalyptus* cell, a fennel cell, a fig cell, a forest tree cell, a gourd cell, a grape cell, a grapefruit cell, a honey dew cell, a jicama cell, kiwifruit cell, a lettuce cell, a leek cell, a lemon cell, a lime cell, a Loblolly pine cell, a mango cell, a maple tree cell, a melon cell, a mushroom cell, a nectarine cell, a nut cell, an oat cell, an okra cell, an onion cell, an orange cell, an ornamental plant cell, a papaya cell, a parsley cell, a pea cell, a peach cell, a peanut cell, a pear cell, a pepper cell, a persimmon cell, a pine cell, a pineapple cell, a plantain cell, a plum cell, a pomegranate cell, a poplar cell, a potato cell, a pumpkin cell, a quince cell, a radiata pine cell, a radicchio cell, a radish cell, a rapeseed cell, a raspberry cell, a rice cell, a rye cell, a sorghum cell, a Southern pine cell, a soybean cell, a spinach cell, a squash cell, a strawberry cell, a sugar beet cell, a sugarcane cell, a sunflower cell, a sweet corn cell, a sweet potato cell, a sweetgum cell, a tangerine cell, a tea cell, a tobacco cell, a tomato cell, a turf cell, a vine cell, watermelon cell, a wheat cell, a yam cell, and a zucchini cell. In another aspect, a plant cell provided herein is selected from the group consisting of a corn cell, a soybean cell, a canola cell, a cotton cell, a wheat cell, and a sugarcane cell.

In still another aspect an engineered plant provided herein is an algae. In yet another aspect, an engineered plant or seed provided herein is selected from the group consisting of a corn plant, a wheat plant, a sorghum plant, a canola plant, a soybean plant, an alfalfa plant, a cotton plant, and a rice plant. In still another aspect, an engineered plant or seed provided herein is selected from the group consisting of an Acacia plant, an alfalfa plant, an aneth plant, an apple plant, an apricot plant, an artichoke plant, an arugula plant, an asparagus plant, an avocado plant, a banana plant, a barley plant, a bean plant, a beet plant, a blackberry plant, a blueberry plant, a broccoli plant, a Brussels sprout plant, a cabbage plant, a canola plant, a cantaloupe plant, a carrot plant, a cassava plant, a cauliflower plant, a celery plant, a Chinese cabbage plant, a cherry plant, a cilantro plant, a citrus plant, a clementine plant, a coffee plant, a corn plant, a cotton plant, a cucumber plant, a Douglas fir plant, an eggplant plant, an endive plant, an escarole plant, an eucalyptus plant, a fennel plant, a fig plant, a forest tree plant, a gourd plant, a grape plant, a grapefruit plant, a honey dew plant, a jicama plant, kiwifruit plant, a lettuce plant, a leek plant, a lemon plant, a lime plant, a Loblolly pine plant, a mango plant, a maple tree plant, a melon plant, a mushroom plant, a nectarine plant, a nut plant, an oat plant, an okra plant, an onion plant, an orange plant, an ornamental plant, a papaya plant, a parsley plant, a pea plant, a peach plant, a peanut plant, a pear plant, a pepper plant, a persimmon plant, a pine plant, a pineapple plant, a plantain plant, a plum plant, a pomegranate plant, a poplar plant, a potato plant, a pumpkin plant, a quince plant, a radiata pine plant, a radicchio plant, a radish plant, a rapeseed plant, a raspberry plant, a rice plant, a rye plant, a sorghum plant, a Southern pine plant, a soybean plant, a spinach plant, a squash plant, a strawberry plant, a sugar beet plant, a sugarcane plant, a sunflower plant, a sweet corn plant, a sweet potato plant, a sweetgum plant, a tangerine plant, a tea plant, a tobacco plant, a tomato plant, a turf plant, a vine plant, watermelon plant, a wheat plant, a yam plant, and a zucchini plant. In another aspect, a plant provided herein is selected from the group consisting of a corn plant, a soybean plant, a canola plant, a cotton plant, a wheat plant, and a sugarcane plant.

In still another aspect a modified plant provided herein is an algae. In yet another aspect, a modified plant provided herein is selected from the group consisting of a corn plant, a wheat plant, a sorghum plant, a canola plant, a soybean plant, an alfalfa plant, a cotton plant, and a rice plant. In still another aspect, a modified plant provided herein is selected from the group consisting of an Acacia plant, an alfalfa plant, an aneth plant, an apple plant, an apricot plant, an artichoke plant, an arugula plant, an asparagus plant, an avocado plant, a banana plant, a barley plant, a bean plant, a beet plant, a blackberry plant, a blueberry plant, a broccoli plant, a Brussels sprout plant, a cabbage plant, a canola plant, a cantaloupe plant, a carrot plant, a cassava plant, a cauliflower plant, a celery plant, a Chinese cabbage plant, a cherry plant, a cilantro plant, a citrus plant, a clementine plant, a coffee plant, a corn plant, a cotton plant, a cucumber plant, a Douglas fir plant, an eggplant plant, an endive plant, an escarole plant, an eucalyptus plant, a fennel plant, a fig plant, a forest tree plant, a gourd plant, a grape plant, a grapefruit plant, a honey dew plant, a jicama plant, kiwifruit plant, a lettuce plant, a leek plant, a lemon plant, a lime plant, a Loblolly pine plant, a mango plant, a maple tree plant, a melon plant, a mushroom plant, a nectarine plant, a nut plant, an oat plant, an okra plant, an onion plant, an orange plant, an ornamental plant, a papaya plant, a parsley plant, a pea plant, a peach plant, a peanut plant, a pear plant, a pepper plant, a persimmon plant, a pine plant, a pineapple plant, a plantain plant, a plum plant, a pomegranate plant, a poplar plant, a potato plant, a pumpkin plant, a quince plant, a radiata pine plant, a radicchio plant, a radish plant, a rapeseed plant, a raspberry plant, a rice plant, a rye plant, a sorghum plant, a Southern pine plant, a soybean plant, a spinach plant, a squash plant, a strawberry plant, a sugar beet plant, a sugarcane plant, a sunflower plant, a sweet corn plant, a sweet potato plant, a sweetgum plant, a tangerine plant, a tea plant, a tobacco plant, a tomato plant, a turf plant, a vine plant, watermelon plant, a wheat plant, a yam plant, and a zucchini plant.

In yet another aspect, a modified seed provided herein is selected from the group consisting of a corn seed, a wheat seed, a sorghum seed, a canola seed, a soybean seed, an alfalfa seed, a cotton seed, and a rice seed. In still another aspect, a modified seed provided herein is selected from the group consisting of an Acacia seed, an alfalfa seed, an aneth seed, an apple seed, an apricot seed, an artichoke seed, an arugula seed, an asparagus seed, an avocado seed, a banana seed, a barley seed, a bean seed, a beet seed, a blackberry seed, a blueberry seed, a broccoli seed, a Brussels sprout seed, a cabbage seed, a canola seed, a cantaloupe seed, a carrot seed, a cassava seed, a cauliflower seed, a celery seed, a Chinese cabbage seed, a cherry seed, a cilantro seed, a citrus seed, a clementine seed, a coffee seed, a corn seed, a cotton seed, a cucumber seed, a Douglas fir seed, an eggplant seed, an endive seed, an escarole seed, an eucalyptus seed, a fennel seed, a fig seed, a forest tree seed, a gourd seed, a grape seed, a grapefruit seed, a honey dew seed, a jicama seed, kiwifruit seed, a lettuce seed, a leek seed, a lemon seed, a lime seed, a Loblolly pine seed, a mango seed, a maple tree seed, a melon seed, a mushroom seed, a nectarine seed, a nut seed, an oat seed, an okra seed, an onion seed, an orange seed, an ornamental plant seed, a papaya seed, a parsley seed, a pea seed, a peach seed, a peanut seed, a pear seed, a pepper seed, a persimmon seed, a pine seed, a pineapple seed, a plantain seed, a plum seed, a pomegranate seed, a poplar seed, a potato seed, a pumpkin seed, a quince seed, a *radiata* pine seed, a radicchio seed, a radish seed, a rapeseed seed, a raspberry seed, a rice seed, a rye seed, a sorghum seed, a Southern pine seed, a soybean seed, a spinach seed, a squash seed, a strawberry seed, a sugar beet seed, a sugarcane seed, a sunflower seed, a sweet corn seed, a sweet potato seed, a sweetgum seed, a tangerine seed, a tea seed, a tobacco seed, a tomato seed, a turf seed, a vine seed, watermelon seed, a wheat seed, a yam seed, and a zucchini seed.

In still another aspect a modified chromosome provided herein is an algae. In yet another aspect, a modified chromosome provided herein is selected from the group consisting of a corn chromosome, a wheat chromosome, a sorghum chromosome, a canola chromosome, a soybean chromosome, an alfalfa chromosome, a cotton chromosome, and a rice chromosome. In still another aspect, a modified chromosome provided herein is selected from the group consisting of an Acacia chromosome, an alfalfa chromosome, an aneth chromosome, an apple chromosome, an apricot chromosome, an artichoke chromosome, an arugula chromosome, an asparagus chromosome, an avocado chromosome, a banana chromosome, a barley chromosome, a bean chromosome, a beet chromosome, a blackberry chromosome, a blueberry chromosome, a broccoli chromosome, a Brussels sprout chromosome, a cabbage chromosome, a canola chromosome, a cantaloupe chromosome, a carrot chromosome, a cassava chromosome, a cauliflower chromosome, a celery chromosome, a Chinese cabbage chromosome, a cherry chromosome, a cilantro chromosome, a citrus chromosome, a clementine chromosome, a coffee chromosome, a corn chromosome, a cotton chromosome, a cucumber chromosome, a Douglas fir chromosome, an eggplant chromosome, an endive chromosome, an escarole chromosome, an *eucalyptus* chromosome, a fennel chromosome, a fig chromosome, a forest tree chromosome, a gourd chromosome, a grape chromosome, a grapefruit chromosome, a honey dew chromosome, a jicama chromosome, kiwifruit chromosome, a lettuce chromosome, a leek chromosome, a lemon chromosome, a lime chromosome, a Loblolly pine chromosome, a mango chromosome, a maple tree chromosome, a melon chromosome, a mushroom chromosome, a nectarine chromosome, a nut chromosome, an oat chromosome, an okra chromosome, an onion chromosome, an orange chromosome, an plant chromosome chromosome, a papaya chromosome, a parsley chromosome, a pea chromosome, a peach chromosome, a peanut chromosome, a pear chromosome, a pepper chromosome, a persimmon chromosome, a pine chromosome, a pineapple chromosome, a plantain chromosome, a plum chromosome, a pomegranate chromosome, a poplar chromosome, a potato chromosome, a pumpkin chromosome, a quince chromosome, a *radiata* pine chromosome, a radicchio chromosome, a radish chromosome, a rapeseed chromosome, a raspberry chromosome, a rice chromosome, a rye chromosome, a sorghum chromosome, a Southern pine chromosome, a soybean chromosome, a spinach chromosome, a squash chromosome, a strawberry chromosome, a sugar beet chromosome, a sugarcane chromosome, a sunflower chromosome, a sweet corn chromosome, a sweet potato chromosome, a sweetgum chromosome, a tangerine chromosome, a tea chromosome, a tobacco chromosome, a tomato chromosome, a turf chromosome, a vine chromosome, watermelon chromosome, a wheat chromosome, a yam chromosome, and a zucchini chromosome.

In one aspect, a cell provided herein is a modified cell. In another aspect, a plant provided herein is a modified plant. In yet another aspect, a plant cell provided herein is a modified plant cell. In still another aspect, a seed provided herein is a modified seed. In a further aspect, a chromosome provided herein is a modified chromosome.

According to one aspect, a modified plant, plant cell, cell, seed, or chromosome provided herein comprises at least one, at least two, at least three, at least four, at least five, at least six, at least seven, at least eight, at least nine, or at least ten deletions generated by a targeted editing technique. According to one aspect, a modified plant, plant cell, cell, seed, or chromosome provided herein comprises at least one, at least two, at least three, at least four, at least five, at least six, at least seven, at least eight, at least nine, or at least ten insertions generated by a targeted editing technique. According to one aspect, a modified plant, plant cell, cell, seed, or chromosome provided herein comprises at least one, at least two, at least three, at least four, at least five, at least six, at least seven, at least eight, at least nine, or at least ten inversions generated by a targeted editing technique. According to one aspect, a modified plant, plant cell, cell, seed, or chromosome provided herein comprises at least one, at least two, at least three, at least four, at least five, at least six, at least seven, at least eight, at least nine, or at least ten deletions generated by a targeted editing technique, at least one, at least two, at least three, at least four, at least five, at least six, at least seven, at least eight, at least nine, or at least ten insertions generated by a targeted editing technique, at least one, at least two, at least three, at least four, at least five, at least six, at least seven, at least eight, at least nine, or at least ten inversions generated by a targeted editing technique, or any combination thereof. In still another aspect, a modified plant, plant cell, cell, seed, or chromosome provided herein comprises at least one, at least two, at least three, at least four, at least five, at least six, at least seven, at least eight, at least nine, or at least ten dominant negative alleles generated by a targeted editing technique. In still another aspect, a modified plant, plant cell, cell, seed, or chromosome provided herein comprises at least one, at least two, at least three, at least four, at least five, at least six, at least seven, at least eight, at least nine, or at least ten dominant positive alleles generated by a targeted editing technique. In still another aspect, a modified plant, plant cell, cell, seed, or chromosome provided herein comprises at least one, at least two, at least three, at least four, at least five, at least six, at least seven, at least eight, at least nine, or at least ten dominant negative alleles generated by a targeted editing technique, at least one, at least two, at least three, at least four, at least five, at least six, at least seven, at least eight, at least nine, or at least ten dominant positive alleles generated by a targeted editing technique, or any combination thereof.

According to another aspect of the present application, a modified plant(s), plant cell(s), seed(s), chromosome(s) and plant part(s) are provided comprising a genome editing event in the genome of at least one plant cell thereof, the genome editing event comprising an insertion, a deletion, a substitution, or an inversion of a targeted locus.

According to one aspect, the present disclosure provides a modified plant cell produced by any one of the methods provided herein. In another aspect, the present disclosure provides a modified chromosome produced by any one of the methods provided herein. In still another aspect, the present disclosure provides a modified cell comprising a modified chromosome provided herein. In still a further aspect, this disclosure provides a modified plant or modified plant tissue regenerated from a modified cell provided herein. In still another aspect, the present disclosure provides a product comprising a modified chromosome provided herein. In an aspect, the present disclosure provides a product comprising a modified cell provided herein. As used herein, a "product" refers to any article or substance that is intended for human use, human consumption, animal use, or animal consumption, including any component, part, or accessory that comprises a modified cell or modified chromosome provided herein.

The methods and compositions provided herein are capable of editing any locus in a genome. Also provided herein are chromosomes edited by using the methods and compositions provided herein. In an aspect, a genome provided herein is a nuclear genome, a mitochondrial genome, or a plastid genome. In another aspect, a plastid genome provided herein comprises a chloroplast genome. In one aspect, a method provided herein generates a double-stranded break on a chromosome. In an aspect, a chromosome provided herein is a nuclear chromosome, a mitochondrial chromosome, or a chloroplast chromosome. In another aspect a chromosome provided herein is a supernumerary chromosome or an artificial chromosome. Supernumerary, or B chromosomes, are extra chromosomes found in addition to the normal diploid complement of chromosomes in a cell. Supernumerary chromosomes are dispensable and not required for normal development of a cell or organism. In an aspect, a supernumerary chromosome provided herein is a maize supernumerary chromosome or a rye supernumerary chromosome.

A method of targeted editing disclosed herein can involve transient transfection or stable transformation of a cell of interest (e.g., a plant cell). According to one aspect of the present application, methods are provided for transforming a cell, tissue or explant with a recombinant DNA molecule or construct comprising a transcribable DNA sequence or transgene operably linked to a promoter to produce a transgenic or genome edited cell. According to another aspect of the present application, methods are provided for transforming a plant cell, tissue or explant with a recombinant DNA molecule or construct comprising a transcribable DNA sequence or transgene operably linked to a plant-expressible promoter to produce a transgenic or genome edited plant or plant cell. As used herein, a "transgene" refers to a polynucleotide that has been transferred into a genome by any method known in the art.

Numerous methods for transforming chromosomes or plastids in a plant cell with a recombinant DNA molecule or construct are known in the art, which can be used according to methods of the present application to produce a transgenic plant cell and plant. Any suitable method or technique for transformation of a plant cell known in the art can be used according to present methods. Effective methods for transformation of plants include bacterially mediated transformation, such as *Agrobacterium*-mediated or *Rhizobium*-mediated transformation and microprojectile bombardment-mediated transformation. A variety of methods are known in the art for transforming explants with a transformation vector via bacterially mediated transformation or microprojectile bombardment and then subsequently culturing, etc., those explants to regenerate or develop transgenic plants. Other methods for plant transformation, such as microinjection, electroporation, vacuum infiltration, pressure, sonication, silicon carbide fiber agitation, PEG-mediated transformation, etc., are also known in the art. Transgenic plants produced by these transformation methods can be chimeric or non-chimeric for the transformation event depending on the methods and explants used.

Methods of transforming plant cells are well known by persons of ordinary skill in the art. For instance, specific instructions for transforming plant cells by microprojectile bombardment with particles coated with recombinant DNA are found in U.S. Pat. Nos. 5,550,318; 5,538,880 6,160,208; 6,399,861; and 6,153,812 and *Agrobacterium*-mediated transformation is described in U.S. Pat. Nos. 5,159,135; 5,824,877; 5,591,616; 6,384,301; 5,750,871; 5,463,174; and 5,188,958, all of which are incorporated herein by reference. Additional methods for transforming plants can be found in, for example, Compendium of Transgenic Crop Plants (2009) Blackwell Publishing. Any appropriate method known to those skilled in the art can be used to transform a plant cell with any of the nucleic acid molecules provided herein.

Recipient cell or explant targets for transformation include, but are not limited to, a seed cell, a fruit cell, a leaf cell, a cotyledon cell, a hypocotyl cell, a meristem cell, an embryo cell, an endosperm cell, a root cell, a shoot cell, a stem cell, a pod cell, a flower cell, an inflorescence cell, a stalk cell, a pedicel cell, a style cell, a stigma cell, a receptacle cell, a petal cell, a sepal cell, a pollen cell, an anther cell, a filament cell, an ovary cell, an ovule cell, a pericarp cell, a phloem cell, a bud cell, or a vascular tissue cell. In another aspect, this disclosure provides a plant chloroplast. In a further aspect, this disclosure provides an epidermal cell, a stomata cell, a trichome cell, a root hair cell, a storage root cell, or a tuber cell. In another aspect, this disclosure provides a protoplast. In another aspect, this disclosure provides a plant callus cell. Any cell from which a fertile plant can be regenerated is contemplated as a useful recipient cell for practice of this disclosure. Callus can be initiated from various tissue sources, including, but not limited to, immature embryos or parts of embryos, seedling apical meristems, microspores, and the like. Those cells which are capable of proliferating as callus can serve as recipient cells for transformation. Practical transformation methods and materials for making transgenic plants of this disclosure (e.g., various media and recipient target cells, transformation of immature embryos, and subsequent regeneration of fertile transgenic plants) are disclosed, for example, in U.S. Pat. Nos. 6,194,636 and 6,232,526 and U. S. Patent Application Publication 2004/0216189, all of which are incorporated herein by reference. Transformed explants, cells or tissues can be subjected to additional culturing steps, such as callus induction, selection, regeneration, etc., as known in the art. Transformed cells, tissues or explants containing a recombinant DNA insertion can be grown, developed or regenerated into transgenic plants in culture, plugs or soil according to methods known in the art. In one aspect, this disclosure provides plant cells that are not reproductive material and do not mediate the natural reproduction of the plant. In another aspect, this disclosure also provides plant cells that are reproductive material and mediate the natural reproduction of the plant. In another aspect, this disclosure provides plant cells that cannot maintain themselves via photosynthesis. In another aspect, this disclosure provides somatic plant cells. Somatic cells, contrary to germline cells, do not mediate plant reproduction. In one aspect, this disclosure provides a non-reproductive plant cell.

Modified plants can be further crossed to themselves or other plants to produce modified seeds and progeny. A modified plant can also be prepared by crossing a first plant comprising a recombinant DNA sequence insertion with a second plant lacking the insertion. For example, a recombinant DNA sequence can be introduced into a first plant line that is amenable to transformation, which can then be crossed with a second plant line to introgress the recombinant DNA sequence into the second plant line. A modified plant can also be prepared by crossing a modified plant with an unmodified plant. Progeny of these crosses can be further back crossed into the more desirable line multiple times, such as through 6 to 8 generations or back crosses, to produce a progeny plant with substantially the same genotype as the original parental line but for the introduction of the recombinant DNA construct or modified sequence.

A modified plant, cell, or explant provided herein can be of an elite variety or an elite line. An elite variety or an elite line refers to any variety that has resulted from breeding and selection for superior agronomic performance. A modified plant, cell, or explant provided herein can be a hybrid plant, cell, or explant. As used herein, a "hybrid" is created by crossing two plants from different varieties, lines, or species, such that the progeny comprises genetic material from each parent. Skilled artisans recognize that higher order hybrids can be generated as well. For example, a first hybrid can be made by crossing Variety C with Variety D to create a C×D hybrid, and a second hybrid can be made by crossing Variety E with Variety F to create an E×F hybrid. The first and second hybrids can be further crossed to create the higher order hybrid (C×D)×(E×F) comprising genetic information from all four parent varieties. A modified plant provided herein is fertile. A modified plant provided herein is a male or female sterile modified plant, which cannot reproduce without human intervention. In one aspect, a modified plant provided herein reproduces via asexual or vegetative reproduction. In still another aspect, a modified plant provided herein reproduces via sexual reproduction.

A recombinant DNA molecule or construct of the present application can comprise or be included within a DNA transformation vector for use in transformation of a target plant cell, tissue or explant. Such a transformation vector of the present application can generally comprise sequences or elements necessary or beneficial for effective transformation in addition to at least one selectable marker gene, at least one expression cassette and/or transcribable DNA sequence encoding one or more site-specific nucleases, and, optionally, one or more sgRNAs or crRNAs. For *Agrobacterium*-mediated transformation, the transformation vector can comprise an engineered transfer DNA (or T-DNA) segment or region having two border sequences, a left border (LB) and a right border (RB), flanking at least a transcribable DNA sequence or transgene, such that insertion of the T-DNA into the plant genome will create a transformation event for the transcribable DNA sequence, transgene or expression cassette. In other words, the transgene, a transcribable DNA sequence, transgene or expression cassette encoding the site-specific nuclease(s), and/or sgRNA(s) or crRNA(s) would be located between the left and right borders of the T-DNA, perhaps along with an additional transgene(s) or expression cassette(s), such as a plant selectable marker transgene and/or other gene(s) of agronomic interest that can confer a trait or phenotype of agronomic interest to a plant. According to an alternative aspect, the transcribable DNA sequence, transgene or expression cassette encoding at least one site-specific nuclease, any necessary sgRNAs or crRNAs, and the plant selectable marker transgene (or other gene of agronomic interest) can be present in separate T-DNA segments on the same or different recombinant DNA molecule(s), such as for co-transformation. A transformation vector or construct can further comprise prokaryotic maintenance elements, which for *Agrobacterium*-mediated transformation can be located in the vector backbone outside of the T-DNA region(s).

A plant selectable marker transgene in a transformation vector or construct of the present application can be used to assist in the selection of transformed cells or tissue due to the presence of a selection agent, such as an antibiotic or herbicide, where the plant selectable marker transgene provides tolerance or resistance to the selection agent. Thus, the selection agent can bias or favor the survival, development, growth, proliferation, etc., of transformed cells expressing the plant selectable marker gene, such as to increase the proportion of transformed cells or tissues in the $R_0$ plant. Commonly used plant selectable marker genes include, for example, those conferring tolerance or resistance to antibiotics, such as kanamycin and paromomycin (nptII), hygromycin B (aph IV), streptomycin or spectinomycin (aadA) and gentamycin (aac3 and aacC4), or those conferring tolerance or resistance to herbicides such as glufosinate (bar or pat), dicamba (DMO) and glyphosate (aroA or Cp4-EPSPS). Plant screenable marker genes can also be used, which provide an ability to visually screen for transformants, such as luciferase or green fluorescent protein (GFP), or a gene expressing a beta glucuronidase or uidA gene (GUS) for which various chromogenic substrates are known. In one aspect, a vector or polynucleotide provided herein comprises at least one marker gene selected from the group consisting of nptII, aph IV, aadA, aac3, aacC4, bar, pat, DMO, EPSPS, aroA, GFP, and GUS.

According to an aspect of the present application, methods for transforming a plant cell, tissue or explant with a recombinant DNA molecule or construct can further include site-directed or targeted integration using site-specific nucleases. According to these methods, a portion of a recombinant DNA donor molecule (i.e., an insertion sequence) can be inserted or integrated at a desired site or locus within a genome. The insertion sequence of the donor template can comprise a transgene or construct, such as a designed element or a tissue-specific promoter. The donor molecule can also have one or two homology arms flanking the insertion sequence to promote the targeted insertion event through homologous recombination and/or homology-directed repair. Thus, a recombinant DNA molecule of the present application can further include a donor template for site-directed or targeted integration of a transgene or construct, such as a transgene or transcribable DNA sequence encoding a designed element or a tissue-specific promoter into a genome.

As used herein, a "portion" of a nucleic acid sequence or molecule refers to any number of nucleotides less than the full length of the nucleic sequence. For example, a portion of a 100 nucleotide nucleic acid sequence can be any number of nucleotides from 1 to 99 nucleotides. Alternatively, a "portion" of a nucleic sequence refers to anywhere from 0.01% to 99.99% of the full length of a given nucleic acid sequence.

Provided herein are methods of generating dominant alleles of gene regions using targeted editing techniques. Also provided herein are cells generated by such methods and compositions used in such methods. The instant description further provides modified plants regenerated from cells subjected to the methods provided herein. In one aspect, a dominant negative allele provided herein is capable of suppressing transcription of a locus or a gene in a heterozygous state. In another aspect, a dominant negative allele provided herein is capable of suppressing transcription of a locus or a gene in a homozygous state.

Dominant negative alleles of a gene region can reduce or eliminate the function of a gene region product in a heterozygous state. Without being limiting, a dominant negative allele can be generated by editing an allele of a gene region such that at least a portion of the polynucleotide encoding the gene region is inverted in orientation (e.g., a portion of the gene is flipped to a 3' to 5' orientation while the rest of the gene remains in a 5' to 3' orientation). Expression of the edited allele of the gene region will comprise an antisense RNA segment that is complementary to the sense RNA expressed by the unedited gene region. Without being bound by any scientific theory, the complementary segment between the sense and antisense portions of the gene region RNAs can be processed by RNA silencing mechanisms native to the cell to reduce the expression of the edited and unedited gene region alleles in a dominant negative manner. In one aspect, an antisense RNA transcript provided herein is capable of suppressing a complementary sense RNA transcript. In another aspect, an antisense RNA transcript provided herein is suppresses a complementary sense RNA transcript.

In one aspect, this disclosure provides a method of generating a dominant negative allele of a gene in a cell comprising inverting a portion of the gene using a targeted editing technique, generating an antisense RNA transcript capable of triggering suppression of an unmodified allele. In one aspect, expression of the unmodified allele is reduced as compared to a control cell that does not comprise the antisense RNA transcript. In another aspect, a targeted editing technique provided here comprises the use of at least one site-specific nuclease. In an aspect, an antisense RNA transcript provided herein is a partial antisense RNA transcript. In another aspect, an antisense RNA transcript provided herein is a complete antisense RNA transcript. Without being limiting, a partial antisense RNA transcript can be generated by inverting only one region of a gene as opposed to inverting the entire gene. For instance, if an mRNA transcript is encoded by three exons, inverting only the second exon would enable the generation of a partial antisense RNA transcript. It will be appreciated that inverting any number of nucleotides of a gene region that is less than the length of the entire gene region can give rise to a partial antisense RNA transcript. As an example, if a gene region comprises 500 nucleotides, inverting a 200 nucleotide region will give rise to a partial antisense RNA transcript. If all 500 nucleotides were inverted a complete antisense RNA transcript would be generated. In an aspect, an antisense RNA transcript provided herein is capable of suppressing expression of a complementary nucleic acid sequence. In an aspect, an anti sense RNA transcript provided herein is capable of suppressing expression of at least one, at least two, at least three, at least four, at least five, at least six, at least seven, at least eight, at least nine, or at least ten genes. In an aspect, an antisense RNA transcript provided herein is capable of suppressing expression of a first gene region. In an aspect, an antisense RNA transcript provided herein is capable of suppressing expression of a protein encoded by a complementary nucleic acid sequence. One of skill in the art would recognize that 100% complementarity is not required between an antisense RNA transcript and a second nucleic acid in order to induce suppressed expression of the second nucleic acid. For example, an antisense RNA transcript comprising at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, or 100% complementarity to a second nucleic acid sequence can be capable of suppressing expression of the second nucleic acid sequence.

In one aspect, an antisense RNA transcript transcribed by a dominant negative allele provided herein is capable of downregulating expression of itself. In another aspect, an antisense RNA transcript transcribed by a dominant negative allele provided herein is capable of downregulating expression of an unmodified allele of the same locus. In one aspect, expression of the unmodified allele is reduced as compared to a control cell that does not comprise the antisense RNA transcript.

In one aspect, this disclosure provides a method of generating a dominant negative allele of a gene in one or more cells comprising: a) inducing a first double-stranded break and a second double-stranded break flanking a targeted region of the gene; b) identifying one or more cells comprising an inversion of the targeted region of the gene, where the inversion results in the production of an antisense RNA transcript from the targeted region of the gene; and c) selecting one or more cells comprising the inversion of the targeted region of the gene.

In another aspect, this disclosure provides a method of reducing the expression of a protein in a cell comprising: a) inducing a first double-stranded break and a second double-stranded break flanking a targeted region of a chromosome; and b) identifying one or more cells comprising an inversion in the targeted region of the chromosome, where expression of the protein is reduced as compared to a control cell that does not comprise the inversion in the targeted region.

In a further aspect, this disclosure provides a method of generating an inversion in a targeted region of a gene comprising: a) providing to one or more cells at least one RNA-guided nuclease or one or more vectors encoding an RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a first target site and a second target site flanking the targeted region of the gene, where the first target site and the second target site are linked, where the at least one RNA-guided nuclease creates double-stranded breaks in the gene at the first target site and the second target site; b) identifying one or more cells comprising an inversion in the targeted region of the gene, where the inversion results in the production of an antisense RNA transcript from the targeted region; and c) selecting one or more cells comprising the inversion in the targeted region of the gene.

In one aspect, a method or composition provided herein comprises at least one, at least two, at least three, at least four, at least five, at least six, at least seven, at least eight, at least nine, or at least ten site-specific nucleases. In another aspect, a method or composition provided herein comprises at least one, at least two, at least three, at least four, at least five, at least six, at least seven, at least eight, at least nine, or at least ten sgRNAs. In a further aspect, a method or composition provided herein comprises at least one, at least two, at least three, at least four, at least five, at least six, at least seven, at least eight, at least nine, or at least ten tgOligos. In another aspect, a method or composition provided herein comprises at least one, at least two, at least three, at least four, at least five, at least six, at least seven, at least eight, at least nine, or at least ten donor molecules. In another aspect, a method or composition provided herein comprises at least one, at least two, at least three, at least four, at least five, at least six, at least seven, at least eight, at least nine, or at least ten donor sequences.

In another aspect, a method or composition provided herein comprises at least one, at least two, at least three, at least four, at least six, at least seven, at least eight, at least nine, or at least ten vectors encoding at least one, at least two, at least three, at least four, at least five, at least six, at least seven, at least eight, at least nine, or at least ten site-specific nucleases. In another aspect, a method or composition provided herein comprises at least one, at least two, at least three, at least four, at least six, at least seven, at least eight, at least nine, or at least ten vectors encoding at least one, at least two, at least three, at least four, at least five, at least six, at least seven, at least eight, at least nine, or at least ten sgRNAs. In another aspect, a method or composition provided herein comprises at least one, at least two, at least three, at least four, at least six, at least seven, at least eight, at least nine, or at least ten vectors encoding at least one, at least two, at least three, at least four, at least five, at least six, at least seven, at least eight, at least nine, or at least ten tgOligos. In another aspect, a method or composition provided herein comprises at least one, at least two, at least three, at least four, at least six, at least seven, at least eight, at least nine, or at least ten vectors encoding at least one, at least two, at least three, at least four, at least five, at least six, at least seven, at least eight, at least nine, or at least ten donor molecules. In another aspect, a method or composition provided herein comprises at least one, at least two, at least three, at least four, at least six, at least seven, at least eight, at least nine, or at least ten vectors encoding at least one, at least two, at least three, at least four, at least five, at least six, at least seven, at least eight, at least nine, or at least ten donor sequences.

In one aspect, a vector provided herein encodes at least one, at least two, at least three, at least four, or at least five site-specific nucleases. In one aspect, a vector provided herein encodes at least one, at least two, at least three, at least four, or at least five RNA-guided nucleases. In another aspect, a vector provided herein encodes at least one, at least two, at least three, at least four, or at least five sgRNAs. In one aspect, a method or composition provided herein comprises one or more vectors comprising a first sgRNA and a second sgRNA. In aIn a further aspect, a vector provided herein encodes at least one, at least two, at least three, at least four, or at least five donor molecules.

In an aspect, a vector provided herein encodes at least one, at least two, at least three, at least four, or at least five site-specific nucleases and at least one, at least two, at least three, at least four, or at least five sgRNAs. In another aspect, a vector provided herein encodes at least one, at least two, at least three, at least four, or at least five RNA-guided nuclease and at least one, at least two, at least three, at least four, or at least five sgRNAs. In an aspect, a vector provided herein encodes at least one, at least two, at least three, at least four, or at least five sgRNAs and at least one, at least two, at least three, at least four, or at least five donor molecules.

In another aspect a vector provided herein encodes at least one RNA-guided nuclease, a first sgRNA, and a second sgRNA. In a further aspect, at least one RNA-guided nuclease, a first sgRNA, and a second sgRNA are encoded by two or more or three or more vectors. In another aspect, a vector provided herein encodes at least one RNA-guided nuclease, a sgRNA, and a donor molecule. In a further aspect, at least one RNA-guided nuclease, a sgRNA, and a donor molecule are encoded by two or more or three or more vectors.

In another aspect, a vector provided herein encodes at least one, at least two, at least three, at least four, or at least five site-specific nucleases and at least one, at least two, at least three, at least four, or at least five donor molecules. In one aspect, a vector provided herein encodes at least one, at least two, at least three, at least four, or at least five RNA-guided nucleases and at least one, at least two, at least three, at least four, or at least five donor molecules. In another aspect, a vector provided herein encodes at least one, at least two, at least three, at least four, or at least five site-specific nucleases, at least one, at least two, at least three, at least four, or at least five sgRNAs, and at least one, at least two, at least three, at least four, or at least five donor molecules. In another aspect, a vector provided herein encodes at least one, at least two, at least three, at least four, or at least five RNA-guided nucleases, at least one, at least two, at least three, at least four, or at least five sgRNAs, and at least one, at least two, at least three, at least four, or at least five donor molecules. In another aspect, a vector provided herein encodes at least one site-specific nuclease, at least one donor molecule, and at least one sgRNA. In another aspect, a vector provided herein encodes at least one RNA-guided nuclease, at least one donor molecule, and at least one sgRNA.

In one aspect, one or more site-specific nucleases, one or more sgRNAs, and one or more donor molecule provided herein are encoded by one vector. In one aspect, one or more site-specific nucleases, one or more sgRNAs, and one or more donor molecule provided herein are encoded by two or more or three or more vectors. In still another aspect, one or more sgRNAs, and one or more donor molecule provided herein are encoded by two or more, three or more, four or more, five or more, six or more, seven or more, eight or more, nine or more, or ten or more vectors. In one aspect, at least one RNA-guided nuclease, a first sgRNA, and a second sgRNA are encoded by one vector. In another aspect, at least one RNA-guided nuclease, a first sgRNA, and a second sgRNA are encoded by two or more or three or more vectors. In one aspect, at least one site-specific nuclease, a first sgRNA, and a second sgRNA are encoded by one vector. In another aspect, at least one site-specific nuclease, a first sgRNA, and a second sgRNA are encoded by two or more or three or more vectors. In one aspect, at least one RNA-guided nuclease, at least one sgRNA, and at least one donor molecule are encoded by one vector. In one aspect, at least one RNA-guided nuclease, at least one sgRNA, and at least one donor molecule are encoded by two or more or three or more vectors. In one aspect, at least one site-specific nuclease, at least one sgRNA, and at least one donor molecule are encoded by one vector. In one aspect, at least one site-specific nuclease, at least one sgRNA, and at least one donor molecule are encoded by two or more or three or more vectors.

In one aspect, one or more Cas9 nucleases, one or more sgRNAs, and one or more donor molecule provided herein are encoded by one vector. In one aspect, one or more Cas9 nucleases, one or more sgRNAs, and one or more donor molecule provided herein are encoded by two or more or three or more vectors. In one aspect, at least one Cas9 nuclease, a first sgRNA, and a second sgRNA are encoded by one vector. In another aspect, at least one Cas9 nuclease, a first sgRNA, and a second sgRNA are encoded by two or more or three or more vectors. In one aspect, at least one Cas9 nuclease, at least one sgRNA, and at least one donor molecule are encoded by one vector. In one aspect, at least one Cas9 nuclease, at least one sgRNA, and at least one donor molecule are encoded by two or more or three or more vectors.

In still another aspect, any vector described herein further encodes at least one, at least two, at least three, at least four, or at least five marker genes. In one aspect, a marker gene provided herein is selected from the group consisting of nptII, aph IV, aadA, aac3, aacC4, bar, pat, DMO, EPSPS, aroA, GFP, and GUS.

Targeted editing techniques can be used to convert a genomic locus into a locus that is capable of generating an RNAi-inducing hairpin when the edited locus is transcribed into RNA. In a cell that is heterozygous at the locus of interest (e.g., two polymorphic alleles are present), two or more nucleases are used to generate two double-stranded breaks (e.g., a first double-stranded break and a second double-stranded break) in the first allele, and one double-stranded break (e.g., a third double-stranded break) in the second allele. When the nucleases cut the alleles, the portion of the first allele that is flanked by the first and second double-stranded breaks is released from the genomic DNA. In one outcome, the released portion of the first allele is inverted and integrated into the third double-stranded break in the second allele, thereby creating an edited locus that is capable of generating an RNAi-inducing hairpin when the edited locus is transcribed.

This disclosure provides a method comprising: a) generating a first double-stranded break and a second double-stranded break in a first allele of a gene in a cell using a targeted editing technique; generating a third double-stranded break in a second allele of the gene in the cell using a targeted editing technique; and c) identifying a cell comprising an insertion of a region of the first allele in inverted orientation at the third double-stranded break site in the second allele, thereby generating a modified second allele. In one aspect, a modified second allele is a dominant negative allele. In another aspect, a modified second allele is a dominant positive allele. In an aspect, a first double-stranded break and a second double-stranded break are at the same nucleotide sequence or the same nucleotide position in the first allele and the second allele. In an aspect, a first double-stranded break and a second double-stranded break are at the same nucleotide sequence in the first allele and the second allele. In an aspect, a first double-stranded break and a second double-stranded break are at the same nucleotide position in the first allele and the second allele. In an aspect, the nucleotide sequence of a first allele is not identical to the nucleotide sequence of the second allele (e.g., the cell is heterozygous for the locus). In an aspect, the nucleotide sequence at the third double-stranded break site in the second allele is not present in the first allele. In an aspect, a modified second allele provided herein transcribes an RNA capable of forming a hairpin loop secondary structure. In an aspect, a region of the first allele can comprise any number of nucleotides up to and including the full length of the first allele. In an aspect, a region of the first allele comprises at least 10, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, at least 1500, at least 2000, at least 3000, at least 4000, at least 5000, or at least 10,000 nucleotides. In another aspect, a region of the first allele comprises between 18 and 5000, between 18 and 4000, between 18 and 3000, between 18 and 2000, between 18 and 1000, between 18 and 500, between 18 and 400, between 18 and 300, between 18 and 200, between 18 and 100, between 18 and 50, between 18 and 30, between 50 and 500, between 50 and 1000, between 100 and 500, between 100 and 1000, or between 500 and 5000 nucleotides.

In one aspect, this disclosure provides a modified cell comprising at least one dominant negative allele of at least one gene generated by a targeted editing technique, where the allele generates an RNA transcript capable of forming a hairpin-loop secondary structure when the at least one dominant negative allele is transcribed.

This disclosure provides a method of generating a dominant negative allele of a gene in a cell comprising inserting an inverted copy of the gene, or a portion thereof, adjacent to a native copy of the gene using a targeted editing technique to generate an inverted repeat sequence capable of producing an antisense RNA transcript of the gene, or a portion thereof. In one aspect, the inverted repeat sequence is capable of forming a hairpin-loop secondary structure. In another aspect, the dominant negative allele generates at least one RNA transcript capable of forming a hairpin-loop secondary structure. In one aspect, the inverted copy of the gene and the native copy of the gene are separated by a spacer sequence. In an aspect, a spacer sequence comprises at least 1, at least 2, at least 3, at least 4, at least 5, at least 10, at least 25, at least 50, at least 75, at least 100, at least 150, at least 250, at least 500, or at least 1000 nucleotides. In yet another aspect, the dominant negative allele is operably linked to a promoter of the native copy of the gene.

In another aspect, this disclosure provides a modified cell comprising a dominant negative allele of at least one gene comprising an inverted copy of the gene adjacent to a native copy of the gene at the endogenous locus of the gene.

A dominant negative allele can also be generated by editing a genome to delete a region of DNA between a first gene region and a second, neighboring gene region, where the first gene region and the second gene region are present on the chromosome in opposite orientations (e.g., the first gene region is present in 5' to 3' orientation, while the second gene region is present on the same DNA strand of the chromosome in 3' to 5' orientation). Without being bound by any scientific theory, such a deletion allows the expression of an antisense RNA transcript of the first gene region by the promoter of the second gene region, while the native promoter of the first gene region expresses a sense RNA transcript. The sense and antisense RNA transcripts are complementary to each other and can be processed by RNA silencing mechanisms native to the cell to reduce the expression of the edited and unedited first gene region alleles in a dominant negative manner. Without being bound by any scientific theory, it is also contemplated that the antisense RNA molecule transcribed from the mutant or edited allele of the endogenous gene or locus may affect the expression level(s) of the gene through different mechanisms, such as nonsense mediated decay, non-stop decay, no-go decay, DNA or histone methylation or other epigenetic changes, inhibition or decreased efficiency of transcription and/or translation, ribosomal interference, interference with mRNA processing or splicing, and/or ubiquitin-mediated protein degradation via the proteasome. See, e.g., Nickless, A. et al., "Control of gene expression through the nonsense-mediated RNA decay pathway", *Cell Biosci* 7:26 (2017); Karamyshev, A. et al., "Lost in Translation: Ribosome-Associated mRNA and Protein Quality Controls", *Frontiers in Genetics* 9:431 (2018); Inada, T., "Quality controls induced by aberrant translation", *Nucleic Acids Res* 48:3 (2020); and Szadeczky-Kardoss, I. et al., "The nonstop decay and the RNA silencing systems operate cooperatively in plants", *Nucleic Acids Res* 46:9 (2018), the entire contents and disclosures of which are incorporated herein by reference. Each of these different mechanisms may act alternatively or in addition to RNA interference (RNAi), transcriptional gene silencing (PGS) and/or post transcriptional gene silencing (PTGS) mechanisms. See, e.g., Wilson, R. C. et al., "Molecular Mechanisms of RNA Interference", *Annu Rev Biophysics* 42:217-39 (2013); and Guo, Q. et al., "RNA Silencing in Plants: Mechanism, Technologies and Applications in Horticulture Crops", *Current Genomics* 17:476-489 (2016), the entire contents and disclosures of which is incorporated herein by reference. Some of the above mechanisms may reduce expression of the edited allele itself, while others may also reduce the expression of other copy/-ies or allele(s) of the endogenous locus/loci or gene(s). Such dominant or semi-dominant effect(s) on the gene(s) may operate through non-canonical suppression mechanisms that do not involve RNAi and/or formation of targeted small RNAs at a significant or detectable level.

In one aspect, this disclosure provides a method of generating a dominant negative allele of a gene in a cell comprising deleting a portion of a chromosome between a first gene region and a second gene region using a targeted editing technique, where an antisense mRNA transcript of the first gene region is generated following the deletion of the portion of the chromosome. In another aspect, a targeted editing technique provided here comprises the use of at least one site-specific nuclease. In an aspect, an antisense RNA transcript provided herein is a partial antisense RNA transcript. In an aspect, a partial antisense RNA transcript is shorter than the corresponding sense RNA transcript. In an aspect, a partial antisense RNA transcript is at least 1, at least 2, at least 3, at least 4, at least 5, at least 6, at least 7, at least 8, at least 9, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, at least 1500, at least 2000, or at least 2500 nucleotides shorter than a corresponding sense RNA transcript. In another aspect, a partial antisense RNA transcript is at least 1%, at least 2%, at least 3%, at least 4%, at least 5%, at least 10%, at least 20%, at least 30%, at least 40%, at least 50%, at least 60%, at least 70%, at least 80%, at least 90%, or at least 95% shorter than a corresponding sense RNA transcript. In another aspect, an antisense RNA transcript provided herein is a complete antisense RNA transcript. In an aspect, a complete antisense RNA transcript is the same length as a corresponding sense RNA transcript. In an aspect, an antisense RNA transcript provided herein suppresses expression of a first gene region. In an aspect, an antisense RNA transcript provided herein is capable of suppressing expression of a first gene region.

In another aspect, this disclosure provides a method comprising: a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; b) inducing a first double-stranded break and a second double-stranded break flanking a targeted region; c) identifying one or more cells comprising a deletion of the targeted region of the chromosome; and d) selecting one or more cells comprising the deletion of the targeted region of the chromosome.

As used herein, an "intervening region" or "intervening sequence" refers to a polynucleotide sequence between a physically linked first polynucleotide sequence and second polynucleotide sequence. In one aspect, an intervening region or intervening sequence is between a first gene and a second gene. In an aspect, an intervening region or intervening sequence is between a first gene region and a second gene region. In one aspect, an intervening region or intervening sequence is between a first coding region and a second coding region. In another aspect, an intervening region or intervening sequence is between a first target site and a second target site. In one aspect, an intervening region or intervening sequence is between a first target gene and a second target gene. In one aspect, all or part of an intervening region or intervening sequence is inverted via a targeted editing technique. In another aspect, all or part of an intervening region or intervening sequence is deleted via a targeted editing technique. In one aspect, an intervening region or intervening sequence comprises at least 1, at least 2, at least 3, at least 4, at least 5, at least 10, at least 25, at least 50, at least 100, at least 150, at least 200, at least 250, at least 500, at least 1000, at least 1250, at least 1500, at least 1750, at least 2000, at least 2500, at least 3000, at least 4000, at least 5000, at least 6000, at least 7000, at least 8000, at least 9000, at least 10,000, at least 15,000, at least 20,000, at least 25,000, or at least 50,000 nucleotides. In an aspect, an intervening region or an intervening sequence comprises at least one, at least two, at least three, at least four, at least five, at least six, at least seven, at least eight, at least nine, or at least ten genes. In one aspect, an intervening region or intervening sequence is positioned on a chromosome. In one aspect, an intervening region or intervening sequence is positioned on a vector. In one aspect, an intervening region or intervening sequence comprises a DNA sequence. In one aspect, an intervening region or intervening sequence comprises an RNA sequence. In one aspect, an intervening region or intervening sequences comprises an endogenous nucleic acid sequence. In another aspect, an intervening region or intervening sequences comprises a transgenic nucleic acid sequence. In one aspect, an intervening region or intervening sequences comprises an endogenous nucleic acid sequence and a transgenic nucleic acid sequence.

In one aspect, a first gene region is selected from the group of a GA20 oxidase gene region, a GA3 oxidase gene region, a brachytic2 gene region, and a Y1 gene region. In another aspect, a first gene region is a GA20 oxidase gene region or a GA3 oxidase gene region. In a further aspect, a first gene region is a GA20 oxidase gene region. In an aspect, a first gene region is a GA3 oxidase gene region. In still another aspect, a first gene region is a brachytic2 gene region. In another aspect, a first gene region is a Y1 gene region.

GA oxidases in cereal plants consist of a family of related GA oxidase genes. For example, corn has a family of at least nine GA20 oxidase genes that includes GA20 oxidase_1, GA20 oxidase_2, GA20 oxidase_3, GA20 oxidase_4, GA20 oxidase_5, GA20 oxidase_6, GA20 oxidase_7, GA20 oxidase_8, and GA20 oxidase_9. The DNA and protein sequences by SEQ ID NOs for each of GA20 oxidase_3 and GA20 oxidase_5 are provided in Table 1.

TABLE 1

DNA and protein sequences by sequence identifier for GA20 oxidase_3 and GA20 oxidase_5 genes in corn.

| GA20 oxidase Gene | Genomic DNA | cDNA | Coding Sequence (CDS) | Protein |
|---|---|---|---|---|
| GA20 oxidase_3 | SEQ ID NO: 27 | SEQ ID NO: 28 | SEQ ID NO: 29 | SEQ ID NO: 30 |
| GA20 oxidase_5 | SEQ ID NO: 31 | SEQ ID NO: 32 | SEQ ID NO: 33 | SEQ ID NO: 34 |

A wild-type genomic DNA sequence of the GA20 oxidase_3 locus from a reference genome is provided in SEQ ID NO: 27, and A wild-type genomic DNA sequence of the GA20 oxidase_5 locus from a reference genome is provided in SEQ ID NO: 31.

For the corn GA20 oxidase_3 gene (also referred to as Zm.GA20ox3), SEQ ID NO: 27 provides 3000 nucleotides upstream (5') of the GA20 oxidase_3 5'-UTR; nucleotides 3001-3096 correspond to the 5'-UTR; nucleotides 3097-3665 correspond to the first exon; nucleotides 3666-3775 correspond to the first intron; nucleotides 3776-4097 correspond to the second exon; nucleotides 4098-5314 correspond to the second intron; nucleotides 5315-5584 correspond to the third exon; and nucleotides 5585-5800 correspond to the 3'-UTR. SEQ ID NO: 27 also provides 3000 nucleotides downstream (3') of the end of the 3'-UTR (nucleotides 5801-8800).

For the corn GA20 oxidase_5 gene (also referred to as Zm.GA20ox5), SEQ ID NO: 31 provides 3000 nucleotides upstream of the GA20 oxidase_5 start codon (nucleotides 1-3000); nucleotides 3001-3791 correspond to the first exon; nucleotides 3792-3906 correspond to the first intron; nucleotides 3907-4475 correspond to the second exon; nucleotides 4476-5197 correspond to the second intron; nucleotides 5198-5473 correspond to the third exon; and nucleotides 5474-5859 correspond to the 3'-UTR. SEQ ID NO: 31 also provides 3000 nucleotides downstream (3') of the end of the 3'-UTR (nucleotides 5860-8859).

In the corn genome, the Zm.GA20ox5 gene located next to the Zm.SAMT gene. These two genes are separated by an intergenic region of about 550 bp, with the Zm.SAMT gene positioned downstream and oriented in the opposite orientation relative to the Zm.GA20ox5 gene. A reference genomic sequence of the region encompassing the Zm.GA20ox5 and Zm.SAMT genes is provided in SEQ ID NOs. 35 and 36. SEQ ID NO. 35 represents the sequence of the sense strand of the Zm.GA20ox5 gene encompassing both Zm.GA20ox5 and Zm.SAMT genes (the "GA20ox5_SAMT genomic sequence" in Table 2). SEQ ID NO: 35 partially overlaps with SEQ ID NO: 31 and has a shorter Zm.GA20ox5 upstream sequence and a longer Zm.GA20ox5 downstream sequence compared to the SEQ ID NO: 31. SEQ ID NO. 36 represents the sequence of the sense strand of the Zm.SAMT gene (i.e., the antisense strand of the Zm.GA20ox5 gene) encompassing both Zm.GA20ox5 and Zm.SAMT genes (the "SAMT_GA20ox5 genomic sequence" in Table 2). The elements or regions of the reference genomic Zm.GA20ox5/Zm.SAMT sequence are annotated in Table 2 below by reference to the nucleotide coordinates of those elements or regions in SEQ ID NO. 35 or 36.

It was previously shown that suppression of GA20 oxidase gene(s) and/or targeting of a subset of one or more GA oxidase genes via transgenic suppression (e.g., an artificial microRNA-mediated suppression of both GA20 oxidase_3 and GA20 oxidase_5 genes) can be effective in achieving a short stature, semi-dwarf phenotype with increased resistance to lodging, but without reproductive off-types in the ear. See PCT Application No. PCT/US2017/047405 and U.S. application Ser. No. 15/679,699, both filed on Aug. 17, 2017, and published as WO/2018/035354 and US20180051295, respectively. Furthermore, knocking out GA20 oxidase_3, GA20 oxidase_5, or both genes via genome editing also can cause reduced plant height and increased lodging resistance, and impacts GA hormonal levels. See PCT Application Nos. PCT/US2019/018128, PCT/US2019/018131, and PCT/US2019/018133, all filed on Feb. 15, 2019.

In one aspect, a first gene region comprises a polynucleotide sequence having at least 80%, at least 85%, at least 90%, at least 91%, at least 92%, at least 93%, at least 94%, at least 95%, at least 96%, at least 97%, at least 98%, at least 99%, at least 99.5%, or 100% identity or complementarity to a sequence selected from the group consisting of SEQ ID NOs: (insert GA20 cDNA sequences).

In another aspect, a first gene region comprises a polynucleotide sequence having at least 80%, at least 85%, at least 90%, at least 91%, at least 92%, at least 93%, at least 94%, at least 95%, at least 96%, at least 97%, at least 98%, at least 99%, at least 99.5%, or 100% identity or complementarity to a sequence selected from the group consisting of SEQ ID NOs: (insert BR2 cDNA sequences).

In one aspect, a first gene region comprises a polynucleotide sequence having at least 80%, at least 85%, at least 90%, at least 91%, at least 92%, at least 93%, at least 94%, at least 95%, at least 96%, at least 97%, at least 98%, at least 99%, at least 99.5%, or 100% identity or complementarity to a sequence selected from the group consisting of SEQ ID NOs: (insert GA3 cDNA sequences).

In one aspect, a first gene region comprises a polynucleotide sequence having at least 80%, at least 85%, at least 90%, at least 91%, at least 92%, at least 93%, at least 94%, at least 95%, at least 96%, at least 97%, at least 98%, at least 99%, at least 99.5%, or 100% identity or complementarity to a sequence selected from the group consisting of SEQ ID NOs: (insert Y1 cDNA sequences).

In an aspect, a deletion provided herein comprises all or part of a second gene region. In another aspect, a deletion provided herein comprises all of a second gene region. In still another aspect, a deletion provided herein comprises part of a second gene region.

In still another aspect, this disclosure provides a method of reducing expression of a gene in a cell comprising: a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; b) inducing a first double-stranded break and a second double-stranded break flanking a targeted region using a targeted editing technique, where the targeted region comprises the second coding region and the intervening region; and c) identifying one or more cells comprising a deletion of the targeted region of the chromosome, where the second promoter generates at least one antisense RNA of the first coding region, and where expression of the first coding region is reduced as compared to a control cell that does not comprise the deletion of the targeted region. In one aspect, a deletion leads to a portion of a first coding region being transcribed in reverse orientation.

In a further aspect, this disclosure provides a method comprising: a) identifying a chromosomal region comprising a first gene region comprising a first promoter and a first coding region, and a second gene region comprising a second promoter and a second coding region, where the first coding region and the second coding region are separated by an intervening region, and where the first promoter and the second promoter are positioned in opposite orientations; b) providing to one or more cells at least one RNA-guided nuclease or one or more vectors encoding at least one RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a first target site and a second target site flanking a targeted region of a chromosome, where the targeted region comprises the second coding region and the intervening region, where the RNA-guided nuclease creates double-stranded breaks in the chromosome at the first target site and the second target site; b) identifying one or more cells comprising a deletion of the targeted region; and c) selecting one or more cells comprising the deletion of the targeted region.

In one aspect, this disclosure provides a modified plant, or part thereof, comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In one aspect, this disclosure provides a modified plant cell comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In another aspect, this disclosure provides a modified plant or modified plant tissue comprising a modified plant cell comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof.

It is known in the art that transposons, or transposable elements, are DNA sequences that can change their position within a genome. Transposons can create insertions, deletions, or inversions in a genome. In an aspect, methods, compositions, and cells provided herein do not comprise the use of a transposon (e.g., "non-transposon mediated").

In one aspect, this disclosure provides a modified chromosome comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In one aspect, this disclosure provides a modified cell comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In another aspect, this disclosure provides a modified cell comprising a modified chromosome comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof.

In one aspect, this disclosure provides a product comprising a modified chromosome comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In one aspect, this disclosure provides a product comprising a modified plant, or part thereof, comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In one aspect, this disclosure provides a product comprising a modified plant cell comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In one aspect, this disclosure provides a product comprising a modified cell comprising a non-transposon mediated genome deletion or inversion of a gene or a portion thereof, at the endogenous locus of the gene, where the deletion or inversion results in the production of an RNA transcript comprising a sequence complementary to a native transcript sequence of the gene, or portion thereof. In an aspect, a product comprises silage, flour, cellulose, sugar, starch, fat, syrup, or protein derived from a plant, plant part, or plant cell.

In an aspect, this disclosure provides a modified cell comprising a) a non-transposon mediated genome deletion of at least one gene or a portion thereof, at the endogenous locus of the at least one gene, or b) a non-transposon mediated and non-T-DNA mediated insertion of a polynucleotide sequence into the at least one gene, where the deletion or insertion creates a dominant positive allele of the at least one gene. In one aspect, an insertion comprises a regulatory element. In another aspect, a regulatory element is selected from the group consisting of a promoter sequence, a transcriptional start site sequence, a transcriptional termination site sequence, an enhancer sequence, and a designed element.

In another aspect, the present disclosure provides a modified cell comprising a non-transposon mediated genome deletion or inversion of at least one gene or a portion thereof, at the endogenous locus of the at least one gene, where the deletion or inversion creates a dominant negative allele of the at least one gene. In still another aspect, this disclosure provides a modified cell comprising a non-transposon mediated genome deletion or inversion of a gene or a portion thereof, at the endogenous locus of the at least one gene, where the deletion or inversion results in the production of an RNA transcript comprising a sequence complementary to a native transcript sequence of the gene. In an aspect, this disclosure provides a modified cell comprising a targeted edit of at least one gene or a portion thereof, where the targeted edit generates an RNA transcript that is complementary to a native transcript sequence of the gene. In an aspect, an RNA transcript is a complete antisense transcript. In another aspect, an RNA transcript is a partial antisense transcript. In a further aspect, an RNA transcript is a partial sense transcript. In still another aspect, an RNA transcript is a complete sense transcript. In another aspect, an RNA transcript is a native transcript of a gene. In a further aspect, a native transcript of a gene is a partial or complete sense transcript.

A dominant allele of a gene region can also be created by inserting a designed element into the promoter of a gene region to induce constitutive expression of the gene region.

In one aspect, this disclosure provides a method of modifying gene expression comprising: a) inducing a double-stranded break using a targeted editing technique at a target site of the gene; b) inserting a donor sequence at the double-stranded break, where the donor sequence comprises a designed element capable of inducing increased or ectopic expression of the gene; and c) identifying at least one cell comprising the insertion of the donor sequence, where expression of the gene is increased in at least one tissue as compared to a control cell that does not comprise the insertion of the donor sequence.

In another aspect, this disclosure provides a method comprising a) providing to one or more cells at least one RNA-guided nuclease and at least one donor molecule or one or more vectors encoding at least one RNA-guided nuclease and at least one donor molecule, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the donor molecule comprises a designed element, where the RNA-guided nuclease creates a double-stranded break at the target site, and where the donor molecule is inserted at the double-stranded break; b) identifying one or more cells comprising the insertion of the donor molecule at the target site; and c) selecting one or more cells comprising the insertion of the donor molecule at the target site.

In an aspect, the target site is positioned downstream of a TATA box upstream of the gene. In an aspect, the target site is positioned upstream of a TATA box upstream of the gene. In an aspect, a target site is positioned upstream of a TATA box that is operably linked to at least one gene. In another aspect, a target site is positioned downstream of a TATA box that is operably linked to at least one gene. In an aspect, a target site is positioned within 10, within 20, within 30, within 40, within 50, within 60, within 70, within 80, within 90, within 100, within 200, within 300, within 400, within 500, within 600, within 700, within 800, within 900, within 1000, within 1500, within 2000, within 2500, or within 5000 nucleotides of a TATA box that is operably linked to at least one gene. In still another aspect, a target site is positioned between 10 and 5000, between 10 and 2500, between 10 and 1500, between 10 and 1000, between 10 and 750, between 10 and 500, between 10 and 250, between 10 and 100, between 20 and 100, between 20 and 250, between 20 and 500, or between 50 and 500 nucleotides of a TATA box that is operably linked to at least one gene. In still another aspect the target site is positioned within 10, within 20, within 30, within 40, within 50, within 60, within 70, within 80, within 90, within 100, within 200, within 300, within 400, within 500, within 600, within 700, within 800, within 900, within 1000, within 1500, within 2000, within 2500, or within 5000 nucleotides of a promoter of a gene. In still another aspect, the target site is positioned upstream of an initiator element upstream of the gene. In still another aspect, the target site is positioned downstream of an initiator element upstream of the gene. In still another aspect the target site is positioned within 10, within 20, within 30, within 40, within 50, within 60, within 70, within 80, within 90, within 100, within 200, within 300, within 400, within 500, within 600, within 700, within 800, within 900, within 1000, within 1500, within 2000, within 2500, or within 5000 nucleotides of an initiator element of a gene.

In one aspect, a "TATA box" comprises a core DNA sequence of 5'-TATAAA-3' or a variant thereof, and is frequently associated with the promoters of eukaryotic genes. Typically, but not always, a TATA box is positioned approximately 25 to 35 nucleotides upstream of a transcription start site of a gene. TATA boxes often serve as a binding site for a transcription factor to enable expression of an operably linked gene, or a histone to block expression of an operably linked gene. In one aspect, a TATA box is an initiator element. An initiator element is a core promoter that facilitates the binding of a transcription factor to promote expression of an operably linked gene. In one aspect, an initiator sequence provided herein comprises the sequence of 5'-[C/T][C/T]AN[A/T][C/T][C/T]-3'.

A dominant negative allele can also be created by editing a genome to comprise a tissue-specific or a tissue-preferred promoter of a gene region, such that the tissue-specific or tissue-preferred promoter is in opposite orientation of a targeted gene. For example, placing an tissue-specific promoter downstream of the 3'-UTR of a gene region in reverse orientation would allow the tissue-specific promoter to generate a complete antisense gene region RNA transcript. Without being bound to any theory, the antisense gene region RNA transcript expressed by the antisense tissue-specific promoter is able to suppress the expression of the gene region in a tissue-specific manner.

In one aspect, this disclosure provides a method of reducing the expression of a gene in at least one cell comprising a) inducing a double-stranded break using a targeted editing technique at a target site of the gene; b) inserting a donor sequence at the double-stranded break, where the donor sequence comprises a tissue-specific or tissue-preferred promoter, and where the donor sequence is inserted into the target site such that the tissue-specific or tissue-preferred promoter is in reverse orientation as compared to the gene; and c) identifying at least one cell comprising the insertion of the donor sequence in reverse orientation, where expression of the gene is reduced as compared to a control cell that does not comprise the insertion of the donor sequence. In one aspect, a method provided herein further comprises using a targeted editing technique to remove the native promoter of the gene. As used herein, a "native promoter" refers to a promoter that generates a sense mRNA transcript of an operably linked gene.

In another aspect, this disclosure provides a method comprising a) providing to one or more cells at least one RNA-guided nuclease and at least one donor molecule or one or more vectors encoding at least one RNA-guided nuclease and at least one donor molecule, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the donor molecule comprises a sequence encoding a tissue-specific or tissue-preferred promoter, where the RNA-guided nuclease creates a double-stranded break at the target site, and where the donor molecule is inserted at the double-stranded break; b) identifying one or more cells comprising the insertion of the donor molecule at the target site such that the tissue-specific or tissue-preferred promoter is in reverse orientation as compared to the gene; and c) selecting one or more cells comprising the insertion of the donor molecule at the target site.

In an aspect, a target site is positioned downstream of the 3'-UTR of a gene. In another aspect, a target site is positioned within the 3'-UTR of a gene. In another aspect, a target site is positioned within an intron of a gene. In a further aspect, a target site is positioned within an exon of a gene. In an aspect, a target site is positioned with a 5'-UTR of a gene. In another aspect, a target site is positioned upstream of a 5'-UTR of a gene. In a still further aspect, a target site is positioned within a promoter of a gene.

In one aspect, the donor molecule comprises a polynucleotide that encodes a promoter. In one aspect, the donor molecule comprises a polynucleotide that encodes a promoter that is selected from the group consisting of a tissue-specific promoter, a tissue-preferred promoter, a constitutive promoter, and an inducible promoter. In another aspect, the donor molecule provided herein comprises a polynucleotide that encodes a tissue-specific or tissue-preferred promoter. In still another aspect, the donor molecule provided herein comprises a polynucleotide that encodes a constitutive promoter. In another aspect, the donor molecule provided herein comprises a polynucleotide that encodes an inducible promoter.

In an aspect, a tissue-specific or tissue-preferred promoter is selected from the group consisting of a leaf-specific promoter, a leaf-preferred promoter, a stem-specific promoter, a stem-preferred promoter, a vascular-specific promoter, a vascular-preferred promoter, a root-specific promoter, a root-preferred promoter, an inflorescence-specific promoter, an inflorescence-preferred promoter, a pollen-specific promoter, a pollen-preferred promoter, an anther-specific promoter, an anther-preferred promoter, an ovule-specific promoter, an ovule-preferred promoter, a seed-specific promoter, a seed-preferred promoter, an embryo-specific promoter, an embryo-preferred promoter, an endosperm-specific promoter, an endosperm-preferred promoter, a pericarp-specific promoter, a pericarp-preferred promoter, an aleurone-specific promoter, an aleurone-preferred promoter, a meristem-specific promoter, a meristem-preferred promoter, a fruit-specific promoter, a fruit-preferred promoter, a pod-specific promoter, a pod-preferred promoter, an epidermis-specific promoter, an epidermis-preferred promoter, a mitochondrial-specific promoter, a mitochondrial-preferred promoter, a chloroplast-specific promoter, and a chloroplast-preferred promoter. In another aspect, a tissue-specific or tissue-preferred promoter provided herein is an RTBV promoter. In an aspect, a tissue-specific or tissue-preferred promoter provided herein expresses an antisense mRNA transcript of a gene. In an aspect, a tissue-specific or tissue-preferred promoter provided herein is expresses an antisense mRNA transcript of a gene.

Targeted editing techniques can be used to insert a donor molecule into a target site in a genomic locus. If a donor molecule comprising a non-coding RNA target site is inserted into a 5'-UTR, an exon, an intron, or a 3'-UTR of a gene of interest, RNA transcription or protein translation of the gene of interest can be suppressed by a complementary non-coding RNA. When a gene of interest is a target of a non-coding RNA (e.g., a miRNA or an siRNA), a cleaved mRNA from the gene of interest can generate secondary siRNAs, which can further suppress the transcription or translation of the gene of interest. Such secondary suppression can act in a dominant manner, as the secondary siRNAs are complementary to alleles with and without the insertion of the non-coding RNA target site.

In one aspect, an engineered or artificial miRNA is created to target a native gene region. In another aspect, a gene region is edited to be complementary to a native miRNA. Engineered miRNAs are useful for targeted gene suppression with increased specificity. See, e.g., Parizotto et al., *Genes Dev.* 18:2237-2242 (2004), and U.S. Patent Application Publication Nos. 2004/0053411, 2004/0268441, 2005/0144669, and 2005/0037988, the contents and disclosures of which are incorporated herein by reference. miRNAs are non-protein coding RNAs. When a miRNA precursor molecule is cleaved, a mature miRNA is formed that is typically from about 19 to about 25 nucleotides in length (commonly from about 20 to about 24 nucleotides in length in plants), such as 19, 20, 21, 22, 23, 24, or 25 nucleotides in length, and has a sequence corresponding to the gene targeted for suppression and/or its complement. The mature miRNA hybridizes to target mRNA transcripts and guides the binding of a complex of proteins to the target transcripts, which can function to inhibit translation and/or result in degradation of the transcript, thus negatively regulating or suppressing expression of the targeted gene. miRNA precursors are also useful in plants for directing in-phase production of siRNAs, trans-acting siRNAs (ta-siRNAs), in a process that requires a RNA-dependent RNA polymerase to cause suppression of a target gene. See, e.g., Allen et al., *Cell* 121:207-221 (2005), Vaucheret *Science STKE,* 2005:pe43 (2005), and Yoshikawa et al. *Genes Dev.,* 19:2164-2175 (2005), the contents and disclosures of which are incorporated herein by reference.

Plant miRNAs regulate their target genes by recognizing and binding to a near-perfectly complementary sequence (miRNA recognition site) in the target transcript, followed by cleavage of the transcript by RNase III enzymes such as ARGONAUTE1. In plants, certain mismatches between a given miRNA recognition site and the corresponding mature miRNA are not tolerated, particularly mismatched nucleotides at positions 10 and 11 of the mature miRNA. Positions within the mature miRNA are given in the 5' to 3' direction. Perfect complementarity between a given miRNA recognition site and the corresponding mature miRNA is usually required at positions 10 and 11 of the mature miRNA. See, for example, Franco-Zorrilla et al. (2007) Nature Genetics, 39:1033-1037; and Axtell et al. (2006) Cell, 127:565-577.

Many microRNA genes (MIR genes) have been identified and made publicly available in a database ("miRBase", available on line at microrna.sanger.ac.uk/sequences; also see Griffiths-Jones et al. (2003) Nucleic Acids Res., 31:439-441). MIR genes have been reported to occur in intergenic regions, both isolated and in clusters in the genome, but can also be located entirely or partially within introns of other genes (both protein-coding and non-protein-coding). For a recent review of miRNA biogenesis, see Kim (2005) Nature Rev. Mol. Cell. Biol., 6:376-385. Transcription of MIR genes can be, at least in some cases, under promotional control of a MIR gene's own promoter. The primary transcript, termed a "pri-miRNA", can be quite large (several kilobases) and can be polycistronic, containing one or more pre-miRNAs (fold-back structures containing a stem-loop arrangement that is processed to the mature miRNA) as well as the usual 5' "cap" and polyadenylated tail of an mRNA. See, for example, FIG. 1 in Kim (2005) Nature Rev. Mol. Cell. Biol., 6:376-385.

Transgenic expression of miRNAs (whether a naturally occurring sequence or an artificial sequence) can be employed to regulate expression of the miRNA's target gene or genes. Recognition sites of miRNAs have been validated in all regions of a mRNA, including the 5' untranslated region, coding region, and 3' untranslated region, indicating that the position of the miRNA target site relative to the coding sequence may not necessarily affect suppression (see, e.g., Jones-Rhoades and Bartel (2004). Mol. Cell, 14:787-799, Rhoades et al. (2002) Cell, 110:513-520, Allen et al. (2004) Nat. Genet., 36:1282-1290, Sunkar and Zhu (2004) Plant Cell, 16:2001-2019). Because miRNAs are important regulatory elements in eukaryotes, transgenic suppression of miRNAs is useful for manipulating biological pathways and responses. Promoters of MIR genes can have very specific expression patterns (e.g., cell-specific, tissue-specific, temporally specific, or inducible), and thus are useful in recombinant constructs to induce such specific transcription of a DNA sequence to which they are operably linked. Various utilities of miRNAs, their precursors, their recognition sites, and their promoters are described in detail in U.S. Patent Application Publication 2006/0200878 A1, incorporated by reference herein. Non-limiting examples of these utilities include: (1) the expression of a native miRNA or miRNA precursor sequence to suppress a target gene; (2) the expression of an artificial miRNA or miRNA precursor sequence to suppress a target gene; (3) expression of a transgene with a miRNA recognition site, where the transgene is suppressed when the mature miRNA is expressed; (4) expression of a transgene driven by a miRNA promoter.

Designing an artificial miRNA sequence can be as simple as substituting sequence that is complementary to the intended target for nucleotides in the miRNA stem region of the miRNA precursor, as demonstrated by Zeng et al. (2002) Mol. Cell, 9:1327-1333. One non-limiting example of a general method for determining nucleotide changes in the native miRNA sequence to produce the engineered miRNA precursor includes the following steps: (a) Selecting a unique target sequence of at least 18 nucleotides specific to the target gene, e.g., by using sequence alignment tools such as BLAST (see, for example, Altschul et al. (1990) J. Mol. Biol., 215:403-410; Altschul et al. (1997) Nucleic Acids Res., 25:3389-3402), for example, of both tobacco cDNA and genomic DNA databases, to identify target transcript orthologues and any potential matches to unrelated genes, thereby avoiding unintentional silencing of non-target sequences; (b) Analyzing the target gene for undesirable sequences (e.g., matches to sequences from non-target species), and score each potential 19-mer segment for GC content, Reynolds score (see Reynolds et al. (2004) Nature Biotechnol., 22:326-330), and functional asymmetry characterized by a negative difference in free energy (".DELTA..DELTA.G" or "ΔΔG") (see Khvorova et al. (2003) Cell, 115:209-216). Preferably 19-mers are selected that have all or most of the following characteristics: (1) a Reynolds score>4, (2) a GC content between about 40% to about 60%, (3) a negative ΔΔG, (4) a terminal adenosine, (5) lack of a consecutive run of 4 or more of the same nucleotide; (6) a location near the 3' terminus of the target gene; (7) minimal differences from the miRNA precursor transcript. Positions at every third nucleotide in an siRNA have been reported to be especially important in influencing RNAi efficacy and an algorithm, "siExplorer" is publicly available at ma.chem.t.u-tokyo.ac.jp/siexplorer.htm (see Katoh and Suzuki (2007) Nucleic Acids Res., 10.1093/nar/gkl1120); (c) Determining the reverse complement of the selected 19-mers to use in making a modified mature miRNA. The additional nucleotide at position 20 is preferably matched to the selected target sequence, and the nucleotide at position 21 is preferably chosen to either be unpaired to prevent spreading of silencing on the target transcript or paired to the target sequence to promote spreading of silencing on the target transcript; and (d) transforming the artificial miRNA into a plant.

The siRNA pathway involves the non-phased cleavage of a longer double-stranded RNA intermediate (an RNA duplex) into small interfering RNAs (siRNAs). The size or length of siRNAs ranges from about 19 to about 25 nucleotides or base pairs, but common classes of siRNAs include those containing 21 base pairs or 24 base pairs. Thus, a transcribable DNA sequence or suppression element of the present application can encode a RNA molecule that is at least about 19 to about 25 nucleotides in length, such as 19, 20, 21, 22, 23, 24, or 25 nucleotides in length.

In the ta-siRNA pathway, miRNAs serve to guide in-phase processing of siRNA primary transcripts in a process that requires an RNA-dependent RNA polymerase for production of a double-stranded RNA precursor; ta-siRNAs are defined by lack of secondary structure, a miRNA target site that initiates production of double-stranded RNA, requirements of DCL4 and an RNA-dependent RNA polymerase (RDR6), and production of multiple perfectly phased ~21-nt small RNAs with perfectly matched duplexes with 2-nucleotide 3' overhangs (see Allen et al. (2005) Cell, 121:207-221). The size or length of ta-siRNAs ranges from about 20 to about 22 nucleotides or base pairs, but are mostly commonly 21 base pairs. Thus, a donor molecule or vector of the present application can encode a RNA molecule that is at least about 20 to about 22 nucleotides in length, such as 20, 21, or 22 nucleotides in length. Donor molecules and vectors provided herein can also comprise a ta-siRNA scaffold. For methods of constructing suitable ta-siRNA scaffolds, see U.S. Pat. No. 9,309,512, which is incorporated herein by reference in its entirety.

This disclosure provides a method of generating a dominant negative allele of a gene comprising using a targeted editing technique to introduce at least one non-coding RNA target site into the gene. In an aspect, the dominant negative allele of the gene is downregulated as compared to an allele of the gene that does not comprise the at least one non-coding RNA target site. In another aspect, secondary siRNAs complementary to the gene are generated. In another aspect, the at least one non-coding RNA target site is a miRNA target site or a siRNA target site. In a further aspect, the at least one non-coding RNA target site is introduced into a region of the gene selected from the group consisting of a 5'-UTR, an exon, an intron, and a 3'-UTR. In another aspect, the at least one non-coding RNA target site is introduced into an exon of the gene. In another aspect, the at least one non-coding RNA target site is introduced into an intron of the gene. In another aspect, the at least one non-coding RNA target site is introduced into a 5'-UTR of the gene. In still another aspect, the at least one non-coding RNA target site is introduced into a 3'-UTR of the gene.

In another aspect, this disclosure provides a modified cell comprising a non-transgenic dominant negative allele of a gene, the dominant negative allele comprising a heterologous non-coding RNA target site in the endogenous locus of the gene.

A dominant allele can also be created by editing an allele of a protein-coding gene region such that a truncated protein is generated, where the edited, truncated protein interferes with the activity of the wild-type protein and produces a dominant effect. In one aspect, the introduction of a targeted edit to a protein-coding gene to generate a truncated protein creates a dominant positive allele. In one aspect, the introduction of a targeted edit to a protein-coding gene to generate a truncated protein creates a dominant negative allele. In an aspect, a truncated protein provided herein interferes with protein-protein binding, DNA-protein binding, or RNA-protein binding. In one aspect, a truncated protein provided herein is a microprotein. As used herein, a microprotein refers to a ~100-200 amino acid long protein that only encodes a protein-protein interaction or binding domain (see, for example, Seo et al., Trends in Plant Sciences, 2011, 10:541-549). Microproteins often evolve from functional genes that underwent mutations to eliminate functional protein domains. In one aspect, a microprotein is at least 50, at least 75, at least 100, at least 125, at least 150, at least 175, at least 200, or at least 225 amino acids in length. In one aspect a microprotein suppresses activity of at least one, at least two, at least three, at least four, at least five, at least six, at least seven, at least eight, at least nine, or at least ten protein in a cell. In another aspect, a microprotein enhances activity of at least one, at least two, at least three, at least four, at least five, at least six, at least seven, at least eight, at least nine, or at least ten proteins in a cell. Without being limiting, a microprotein can compete with a second protein for a binding site in a third protein. In one aspect, a microprotein blocks the binding of a second protein to a third protein a suppression of activity can occur. Alternatively, in another aspect, the binding of the microprotein to the third protein, in place of the second protein, enhances the activity of the third protein.

In one aspect, plant comprising a dominant negative allele encoding a microprotein comprises an improvement in a trait selected from the group consisting of flowering time, meristem size, insect resistance, herbicide tolerance, and shade avoidance. In one aspect, plant comprising a dominant positive allele encoding a microprotein comprises an improvement in a trait selected from the group consisting of flowering time, meristem size, insect resistance, herbicide tolerance, and shade avoidance.

In one aspect, a truncated protein provided herein is selected from the group consisting of a truncated CLAVATA protein, a truncated CORYNE protein, a truncated BAM receptor, a truncated RECEPTOR-LIKE PROTEIN KINASE2 (RPK2) protein, and a truncated G PROTEIN BETA-SUBUNIT1 (AGB1) protein. In another aspect, a CLAVATA protein provided herein is a CLAVATA1 protein, a CLAVATA2 protein, or a CLAVATA3 protein.

In one aspect, this disclosure provides a method of generating a dominant negative allele of a gene comprising a) inducing a double-stranded break in a genome of at least one cell using a targeted editing technique at a target site of the gene, where the double-stranded break is repaired by non-homologous end-joining; and b) identifying at least one cell comprising an insertion or deletion at the target site, where the insertion or deletion at the target site results in the generation of a dominant negative allele of the gene.

In still another aspect, this disclosure provides a modified cell comprising at least one insertion or deletion at the endogenous locus of the at least one gene generated by a targeted editing technique, where the insertion or deletion results in expression of a truncated protein.

In another aspect, this disclosure provides a method comprising a) providing to one or more cells at least one RNA-guided nuclease or one or more vectors encoding at least one RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the RNA-guided nuclease creates a double-stranded break at the target site; b) identifying at least one cell comprising an insertion or deletion at the target site, where the insertion or deletion at the target site results in the generation of a dominant negative allele of the at least one gene; and, c) selecting one or more cells comprising the dominant negative allele of the at least one gene.

This disclosure also provides a method of generating a dominant allele of a gene comprising using a targeted editing technique to introduce a nonsense mutation in the gene to create a truncated protein. In an aspect, the truncated protein is a microprotein. In an aspect, the targeted editing technique comprises a deletion of at least 1, at least 2, at least 3, at least 4, at least 5, at least 6, at least 7, at least 8, at least 9, at least 10, at least 25, at least 50, at least 75, at least 100, at least 150, at least 200, at least 250, at least 500, at least 1000, at least 2500, or at least 5000 nucleotides. In an aspect, the targeted editing technique comprises an insertion of at least 1, at least 2, at least 3, at least 4, at least 5, at least 6, at least 7, at least 8, at least 9, at least 10, at least 25, at least 50, at least 75, at least 100, at least 150, at least 200, at least 250, at least 500, at least 1000, at least 2500, or at least 5000 nucleotides. In an aspect, the targeted editing technique comprises an inversion of at least 1, at least 2, at least 3, at least 4, at least 5, at least 6, at least 7, at least 8, at least 9, at least 10, at least 25, at least 50, at least 75, at least 100, at least 150, at least 200, at least 250, at least 500, at least 1000, at least 2500, or at least 5000 nucleotides.

In one aspect, the introduction of a targeted edit to a protein-coding gene to generate a truncated protein creates a dominant positive allele. In one aspect, this disclosure provides a method of generating a dominant positive allele of a gene comprising a) inducing a double-stranded break in a genome of at least one cell using a targeted editing technique at a target site of the gene, where the double-stranded break is repaired by non-homologous end-joining; and b) identifying at least one cell comprising an insertion or deletion at the target site, where the insertion or deletion at the target site results in the generation of a dominant positive allele of the gene.

In another aspect, this disclosure provides a method comprising a) providing to one or more cells one or more vectors, where the one or more vectors comprises at least one polynucleotide encoding at least one RNA-guided nuclease, where the at least one RNA-guided nuclease is capable of binding to at least 18, at least 19, at least 20, at least 21, at least 22, at least 23, at least 24, at least 25, or at least 26 consecutive nucleotides of a target site of at least one gene, where the RNA-guided nuclease creates a double-stranded break at the target site, and where the double-stranded break is repaired by non-homologous end-joining; b) identifying at least one cell comprising an insertion or deletion at the target site, where the insertion or deletion at the target site results in the generation of a dominant positive allele of the at least one gene; and, c) selecting one or more cells comprising the dominant positive allele of the at least one gene.

In one aspect, an insertion or deletion provided herein abrogates an intron/exon splice site. An intron/exon splice site refers to the boundary between an intron and an exon in a gene. In eukaryotes, introns are typically, but not always, processed out of an RNA transcript by a spliceosome to produce an mRNA transcript that comprises only exonic sequence. If an intron/exon splice site is perturbed the spliceosome can fail to properly remove the intron sequence leading to a protein with one or more nonsense mutations to generate a premature stop codon. In an aspect, a nonsense mutation generates a truncated protein. In an aspect, a truncated protein comprises at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100, at least 125, at least 150, at least 175, at least 200, at least 225, at least 250, at least 275, at least 300, at least 350, at least 400, at least 450, or at least 500 fewer amino acids than an endogenous protein encoded by a gene lacking a nonsense mutation.

In one aspect, a nonsense mutation is a mutation that results in a premature stop codon in a transcribed mRNA. In another aspect, an insertion or deletion provided herein is located in an exon. In another aspect, an insertion or deletion provided herein is located in an intron. In another aspect, an insertion or deletion provided herein is located in a 5'-UTR or a 3'-UTR. In an aspect, an insertion or deletion provided herein is located in a structure selected from the group consisting of an intron/exon splice site, an exon, an intron, a 5'-UTR, and a 3'-UTR. In still another aspect, a dominant negative allele provided herein comprises one or more, two or more, three or more, four or more, or five or more insertions and/or deletions. In still another aspect, a dominant positive allele provided herein comprises one or more, two or more, three or more, four or more, or five or more insertions and/or deletions.

In another aspect, a nonsense mutation provided herein is located in an exon. In an aspect, an insertion or deletion provided herein is located in a structure selected from the group consisting of an intron/exon splice site and an exon. An insertion or deletion provided herein can generate a protein with one or more, two or more, three or more, four or more, five or more, six or more, seven or more, eight or more, nine or more, or ten or more nonsense mutations.

In an aspect, a dominant negative allele provided herein comprises a polynucleotide comprising a premature stop codon as compared to a polynucleotide of a control allele. A premature stop codon is a stop codon positioned upstream of the normal stop codon of a gene. A premature stop codon generates a truncated protein. A stop codon is a nucleotide triplet in an mRNA that signals the termination of protein translation from the mRNA. In one aspect, a dominant negative allele provided herein comprises a polynucleotide encoding a truncated protein. In one aspect, a truncated protein provided herein is at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 125, at least 150, at least 175, at least 200, at least 225, at least 250, at least 275, at least 300, at least 400, or at least 500 amino acids shorter than a full-length protein. In an aspect, a truncated protein provided herein is generated by the insertion or deletion of at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 125, at least 150, at least 175, at least 200, at least 250, at least 300, at least 400, at least 500, at least 1000, at least 1500, or at least 2000 nucleotides.

In an aspect, a dominant positive allele provided herein comprises a polynucleotide comprising a premature stop codon as compared to a polynucleotide of a control allele. A premature stop codon is a stop codon positioned upstream of the normal stop codon of a gene. A premature stop codon generates a truncated protein. A stop codon is a nucleotide triplet in an mRNA that signals the termination of protein translation from the mRNA. In one aspect, a dominant positive allele provided herein comprises a polynucleotide encoding a truncated protein. In one aspect, a truncated protein provided herein is at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 125, at least 150, at least 175, at least 200, at least 225, at least 250, at least 275, at least 300, at least 400, or at least 500 amino acids shorter than a full-length protein. In an aspect, a truncated protein provided herein is generated by the insertion or deletion of at least 1, at least 2, at least 3, at least 4, at least 5, at least 6, at least 7, at least 8, at least 9, at least 10, at least 15, at least 20, at least 25, at least 30, at least 40, at least 50, at least 60, at least 70, at least 80, at least 90, at least 100, at least 125, at least 150, at least 175, at least 200, at least 250, at least 300, at least 400, at least 500, at least 1000, at least 1500, or at least 2000 nucleotides.

This disclosure provides a method of generating a dominant negative allele of a gene in a cell comprising deleting a portion of a gene using a targeted editing technique, where a microprotein is generated following the deletion of the portion of the gene. In one aspect, a truncated protein is a microprotein. In another aspect, a dominant negative allele provided herein encodes a microprotein. In a further aspect, a dominant positive allele provided herein encodes a microprotein. As used herein, a "microprotein" refers to short, single-domain proteins that possess the ability to interfere with larger multi-domain proteins. In one aspect, a microprotein provided herein interferes with at least one, at least two, at least three, at least four, at least five, at least six, at least seven, at least eight, at least nine, or at least ten other proteins. In one aspect, a microprotein provided herein is capable of preventing a second protein from binding to a nucleic acid molecule. In another aspect, a microprotein provided herein is capable of preventing a second protein from binding to a third protein. The third protein can be identical or non-identical to the second protein. In another aspect, a microprotein provided herein is capable of binding to at least two, at least three, at least four, at least five, at least six, at least seven, at least eight, at least nine, or at least ten other proteins. In one aspect, a microprotein provided herein can form heterodimers with at least two, at least three, at least four, at least five, at least six, at least seven, at least eight, at least nine, or at least ten other proteins. In another aspect, a microprotein provided herein is capable of forming a homodimer. As used herein, a "homodimer" refers to hybridization or binding of two identical molecules (e.g., protein A and protein A), while a "heterodimer" refers to the hybridization or binding of two different macromolecules (e.g., protein A and protein B; protein A and DNA; protein A and RNA).

Members of the pentatricopeptide repeat (PPR) gene family are common in plant genomes. Many PPR proteins are capable of binding RNA molecules in a sequence-specific manner. PPR proteins comprise 2-30 PPR motifs, each of which aligns to a single nucleotide in an RNA molecule. Within the PPR motifs, the amino acids present at two or three specific positions confer nucleotide specificity. For example, without being limiting, a PPR motif binds an adenine nucleotide when a threonine is in position 6 and an asparagine is at the 1' position; a PPR motif binds a guanine nucleotide when a threonine is in position 6 and an aspartic acid is at the 1' position; a PPR motif binds a uracil (or thymine) nucleotide when an asparagine is at position 6 and an aspartic acid is at the 1' position; and a PPR motif binds a cytosine nucleotide when an asparagine is at position 6 and an asparagine or a serine is at the 1' position.

Without being limiting, an engineered PPR protein can be generated by at least two building strategies. In the first strategy, a PPR protein is constructed by treating each PPR motif as a separate block, such that a PPR protein is constructed by putting multiple desired motifs in order. The resulting engineered PPR protein is then capable of binding a target RNA molecule. However, such a strategy may not always work because each PPR motif comprises an internal scaffolding between the 1' and 6 positions, and that intra-motif scaffold is not shared across different PPR proteins. The second strategy makes use of the preexisting intra-motif scaffolding. In the second strategy, site-directed mutagenesis of the 1' and 6 positions is used to edit an existing PPR protein such that it will be specific to a new target RNA molecule.

As used herein, an "engineered PPR protein," "engineered PPR motif," refers to a synthetically created PPR protein or PPR motif that does not exist in nature and is capable of binding an RNA sequence in a site-specific manner.

This disclosure provides a method comprising: a) providing to a cell an engineered PPR protein or a vector encoding the engineered PPR protein operably linked to a promoter, where the engineered PPR protein is capable of binding to an RNA transcript of a target gene; b) selecting one or more cells from step (a) expressing the engineered PPR protein; and c) identifying one or more cells selected in step (b) comprising altered expression of the target gene. In one aspect, the engineered PPR protein is capable of binding to at least one non-coding RNA target site of the RNA transcript. In one aspect, the engineered PPR protein binds to at least one non-coding RNA target site of the RNA transcript. In one aspect, the altered expression is increased expression. In another aspect, the altered expression is reduced expression. In an aspect, the promoter is the native promoter of the target gene. In another aspect, the promoter is selected from the group consisting of a constitutive promoter, a tissue-specific promoter, a tissue-preferred promoter, and an inducible promoter.

In one aspect, an engineered PPR protein provided herein binds to a non-coding RNA target site of a target RNA molecule and blocks the non-coding RNA from cleaving the target RNA or inhibiting translation of the target RNA. In another aspect, an engineered PPR protein provided herein directs the degradation of a target RNA molecule. In one aspect, an engineered PPR protein provided herein comprises at least one RNA nuclease domain. In another aspect, an RNA nuclease domain provided herein is a NYN nuclease domain or a small MutS-related (SMR) domain.

In an aspect, an engineered PPR protein or an engineered PPR motif provided herein binds to at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, or at least 35 nucleotides of an RNA molecule. In another aspect, an engineered PPR protein or an engineered PPR motif provided herein binds to between 5 and 35, between 5 and 30, between 5 and 25, between 5 and 20, between 5 and 15, between 5 and 14, between 5 and 13, between 5 and 12, between 5 and 11, between 5 and 10, between 10 and 35, between 10 and 30, between 10 and 25, between 10 and 20, between 10 and 15, between 10 and 14, between 10 and 13, between 10 and 12, or between 15 and 30 nucleotides of an RNA molecule.

In an aspect, an engineered PPR protein provided herein is capable of acting as a dominant negative allele. In an aspect, an engineered PPR protein provided herein is capable of acting as a dominant positive allele.

In one aspect, an engineered PPR protein is targeted to a mitochondria or a chloroplast. In another aspect, an engineered PPR protein is targeted to a nucleus. In still another aspect, an engineered PPR protein is targeted to a cytoplasm of a cell. Without being limited by any theory, a protein can be targeted to a specific cellular structure by adding or editing a transit peptide on the N-terminus of the protein.

In one aspect, a genome editing system provided here comprises a tgOligo as a tether molecule. In another aspect, a tether molecule is a cross-linker coupled to a nuclease or a DNA-targeting guide molecule. In a further aspect, a tether molecule is a dimerization domain coupled to a nuclease.

In one aspect, a tether molecule is capable of tethering two or more DNA binding machineries bound to two genomic loci. In another aspect, a tether molecule is capable of tethering two or more DNA binding machineries bound to two genomic loci located in in a single chromosome flanking a target genomic region. In another aspect, a tether molecule is capable of tethering two or more DNA binding machineries bound to two genomic loci are on separate chromosomes.

In one aspect, this disclosure provides a method of generating a dominant negative allele of at least one gene in at least one cell comprising: a) introducing to the at least one cell a genome editing system comprising: i) a site-specific nuclease, or a molecule encoding a site-specific nuclease, ii) a sgRNA, or a molecule encoding a sgRNA, and iii) at least a first tether-guided oligo (tgOligo) and a second tgOligo, or one or more molecules encoding a first and a second tgOligo, operably linked to at least one promoter; b) generating a first double-stranded break and a second double-stranded break in the at least one gene, where the first tgOligo and the second tgOligo hybridize to the 3' free ends of opposing strands at the first double-stranded break and the second double-stranded break, where at least 1, at least 2, at least 3, at least 4, at least 5, at least 10, at least 25, at least 50, at least 100, at least 250, at least 500, at least 750, at least 1000, at least 2500, or at least 5000 nucleotides of the at least one gene are deleted, thereby generating a dominant negative allele of the gene that encodes a truncated protein; and c) identifying and selecting at least one cell comprising the truncated protein.

In one aspect, this disclosure provides a method of generating a dominant negative allele of at least one gene in at least one cell comprising: a) introducing to the at least one cell a genome editing system comprising: i) a site-specific nuclease, or a molecule encoding a site-specific nuclease, ii) a sgRNA, or a molecule encoding a sgRNA, and iii) at least a first tether-guided oligo (tgOligo) and a second tgOligo, or one or more molecules encoding a first and a second tgOligo, operably linked to at least one promoter; b) generating a first double-stranded break and a second double-stranded break in the at least one gene, where the first tgOligo and the second tgOligo hybridize to the 3' free ends of opposing strands at the first double-stranded break and the second double-stranded break, where between land 5000, between 5 and 5000, between 10 and 5000, between 25 and 2500, between 25 and 1000, between 25 and 750, between 25 and 500, between 25 and 100, between 50 and 5000, between 50 and 1000, between 50 and 500, between 100 and 1000, or between 1000 and 5000 nucleotides of the at least one gene are deleted, thereby generating a dominant negative allele of the gene that encodes a truncated protein; and c) identifying and selecting at least one cell comprising the truncated protein.

In another aspect, this disclosure provides a method of generating a dominant negative allele of at least one gene in at least one cell comprising: a) introducing to the at least one cell one or more vectors encoding: i) at least one site-specific nuclease, ii) at least one sgRNA, and iii) at least a first tgOligo and a second tgOligo operably linked to at least one promoter; b) generating a first double-stranded break and a second double-stranded break in the gene, where the first tgOligo and the second tgOligo hybridize to the 3' free ends of opposing strands at the first double-stranded break and the second double-stranded break, where the region of the at least one gene between the first double-stranded break and the second double-stranded break is inverted in orientation, thereby generating a dominant negative allele of the at least one gene that encodes an antisense RNA transcript of the gene; and c) identifying and selecting at least one cell comprising the antisense RNA transcript of the at least one gene.

As used herein, a "tether guide oligo" (tgOligo) refers to an oligonucleotide comprising a sequence segment capable of hybridizing with the 3' free end of the non-target strand of a double-stranded DNA molecule recognized and cleaved by a CRISPR gRNA-Cas complex (this 3' free end is also referred to as 3' free flap). A tgOligo corresponds to a gRNA when that tgOligo recognizes and hybridizes the 3' free end of the non-target strand of that gRNA's target site. A tgOligo can be a DNA molecule, a RNA molecule, or a mix of nucleotides. A hybrid tgOligo is a tgOligo that can recognize and hybridize with two non-target 3' free ends created by two separate CRISPR gRNA-Cas complexes.

As used herein, a "tether guide RNA" (tgRNA) refers to a RNA molecule comprising both a guide RNA (gRNA) sequence and a tether RNA sequence, where the tether RNA sequence is capable of hybridizing with a desired genomic site (which site is called "tether site").

In one aspect, a method provided herein comprises the use of one or more, two or more, three or more, four or more, five or more, six or more, seven or more, eight or more, nine or more, or ten or more tgOligos. In one aspect, a tgOligo is a DNA molecule. In another aspect, a tgOligo is an RNA molecule. In a still further aspect, a tgOligo is a mixture of DNA and RNA molecules. In one aspect, a tgOligo is single-stranded. In another asked, a tgOligo is double-stranded. In one aspect, at least one or at least two tgOligos are used concurrently with at least one, at least two, at least three, at least four, at least five, at least six, at least seven, at least eight, at least nine, or at least ten site-specific nucleases. In another aspect, at least one tgOligo is not used concurrently with a site-specific nuclease. In an aspect, at least one or at least two tgOligos are tethered to at least one or at least two Cas9 proteins. In one aspect, a first tgOligo is tethered to a first Cas9 protein and a second tgOligo is tethered to a second Cas9 protein. In another aspect, at least one or at least two tgOligos are tethered to at least one or at least two deactivated Cas9 proteins.

In still another aspect, a tgOligo provided herein comprises at least 2, at least 3, at least 4, at least 5, at least 6, at least 7, at least 8, at least 9, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 500, at least 1000, at least 2500, at least 5000, at least 10,000, or at least 25,000 nucleotides. In a further aspect, a tgOligo provided herein comprises between 5 and 25,000 nucleotides, between 5 and 10,000 nucleotides, between 5 and 5000 nucleotides, between 20 and 10,000 nucleotides, between 20 and 5000 nucleotides, between 20 and 1000 nucleotides, between 20 and 500 nucleotides, between 20 and 250 nucleotides, between 50 and 2500 nucleotides, between 50 and 1000 nucleotides, between 50 and 500 nucleotides, between 50 and 250 nucleotides, between 100 and 2500 nucleotides, between 100 and 1000 nucleotides, between 100 and 500 nucleotides, or between 1000 and 10,000 nucleotides.

In one aspect, a first tgOligo and a second tgOligo are at least 80%, at least 85%, at least 90%, at least 91%, at least 92%, at least 93%, at least 94%, at least 95%, at least 96%, at least 97%, at least 98%, at least 99%, at least 99.5%, or 100% complementary to each other. In one aspect, a first tgOligo and a second tgOligo are at least 80%, at least 85%, at least 90%, at least 91%, at least 92%, at least 93%, at least 94%, at least 95%, at least 96%, at least 97%, at least 98%, at least 99%, at least 99.5%, or 100% complementary to each other for at least 10, at least 11, at least 12, at least 13, at least 14, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 500, at least 1000, at least 2500, or at least 5000 nucleotides. In one aspect, a first tgOligo comprises a sense strand and a second tgOligo comprises an antisense strand.

In an aspect, a tgOligo is provided to a cell. In another aspect, a tgOligo is encoded by a vector. In another aspect, a site-specific nuclease and a tgOligo are encoded by one vector. In yet another aspect, a site-specific nuclease and a tgOligo are encoded by two or more vectors.

Methods provided herein are suitable for generating dominant alleles of protein-coding genes and non-coding RNAs. Without being limiting, examples of target genes of envisioned by the present disclosure in a plant genome would include genes for disease, insect, or pest tolerance; herbicide tolerance; genes for quality improvements such as yield, nutritional enhancements, environmental or stress tolerances; or any desirable changes in plant physiology, growth, development, morphology or plant product(s) including starch production (U.S. Pat. Nos. 6,538,181;

6,538,179; 6,538,178; 5,750,876; 6,476,295); modified oils production (U.S. Pat. Nos. 6,444,876; 6,426,447; 6,380, 462); high oil production (U.S. Pat. Nos. 6,495,739; 5,608, 149; 6,483,008; 6,476,295); modified fatty acid content (U.S. Pat. Nos. 6,828,475; 6,822,141; 6,770,465; 6,706,950; 6,660,849; 6,596,538; 6,589,767; 6,537,750; 6,489,461; 6,459,018); high protein production (U.S. Pat. No. 6,380, 466); fruit ripening (U.S. Pat. No. 5,512,466); enhanced animal and human nutrition (U.S. Pat. Nos. 6,723,837; 6,653,530; 6,5412,59; 5,985,605; 6,171,640); or biopolymers (U.S. Pat. Nos. RE37,543; 6,228,623; 5,958,745 and U.S. Patent Publication No. US20030028917). Also environmental stress resistance (U.S. Pat. No. 6,072,103); pharmaceutical peptides and secretable peptides (U.S. Pat. Nos. 6,812,379; 6,774,283; 6,140,075; 6,080,560); improved processing traits (U.S. Pat. No. 6,476,295); improved digestibility (U.S. Pat. No. 6,531,648); low raffinose (U.S. Pat. No. 6,166,292); industrial enzyme production (U.S. Pat. No. 5,543,576); improved flavor (U.S. Pat. No. 6,011,199); nitrogen fixation (U.S. Pat. No. 5,229,114); hybrid seed production (U.S. Pat. No. 5,689,041); fiber production (U.S. Pat. Nos. 6,576,818; 6,271,443; 5,981,834; 5,869,720); and biofuel production (U.S. Pat. No. 5,998,700).

In one aspect, a gene edited by the methods provided herein is selected from the group consisting of a Y1 gene, a brachytic2 gene, a GA3 oxidase gene, and a GA20 oxidase gene. In another aspect, a gene edited by the methods provided herein encodes a non-coding RNA. In an aspect, a non-coding RNA edited by the methods provided herein is selected from the group consisting of a microRNA, a small interfering RNA, a transfer RNA, a ribosomal RNA, a trans-acting small interfering RNA, a naturally occurring antisense small interfering RNA, a heterochromatic small interfering RNA, and precursors thereof. In still another aspect, a gene edited by the methods provided herein encodes a miRNA. In a further aspect, a gene edited by the methods provided herein encodes a precursor miRNA (pre-miRNA).

In one aspect, a GA20 oxidase gene provided herein is encoded by an mRNA that encodes a protein having at least 80%, at least 85%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: (insert protein sequences for GA20). In another aspect, a brachytic2 gene provided herein is encoded by an mRNA that encodes a protein having at least 80%, at least 85%, at least 90%, at least 91%, at least 92%, at least 93%, at least 94%, at least 95%, at least 96%, at least 97%, at least 98%, at least 99%, at least 99.5%, or 100% identical to a sequence selected from the group consisting of SEQ ID NOs: (insert protein sequences for BR2).

In one aspect, an unmodified allele provided herein comprises a polynucleotide sequence having at least 80%, at least 85%, at least 90%, at least 91%, at least 92%, at least 93%, at least 94%, at least 95%, at least 96%, at least 97%, at least 98%, at least 99%, at least 99.5%, or 100% identity or complementarity to a sequence selected from the group consisting of SEQ ID NOs: (list GA and BR2 sequences).

In another aspect, a non-coding RNA edited by the methods provided herein is selected from the group consisting of a microRNA, a small interfering RNA, a transfer RNA, a ribosomal RNA, a trans-acting small interfering RNA, a naturally occurring antisense small interfering RNA, a heterochromatic small interfering RNA, and precursors thereof.

EXAMPLES

Example 1. Generating a Dominant Allele of GA20 Oxidase Via Targeted Genomic Inversion Two functional guide RNAs (gRNAs) for a CRISPR/RNA-guided nuclease system are created to target flanking regions (a left target site and a right target site) of a GA20 oxidase_5 gene in the corn genome. See FIG. 1, Panel A. Each of the two target sites are unique within the corn genome. The plant hormone gibberellin plays an important role in a number of plant developmental processes including germination, cell elongation, flowering, embryogenesis and seed development. Certain biosynthetic enzymes (e.g., GA20 oxidase and GA3 oxidase) and catabolic enzymes (e.g., GA2 oxidase) in the GA pathway are critical to affecting GA levels in plant tissues.

A transfer DNA (T-DNA) vector suitable for use in *Agrobacterium* transformation is used. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising promoters operable in a plant cell operably linked to polynucleotides encoding the two gRNAs described above.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the gRNAs guide the nuclease to each of the two target sites in the GA20 oxidase_5 gene, where the nuclease creates a double-stranded break at each target site.

In the majority of events, the region between the target sites is deleted and non-homologous end-joining repair mechanisms joins the flanking regions. Less frequently, some events create insertion/deletion mutations at the left target site, the right target site, or both. In still other events the entire targeted region is inverted in what is referred to as a "complete inversion." See FIG. 1, Panel B. Suitable methods known in the art (e.g., PCR, DNA hybridization (Southern) blots, sequencing) are used to identify transformation events comprising a complete inversion. Transformed embryos comprising a targeted complete inversion in the 5' end of the GA20 oxidase_5 gene are selected and used to regenerate modified plants using techniques standard in the field.

Without being bound to any scientific theory, the presence of a complete inversion in one allele of the GA20 oxidase_5 creates a population of antisense mRNAs under the control of the native GA20 oxidase_5 promoter. The inverted region of the edited GA20 oxidase_5 allele mRNA and the corresponding region in the unedited GA20 oxidase_5 allele mRNA are complementary to each other and are capable of forming a dsRNA. Therefore, even though the modified corn plant can be heterozygous for an edited GA20 oxidase_5 allele, the edited allele can reduce the expression of the GA20 oxidase_5 gene in the modified corn plant.

RNA is extracted from modified corn plants identified as comprising a complete inversion of the targeted region of the GA20 oxidase_5 gene. RNA is also extracted from control corn plants that lack a complete inversion. Suitable methods known in the art (e.g., quantitative reverse-transcriptase PCR, reverse-transcriptase PCR, RNA sequencing) are used to confirm that down-regulation of GA20 oxidase_5 occurs in modified corn plants comprising a complete inversion of the targeted region.

Example 2. Generating a Dominant Allele of BR2 Via Targeted Genomic Inversion Two functional guide RNAs (gRNAs) for an RNA guided nuclease system are created to target flanking regions (a left target site and a right target site) of a BRACHYTIC2 (BR2) gene in the corn genome. Each of the two target sites are unique within the corn genome.

A transfer DNA (T-DNA) vector suitable for use in *Agrobacterium tumefaciens* transformation is used. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising promoters operable in a plant cell operably linked to polynucleotides encoding the two gRNAs described above.

Immature corn embryos are co-cultured with *Agrobacterium tumefaciens* containing the T-DNA vector for three days. The polynucleotides between the LB and RB sequences are integrated into the nuclear genome of the immature corn embryos. Upon expression of the integrated polynucleotides, the gRNAs guide the CRISPR endonuclease to each of the two target sites in the BR2 gene, where the CRISPR endonuclease creates a double-stranded break at each target site.

In the majority of events, the region between the target sites is deleted and non-homologous end-joining repair mechanisms joins the flanking regions. Less frequently, some events create insertion/deletion mutations at the left target site, the right target site, or both. In still other events the entire targeted region is inverted in what is referred to as a "complete inversion." Suitable methods known in the art (e.g., PCR, DNA hybridization (Southern) blots, sequencing) are used to identify transformation events comprising a complete inversion. Transformed embryos comprising a targeted complete inversion in the 5' end of the BR2 gene are selected and used to regenerate plants using techniques standard in the field.

Without being bound to any scientific theory, the presence of a complete inversion in one allele of the BR2 gene creates a population of anti-sense mRNAs under the control of the native BR2 promoter. The inverted region of the edited BR2 allele mRNA and the corresponding region in the unedited BR2 allele mRNA are complementary to each other and are capable of forming a dsRNA. Therefore, even though the corn plant may be heterozygous for an edited BR2 allele, the edited allele can reduce the expression both alleles of the BR2 gene in the corn plant, and thus results in a brachytic phenotype.

Figure 2:
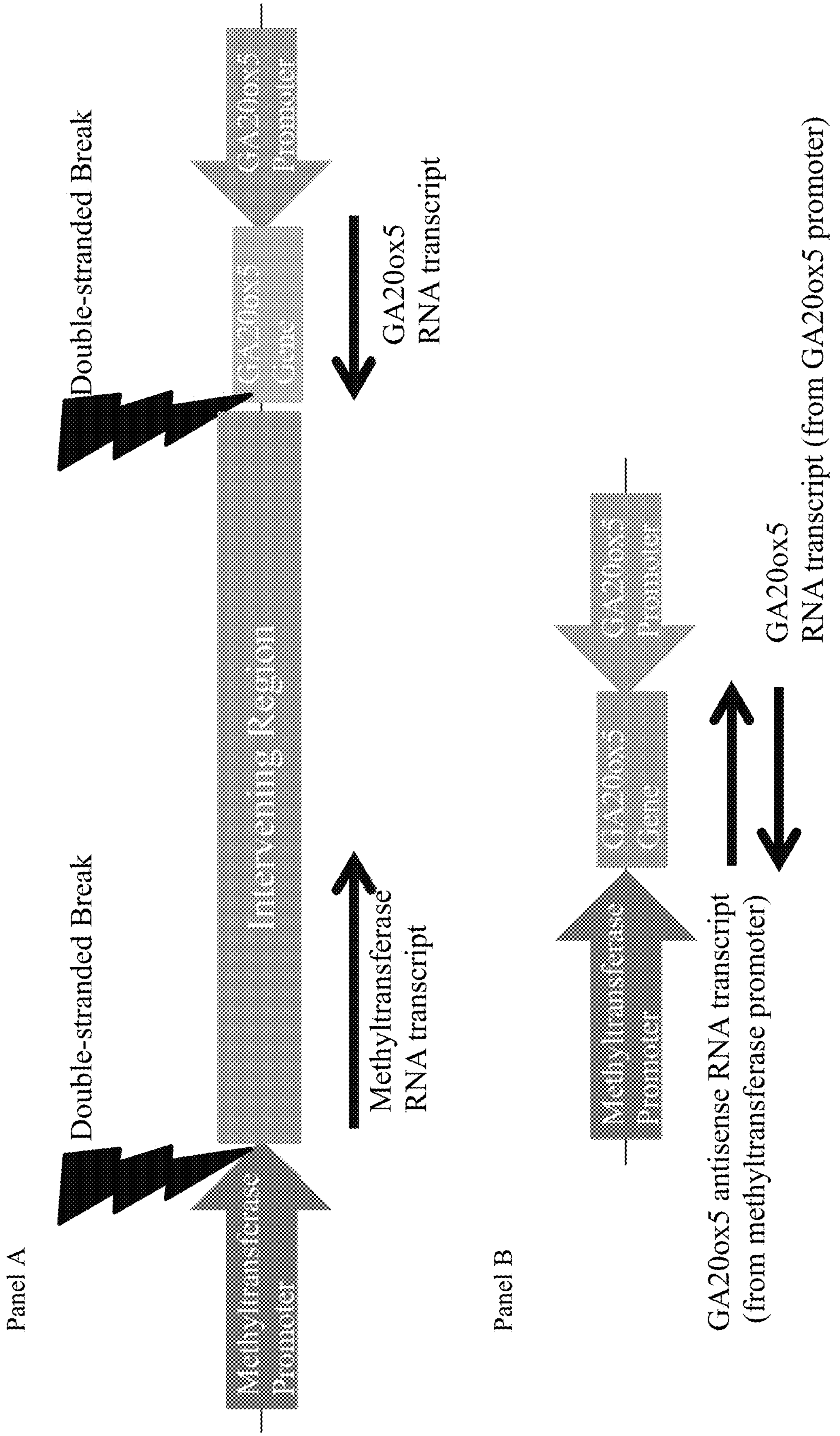
FIG. 2 comprises Panel A and Panel B. Panel A shows a representation of the maize genomic region near the GA20 oxidase_5 gene. As shown in Panel A, a methyltransferase/SAMT gene is adjacent to the GA20 oxidase_5 gene, but it is in an opposite orientation. The intervening region between the SAMT promoter and the GA20 oxidase_5 coding gene is deleted after generating a double-stranded break on each end. Panel B shows the structure of the region following the deletion of the intervening region. By removing the intervening region the SAMT promoter can drive the expression of an antisense GA20 oxidase_5 RNA transcript, which can form a double-stranded RNA with sense GA20 oxidase_5 RNA transcripts generated by the native GA20 oxidase_5 promoter.

Example 3. Generating a Dominant Allele of GA20 Oxidase Via a Targeted Genomic Deletion to Render a GA20 Oxidase Gene Under the Control of Two Reverse Oriented Promoters A gene encoding GA20 oxidase_5 (also called GA20ox5) is located on corn chromosome 8. It is adjacent to the corn gene GRMZM2G049269, which encodes an S-adenosyl-L-methionine-dependent methyltransferase superfamily protein ("SAMT" hereinafter). The SAMT is a member of a large, redundant gene family, and no phenotypes associated with mutations to this gene have been reported in corn or *Arabidopsis*. The SAMT gene is positioned in the opposite orientation as compared to the GA20 oxidase_5 gene (i.e., the SAMT gene is oriented to read 5' to 3', while the GA20 oxidase_5 gene is oriented to read 3' to 5' on the same DNA strand). See FIG. 2, Panel A.

Two functional guide RNAs (gRNAs) for an RNA guidednuclease system are created to target the genomic DNA region between the GA20 oxidase_5 gene and the SAMT gene. The first gRNA targets an area near the transcriptional start site of the SAMT gene, and the second gRNA targets a region near the transcriptional stop site of the GA20 oxidase_5 gene. Each of the two target sites are unique within the corn genome. A transfer DNA (T-DNA) vector suitable for use in *Agrobacterium* transformation is used. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising promoters operable in a plant cell operably linked to polynucleotides encoding the two gRNAs described above.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the gRNAs guide the nuclease to each of the two target sites in the genomic DNA region between the GA20 oxidase_5 gene and the SAMT gene, where the nuclease creates a double-stranded break at each target site.

In the majority of events, the region between the target sites is deleted and non-homologous end-joining repair mechanisms joins the flanking regions. Suitable methods known in the art (e.g., PCR, DNA hybridization (Southern) blots, sequencing) are used to identify transformation events comprising a complete deletion. Transformed embryos comprising a targeted deletion between the GA20 oxidase_5 gene and SAMT gene are selected and used to regenerate modified plants using techniques standard in the field.

Without being bound to any scientific theory, by removing the genomic DNA between the GA20 oxidase_5 gene and the SAMT promoter, the native SAMT promoter can generate an antisense mRNA transcript of the GA20 oxidase_5 gene, while the native GA20 oxidase_5 promoter generates a sense mRNA transcript of the GA20 oxidase_5 gene. The complementary sense and antisense mRNA transcripts of the GA20 oxidase_5 gene are capable of forming a dsRNA that can be processed by RNA silencing mechanisms native to the corn cell. See FIG. 2, Panel B. The processed dsRNA can then suppresses the expression of both GA20 oxidase_5 alleles. Additionally, because the mRNA encoding GA20 oxidase_3 is so similar to the sense GA20 oxidase_5 transcript, it is expected that the deletion between the SAMT promoter and the GA20 oxidase_5 gene will also down-regulate the expression of GA20 oxidase_3. It is also envisioned that suppression or silencing of the GA20 oxidase_5 gene may occur through other mechanisms as provided herein (e.g., nonsense-mediated decay), alternatively or in addition to any RNAi or PTGS forms of suppression.

RNA is extracted from modified corn plants identified as comprising a targeted deletion between the SAMT promoter and the GA20 oxidase_5 gene. RNA is also extracted from control corn plants that lack the deletion. Suitable methods known in the art (e.g., quantitative reverse-transcriptase PCR, reverse-transcriptase PCR, RNA sequencing) are used to confirm that down-regulation of GA20 oxidase_5 and/or GA20 oxidase_3 occurs in corn modified plants comprising a deletion of the targeted region.

Example 4. Generating a Dominant Allele of BR2 Via a Targeted Genomic Deletion to Render a BR2 Gene Under the Control of Two Reverse Oriented Promoters A gene encoding BR2 is located on corn chromosome 1. It is adjacent to the corn gene GRMZM2G491632 which is expressed in the opposite orientation to BR2. Two functional guide RNAs (gRNAs) for an RNA guided nuclease system are created to target the genomic DNA region between the BR2 gene and the GRMZM2G491632 gene. The first gRNA targets an area near the end of the BR2 gene exon 1, and the second gRNA targets a region near the beginning of the coding sequence of the GRMZM2G491632 gene exon 1.

A transfer DNA (T-DNA) vector suitable for use in *Agrobacterium* transformation is used. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising promoters operable in a plant cell operably linked to polynucleotides encoding the two gRNAs described above Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the gRNAs guide the endonuclease to each of the two target sites in the genomic DNA region between the BR2 gene and the GRMZM2G491632 gene, where the endonuclease creates a double-stranded break at each target site.

In the majority of events, the region between the target sites is deleted and non-homologous end-joining repair mechanisms joins the flanking regions. Suitable methods known in the art (e.g., PCR, DNA hybridization (Southern) blots, sequencing) are used to identify transformation events comprising a deletion. Transformed embryos comprising a targeted deletion between the BR2 gene and the GRMZM2G491632 gene are selected and used to regenerate plants using techniques standard in the field.

Without being bound to any scientific theory, by removing the genomic DNA between the BR2 gene and the GRMZM2G491632 promoter, the native GRMZM2G491632 promoter can generate an anti-sense mRNA transcript of the BR2 gene while the native BR2 promoter generates a sense mRNA transcript of the BR2 gene. The complementary sense and anti-sense mRNA transcripts of the BR2 gene can form a dsRNA that can be processed by RNAi machinery native to the corn cell. The processed dsRNA could then suppress the expression of both BR2 alleles, resulting in a brachytic phenotype.

Figure 3:
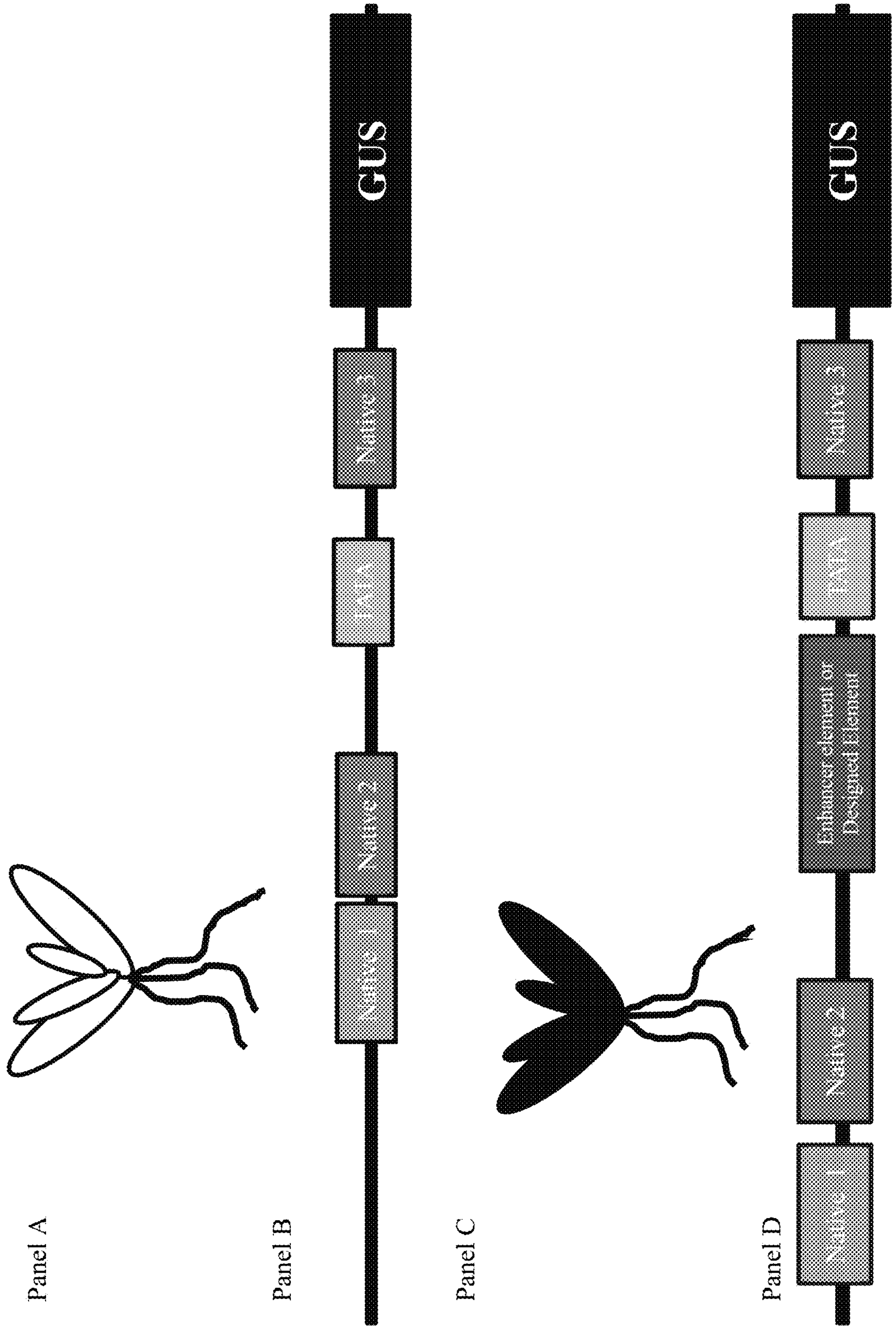
FIG. 3 comprises Panels A, B, C, and D. Panel A shows GUS staining of an *Arabidopsis thaliana* plant, which demonstrates that the Native 3 promoter expresses GUS only in root tissue. Panel B shows the genomic structure around the Native 3 promoter and GUS transgene. Panel C shows expanded GUS staining after insertion of a native genomic expression element such as an enhancer element or designed expression element upstream of the Native 3 TATA box. Panel D shows the genomic structure around the Native 3 promoter after targeted insertion of the native enhancer or designed element.

Example 5. Insertion of Designed Elements into Native Promoters Using Genome Editing Techniques to Create a Dominant Allele A gene comprising a root-specific promoter is identified in the *Arabidopsis thaliana* genome. See FIG. 3, Panel A. This promoter is used to drive the expression of GUS in the roots of the plant. See FIG. 3, Panel B. A functional gRNA is designed to target a region upstream of a TATA box of the root-specific promoter (the "target site"). A transfer DNA (T-DNA) vector suitable for use in *Agrobacterium* transformation is used to introduce the gRNA to *Arabidopsis*. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the gRNA described above. A second T-DNA construct comprises a polynucleotide encoding a donor molecule comprising a designed element to be inserted at the target site, between a LB sequence and a RB sequence. In one embodiment, the donor molecule comprises the designed element flanked by homologous regions that are homologous to sequences present on either side of the target site. The designed element enables the formerly root-specific gene to be expressed constitutively in all tissues of the plant when it is inserted into the promoter region of a gene. In another embodiment, the donor molecule comprises the designed sequence flanked by target sites that are targeted by the gRNA in T-DNA vector 1.

The floral dip method is used to transform *Arabidopsis* using the vector described above. See Clough and Bent, 1998, *Plant J*, 16: 735-743, which is incorporated herein in its entirety. Upon expression of the integrated polynucleotides, the gRNA guides the nuclease to the target site and creates a double-stranded break at the target site. For donor molecules comprising designed sequence flanked by Homology arms, homologous repair mechanisms native to the *Arabidopsis* cells insert the designed element at the site of the double-stranded break. For donor molecules comprising the designed sequence flanked by gRNA target sites, the gRNAs guide the nuclease to create double standed breaks within the second T-DNA thereby releasing the designed sequence, which can then integrate within the genomic target site via NHEJ (Non Homologous End Joining) repair mechanisms. In a subset of the insertion events, the promoter inserts in the desired orientation. Without being bound by any particular theory, the presence of the designed element upstream of the TATA box induces constitutive expression of the gene throughout the modified plant, thereby creating a dominant allele of the gene.

Suitable methods known in the art (e.g., PCR, DNA hybridization (Southern) blots, sequencing) are used to identify transformation events comprising a targeted insertion of the designed element in the desired orientation. Transformed *Arabidopsis* plants comprising the designed element at the target site are selected and further examined.

Plants identified as comprising the designed element upstream of the TATA box (see FIG. 3, Panel D) are examined for the expression of GUS using techniques standard in the art. Plants comprising the designed element exhibit GUS expression throughout the plant. See FIG. 3, Panel C. Additionally, RNA is extracted from various tissues (e.g., roots, stem, leaf, inflorescence) of the modified *Arabidopsis* plants identified as comprising the designed element. RNA is also extracted from control *Arabidopsis* plants that lack the designed element. Suitable methods known in the art (e.g., quantitative reverse-transcriptase PCR, reverse-transcriptase PCR, RNA sequencing) are used to confirm that GUS is more broadly expressed and/or more strongly expressed in the modified *Arabidopsis* plants.

Figure 4:
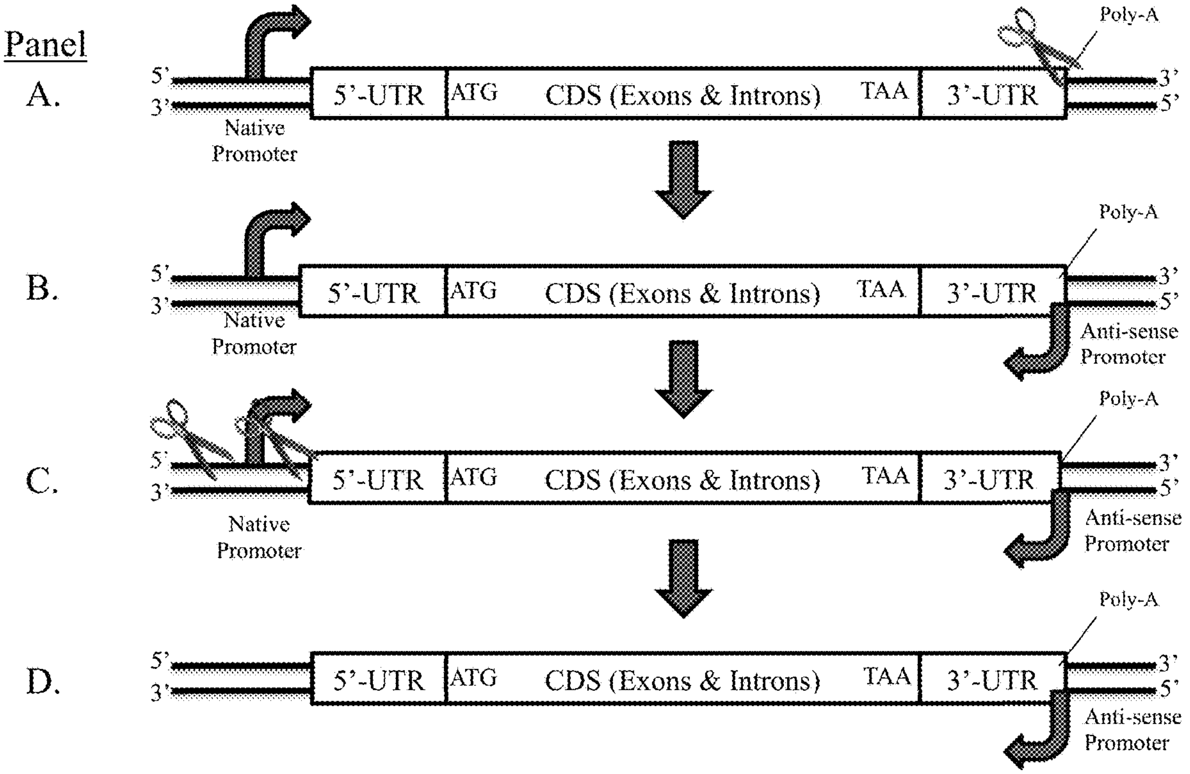
FIG. 4 comprises Panels A, B, C, and D. Panel A shows the structure of a gene of interest and indicates that a double-stranded break can be generated immediately upstream of the poly-adenylation site in the 3'-UTR of the gene of interest. Panel B shows the insertion of an anti-sense promoter at the double-stranded break site. The promoter can be the native promoter of the gene or any promoter of interest. Panel C shows the optional generation of two double-stranded breaks surrounding the native promoter of the gene of interest, leading to its deletion (Panel D).
Figure 5:
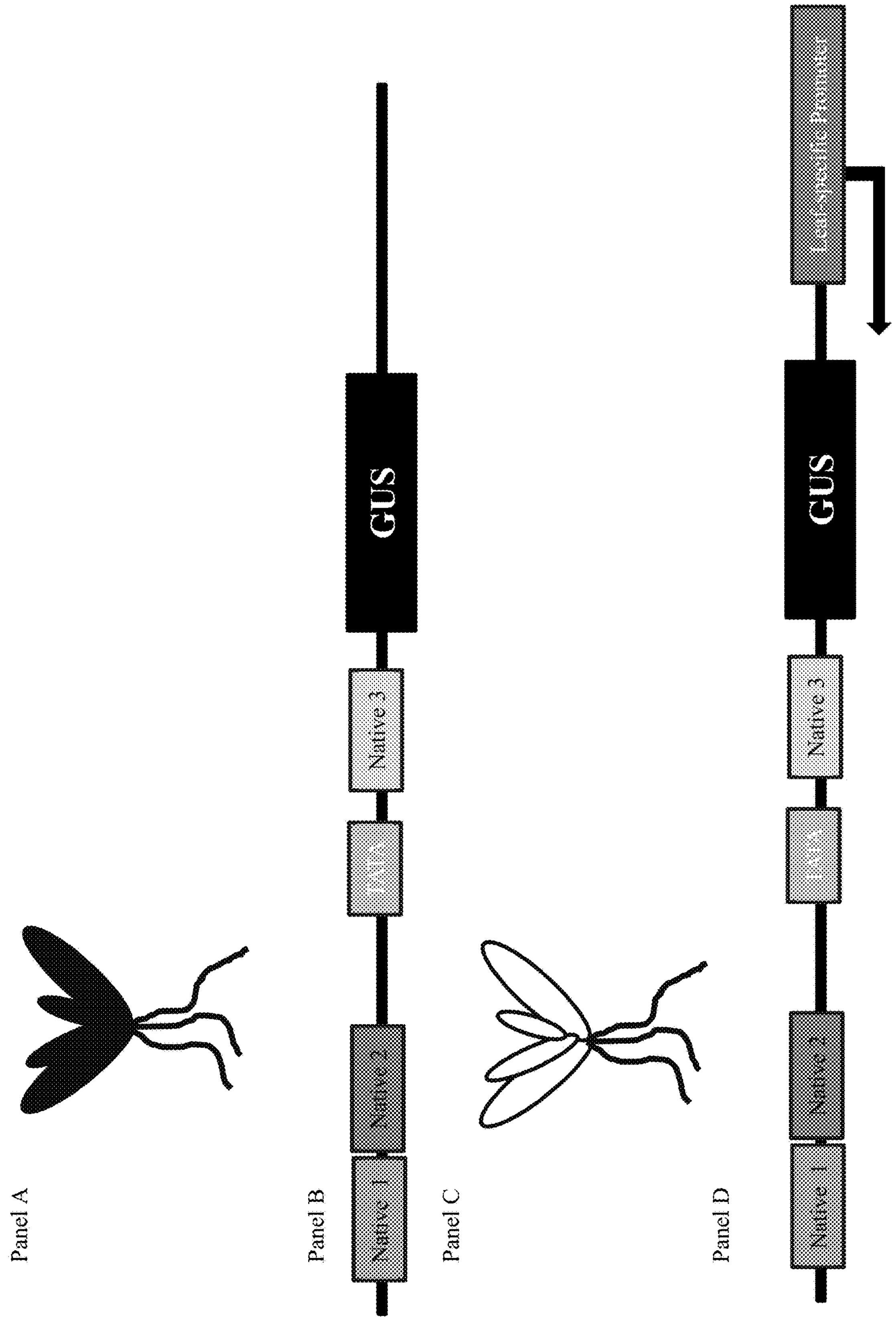
FIG. 5 comprises Panels A, B, C, and D. Panel A shows GUS staining of an *Arabidopsis thaliana* plant comprising a GUS transgene under the control of the Native 3 promoter. GUS is expressed throughout the plant. Panel B shows the genomic region around the Native 3 promoter and the GUS transgene. Panel C shows the reduction of GUS staining when a leaf-specific promoter is inserted downstream of the GUS transgene such that it transcribes antisense GUS RNA. Panel D shows the genomic region around the Native 3 promoter and GUS transgene following the insertion of the antisense leaf-specific promoter.

Example 6. Insertion of Tissue-Specific Suppression Elements Using Genome Editing Techniques to Create a Dominant Allele An *Arabidopsis thaliana* plant comprising a GUS transgene under the control of a promoter that is functional in leaf, vascular, and root tissue is created using standard techniques in the art. See FIG. 4 for a general overview of the concept provided in this Example; and FIG. 5, Panels A and B. A functional gRNA is designed to target a region downstream of the GUS gene (the "target site"). A transfer DNA (T-DNA) vector suitable for use in *Agrobacterium* transformation is used to introduce the gRNA to *Arabidopsis*. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the gRNA described above. A second T-DNA construct comprises a donor molecule comprising a leaf-specific promoter such as the COOLAIR promoter (see Chen and Penfield, Science, 2018, 360: 6392) between a LB sequence and a RB sequence. In one embodiment, the donor molecule comprises the promoter in an antisense orientation flanked by homologous regions that are homologous to sequences present on either side of the target site. The antisense oriented leaf-specific promoter enables the expression of a GUS antisense mRNA in tissues where the promoter is expressed (e.g., leaf tissue). Without being bound by any particular theory, the antisense RNA transcript of the GUS gene leads to the silencing of GUS in leaf tissue, but not root tissue. In another embodiment, the donor molecule comprises the promoter sequence flanked by target sites that are targeted by the gRNA in T-DNA vector 1.

The floral dip method is used to transform *Arabidopsis* using the vector described above. See Clough and Bent, 1998, *Plant J*, 16: 735-743, which is incorporated herein in its entirety. Upon expression of the polynucleotides, the gRNA guides the nuclease to the target site and creates a double-stranded break at the target site. For donor molecules comprising the antisense oriented promoter flanked by homology arms, homologous repair mechanisms native to the *Arabidopsis* cells insert the leaf-specific promoter at the site of the double-stranded break downstream of the GUS gene, thereby placing the promoter in an anti-sense orientation to the GUS gene. For donor molecules comprising the promoter flanked by gRNA target sites, the gRNAs guide the nuclease to create double standed breaks within the second T-DNA thereby releasing the promoter sequence that can then integrate within the genomic target site via NHEJ (Non Homologous End Joining) repair mechanisms. In a subset of the insertion events, the promoter inserts in an anti-sense orientation. Without being bound by a particular theory, the presence of the antisense leaf-specific promoter induces reduced expression of GUS throughout leaf tissue of the plant, thereby creating a dominant allele of the gene.

Suitable methods known in the art (e.g., PCR, DNA hybridization (Southern) blots, sequencing) are used to identify transformation events comprising a targeted insertion of the promoter in the desired orientation. Transformed *Arabidopsis* plants comprising the leaf-specific promoter at the target site are selected and further examined.

Plants identified as comprising the leaf-specific promoter downstream of the GUS gene in antisense orientation to the GUS gene (see FIG. 5, Panel D) are examined for the expression of GUS using techniques standard in the art. Plants comprising the leaf-specific promoter in antisense orientation to the GUS gene exhibit GUS expression only in root tissues. See FIG. 5, Panel C. Additionally, RNA is extracted from various tissues (e.g., roots, stem, leaf, inflorescence) of the modified *Arabidopsis* plants identified as comprising the leaf-specific promoter. RNA is also extracted from control *Arabidopsis* plants that lack the leaf-specific promoter in antisense orientation to the GUS gene. Suitable methods known in the art (e.g., quantitative reverse-transcriptase PCR, reverse-transcriptase PCR, RNA sequencing) are used to confirm that expression of GUS is reduced in leaf tissues.

Example 7. Insertion of Tissue-Specific Suppression Elements Using Genome Editing Techniques to Create a Dominant GA20 Oxidase_5 Allele A functional gRNA is designed to target a region downstream of the 3'-UTR of the GA20 oxidase_5 gene (the "target site"). A transfer DNA (T-DNA) vector suitable for use in *Agrobacterium* transformation is used to introduce the gRNA to a corn cell. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the gRNA described above. A second T-DNA construct comprises a donor molecule comprising an RTBV promoter between a LB sequence and a RB sequence. In one embodiment, the donor molecule comprises the RTBV promoter in an antisense orientation, flanked by homologous regions that are homologous to sequences present on either side of the target site. In another embodiment, the donor molecule comprises the promoter sequence flanked by target sites that are targeted by the gRNA in T-DNA vector 1. The antisense oriented RTBV promoter enables the expression of a GA20 oxidase_5 antisense mRNA in tissues where RTBV is expressed (e.g., stem and vascular tissue). Without being bound by any particular theory, the antisense RNA transcript of the GA20 oxidase_5 gene leads to the silencing of both GA20 oxidase_5 and GA20 oxidase_3 in stem and vascular tissue.

Immature corn embryos are co-cultured with *Agrobacterium* containing the T-DNA vectors for three days. Upon expression of the polynucleotides, the gRNA guides the nuclease to the target site and creates a double-stranded break at the target site. For donor molecules comprising the antisense oriented RTBV promoter flanked by Homology arms, homologous repair mechanisms native to the corn cell insert the the antisense RTBV promoter at the target site downstream of the 3' end of the GA20 oxidase_5 gene. For donor molecules comprising the promoter flanked by gRNA target sites, the gRNAs guide the nuclease to create double standed breaks within the second T-DNA there by releasing the promoter sequence that can then integrate within the genomic target site via NHEJ (Non Homologous End Joining) repair mechanisms. In a subset of the insertion events, the promoter inserts in an anti-sense orientation.

Suitable methods known in the art (e.g., PCR, DNA hybridization (Southern) blots, sequencing) are used to identify transformation events comprising a targeted insertion of the antisense RTBV promoter. Transformed embryos comprising the antisense RTBV promoter at the target site are selected and used to regenerate modified plants using techniques standard in the field.

RNA is extracted from various tissues (e.g., roots, stem, leaf, inflorescence) of the modified corn plants identified as comprising the antisense RTBV promoter. RNA is also extracted from control corn plants that lack the antisense RTBV promoter at the target site. Suitable methods known in the art (e.g., quantitative reverse-transcriptase PCR, reverse-transcriptase PCR, RNA sequencing) are used to confirm that expression of GA20 oxidase_5 and/or GA20 oxidase_3 are reduced in stem and vascular tissue in the modified corn plants comprising the antisense RTBV promoter as compared to control corn plants.

Figure 6:
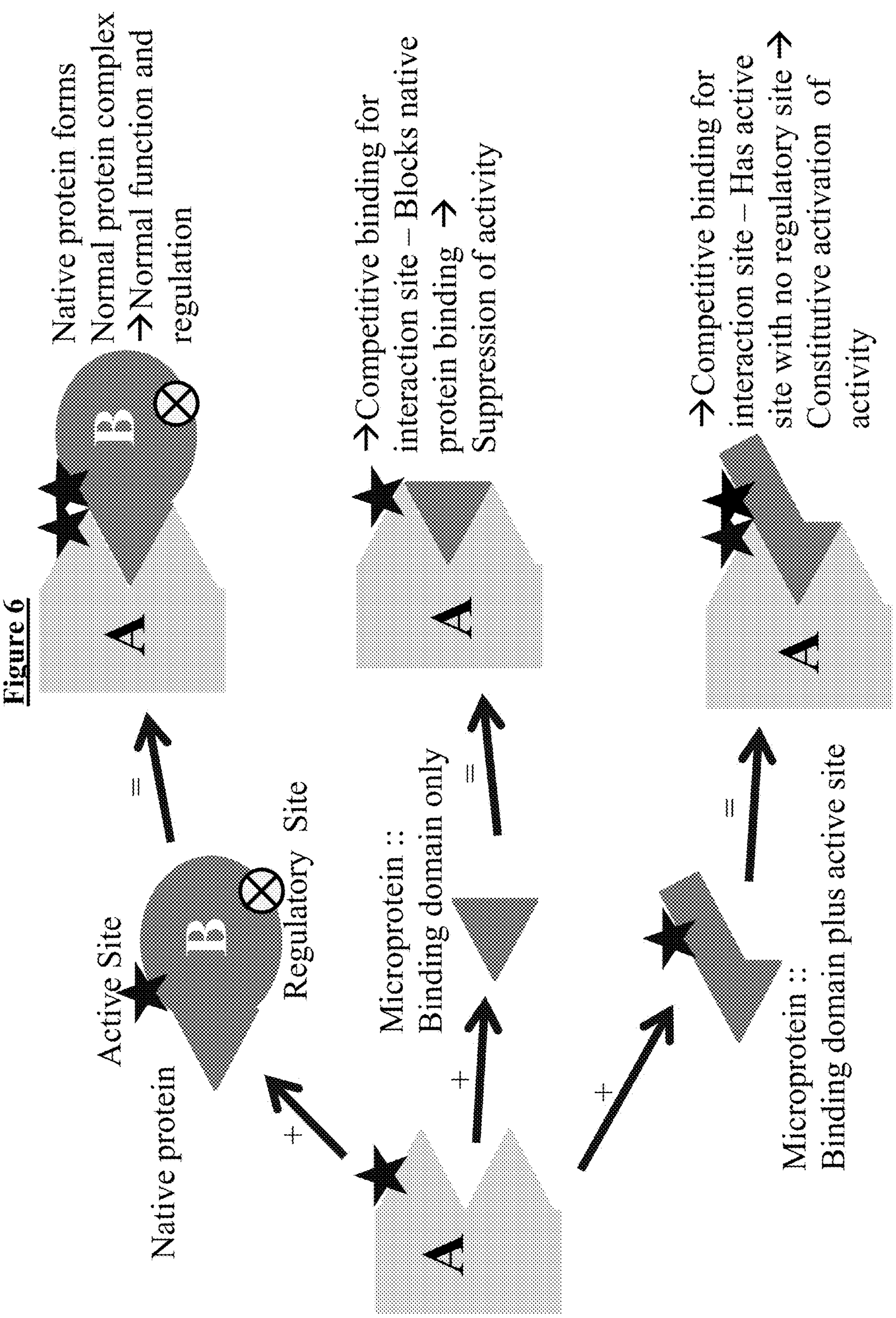
FIG. 6 shows potential outcomes of protein truncation. The upper flow shows normal protein interactions that brings all of the encoded components together in the correct conformation to allow function of a protein complex. The center flow shows a truncation of one of the protein components that removes a functional unit of the protein but retains the interaction domain that can still bind the interacting protein and block the interaction site from a complete fully functional version of the truncated protein. In the center case—this would act as a dominant negative allele. The lower flow shows the strategic deletion of part of a protein that encodes a regulatory element for activity and leaves the functional domain and the interaction domain intact—thus leading to a protein complex that is stuck in either a constitutively active or suppressed state of activity.

Example 8. Engineering a Truncated Protein Using Genome Editing Techniques to Create a Dominant Allele A) Engineering GA20 Oxidase Truncated Proteins:

Targeted editing of genes that result in truncated proteins or non-sense mutations to the proteins can create dominant alleles. See FIG. 6. The corn GA20 Oxidase_5 gene and GA20 Oxidase_3 gene are highly similar in sequence and structure. Both genes comprise three exons. A gRNA is designed to introduce an edit in an exon of both genes.

A transfer DNA (T-DNA) vector suitable for use in *Agrobacterium* transformation is used to introduce the gRNA to a corn cell. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the gRNA described above.

Immature corn embryos are co-cultured with *Agrobacterium* containing the T-DNA vectors for three days. The polynucleotides between the LB and RB sequences are integrated into the nuclear genome of the immature corn embryos. Upon expression of the integrated polynucleotides, the gRNA guides the nuclease to the target site and creates a double-stranded break at the target site. Without being bound by a particular theory, the non-homologous end-joining repair mechanisms native to the cell frequently repair such breaks imperfectly, which can lead to the insertion or deletion of one or more nucleotides. These insertions or deletions to an exon can produce premature stop codons (which would generate a truncated protein), or non-sense mutations. A premature stop codon has the capability of generating a dominant allele of GA20 Oxidase_5 and GA20 Oxidase_3.

Suitable methods known in the art (e.g., PCR, DNA hybridization (Southern) blots, sequencing) are used to identify transformation events comprising a targeted insertion or deletion in the GA20 Oxidase_5 and/or GA20 Oxidase_3 genes. Transformed embryos comprising an insertion or deletion capable of introducing a premature stop codon causing a truncated protein or a non-sense mutation at the target site are selected and used to regenerate modified plants using techniques standard in the field.

Protein is extracted from the modified corn plants identified as comprising the identified insertion/deletion. Suitable methods known in the art (e.g., Western blot; HPLC; LC/MS; ELISA; immunoprecipitation) are used to confirm that a truncated protein or a non-sense mutation has been introduced to GA20 Oxidase_5 and/or GA20 Oxidase_3 genes. Additional experiments to confirm a reduction in gibberellin acid in stem and/or vascular tissue are performed as described in Bensen et al., *Plant Physiol.* 1990, 94: 77-84, which is incorporated by reference herein in its entirety.

B) Engineering Brachytic 2 (Br2) Truncated Protein:

A gRNA is designed to introduce an edit within an exon of the Brachytic 2 gene from corn.

A transfer DNA (T-DNA) vector suitable for use in *Agrobacterium* transformation is used to introduce the gRNA to a corn cell. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the gRNA described above.

Immature corn embryos are co-cultured with *Agrobacterium* containing the T-DNA vectors for three days. The polynucleotides between the LB and RB sequences are integrated into the nuclear genome of the immature corn embryos. Upon expression of the integrated polynucleotides, the gRNA guides the nuclease to the target site where the nuclease creates a double-stranded break at the target site. Without being bound by a particular theory, the non-homologous end-joining repair mechanisms native to the cell frequently repair such breaks imperfectly, which can lead to the insertion or deletion of one or more nucleotides. These insertions or deletions to an exon can produce premature stop codons (which would generate a truncated protein), or non-sense mutations. A premature stop codon has the capability of generating a dominant allele of Brachytic 2 (Br2).

Suitable methods known in the art (e.g., PCR, DNA hybridization (Southern) blots, sequencing) are used to identify transformation events comprising a targeted insertion or deletion in the Br2 gene. Transformed embryos comprising an insertion or deletion capable of introducing a premature stop codon (causing a truncated protein) or a non-sense mutation at the target site are selected and used to regenerate modified plants using techniques standard in the field.

Protein is extracted from the modified corn plants identified as comprising the identified insertion/deletion. Suitable methods known in the art (e.g., Western blot; HPLC;

LC/MS; ELISA; immunoprecipitation) are used to confirm that a Br2 truncated protein is generated.

Example 9. Generating an Inverted Repeat within a Target Gene

Figure 7:
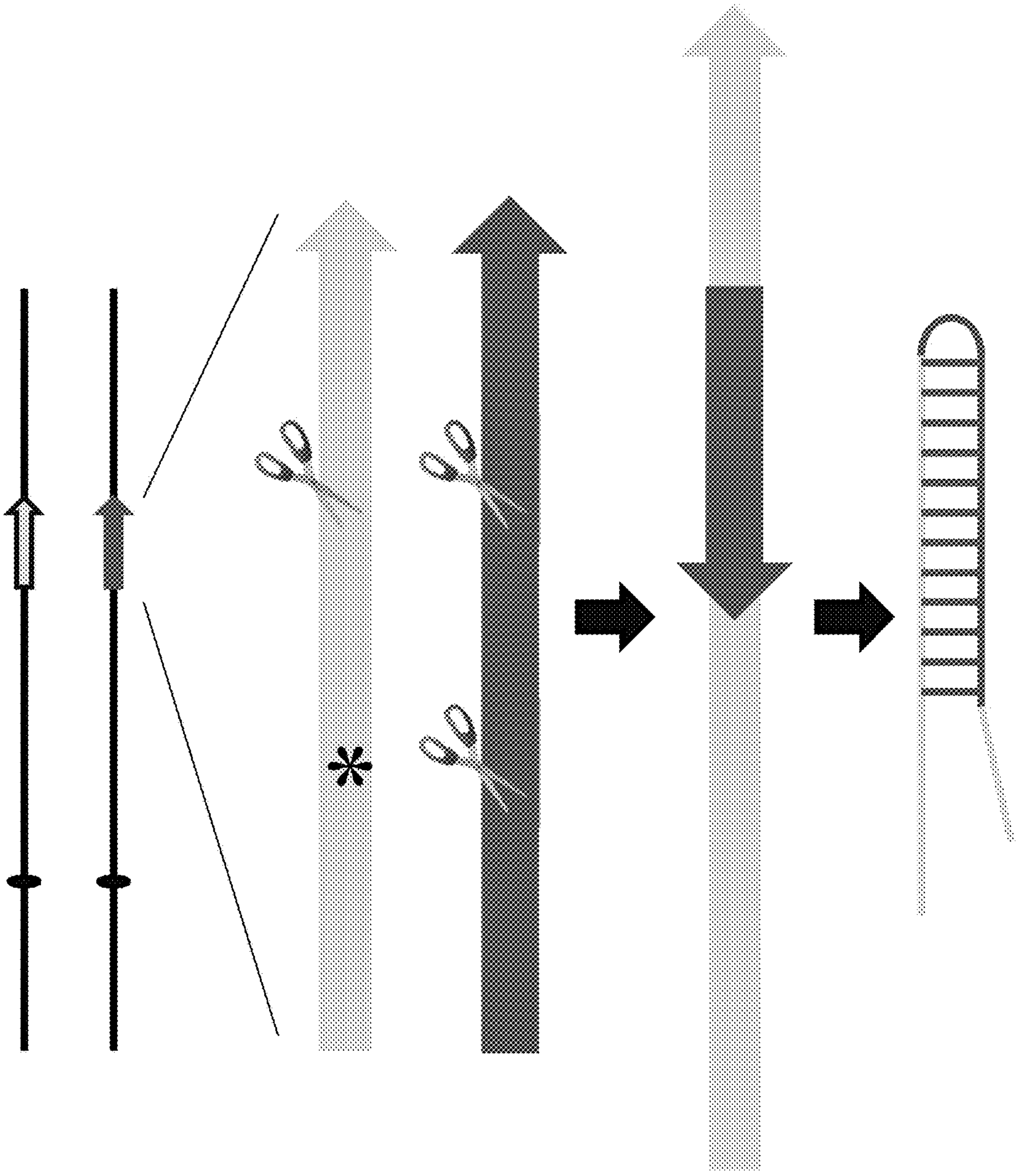
FIG. 7 comprises Panels A, B, C, D, and E. Panel A shows a heterozygous genomic locus. Panel B shows that a nuclease (represented by scissors) generates one DSB in the first allele. Panel C shows that a nuclease generates two DSBs in the second allele. In one possible outcome (Panel D) the region between the two DSBs on the second allele (Panel C) is inverted and inserted into the single DSB in the first allele. Panel E shows a hairpin RNA transcript produced form transcribing the allele structure in Panel D.

Targeted editing techniques can be used to convert a genomic locus into a locus that is capable of generating an RNAi-inducing hairpin when the edited locus is transcribed into RNA. See FIG. 7. In a cell that is heterozygous at the locus of interest (e.g., two polymorphic alleles are present), one or more nucleases are used to generate two double-stranded breaks (e.g., a first double-stranded break and a second double-stranded break) in the first allele, and one double-stranded break (e.g., a third double-stranded break) in the second allele. When the nucleases cut the first and second alleles, the portion of the first allele that is flanked by the first and second double-stranded breaks is released from the genomic DNA. In one outcome, the released portion of the first allele is inverted in orientation and integrated into the third double-stranded break in the second allele, thereby creating an edited locus that is capable of generating an RNAi-inducing hairpin when the edited locus is transcribed.

A first and a second functional guide RNA (gRNA) for a RNA guided nuclease system are created. The first and second gRNAs are complementary to a first target site and a second target site, respectively, flanking a portion of a first allele of a GA20 oxidase_5 gene in the corn genome. The first gRNA is also complementary to a second allele of the GA20 oxidase_5 gene at a third target site (which is homologous to the first target site), but the second gRNA is not complementary to the second allele due to a polymorphism between the first and second GA20 oxidase_5 alleles at the second target site.

A transfer DNA (T-DNA) vector suitable for use in *Agrobacterium* transformation is constructed. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises an expression cassette comprising a promoter operable in a plant cell operably linked to a polynucleotide encoding the first and second gRNAs described above.

Immature corn embryos are co-cultured with *Agrobacterium* containing the T-DNA vector for three days. Upon expression of the polynucleotides, the gRNAs guide the nuclease to each of the three target sites in the GA20 oxidase_5 alleles, where the nuclease creates a double-stranded break at each target site.

In the majority of events, the region between the first and second target sites in the first GA20 oxidase_5 allele is deleted and non-homologous end-joining repair mechanisms joins the flanking regions. Less frequently, some events create insertion/deletion mutations at the first target site, the second target site, or both. In still other events the entire targeted region of the first allele integrates into the double-stranded break at the third target site in an inverted orientation. See FIG. 7, Panel D. Suitable methods known in the art (e.g., PCR, DNA hybridization (Southern) blots, sequencing) are used to identify transformation events comprising an inversion in the second GA20 oxidase_5 allele. Transformed embryos comprising an inversion in the second GA20 oxidase_5 allele are selected and used to regenerate modified plants using techniques standard in the field.

Without being bound to any scientific theory, the presence of an inversion in one allele of the GA20 oxidase_5 creates a population of RNA transcripts capable of forming a hairpin structure. Such a hairpin induces RNAi machinery in the cell, which leads to down-regulation of GA20 oxidase_5 RNA transcripts in a dominant manner (e.g., edited and unedited alleles are both down-regulated).

RNA is extracted from modified corn plants identified as comprising an inversion in the second allele capable of generating a hairpin RNA transcript. RNA is also extracted from control corn plants that lack edited GA20 oxidase_5 alleles. Suitable methods known in the art (e.g., quantitative reverse-transcriptase PCR, reverse-transcriptase PCR, RNA sequencing) are used to confirm that down-regulation of GA20 oxidase_5 occurs in modified corn plants comprising an inversion in the second allele capable of generating a hairpin RNA transcript. Additionally, due to the sequence similarities between GA20 oxidase_5 and GA20 oxidase_3, the inversion in the second allele of GA20 oxidase_5 also causes down-regulation of GA20 oxidase_3 RNA transcripts.

Example 10. Inserting a miRNA Target Site into a Desired Genomic Locus

Figure 8:
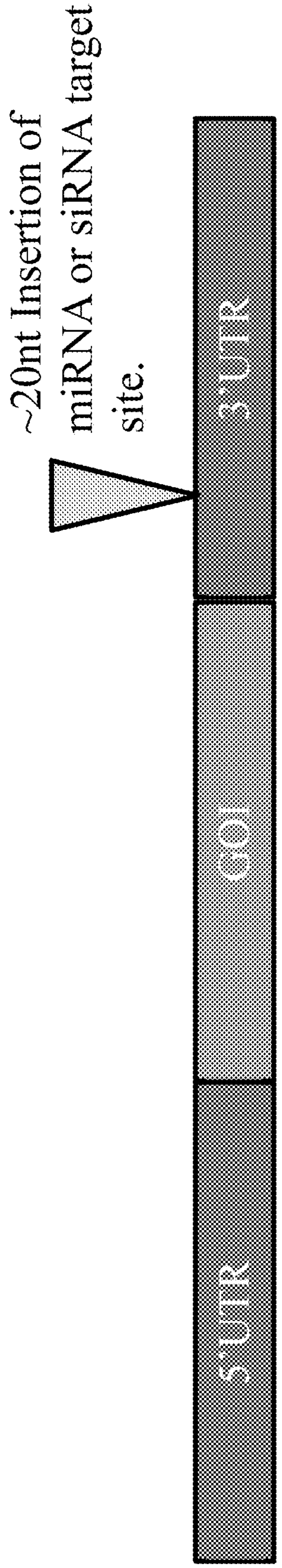
FIG. 8 provides a schematic of a non-coding RNA target site insertion in a gene of interest. Such an insertion can lead to the production of transient secondary siRNAs to down-regulate the gene of interest (GOI).

Targeted editing techniques can be used to insert a donor molecule into a target site in a genomic locus. See FIG. 8. If a donor molecule comprising a non-coding RNA target site is inserted into a 5'-UTR, an exon, an intron, or a 3'-UTR of a gene of interest, RNA transcription or protein translation of the gene of interest can be suppressed by a complementary non-coding RNA. When a gene of interest is a target of a non-coding RNA (e.g., a miRNA or an siRNA), a cleaved mRNA from the gene of interest can generate secondary siRNAs, which can further suppress the transcription or translation of the gene of interest. Such secondary suppression can act in a dominant manner, as the secondary siRNAs are complementary to alleles with and without the insertion of the non-coding RNA target site.

A functional guide RNA (gRNA) is created that is complementary to a target site in the 3'-UTR of a GA20 oxidase_5 gene. A transfer DNA (T-DNA) vector suitable for use in *Agrobacterium* transformation is constructed. The T-DNA construct comprises a promoter that is operable in a plant cell operably linked to polynucleotides encoding a) an RNA guided/nuclease; b) CP4-EPSPS marker gene; c) the gRNA described above; and d) a donor molecule, between a left border (LB) sequence and a right border (RB) sequence. The donor molecule comprises a 21 nucleotide sequence homologous to miR166, as well as a first and a second homologous region that are homologous to the 3'-UTR of the GA20 oxidase_5 gene on either side of the target site.

Immature corn embryos are co-cultured with *Agrobacterium* containing the T-DNA vector for three days. Upon expression of the polynucleotides, the gRNA guides the nuclease to the target site in the GA20 oxidase_5 3'-UTR, where the nuclease creates a double-stranded break. Homologous recombination repair mechanisms then insert the donor molecule into the target site, thereby incorporating a miR166 target site into the 3'-UTR of the GA20 oxidase_5 gene.

Suitable methods known in the art (e.g., PCR, DNA hybridization (Southern) blots, sequencing) are used to identify transformation events comprising the insertion of the miR166 target site into the 3'-UTR of the GA20 oxidase_5 gene. Transformed embryos comprising the insertion of the miR166 target site into the 3'-UTR of the GA20 oxidase_5 gene are selected and used to regenerate modified plants using techniques standard in the field.

Without being bound to any scientific theory, the presence of a miRNA binding site in GA20 oxidase_5 creates a population of secondary siRNA transcripts capable of suppressing GA20 oxidase_5 RNA transcription in a dominant negative manner.

RNA is extracted from modified corn plants identified as comprising a miR166 target site insertion in the 3'-UTR of a GA20 oxidase_5 gene. RNA is also extracted from control corn plants that lack an edited GA20 oxidase_5 gene. Suitable methods known in the art (e.g., quantitative reverse-transcriptase PCR, reverse-transcriptase PCR, RNA sequencing) are used to confirm that down-regulation of GA20 oxidase_5 occurs in modified corn plants. Additionally, due to the sequence similarities between GA20 oxidase_5 and GA20 oxidase_3, the miRNA target site in the GA20 oxidase_5 gene is also capable of causing down-regulation of GA20 oxidase_3 RNA transcripts.

Example 11. Generating Dominant Negative Alleles by Creating Truncated Proteins Targeted editing of genes that result in truncated proteins (e.g., non-sense mutations) can create dominant negative alleles. In one embodiment, the targeted gene encodes a protein that has protein: protein interaction domains. See FIG. 6. Examples of dominant truncated proteins are known in various plant species. For example, dominant mutant phenotypes caused by truncated proteins are known for FAZ1 in rice and AGAMOUS and SOC1 in *Arabidopsis thaliana*. The peptide CLAVATA3 (CLV3) is processed to a signaling peptide (CLE), which is bound by the receptor-like kinases CLV1 and CORYNE (CRN) and the receptor-like protein CLV2 to regulate the expression of WUSCHEL (WUS) in meristems. Corn plants comprising mutant alleles of CLV2 often exhibit ears with increased number of kernel rows. Without being limited by a particular theory, when CLV2 is mutated, WUS expression can increase, which leads to an increased meristem size, which in turn gives rise to an increased number of kernel rows on the ear. CLV2 comprises an extracellular domain and a transmembrane domain, which forms a complex with CRN. A truncated CLV2 protein could function in a dominant manner to increase meristem size in corn.

A gRNA is designed to introduce a stop codon in the extracellular domain of CLV2 in corn. A transfer DNA (T-DNA) vector suitable for use in *Agrobacterium* transformation is used to introduce the gRNA to a corn cell. The T-DNA construct comprises a promoter that is operable in a plant cell operably linked to polynucleotides encoding a) a RNA guided nuclease; b) CP4-EPSPS marker gene; and c) the gRNA described above, between a left border (LB) sequence and a right border (RB) sequence.

Immature corn embryos are co-cultured with *Agrobacterium* containing the T-DNA vectors for three days. The polynucleotides between the LB and RB sequences are integrated into the nuclear genome of the immature corn embryos. Upon expression of the integrated polynucleotides, the gRNA guides the nuclease to the target site and creates a double-stranded break at the target site. Without being bound by any theory, the non-homologous end-joining repair mechanisms native to the cell frequently repair such breaks imperfectly, which can lead to the insertion or deletion of one or more nucleotides. These insertions or deletions to an exon can produce premature stop codons (which would generate a truncated protein), or non-sense mutations. Such a mutation can generate a dominant negative allele of CLV2.

Suitable methods known in the art (e.g., PCR, DNA hybridization (Southern) blots, sequencing) are used to identify transformation events comprising a targeted insertion or deletion in the CLV2 gene. Transformed embryos comprising an insertion or deletion capable of causing a truncated protein at the target site are selected and used to regenerate modified plants using techniques standard in the field.

Protein is extracted from the modified corn plants identified as comprising the identified insertion/deletion. Suitable methods known in the art (e.g., Western blot; HPLC; LC/MS; ELISA; immunoprecipitation) are used to confirm that a non-sense mutation has been introduced to the CLV2 gene. Additional phenotypic screening of ear kernel rows is done to an increase in meristem size. Light microscopy of sectioned meristems from modified and control plants is also done to quantify the increase in meristem size.

Example 12. Preventing Cleavage of a Target Gene Using an Engineered PPR Protein Members of the pentatricopeptide repeat (PPR) gene family are common in plant genomes. Many PPR proteins are capable of binding RNA molecules in a sequence-specific manner. PPR proteins comprise 2-30 PPR motifs, each of which aligns to a single nucleotide in an RNA molecule. Within the PPR motifs, the amino acids present at two or three specific positions confer nucleotide specificity. For example, without being limiting, a PPR motif binds an adenine nucleotide when a threonine is in position 6 and an asparagine is at the 1' position; a PPR motif binds a guanine nucleotide when a threonine is in position 6 and an aspartic acid is at the 1' position; a PPR motif binds a uracil (or thymine) nucleotide when an asparagine is at position 6 and an aspartic acid is at the 1' position; and a PPR motif binds a cytosine nucleotide when an asparagine is at position 6 and an asparagine or a serine is at the 1' position.

Without being limiting, an engineered PPR protein can be generated by at least two building strategies. In the first strategy, a PPR protein is constructed by treating each PPR motif as a separate block, such that a PPR protein is constructed by putting multiple desired motifs in order. The resulting engineered PPR protein is then capable of binding a target RNA molecule. However, such a strategy may not always work because each PPR motif comprises an internal scaffolding between the 1' and 6 positions, and that intra-motif scaffold is not shared across different PPR proteins. The second strategy makes use of the preexisting intra-motif scaffolding. In the second strategy, site-directed mutagenesis of the 1' and 6 positions is used to edit an existing PPR protein such that it will be specific to a new target RNA molecule.

An engineered PPR protein comprising PPR motifs is engineered such that the PPR protein can specifically bind to nucleotides of the miRNA target site of a suitable gene and the PPR protein is targeted to the cytoplasm. A nucleic acid sequence encoding the engineered PPR protein is inserted into a transfer DNA (T-DNA) vector suitable for use in *Agrobacterium* transformation. The nucleic acid sequence encoding the engineered PPR protein is operably linked to the promoter of the target gene or a constitutive promoter to ensure overlapping expression of the engineered PPR protein and the target gene mRNA. The nucleic acid molecule encoding the engineered PPR protein and operably linked promoter is positioned between a left border (LB) sequence and a right border (RB) sequence within the T-DNA construct.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the engineered PPR protein is expressed and binds to complementary target mRNAs.

Suitable methods known in the art (e.g., PCR, DNA hybridization (Southern) blots, sequencing) are used to identify transformation events comprising the insertion of the engineered PPR protein encoding nucleic acid molecule. Transformed embryos comprising the insertion of the engineered PPR protein encoding nucleic acid molecule are selected and used to regenerate modified plants using techniques standard in the field.

Without being bound to any scientific theory, the engineered PPR protein binds to the target gene mRNA and prevents the microRNA from suppressing the target gene.

RNA and protein is extracted from modified corn plants identified as comprising the engineered PPR protein. RNA and protein is also extracted from control corn plants that lack the engineered PPR protein. Suitable methods known in the art (e.g., quantitative reverse-transcriptase PCR, reverse-transcriptase PCR, RNA sequencing, Western blot, HPLC, LC/MS, ELISA, immunoprecipitation) are used to confirm that expression of THE TARGET GENE is increased in modified corn plants as compared to unmodified control corn plants.

Example 13. Cleaving a Target Gene Transcript Using an Engineered PPR Protein Coupled to a Nuclease An engineered PPR protein comprising an NYN nuclease domain and PPR motifs is engineered as described in Example 12 such that the PPR protein can specifically bind to certain nucleotides of a target gene and the PPR protein is targeted to the nucleus. A nucleic acid sequence encoding the engineered PPR protein is inserted into a transfer DNA (T-DNA) vector suitable for use in *Agrobacterium* transformation. The nucleic acid sequence encoding the engineered PPR protein is operably linked to the promoter of the target gene or a constitutive promoter to ensure overlapping expression of the engineered PPR protein and the target gene mRNA. The nucleic acid molecule encoding the engineered PPR protein and operably linked promoter is positioned between a left border (LB) sequence and a right border (RB) sequence within the T-DNA construct.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the engineered PPR protein is expressed and binds to complementary target mRNAs.

Suitable methods known in the art (e.g., PCR, DNA hybridization (Southern) blots, sequencing) are used to identify transformation events comprising the insertion of the engineered PPR protein encoding nucleic acid molecule. Transformed embryos comprising the insertion of the engineered PPR protein encoding nucleic acid molecule are selected and used to regenerate modified plants using techniques standard in the field.

Without being bound to any scientific theory, the engineered PPR protein binds to the target gene mRNA, and the NYN nuclease domain cleaves the target gene mRNA. Therefore, expression of the target gene decreases.

RNA and protein are extracted from modified corn plants identified as comprising the engineered PPR protein. RNA and protein are also extracted from control corn plants that lack the engineered PPR protein. Suitable methods known in the art (e.g., quantitative reverse-transcriptase PCR, reverse-transcriptase PCR, RNA sequencing, Western blot, HPLC, LC/MS, ELISA, immunoprecipitation) are used to confirm that expression of the target gene is decreased in modified corn plants as compared to unmodified control corn plants.

Example 14. Blocking Translation of a Target Gene Transcript Using an Engineered PPR Protein An engineered PPR protein comprising PPR motifs is engineered such that the PPR protein can specifically bind to specific nucleotides of an mRNA encoded by the target gene[GENE X], and the PPR protein is targeted to the cytoplasm. A nucleic acid sequence encoding the engineered PPR protein is inserted into a transfer DNA (T-DNA) vector suitable for use in *Agrobacterium* transformation. The nucleic acid sequence encoding the engineered PPR protein is operably linked to the promoter of the target gene or a constitutive promoter to ensure overlapping expression of the engineered PPR protein and the target gene mRNA. The nucleic acid molecule encoding the engineered PPR protein and operably linked promoter is positioned between a left border (LB) sequence and a right border (RB) sequence within the T-DNA construct.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the engineered PPR protein is expressed and binds to complementary target mRNAs.

Suitable methods known in the art (e.g., PCR, DNA hybridization (Southern) blots, sequencing) are used to identify transformation events comprising the insertion of the engineered PPR protein encoding nucleic acid molecule. Transformed embryos comprising the insertion of the engineered PPR protein encoding nucleic acid molecule are selected and used to regenerate modified plants using techniques standard in the field.

Without being bound to any scientific theory, the engineered PPR protein binds to the target gene mRNA and prevents translation of the mRNA into protein. Therefore, protein translation of the target gene decreases.

Protein is extracted from modified corn plants identified as comprising the engineered PPR protein. Protein is also extracted from control corn plants that lack the engineered PPR protein. Suitable methods known in the art (e.g., Western blot, HPLC, LC/MS, ELISA, immunoprecipitation) are used to confirm that protein translation of the target gene is decreased in modified corn plants.

Example 15. Design of a Tether Guide Oligo (tgOligo)

Figure 9:
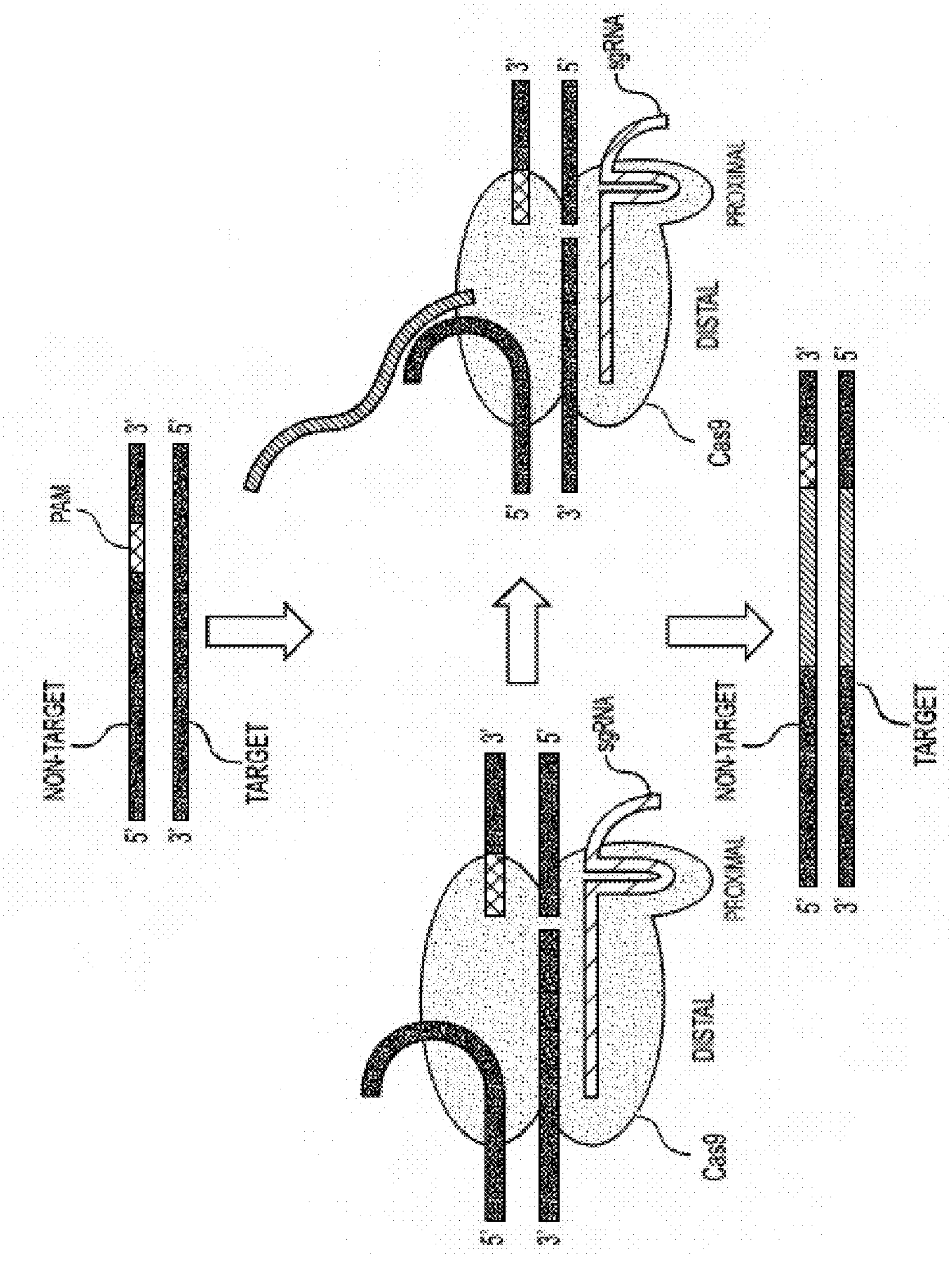
FIG. 9 provides a schematic of a Cas9-mediated double-stranded break (DSB) and a tether guide oligo (tgOligo) bound to a target DNA site. The Cas9-PAM interaction occurs on the non-target strand; sgRNA-DNA annealing occurs on the target strand. The blunt ends at the Cas9 cut site are held in place by Cas9 at the 5' end of the non-target strand (PAM location), and at both cut ends (3' and 5') of the target strand. The 3' cut end of the non-target strand is free and ‘flaps’ around. The 3' free ‘flap’ end of the non-target strand can be up to 35 nucleotides which can be sufficient for specific complementarity binding. A tgOligo (e.g., a ssDNA template) can be included for integration of desired nucleotide modification. The drawing scheme used here is followed in the subsequent figures.

A Cas9/sgRNA complex binds to a dsDNA molecule comprising target and non-target strands (FIG. 9). Cas9-

PAM interaction occurs on the non-target strand; gRNA-DNA annealing occurs on the target strand. RuvC (His840) and HNH (Asp10) nuclease domains cut the non-target and target strands, respectively (triangles). The blunt ends at the Cas9 cut site are held in place by Cas9 at the 5' end of the non-target strand (PAM location), and at both cut ends (3' and 5') of the target strand. The 3' cut end of the non-target strand is free and 'flaps' around. The 3' free 'flap' end of the non-target strand can be up to 35 nucleotides which can be sufficient for specific complementarity binding. A tgOligo (e.g., a ssDNA molecule commentary to the 3' free 'flap' end) is designed and can serve as a template for integration of desired nucleotide modifications. A tgOligo can be DNA, RNA, or a mix of nucleotides depending on the need and design of the edits. In the case of nucleases (e.g., Cpf1) that provide overhangs from a double-stranded break (DSB) cut, the overhangs can act in place of, or in conjunction with, tgOligos.

Example 16. Engineering of Cas9-Like Nuclease

Figure 10:
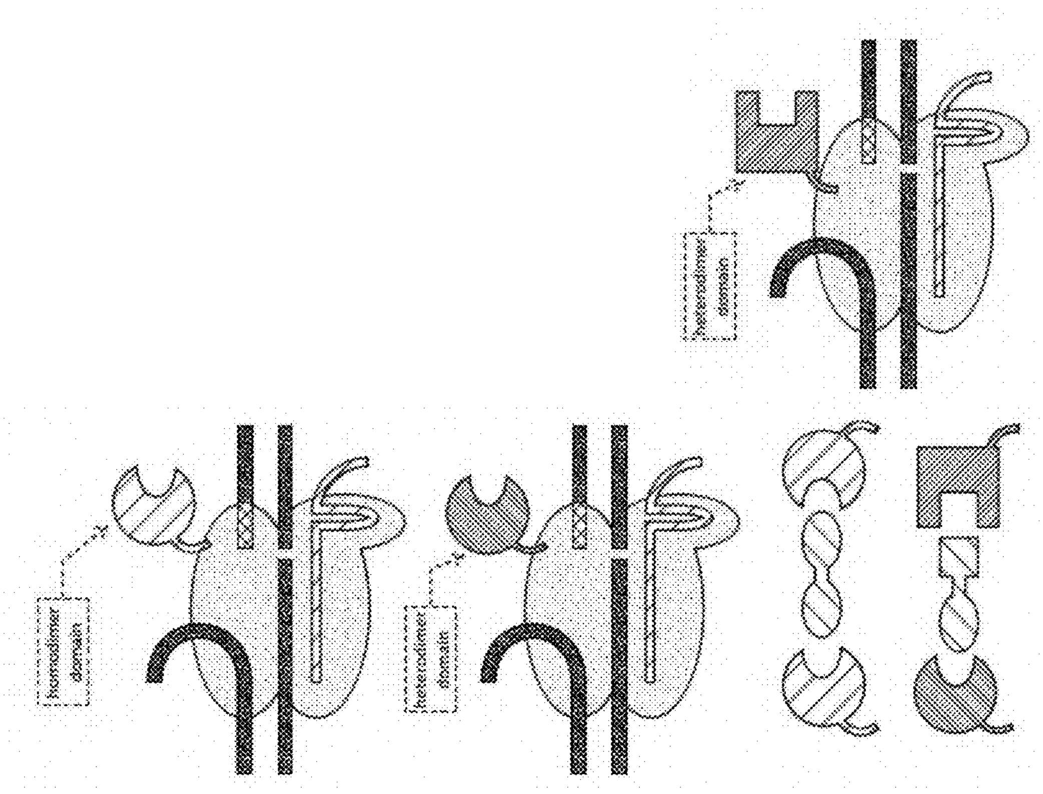
FIG. 10 depicts Cas9 conjugated with a homodimer domain (top) and heterodimer domains (middle and bottom right) to facilitate dimerization. Ligands for the homodimer and heterodimer domains are shown (bottom left). The drawing scheme used here is followed in the subsequent figures; e.g., the ligands, the homodimer or heterodimer domains, ssDNA binding domains. Each component of the Cas9/sgRNA complex and target DNA are shown as illustrated in FIG. 9. The drawing scheme used here for different dimerization domains is followed in the subsequent figures.

Nucleases, such as Cas9, can be repurposed for structural and functional genomics in plants. Various dimerization domains can be conjugated to Cas9 to achieve dimerization (FIG. 10). For example, inducible dimerization domains from Clonetech's homodimerization or heterodimerization iDimerize system can be used to achieve Cas9 dimerization. Additional dimerization systems can also be used such as those described in Andersen et al., *Scientific Reports* 6, Article number: 27766 (2016); and Miyamoto, et al., *Nature Chemical Biology* 8(5):465-70(2012).

Nucleases, such as Cas9, can also be engineered to form a catalytically deactivated from, such catalytically deactivated Cas9 (dCas9). dCas9 binds to DNA at a target site specified by a gRNA and creates a loop structure accessible for template-based editing (FIG. 1). dCas9 can be further modified to form a fusion with a ssDNA binding domain from Affymetrix or NEB for further facilitating template-based editing (FIG. 1). The editing efficiency with this modified dCas9-ssDNA binding scheme is expected to be higher compared to a dCas9-alone approach, because a ssDNA template is bound to dCas9 complex and would be brought into proximity of the gRNA target.

Example 17. Introduction of Multiple tgOligo and gRNA Molecules

Figure 12:
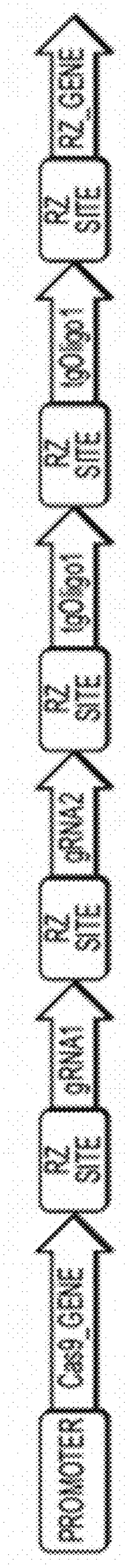
FIG. 12 provides an example construct containing Cas9, gRNAs, and tgOligos. RZ stands for Ribozyme, an enzyme that cleaves a 15 bp recognition site in RNA (RZ site).

Multiple approaches can be used to incorporate tgOligos with editing components (e.g., nuclease, gRNA). Essentially, tgOligos can be incorporated in any manner available to deliver nucleases and gRNAs (transfection, transformation, etc.). The optimal approach depends on the editing component delivery system and the target organism to be edited. For example, in mammalian systems where RNPs (ribonucleoproteins—complexes of nuclease and gRNA) can be transfected across the cell membrane, tgOligos can be simultaneously transfected. Alternatively, a single transcription unit (STU) can be used to incorporate the nuclease (Cas9) and gRNAs in the same transgene construct. Similarly, tgOligos can be incorporated in a similar design (FIG. 12). Multiple constructs could also be used, such as one for the nuclease, one for the gRNAs, and one for tgOligos—or any combination thereof from inclusive in constructs to combining constructs and transfection delivery. For tgOligos included in constructs (such as FIG. 12), these would be RNA-based tgOligos. To utilize DNA-based or mixed nucleotide (DNA+RNA) tgOligos, a transfection or other delivery mechanism would likely be needed. Also if any tgOligo designs result in the tgOligo containing the same gRNA+PAM recognition site as the original gRNA target site, the tgOligo sequence can be modified to eliminate the PAM.

Example 18. Genome Editing Based on a Two-gRNA Approach

Two nuclease/gRNA complexes flanking a target genomic region are designed for achieving INDELs or complete inversion of the flanked genomic region. (FIG. 1). With two nuclease/gRNA complexes, the flanked genomic region is most often deleted and NHEJ repair combining the two cut sites back together. There is also occurrence of INDEL (insertion/deletion) mutations at either nuclease+gRNA flanking site. It is also possible to recover with lower frequency complete inversions of the flanked genomic region.

Example 19. Enhancement of the Two-gRNA Approach

Figure 13:
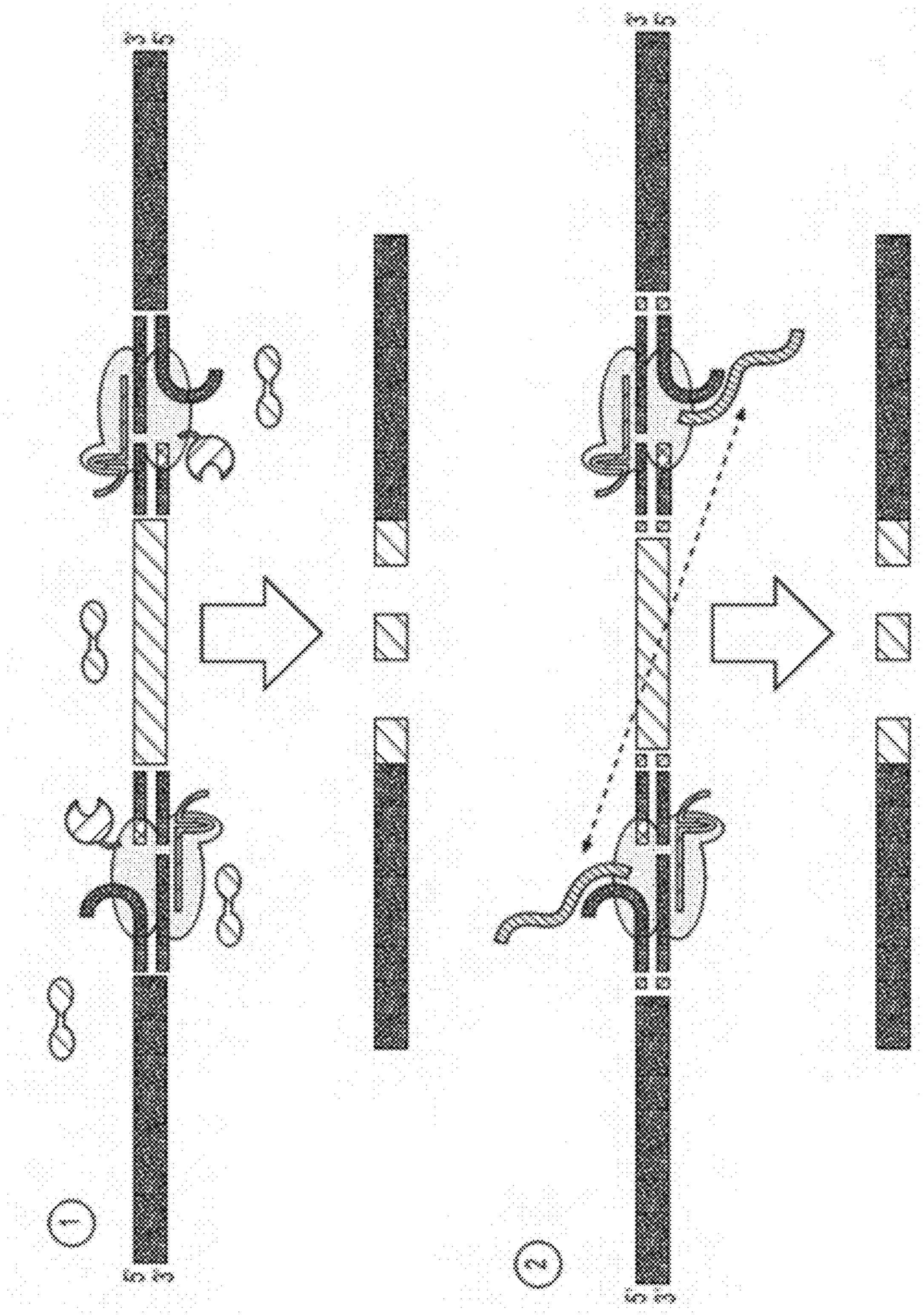
FIG. 13 provides an illustration of various approaches for improving genome editing efficiency. Using dimerization domains (See FIG. 10), tgOligos (See FIG. 9), or a combination of both can enhance recovery of complete knockout (deletion) of the genomic region flanked by the two gRNA target sites. Panel 1 shows a dimerization-enhanced knock out (KO) event. Panel 2 shows a tgOligo-enhanced KO event. Panel 3 shows an enhanced KO event via a combination of dimerization and tgOligos. Panel 4 shows a tgOligo-enhanced inversion event. Panel 5 shows a dimerization-enhanced inversion event. Panel 6 shows an inversion event assisted by a combination of Cas9 dimerization/deactivation and tgOligos. Only shown is the configuration where two gRNAs recognize different strands of a target dsDNA. The same concept is equally applicable to the other configuration where two gRNAs recognize the same strand of a target dsDNA.
Figure 13:
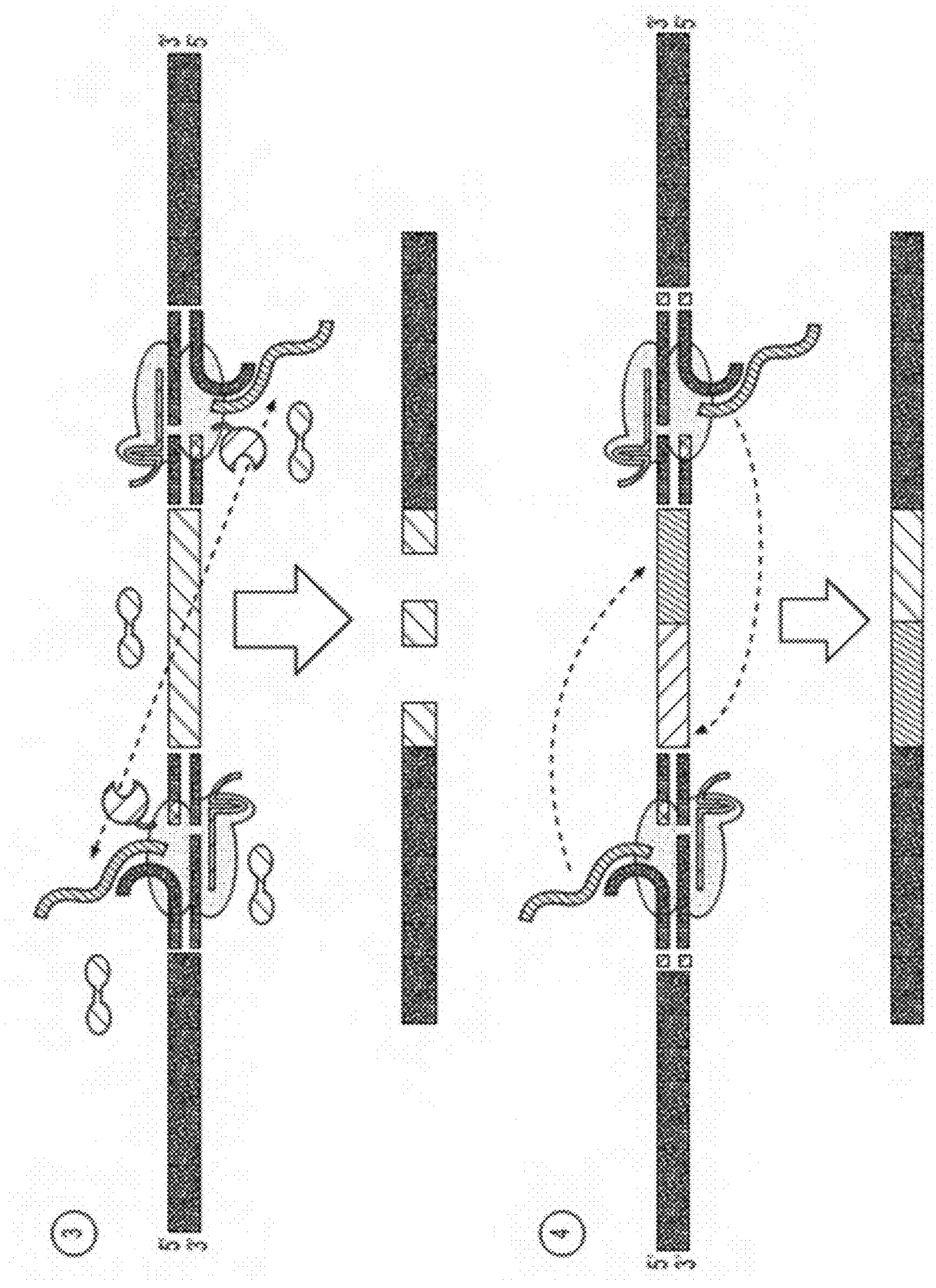
Figure 13:
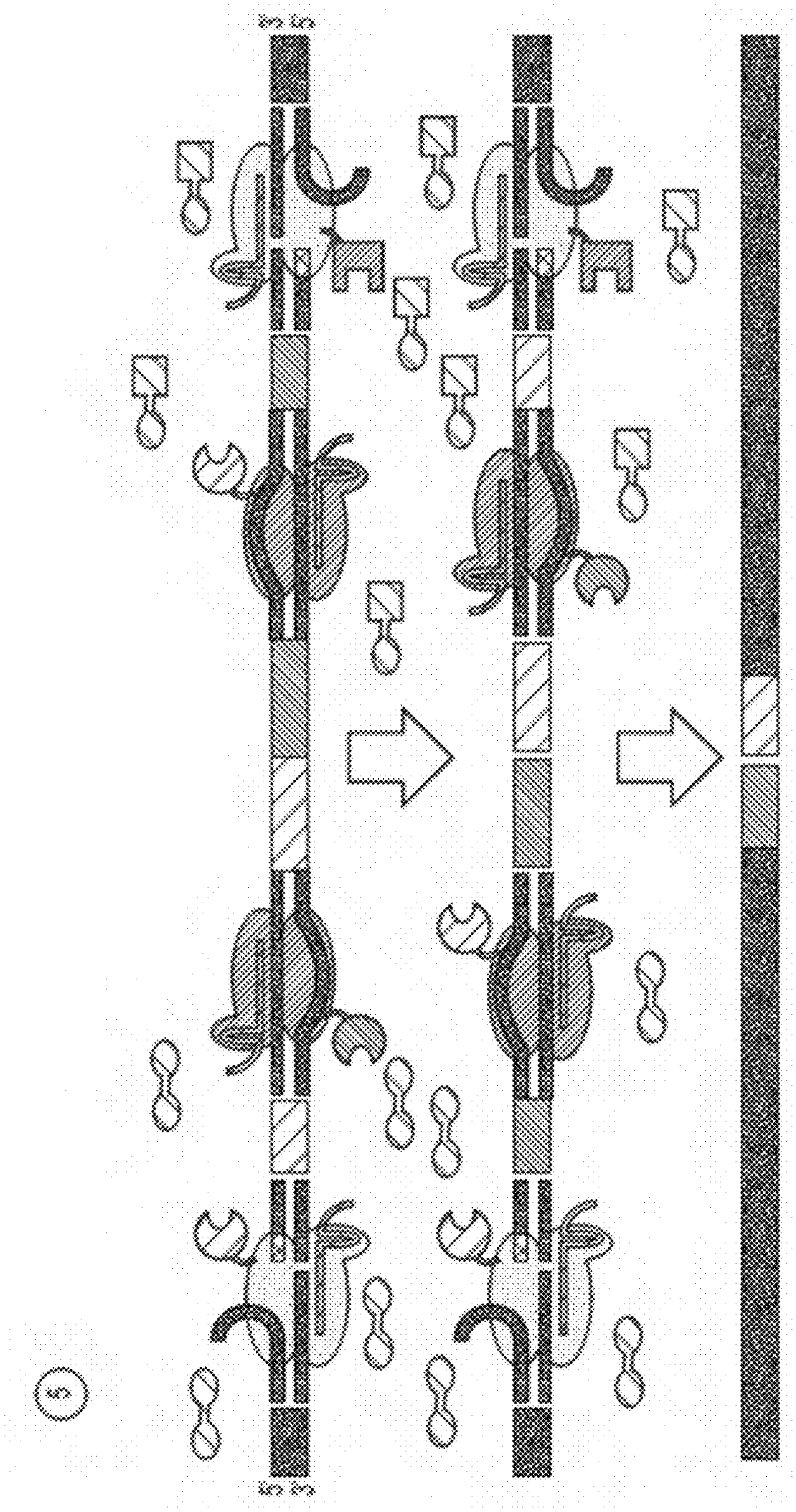
Figure 13:
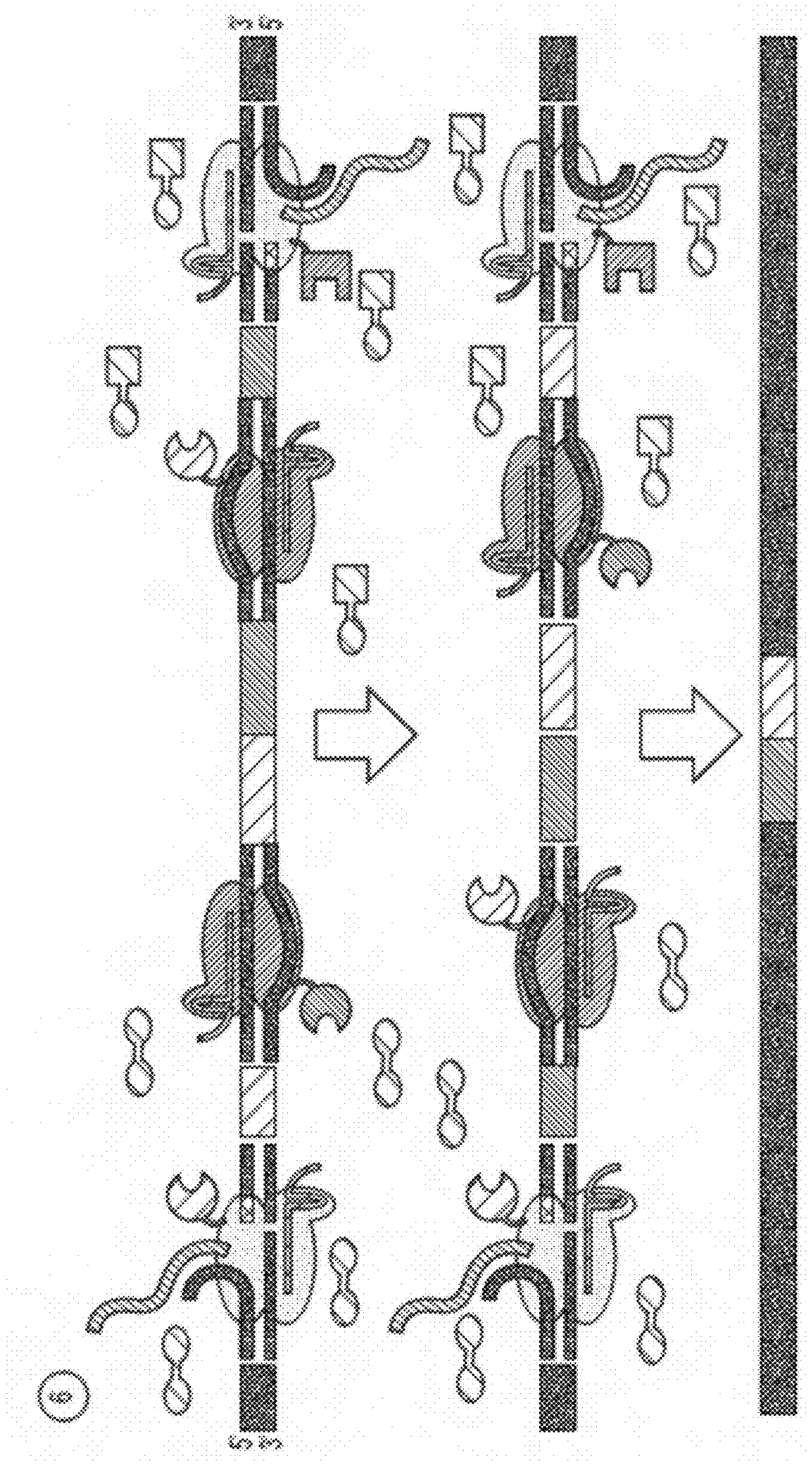

The two-gRNA approach from Example 18 is modified to improve genome editing efficiency. Using dimerization domains (see FIG. 10), tgOligos (see FIG. 9), or combination thereof can enhance recovery of complete knockout (deletion) of the genomic region flanked by the two gRNA target sites (FIG. 13). Panel 1 of FIG. 13 shows a dimerization-enhanced knock out (KO) event. Panel 2 of FIG. 13 shows a tgOligo-enhanced KO event. Panel 3 of FIG. 13 shows an enhanced KO event via a combination of dimerization and tgOligos. Panel 4 of FIG. 13 shows a tgOligo-enhanced inversion event. Without being bound to any theory, tgOligos can facilitate recovery of inversion events by using complementarity of the tether portions to the opposite end of the flanked segment. The tgOligos can vary in length for the complementation to the 3' flap of the non-target strand as well as the template tether extension beyond the flap complementation.

Paired dimerization domains coupled with nuclease (eg: Cas9) or dead nuclease (eg:dCas9) (either alone or in conjunction with tgOligos) can also be used to facilitate inversion of flanked sequence target. Panel 5 of FIG. 13 shows a dimerization-enhanced inversion event. Panel 6 of FIG. 13 shows an inversion event assisted by a combination of nuclease(eg:Cas9) dimerization/deactivation and tgOligos.

Figure 14:
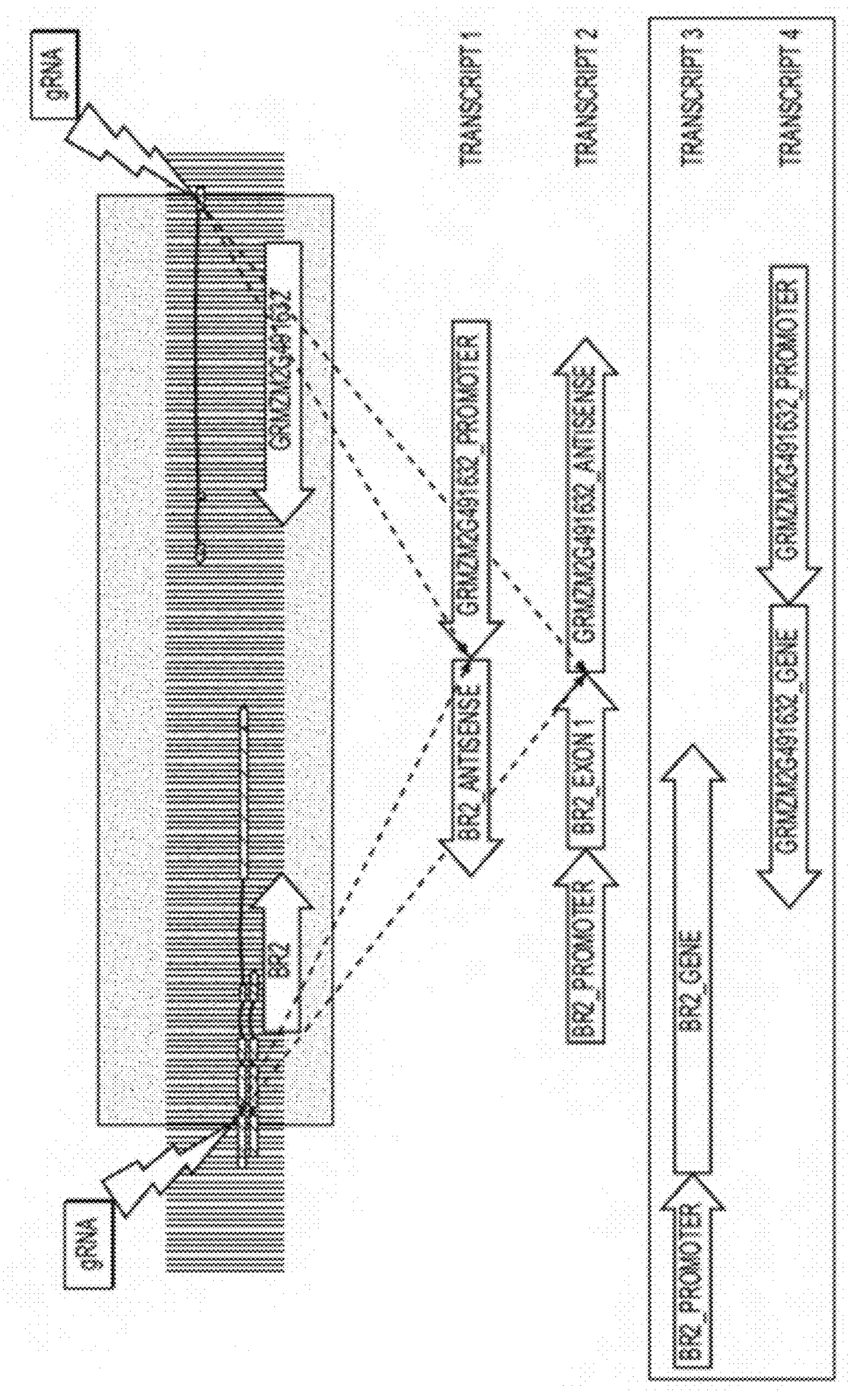
FIG. 14 provides an illustration of editing the corn BR2 gene to generate a dominant knockout allele via genome inversion. Two exemplary gRNAs are used. A first gRNA (shown on the left) targets the end of the first exon of BR2; a second gRNA (shown on the right) recognizes the start codon region of the adjacent GRMZM2G491632 gene. Inversion of the genomic segment flanked by these two gRNAs can lead to a BR2 antisense partial transcript (See Transcript 1). This BR2 antisense transcript is produced via the GRMZM2G491632 promoter activity. Adjusting the relative position of the two gRNAs can achieve a BR2 antisense complete transcript (e.g., moving the first gRNA on the left to target the start codon region of the BR2 gene) or a BR2 antisense transcript under the control of the native BR2 promoter (e.g., moving the second gRNA on the right to target the stop codon region of the BR2 gene).

Example 20. Genome Editing of Corn BR2 Gene by a tgOligo-Assisted Genomic Inversion Approach A tgOligo-assisted inversion approach (as illustrated in Panel 4 of FIG. 13) is used to edit the corn BR2 gene to generate a dominant knockout (KO) mutant allele. The rationale for a genome inversion-based dominant KO mutation approach is depicted in FIG. 14. In essence, two gRNAs are used. A first gRNA (shown on the left) targets the end of the first exon of BR2; a second gRNA (shown on the right) recognizes the start codon region of the adjacent GRMZM2G491632 gene. Inversion of the genomic segment flanked by these two gRNAs can lead to a BR2 antisense partial transcript. This BR2 antisense transcript is produced via the GRMZM2G491632 promoter activity. Adjusting the relative position of the two gRNAs can achieve a BR2 antisense complete transcript (e.g., moving the first gRNA on the left to target the start codon region of the BR2 gene)

or a BR2 antisense transcript under the control of the native BR2 promoter (e.g., moving the second gRNA on the right to target the stop codon region of the BR2 gene).

Reference sequences are listed in SEQ ID NO: 1 for BR2 (NCBI accession AY366085) and SEQ ID NO: 2 for GRMZM2G491632 (from MaizeGDB). GRMZM2G491632 is a gene annotated immediately adjacent to BR2; and these two genes are in reverse orientation of each other. SEQ ID NO: 3 is the gRNA to the sense strand at the proximal end of BR2. SEQ ID NO: 4 is the gRNA to the antisense strand at the proximal end of GRMZM2G491632.

A first RNA tgOligo corresponding to the BR2 gRNA (SEQ ID NO: 3) is designed to complement the sense strand flank gRNA target site, generally about 20 nt long. Optionally, a 20 nt segment upstream of the target site is added. An example of a BR2 RNA tgOligo comprises a DNA-complementary section as set forth in SEQ ID NO: 5 (serving as a DSB 3' flap complement region), which is complementary to SEQ ID NO: 3 with 10 nt included from upstream. Next, a sequence having at least 20 nt starting with the first base of the PAM of the antisense strand gRNA (SEQ ID NO: 4) is selected to give rise to a 50 nt sequence including the PAM (SEQ ID NO: 6, serving as a tether region). Subsequently, the 3' flap complement (SEQ ID NO: 5) is reversed and attached to the end of the tether (SEQ ID NO: 6) to form a complete tgOligo which complements both the sense gRNA and template from antisense gRNA segment for inversion (SEQ ID NO: 7).

A second RNA tgOligo corresponding to the GRMZM2G491632 gRNA (SEQ ID NO: 4) is designed as follows: a) from the reference sequence (SEQ ID NO: 2) reverse complement the antisense strand flank gRNA target site; b) select at least 20 nt starting with the first base of the PAM of the sense strand gRNA (SEQ ID NO: 3) and reverse complement. This example is 50 nt including the PAM (SEQ ID NO: 9); c) attach the 3' flap complement (SEQ ID NO: 8) to the end of the tether (SEQ ID NO: 9) to complete the tgOligo design complementing the sense gRNA and template from antisense gRNA segment for inversion (SEQ ID NO: 10).

A combination of two gRNAs and the first and second tgOligos are used to edit the corn BR2 locus to achieve a genomic inversion. The resulting inversion of BR2 and GRMZM2G491632 is expected to form a sequence with high similarity (95%+) to SEQ ID NO: 11.

Example 21. Enhancement of Template-Based Genome Editing or Site Directed Integration (SDI)

Figure 15:
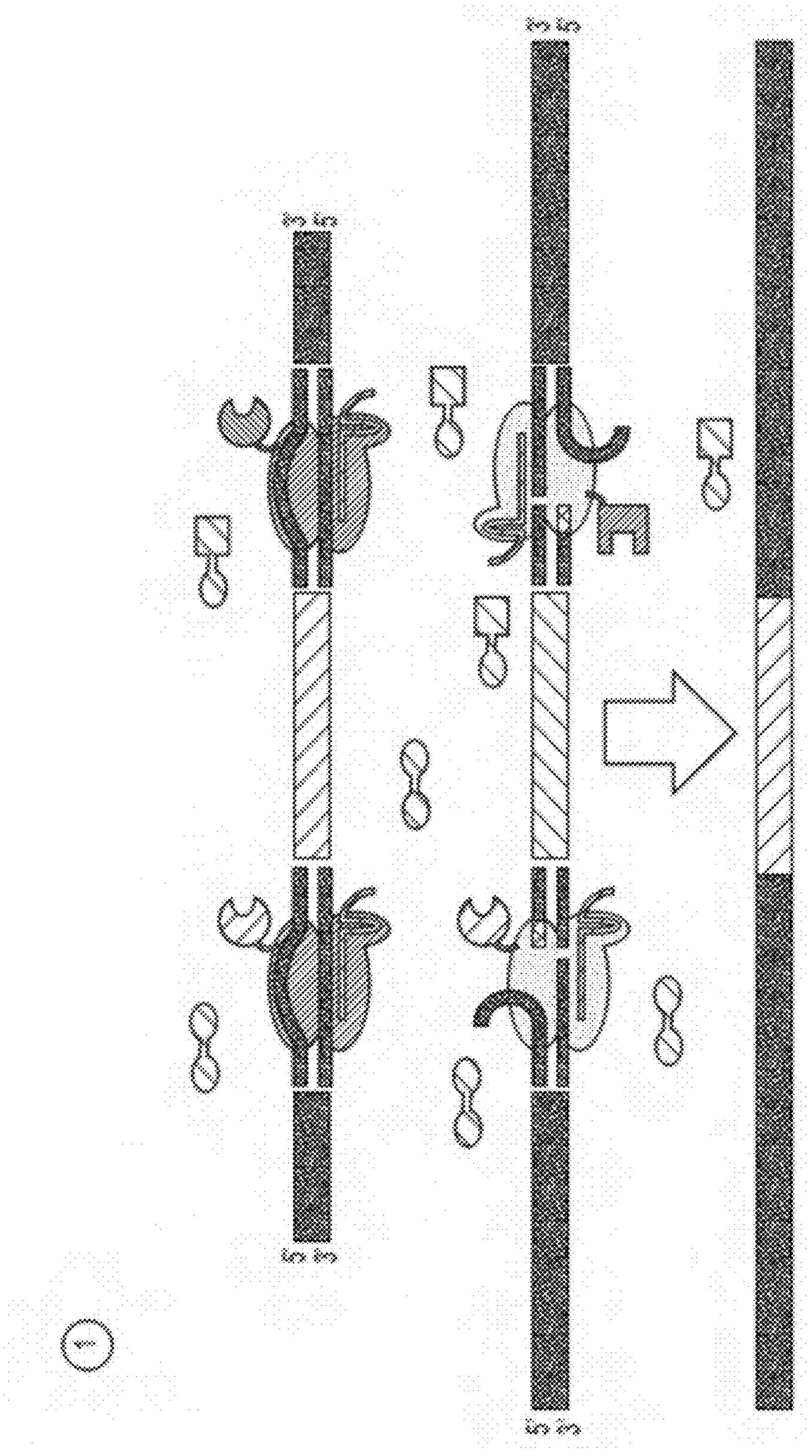
FIG. 15 provides an illustration of dimerization-enhanced template-based editing or site directed integration (SDI) at a single location (Panels 1 and 2) or multiple locations (Panel 3), and dimerization/tgOligo-enhanced template-based editing or SDI (Panel 4).
Figure 15:
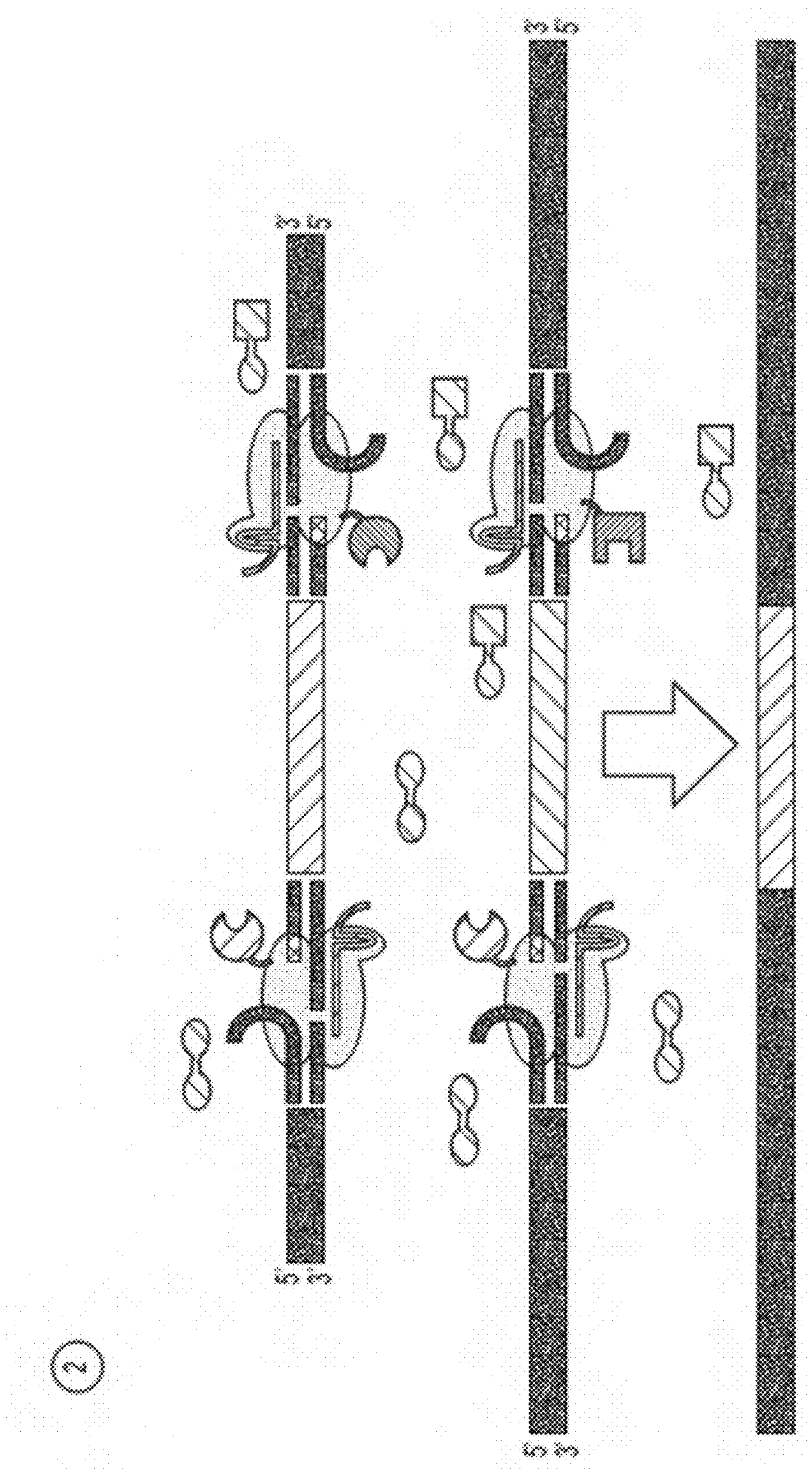
Figure 15:
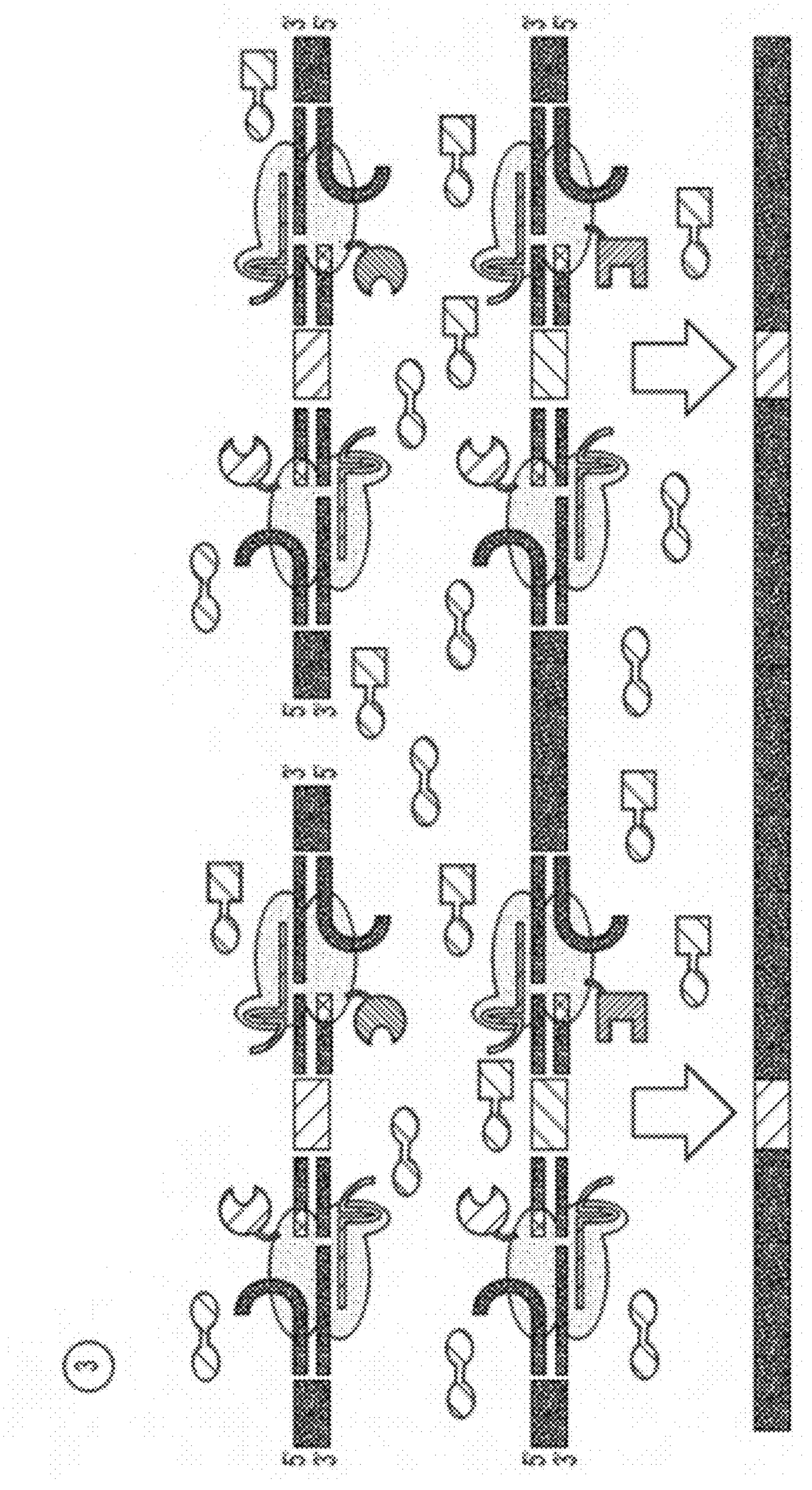
Figure 15:
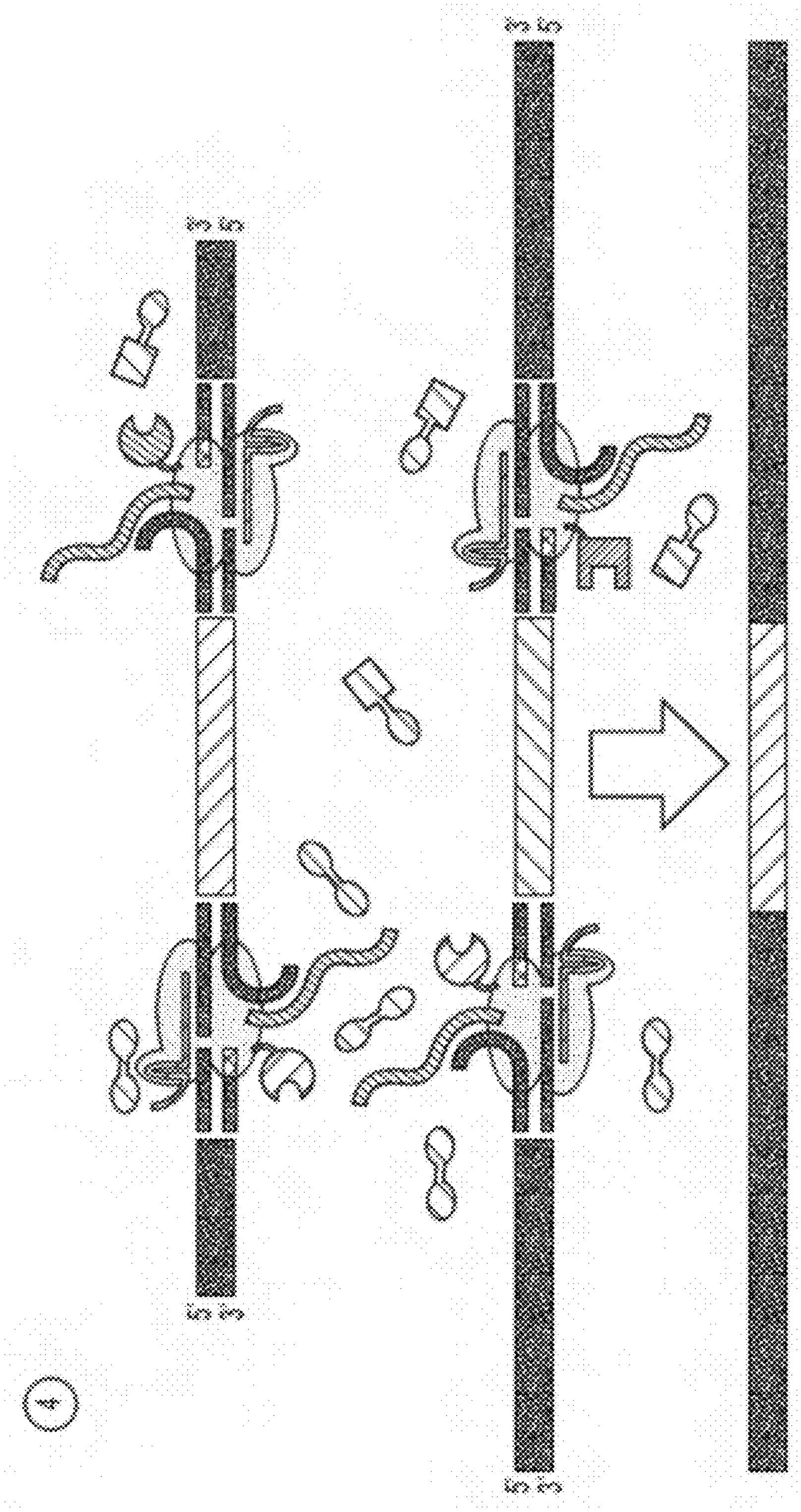

Nuclease dimerization or deactivation, tgOligos, or their combination can be used to enhance targeting of template-based editing or site directed integration (SDI) at a single location or multiple locations. Various representative schemes are depicted in FIG. 15. In these schemes, a template molecule (regardless of its homology to a target site in the genome) is brought into proximity of the target site by nuclease (Cas9) complexes with dimerization domains (Panels 1 to 3 of FIG. 15), tgOligos (not illustrated alone), or a combination thereof (Panel 4 of FIG. 15). dCas9 can be used on the template (Panel 1 of FIG. 15) or active Cas9 can help facilitate integration of the template (Panels 2 to 4 of FIG. 15).

Example 22. Genome Editing of Corn Y1 Gene to Generate Dominant Alleles

The enhanced genome editing schemes depicted in FIG. 15 are tested in creating a dominant allele for a traditionally recessive trait. The following is a summary of the molecular designs for the corn Y1 gene. (SEQ ID NO: 12).

For Y1, the first exon from SEQ ID NO: 12 is shown in SEQ ID NO: 13. To make an antisense template, SEQ ID NO: 13 is reverse complemented into SEQ ID NO: 14 which is used as a template sequence for editing (corresponding to the template sequences between the dCas9 complexes and Cas9 complexes depicted in FIG. 15's Panels 1 and 2). The sense strand gRNA for Y1 (SEQ ID NO: 12) is in the 5-UTR (SEQ ID NO: 15). The antisense strand gRNA for Y1 (SEQ ID NO: 12) is in the 3-UTR (SEQ ID NO: 16). The region between these two gRNAs corresponds to the to-be-replaced genomic sequences between the Cas9 complexes depicted in FIG. 15's Panels 1, 2, and 4.

To provide a template for integration (as depicted in FIG. 15's Panels 1 and 2), SEQ ID NO: 14 is added between the gRNA target sites targeted by (SEQ ID NOs: 15 and 16). The resulting SEQ ID NO: 17 comprises the sense strand gRNA site with 10 nt upstream, SEQ ID NO: 14, and the antisense strand gRNA site with 10 nt downstream.

This template molecule (SEQ ID NO: 17) is then paired with gRNAs (SEQ ID NOs: 15 and 16) and used in editing following the schemes depicted in FIG. 15's Panels 1 and 2. To utilize tgOligos to further help facilitate integration of the template (SEQ ID NO: 17) (see Panel 4 of FIG. 15), two tgOligos are incorporated (SEQ ID NOs: 18 and 19).

Example 23. Genome Editing of Corn BR2 Gene to Generate Dominant Alleles

The enhanced genome editing schemes depicted in FIG. 15 are also tested in creating a dominant allele for corn BR2 gene (SEQ ID NO: 1). The following is a summary of the molecular designs for BR2.

New gRNAs are designed to be able to replace the BR2 gene with an antisense template similar to the Y1 concept described in Example 20. A sense strand gRNA is provided in SEQ ID NO: 20 and an antisense strand gRNA is provided in SEQ ID NO: 21. The region between these two gRNAs corresponds to the to-be-replaced genomic sequences between the Cas9 complexes depicted in FIG. 15's Panels 1, 2, and 4.

The first 250 nt coding sequence of the BR2 gene (SEQ ID NO: 22) is made into an antisense template. SEQ ID NO: 22 is reverse-complemented to create a BR2 Exon 1 antisense sequence template (SEQ ID NO: 23).

To provide a template for integration (as depicted in FIG. 15's Panels 1 and 2), SEQ ID NO: 23 is added between the gRNA target sites targeted by gRNAs SEQ ID NOs: 20 and 21. SEQ ID NO: 24 comprises the sense strand gRNA site with 3 nt upstream, SEQ ID NO: 23, and the antisense strand gRNA site with 10 nt downstream.

This template molecule (SEQ ID NO: 23) is then paired with gRNAs (SEQ ID NOs: 20 and 21) and used in editing following the schemes depicted in FIG. 15's Panels 1 and 2. To utilize tgOligos to further help facilitate integration of the template (SEQ ID NO: 24) (see Panel 4 of FIG. 15), two tgOligos are incorporated (SEQ ID NOs: 25 and 26).

Figure 16:
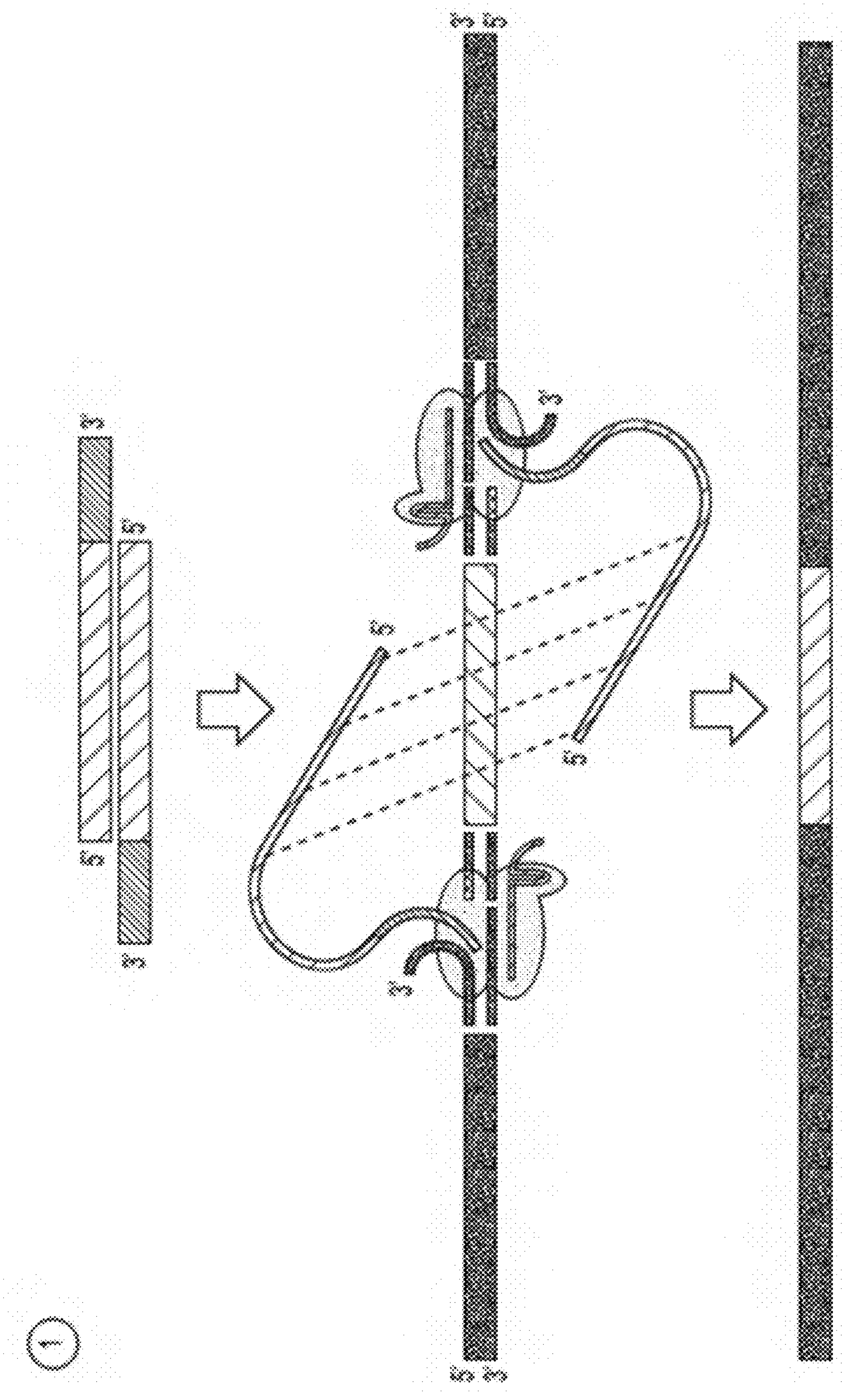
FIG. 16 provides an illustration of template editing (Panel 1), site directed integration (Panel 2), and/or recombination with tgOligos (Panel 3).
Figure 16:
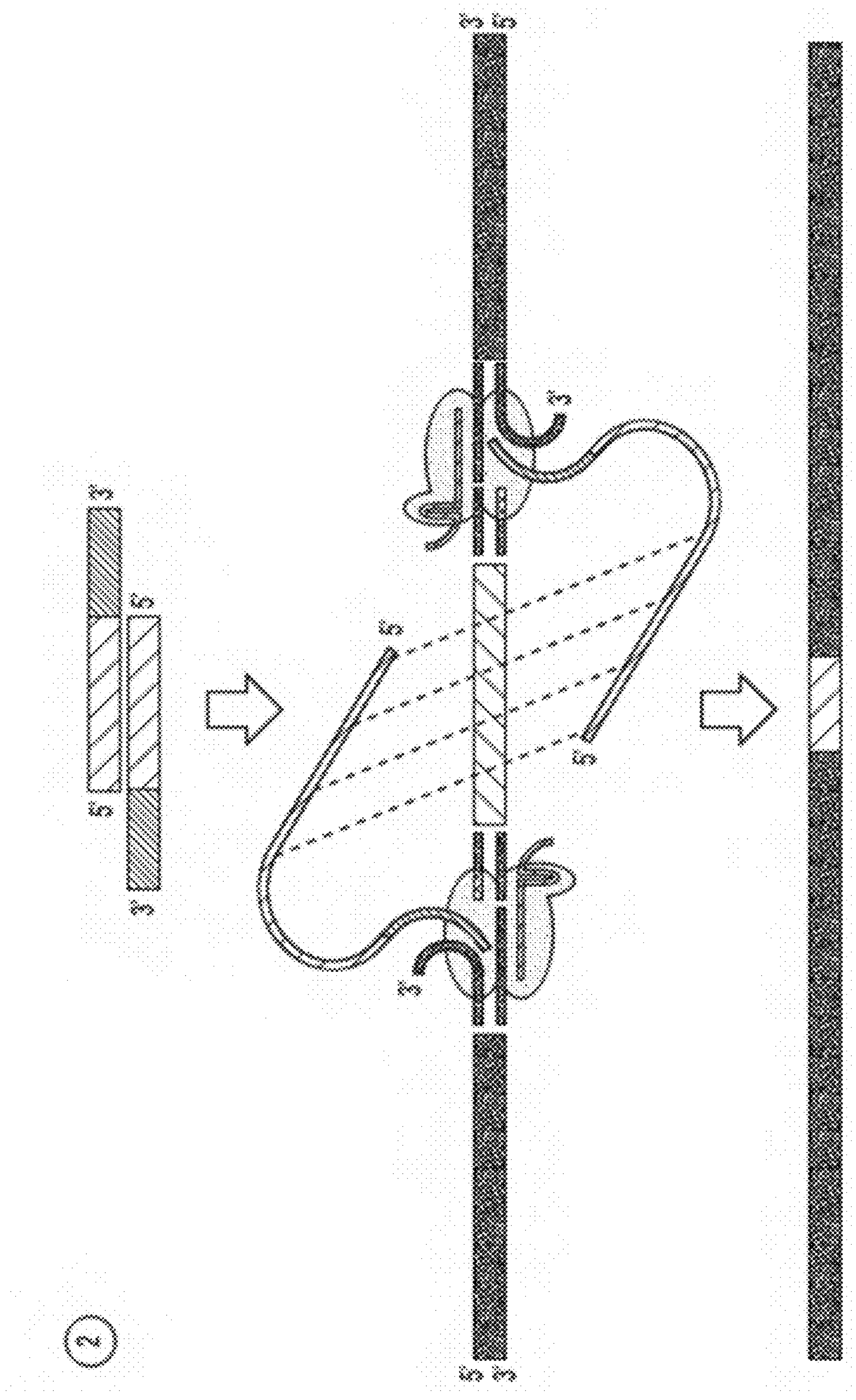
Figure 16:
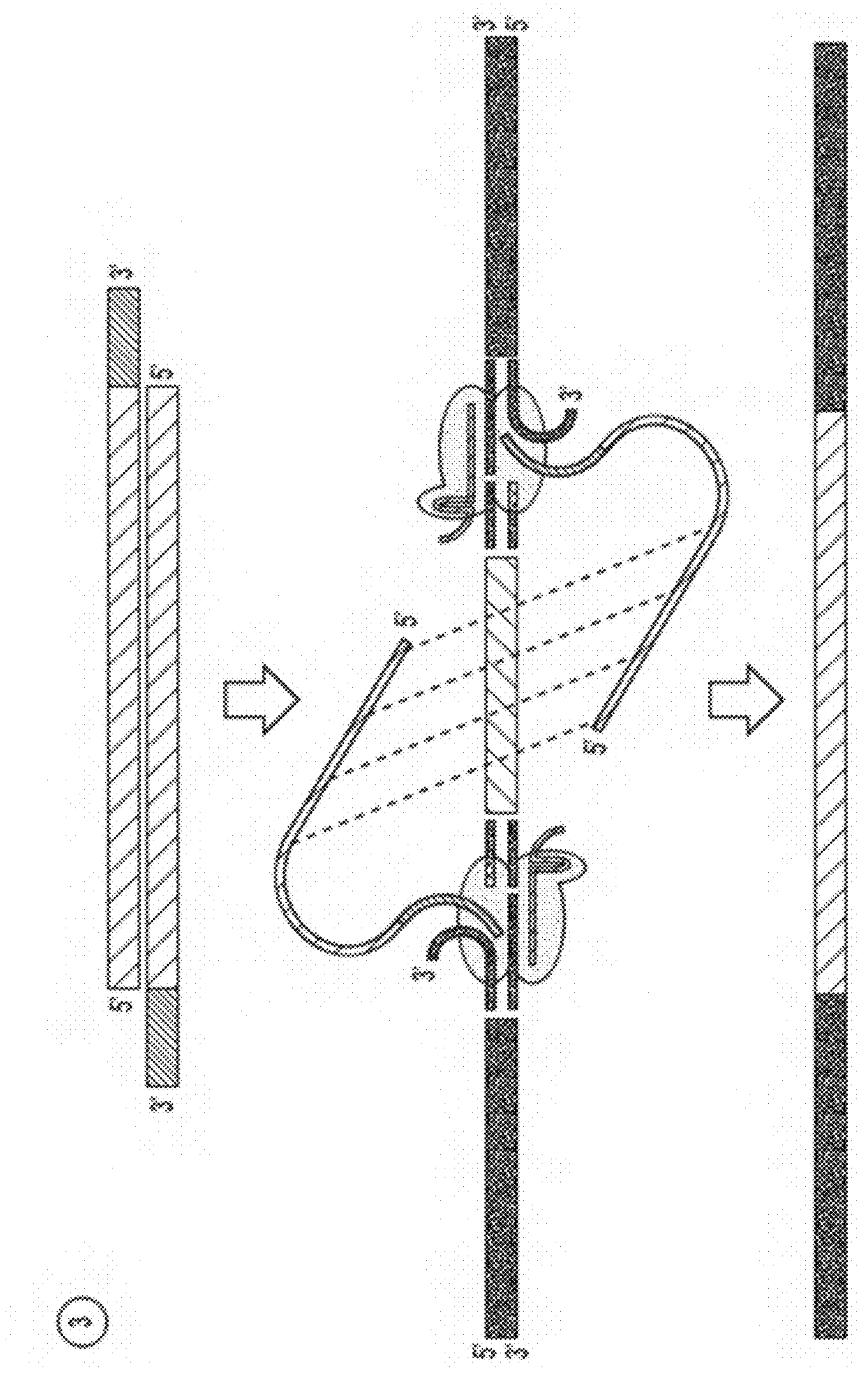

The examples shown above for editing Y1 and BR2 corn genes can be followed to design neighboring template edits or integrations as illustrated in Panel 3 of FIG. 15. It should also be obvious that while the examples provided for Y1 and BR2 use antisense templates of the first exon of these genes, the template integrations could be more subtle, such as changing nucleotides to alter amino acids in the native proteins, or more complex such as integrating a non-native sequence or gene. This is further illustrated in FIG. 16.

A potential advantage to creating antisense templates in the native genomic region of Y1 and BR2 as described above is that the native promoter and gene expression elements are used to regulate the antisense transcript to appropriately achieve gene silencing of a native allele in a heterozygous organism (e.g., in a dominant manner).

Figure 17:
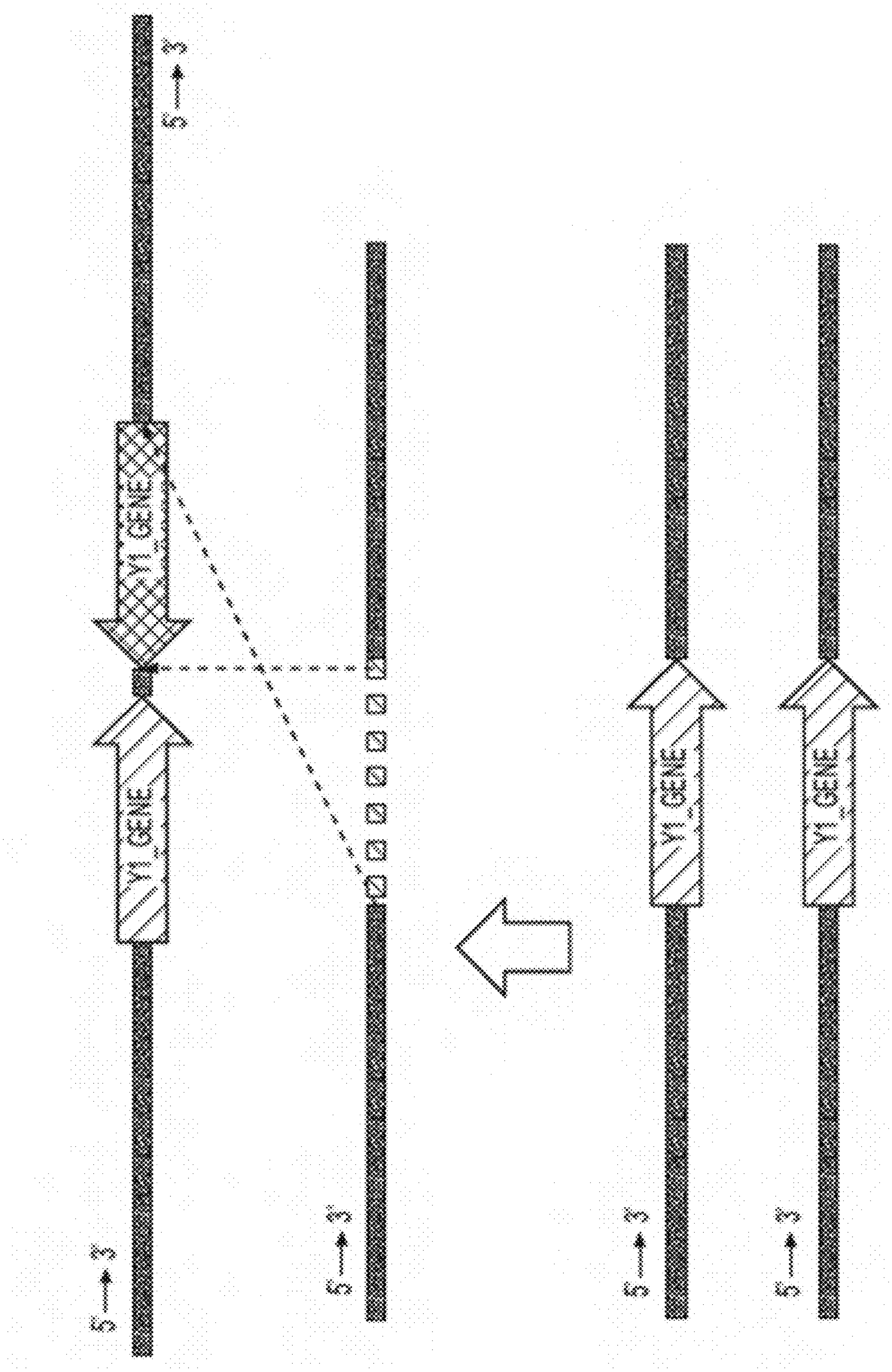
FIG. 17 provides an illustration of the stacking of an inverted Y1 gene head-to-tail to produce an antisense transcript to silence the gene expression. This approach can create a dominant mutant Y1 allele for a normally recessive trait. This dominant allele remains controlled by the native Y1 promoter.

Example 24. Genome Editing-Based Dominant Mutant Allele Via Stacking of an Inverted Y1 Gene Head-to-Tail The tgOligo and nuclease dimerization concepts described in the above examples can also be used to stack an inverted gene head-to-tail next to the native copy. This would result in an antisense transcript to silence the gene expression, and therefore create a dominant mutant allele for a normally recessive trait (e.g., the corn Y1 gene, the corn BR2 gene, the corn GA20 oxidase gene (see FIG. 17).

Figure 18:
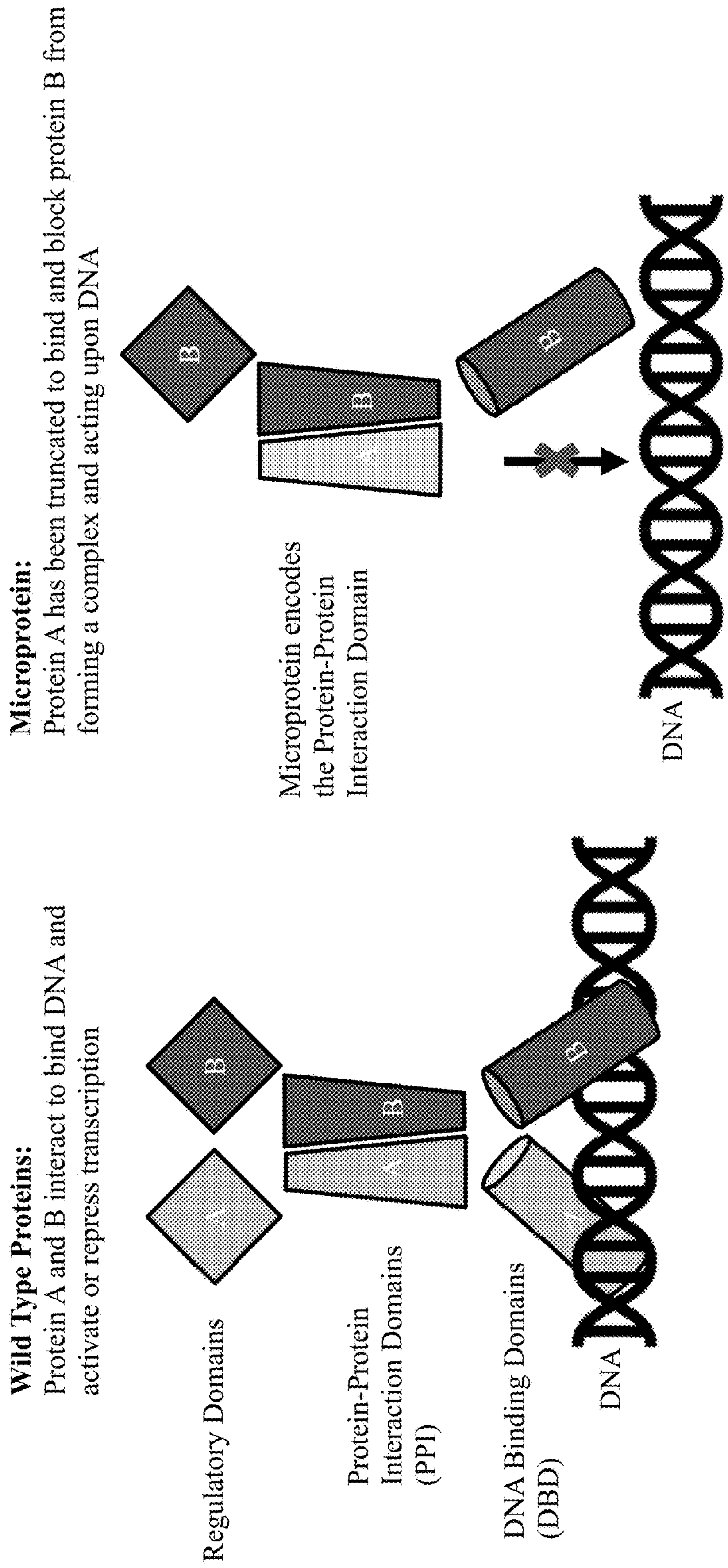
FIG. 18 provides an illustration of a microprotein. Targets of microproteins are often transcriptional regulators that bind to DNA as active homodimers. Microproteins interfere with their targets by forming non-functional heterodimeric complexes that cannot bind to DNA. DBD, DNA-binding domain; PPI, protein-protein interaction domain.

Example 25. Genome Editing to Trigger Microprotein Interference and Dominant Suppression Microproteins are short, single-domain proteins that possess the ability to interfere with larger multi-domain proteins. See FIG. 6 and FIG. 18. Targets of microproteins are often transcriptional regulators that bind to DNA as active homodimers. Microproteins interfere with their targets by forming non-functional heterodimeric complexes that cannot bind to DNA.

Expression of an *Arabidopsis thaliana* microprotein, ATHB17, in maize exhibits a dominant phenotype (e.g., increased ear weight at silking). See Rice et al., 2014, *PLoS ONE,* 9(4):e94238, which is incorporated in its entirety herein. Without being bound to any theory, an ATHB17 microprotein forms non-functional heterodimers with maize transcriptional repressor proteins. The heterodimers are non-functional thus increase the transcription of maize genes that would be normally be repressed in the absence of the ATHB17 microprotein.

The maize homolog of ATHB17, Zmhdz18, is selected as a target for genome editing to create a maize microprotein. Zmhdz18 is an HD-Zip II member comprising a homeodomain immediately adjacent to a leucine zipper domain, a hypothetical N-terminal repression domain, and a redox sensing motif. Without being bound by a particular theory, a Zmhdz18 microprotein will form non-functional heterodimers with transcriptional repressor proteins to increase expression of typically repressed genes and exhibit a dominant phenotype.

A first and a second functional guide RNA (gRNA) for a CRISPR/nuclease system are created. The first and second gRNAs are complementary to a first target site and a second target site, respectively, flanking a portion of the Zmhdz18 gene in the corn genome. The flanked portion encodes the amino terminus of the normal Zmhdz18 protein.

A transfer DNA (T-DNA) vector suitable for use in *Agrobacterium* transformation is constructed. The T-DNA construct comprises comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising a promoter operable in a plant cell operably linked to polynucleotides encoding the two gRNAs described above.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the gRNAs guide the nuclease to the target sites in the Zmhdz18 gene, where the nuclease creates a double-stranded break at each target site.

In the majority of events, the region between the first and second target sites in the Zmhdz18 gene is deleted and non-homologous end-joining repair mechanisms joins the flanking regions. Suitable methods known in the art (e.g., PCR, DNA hybridization (Southern) blots, sequencing) are used to identify transformation events comprising a deletion between the first and second target sites in the Zmhdz18 gene. Transformed embryos comprising the deletion are selected and used to regenerate modified plants using techniques standard in the field.

Without being bound to any scientific theory, the deletion creates a dominant Zmhdz18 allele that encodes a Zmhdz18 microprotein. This microprotein can form homodimers and heterodimers with other proteins to interfere with the transcription of maize genes that results in a dominant phenotype.

RNA and protein are extracted from modified corn plants identified as comprising a deletion in a Zmhdz18 allele capable of encoding a microprotein. RNA and protein are also extracted from control corn plants that lack a deletion in Zmhdz18. Suitable methods known in the art (e.g., quantitative reverse-transcriptase PCR, reverse-transcriptase PCR, RNA sequencing) are used to confirm that expression of maize genes in pathways downstream of Zmhdz18 are altered. Additional suitable methods (e.g., Western blot, HPLC, LC/MS, ELISA, immunoprecipitation) are used to confirm that the deletion in Zmhdz18 generates a microprotein.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples. All references cited herein are incorporated by reference in their entireties.

Figure 19:
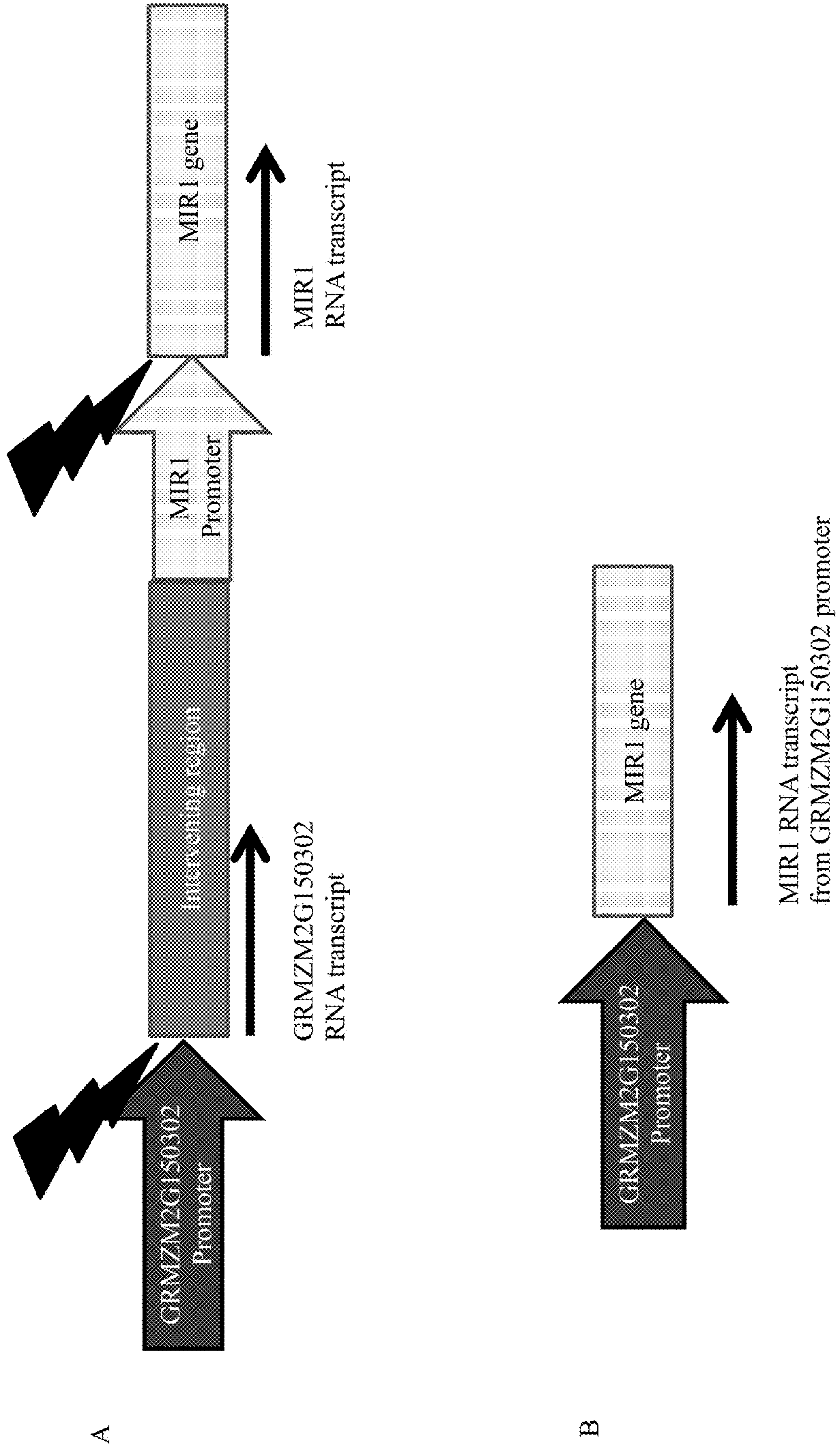
FIG. 19 comprises Panel A and Panel B. Panel A shows a representation of the maize genomic region near the MIR1 gene. As shown in Panel A, the GRMZM2G150302 gene is adjacent and upstream to the GA20 oxidase_5 gene. The intervening region between the GRMZM2G150302 promoter and the MIR1 coding gene is deleted after generating a double-stranded break on each end. Panel B shows the structure of the region following the deletion of the intervening region. By removing the intervening region the GRMZM2G150302 promoter can drive the expression of the MIR1gene.

Example 26: Generating a Dominant Positive Allele of MIR1 Via Targeted Genomic Deletion to Render MIR1 Gene Under the Control of an Upstream Promoter The GRMZM2G150276 gene (SEQ ID NO: 99) encoding the MIR1 protein (SEQ ID NO: 100) is located on corn chromosome 6. MIR1 is predicted to be involved in insect resistance and encodes a cysteine protease that accumulates in the whorls in response to larval feeding in maize genotypes resistant to some lepidopteran pests (see Pechan et al., Plant Cell., 2000 (7):1031-40). The MIR1 gene is adjacent to the gene GRMZM2G150302 and expressed in the same orientation. See FIG. 19, Panel A. The GRMZM2G150302 gene is a member of a large, redundant gene family of xylan synthases. The GRMZM2G150302 promoter (SEQ ID NO: 101) is hypothesized to have a broader/expanded expression profile when compared to the native MIR1 gene expression, which is restricted to the whorls.

Two functional guide RNAs (gRNAs) for an RNA guided nuclease system are created to target the genomic DNA region between the MIR1 gene and the GRMZM2G150302 gene. The first gRNA targets an area near the transcriptional start site of the MIR1 gene and the second gRNA targets a region near the transcriptional start site of the GRMZM2G150302 gene. Each of the two target sites are unique within the corn genome. A transfer DNA (T-DNA) vector suitable for use in *Agrobacterium* transformation is used. The T-DNA construct comprises several expression cassettes between a left border (LB) sequence and a right border (RB) sequence. The first expression cassette comprises a promoter that is operable in a plant cell operably linked to a polynucleotide encoding an RNA guided nuclease. A second expression cassette comprises a promoter that is operable in a plant cell operably linked to the CP4-EPSPS marker gene. The construct also comprises expression cassettes comprising promoters operable in a plant cell operably linked to polynucleotides encoding the two gRNAs described above.

Immature corn embryos are co-cultured with *Agrobacterium* containing the T-DNA vector for three days. The polynucleotides between the LB and RB sequences are integrated into the nuclear genome of the immature corn embryos. Upon expression of the integrated polynucleotides, the gRNAs guide the nuclease to each of the two target sites in the genomic DNA region between the MIR1 gene and the GRMZM2G150302 gene, where the nuclease creates a double-stranded break at each target site.

In the majority of events, the region between the target sites is deleted and non-homologous end-joining repair mechanisms joins the flanking regions. Suitable methods known in the art (e.g., PCR, DNA hybridization (Southern) blots, sequencing) are used to identify transformation events comprising a complete deletion. Transformed embryos comprising a targeted deletion between the MIR1 gene and GRMZM2G150302 gene are selected and used to regenerate modified plants using techniques standard in the field.

Without being bound by a particular theory, by removing the genomic DNA between the MIR1 gene and the GRMZM2G150302 gene, the native GRMZM2G150302 promoter (SEQ ID NO: 101) can drive the transcription of the MIR1 gene (SEQ ID NO: 99) thereby broadening/expanding the expression profile of the MIR1 gene. See FIG. 19, panel B.

RNA is extracted from various tissue types (e.g., roots, stem, leaf, inflorescence) from modified corn plants identified as comprising a targeted deletion between the MIR1 gene and the GRMZM2G150302 gene. RNA is also extracted from control corn plants that lack the deletion. Suitable methods known in the art (e.g., quantitative reverse-transcriptase PCR, reverse-transcriptase PCR, RNA sequencing) are used to confirm that the MIR1 gene is more broadly expressed and/or more strongly expressed in corn modified plants comprising a deletion of the targeted region.

Example 27. Constructs for Creation of Dominant Negative Deletion Mutant Alleles The endogenous Zm.GA20ox5 gene is separated from an endogenous Zm.SAMT gene in the maize genome by an intergenic region of about 550 bp, or by 1170 bp if measured between stop codons, with the Zm.SAMT gene positioned downstream and oriented in the opposite orientation relative to the Zm.GA20ox5 gene. The sequence of the genomic locus or region encompassing the Zm.GA20ox5 and Zm.SAMT genes is provided in SEQ ID NOs. 35 and 36. SEQ ID NO. 35 represents a sequence of the GA20ox5-SAMT genomic locus corresponding to the sense strand of the Zm.GA20ox5 gene and encompassing both Zm.GA20ox5 and Zm.SAMT genes (the "GA20ox5 SAMT genomic sequence" in Table 2). SEQ ID NO. 36 represents a sequence of the GA20ox5-SAMT genomic locus corresponding to the sense strand of the Zm.SAMT gene (the antisense strand of the Zm.GA20ox5 gene) and encompassing both Zm.GA20ox5 and Zm.SAMT genes (the "SAMT_GA20ox5 genomic sequence" in Table 2). The elements or regions of the genomic sequences encompassing both Zm.GA20ox5 and Zm.SAMT genes are annotated in Table 2 below by reference to the nucleotide coordinates of those elements or regions in each of SEQ ID NOs. 35 and 36. As proposed herein, if a genomic region between the neighboring Zm.GA20ox5 and Zm.SAMT genes (including possibly all or part of those genes) were deleted, then the endogenous Zm. SAMT gene promoter may drive expression of an antisense RNA transcript through all or part of the Zm.GA20ox5 gene that can hybridize to a separate RNA transcript expressed from one or both of the copies or alleles of the Zm.GA20ox5 and/or Zm.GA20ox3 gene(s). Since the Zm.GA20ox3 and Zm.GA20ox5 genes share a high level of nucleotide sequence similarity in their respective exon coding regions, the antisense RNA transcript expressed from the oppositely oriented Zm. SAMT gene promoter may hybridize to transcripts of both GA20 oxidase genes and cause the suppression or silencing of one or both of the Zm.GA20ox3 and/or Zm.GA20ox5 gene(s). Thus, a mutant allele having a deletion between the Zm.GA20ox5 and Zm.SAMT genes may behave as a dominant or semi-dominant negative mutation or allele by causing suppression or silencing of one or both (wild-type and/or mutant) copies or alleles of the endogenous Zm.GA20ox5 gene, in addition to possible further suppression or silencing of one or both copies or alleles of the endogenous Zm.GA20ox3 gene.

TABLE 2

Annotation of genomic sequence elements of Zm.GA20ox5 and Zm.SAMT genomic region

| Gene Name or Region | Element/ Feature | Location in the GA20ox5 SAMT genomic sequence (SEQ ID NO: 35) | Location in the SAMT GA20ox5 genomic sequence (SEQ ID NO: 36) |
|---|---|---|---|
| GA20ox5 | Promoter and 5' UTR | 1 . . . 398 | 8670 . . . 9067 |
| GA20ox5 | Exon 1 | 399 . . . 1189 | 7879 . . . 8669 |
| GA20ox5 | Intron 1 | 1190 . . . 1304 | 7764 . . . 7878 |
| GA20ox5 | Exon 2 | 1305 . . . 1629 | 7439 . . . 7763 |
| GA20ox5 | Intron 2 | 1630 . . . 2595 | 6473 . . . 7438 |
| GA20ox5 | Exon 3 | 2596 . . . 2871 | 6197 . . . 6472 |
| GA20ox5 | 3' UTR | 2872 . . . 3180 | 5888 . . . 6196 |
| Intergenic Region | | 3181 . . . 3736 | 5332 . . . 5887 |
| SAMT | 3' UTR | 3737 . . . 4141 | 4927 . . . 5331 |
| SAMT | Exon 8 | 4042 . . . 4258 | 4810 . . . 5026 |
| SAMT | Intron 8 | 4259 . . . 4512 | 4556 . . . 4809 |
| SAMT | Exon 7 | 4513 . . . 4707 | 4361 . . . 4555 |
| SAMT | Intron 7 | 4708 . . . 4989 | 4079 . . . 4360 |
| SAMT | Exon 6 | 4990 . . . 5262 | 3806 . . . 4078 |
| SAMT | Intron 6 | 5263 . . . 5348 | 3720 . . . 3805 |
| SAMT | Exon 5 | 5349 . . . 5523 | 3545 . . . 3719 |
| SAMT | Intron 5 | 5524 . . . 6037 | 3031 . . . 3544 |
| SAMT | Exon 4 | 6038 . . . 6148 | 2920 . . . 3030 |
| SAMT | Intron 4 | 6129 . . . 6239 | 2829 . . . 2939 |
| SAMT | Exon 3 | 6240 . . . 6510 | 2558 . . . 2828 |
| SAMT | Intron 3 | 6511 . . . 6894 | 2174 . . . 2557 |
| SAMT | Exon 2 | 6895 . . . 7044 | 2024 . . . 2173 |
| SAMT | Intron 2 | 7045 . . . 7139 | 1929 . . . 2023 |
| SAMT | Exon 1 | 7140 . . . 8126 | 942 . . . 1928 |
| SAMT | 5' UTR 2 | 8127 . . . 8268 | 800 . . . 941 |

TABLE 2-continued

Annotation of genomic sequence elements of Zm.GA20ox5 and Zm.SAMT genomic region

| Gene Name or Region | Element/ Feature | Location in the GA20ox5 SAMT genomic sequence (SEQ ID NO: 35) | Location in the SAMT GA20ox5 genomic sequence (SEQ ID NO: 36) |
|---|---|---|---|
| SAMT | Intron 1 | 8269 . . . 8771 | 297 . . . 799 |
| SAMT | 5' UTR 1 | 8772 . . . 8942 | 126 . . . 296 |
| SAMT | Promoter | 8943 . . . 9067 | 1 . . . 125 |

Figure 20:
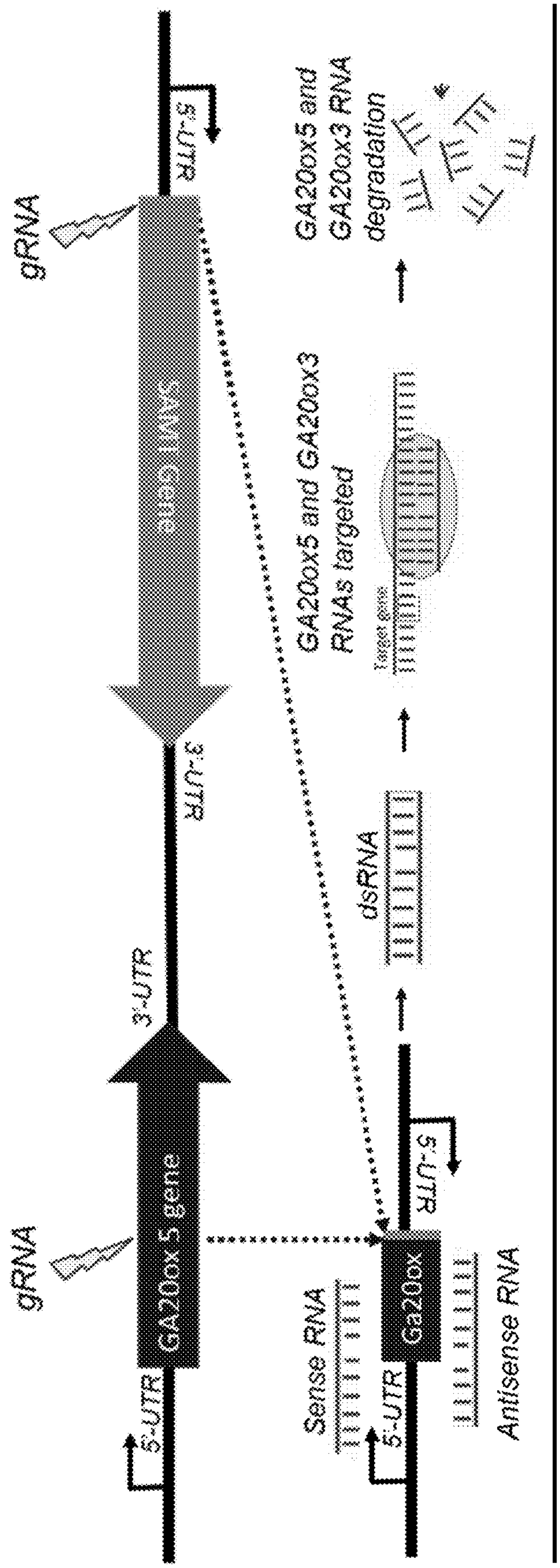
FIG. 20 provides illustrative examples for creating an antisense RNA molecule that targets the Zm.GA20ox5 gene and the Zm.GA20ox3 gene by deleting a genomic region between the Zm.GA20ox5 and its neighboring gene Zm.SAMT oriented in the opposite direction, through genome editing.

FIG. 20 illustrates the concept for creating an antisense RNA molecule that targets the Zm.GA20ox5 gene by deleting a genomic region between the Zm.GA20ox5 and its neighboring Zm.SAMT gene oriented in the opposite direction, through genome editing. The deletion can be generated using two or more guide RNAs that create double stranded breaks in the genome at the two ends of the intended deletion. The antisense RNA molecule generated from the oppositely oriented Zm.SAMT gene promoter can then hybridize to a sense Zm.GA20ox5 RNA transcript and trigger suppression or silencing of one or both copies or alleles (wild-type or mutant) of the endogenous Zm.GA20ox5 gene. FIG. 20 provides an embodiment where small RNAs may be generated through RNA interference. However, it is envisioned that suppression or silencing of the Zm.GA20ox5 gene may occur through other mechanisms as provided herein, alternatively or in addition to any RNAi or PTGS forms of suppression. Given that the Zm.GA20ox3 and Zm.GA20ox5 genes share a high level of nucleotide sequence similarity in their respective coding regions, the antisense RNA transcript may also hybridize to RNA transcripts of the Zm.GA20ox3 gene and cause the suppression or silencing of one or both of the Zm.GA20ox3 and/or Zm.GA20ox5 gene(s). Thus, a deletion between the Zm.GA20ox5 and Zm.SAMT genes may act as a dominant or semi-dominant negative mutation or allele for one or both of the Zm.GA20ox3 and/or Zm.GA20ox5 gene(s).

In the illustrative example provided in FIG. 20, a pair of guide RNAs are used including one guide RNA having a targeting or spacer sequence designed to target a site in the Zm.GA20ox5 gene, and another guide RNA having a targeting or spacer sequence designed to target a site in the Zm. SAMT gene. The size of the deletion and the location of the two breakpoints at the ends of the deletions may be determined by selecting which guide RNAs are used with a RNA-guided endonuclease to create the genome breaks. By creating a double strand break at both target sites, a deletion of the intervening region can be generated that will condense the genomic locus and bring the oppositely oriented Zm.SAMT gene promoter into closer proximity to the GA20ox5 gene, such that the Zm. SAMT gene promoter can drive the expression of an anti sense RNA transcript that reads through at least a portion of the GA20ox5 gene. Even though a 3' portion of the GA20ox5 gene may be deleted, the remaining 5' portion of the GA20ox5 gene can be sufficient for an antisense RNA transcript or molecule to be generated under the control of the Zm. SAMT gene promoter that causes suppression or silencing of the Zm.GA20ox3 and/or GA20ox5 gene(s). Thus, the presence of a single copy or allele of the deletion mutant may act in a dominant or semi-dominant negative manner to cause a corn plant to have a short stature, lodging resistant phenotype.

Deletions in the Zm.GA20ox5/Zm.SAMT genomic region were generated using three different plasmid vector constructs for transformation. Each vector construct comprises a functional cassette for the expression of Cpf1 (or Cas12a), and further comprises one or two functional cassettes for the expression of guide RNAs, in addition to a selectable marker gene and plasmid maintenance elements. For the Vector-1 and Vector-2 constructs, the Cpf1 (or Cas12a) expression cassette comprises a maize ubiquitin promoter (SEQ ID NO: 37) operably linked to a sequence encoding a wild-type *Lachnospiraceae bacterium* Cpf1 RNA-guided endonuclease enzyme (SEQ ID NO: 38) fused to two nuclear localization signals (SEQ ID NOs: 40 and 41). The wild-type Cpf1 expression cassette further contains a synthetic sequence (atggcg) which provides a start codon. For the Vector-3 construct, the Cpf1 (or Cas12a) expression cassette comprises a maize ubiquitin promoter (SEQ ID NO: 37) operably linked to a sequence encoding a *Lachnospiraceae bacterium* G532R/K595R mutant Cpf1 RNA-guided endonuclease enzyme (SEQ ID NO: 39) fused to two nuclear localization signals (SEQ ID NOs: 42 and 43). See, e.g., Gao, L. et al., Nature Biotechnol. 35(8): 789-792 (2017), the entire contents and disclosure of which are incorporated herein by reference.

Table 3 below provides the target site, spacer and targeting/spacer sequence for each guide RNA encoded by the guide RNA cassette(s) in each vector construct. Each guide RNA unit within the guide RNA cassettes comprises a guide RNA scaffold sequence compatible with the LbCpf1 enzyme along with the unique spacer or targeting sequence complementary to its intended target site. For the Vector-2 construct, the guide RNA expression cassette comprises a maize RNA polymerase III (Pol3) promoter (SEQ ID NO: 44) operably linked to a sequence encoding two guide RNAs having targeting/spacer sequences encoded by the SP1b and SP1f DNA sequences in Table 3 below, with one guide RNA (SP1b) targeting a site in the first exon of the Zm.SAMT gene, and the other guide RNA (SP1f) targeting a site in the first intron of the Zm.GA20ox5 gene (see also FIG. 21 (top panel) showing the placement of the two guide RNA target sites for SP1b and SP1f (SAMT_408 and GA20ox5_6531) relative to the genomic region encompassing the endogenous Zm.GA20ox5 and Zm.SAMT genes).

Figure 21:
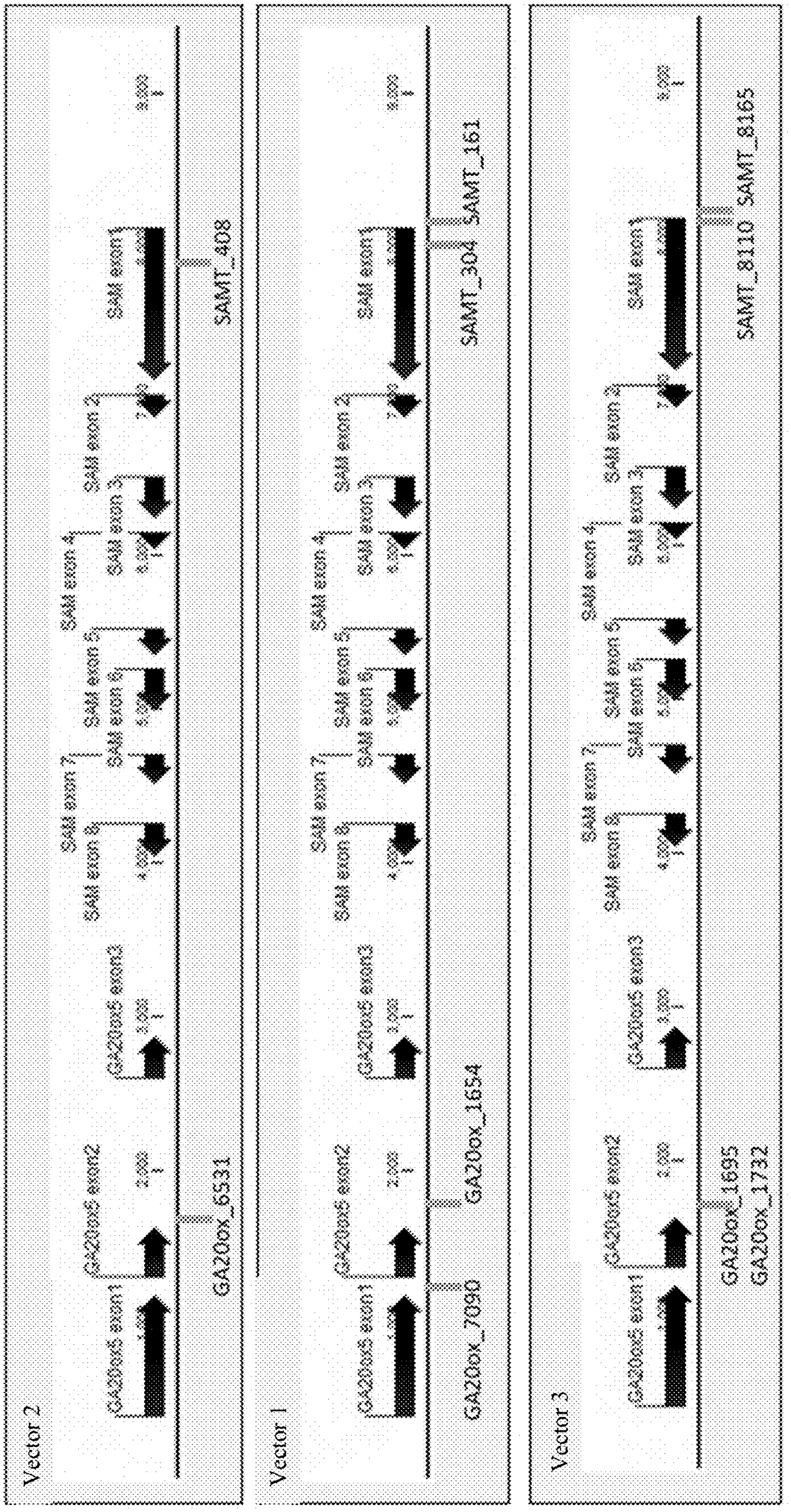
FIG. 21 illustrates the genomic position of various guide RNA target sites in three exemplified vectors for creating a genomic deletion between the Zm.GA20ox5 gene and its neighboring Zm.SAMT gene.

The Vector-1 construct has two guide RNA expression cassettes. One guide RNA expression cassette of the Vector-1 construct comprises a maize Pol3 promoter (SEQ ID NO: 44) operably linked to a sequence encoding two guide RNAs having targeting/spacer sequences encoded by the SP2f1 and SP2f2 DNA sequences in Table 3 below, with one guide RNA (SP2f1) targeting a site in the first exon of the Zm.GA20ox5 gene, and the other guide RNA (SP2f2) targeting a site in the second exon of the Zm.GA20ox5 gene. The other guide RNA expression cassette of the Vector-1 construct comprises a synthetic promoter operably linked to a sequence encoding two guide RNAs having targeting/spacer sequences encoded by the SP2b1 and SP2b2 DNA sequences in Table 3 below, with each guide RNA (SP2b1 and SP2b2) targeting different sites in the first exon of the Zm.SAMT gene. For the Vector-1 construct, see also the middle panel of FIG. 21 showing the placement of the four guide RNA target sites for SP2f1, SP2f1, SP2b1 and SP2b2 (GA20ox5_7090, GA20ox5_1654, SAMT_304 and SAMT_161) relative to the genomic region encompassing the endogenous Zm.GA20ox5 and Zm.SAMT genes.

The Vector-3 construct has two guide RNA expression cassettes. One guide RNA expression cassette of the Vector-3 construct comprises a maize Pol3 promoter (SEQ ID NO: 74) operably linked to a sequence encoding two guide RNAs having targeting/spacer sequences encoded by the SP3f1 and SP3f2 DNA sequences in Table 3 below, with each guide RNA (SP3f1 and SP3f2) targeting different sites in the second intron of the Zm.GA20ox5 gene. The other guide RNA expression cassette of the Vector-1 construct comprises a synthetic promoter operably linked to a sequence encoding two guide RNAs having targeting/spacer sequences encoded by the SP3b1 and SP3b2 DNA sequences in Table 3 below, with one guide RNA (SP3b1) targeting a site in the first exon of the Zm.SAMT gene, and another guide RNA (SP3b2) targeting a site in the 5' UTR of the Zm.SAMT gene. For the Vector-3 construct, see also the lower panel of FIG. 21 showing the placement of the four guide RNA target sites for SP3f1, SP3f1, SP3b1 and SP3b2 (GA20ox5_1695_TYC, GA20ox5_1732 TYC, SAMT_8110_TYC and SAMT_8165_TYC) relative to the genomic region encompassing the endogenous Zm.GA20ox5 and Zm.SAMT genes.

TABLE 3

Transgenic constructs and their respective target sites and guide RNA spacers

| Vector Construct | guide RNA Spacer ID | Target Site | Spacer Sequence | SEQ ID NO |
|---|---|---|---|---|
| Vector-2 | SP1b | SAMT_408 | AGGACACCGACAACAATGATGCC | 45 |
| | SP1f | GA20ox5_6531 | GGTCCACTAGGATTCGGGAAATA | 46 |
| Vector-1 | SP2f1 | GA20ox5_7090 | GAGCCAATGGGGTAAGTAAGGTA | 47 |
| | SP2f2 | GA20ox5_1654 | GTTACCATGAAGGTGTCGCCGAT | 48 |
| | SP2b1 | SAMT_304 | GTCCAATAAGAAGCCGGTGGTGA | 49 |
| | SP2b2 | SAMT_161 | CACCTCGGCCAAATGCCATCAGT | 50 |
| Vector-3 | SP3f2 | GA20ox5_1695_TYC | GTTGAGCTCTCTCTGTGCTGTTA | 51 |
| | SP3f1 | GA20ox5_1732_TYC | CTAGGATTCGGGAAATAACAGCA | 52 |
| | SP3b1 | SAMT_8110_TYC | CCTCGGCCAAATGCCATCAGTGC | 53 |
| | SP3b2 | SAMT_8165_TYC | CGTGGTTTATCTCCACCAACAAC | 54 |

Example 28. Characterization of Deletion Mutant Alleles of GA20Ox5 Gene

An inbred corn plant line was transformed via *Agrobacterium*-mediated transformation with a transformation vector having one of the constructs as described above in Example 27. The transformed plant tissue was grown to mature R0 plants. R0 plants having one or more unique genome edit(s) were selfed to produce R1 plants. To characterize the edits and recover plants with a deletion between the GA20Ox5 and SAMT genes, a PCR-based assay was performed using a pair of PCR primers flanking the intended deletion region. The same pair of primers (SEQ ID NOs: 55 and 56) were used for all three vectors in Table 3. If a deletion is present between the GA20Ox5 and SAMT genes, the PCR assay would result in an amplicon that could be sequenced. However, due to the large size of the intended deletion, the PCR assay would not produce a PCR product in the absence of a larger deletion. For each PCR assay, a 15 μL PCR reaction volume was used containing the Phusion PCR master mix from Thermo Fisher Scientific, 3 μL of genomic DNA template, and two PCR primers. After PCR amplification, a 3 μL PCR mixture was added to 21 μL of Tris-EDTA buffer and then analyzed on a ZAG instrument for the presence or absence of PCR products that indicate a GA20Ox5-SAMT deletion. The PCR products were sequenced to determine the junction sequence generated in each deletion around the GA20ox5-SAMT genomic locus (see Table 4).

R0 plants with a deletion between the GA20ox5 and SAMT genes were selected and selfed to produce R1 plants. The R1 plants were subject to a quantitative PCR assay to determine the zygosity of the GA20ox5-SAMT genomic locus (see Table 5). Each R1 plant was sequenced to determine all of the deletion edits around the GA20Ox5-SAMT genomic locus. Due to multiple gRNAs with a given construct, multiple deletions may occur on the same chromosome of a R0 plant and thus be present in a R1 plant, which may be homozygous or heterozygous for a mutant allele comprising the genomic deletion(s) (see Table 5). In Table 5, "homo" means homozygous for the mutant allele, and "hetero" means heterozygous for the mutant allele.

TABLE 4

Individual deletion junction sequences for edits made using the vectors in Table 3.

| SEQ ID NO. | Deletion Juncfion Number | Junction Sequence (with deletion size shown in the parentheses) | Junction Sequence Description |
|---|---|---|---|
| 57 | 1001 | GCGGCCGTCCATCTTTCCACCTCGGCCAAA-(-8)-GTGCCTGGCGAACATGTACCAGAGCACCAG | 8 nt deletion at SAMT_161 |
| 58 | 1002 | GGCCGTCCATCTTTCCACCTCGGCCAAATG-(-3)-TCAGTGCCTGGCGAACATGTACCAGAGCAC | 3 nt deletion at SAMT_161 |

TABLE 4-continued

Individual deletion junction sequences for edits made using the vectors in Table 3.

| SEQ ID NO. | Deletion Juncfion Number | Junction Sequence (with deletion size shown in the parentheses) | Junction Sequence Description |
|---|---|---|---|
| 59 | 1003 | GGCCGTCCATCTTTCCACCTCGGCCAAATG-(-6)-GTGCCTGGCGAACATGTACCAGAGCACCAG | 6 nt deletion at SAMT_161 |
| 60 | 1004 | GAGTGGCGCCCCGTCCGGCCCGTCCCGGGC-(-6357)-TTCTTATTGGACGAAATCTCCAGCGGGAAG | 6357 nt deletion between GA20ox5_1654 and SAMT_304 |
| 61 | 1005 | CCGGCCCGTCCCGGGCGCCATGGTCATCAA-(-6518)-GTGCCTGGCGAACATGTACCAGAGCACCAG | 6518 nt deletion between GA20ox5_1654 and SAMT_161 |
| 62 | 1006 | GTCCGGCCCGTCCCGGGCGCCATGGTCATC-(-6342)-GGCTTCTTATTGGACGAAATCTCCAGCGGG | 6342 nt deletion between GA20ox5_1654 and SAMT_304 |
| 63 | 1007 | GTCCGGCCCGTCCCGGGCGCCATGGTCATC-(-6348)-TTATTGGACGAAATCTCCAGCGGGAAGACA | 6348 nt deletion between GA20ox5_1654 and SAMT_304 |
| 64 | 1008 | CGTCCGGCCCGTCCCGGGCGCCATGGTCAT-(-6344)-GCTTCTTATTGGACGAAATCTCCAGCGGGA | 6344 nt deletion between GA20ox5_1654 and SAMT_304 |
| 65 | 1009 | CTGTGTGTATATTCAGTTGAGCTCTCTCTG-(-6478)-CACGGCTGGACCAACAGCCCCCCCAAAATC | 6478 nt deletion between GA20ox5_1695 and SAMT_8165 |
| 66 | 1010 | CTTGGCCGCTCTTGTCCTGTGTGTATATTC-(-6160)-GGTGTCCTCAAATTTCTCGGACCCTTCACC | 6160 nt deletion between GA20ox5_6531 and SAMT_408 |
| 67 | 1011 | TGTATATTCAGTTGAGCTCTCTCTGTGCTG-(-6133)-GTTGTCGGTGTCCTCAAATTTCTCGGACCC | 6133 nt deletion between GA20ox5_6531 and SAMT_408 |
| 68 | 1012 | TATATTCAGTTGAGCTCTCTCTGTGCTGTT-(-6130)-TGTTGTCGGTGTCCTCAAATTTCTCGGACC | 6130 nt deletion between GA20ox5_6531 and SAMT_408 |
| 69 | 1013 | ATATTCAGTTGAGCTCTCTCTGTGCTGTTA-(-6130)-GTTGTCGGTGTCCTCAAATTTCTCGGACCC | 6130 nt deletion between GA20ox5_6531 and SAMT_408 |
| 70 | 1014 | ATTCAGTTGAGCTCTCTCTGTGCTGTTATT-(-6131)-GTCGGTGTCCTCAAATTTCTCGGACCCTTC | 6131 nt deletion between GA20ox5_6531 and SAMT_408 |
| 71 | 1015 | CTCGGCCAGGATTTCGAGCCAATGGGGTAA-(-6759)-CTTCTTATTGGACGAAATCTCCAGCGGGAA | 6759 nt deletion between GA20ox5_7090 and SAMT_304 |
| 72 | 1016 | CGGCCAGGATTTCGAGCCAATGGGGTAAGT-(-6753)-CCGGCTTCTTATTGGACGAAATCTCCAGCG | 6753 nt deletion between GA20ox5_7090 and SAMT_304 |
| 73 | 1017 | TCGGCCAGGATTTCGAGCCAATGGGGTAAG-(-12)-AAGGAGCGCCGGTTTACATTTACCGCACGT | 12 nt deletion at GA20ox5_7090 |
| 74 | 1018 | TCGGCCAGGATTTCGAGCCAATGGGGTAAG-(-4)-GTAGTAAGAAGGAGCGCCGGTTTACATTTA | 4 nt deletion at GA20ox5_7090 |
| 75 | 1019 | GGACTACTTCGTCGGCACCCTCGGCCAGGA-(-39)-GCCGGTTTACATTTACCGCACGTCGGCGTG | 39 nt deletion at GA20ox5_7090 |

TABLE 5

Deletion edits and genotype of R0 ad R1 plants.

| R0 Edit ID | R1 Plant ID | Editing Deletion Type | R1 zygosity call for deletion mutant | Deletion Junction Number(s) (Table 4) |
|---|---|---|---|---|
| E221089 | P43596818 | 6759 nt deletion between GA20ox5_7090 and SAMT_304; 6 nt deletion at T161 | Homozygous | 1015; 1003 |
| E221089 | P43596820 | 6759 nt deletion between GA20ox5_7090 and SAMT_304; 6 nt deletion at T161 | Homozygous | 1015; 1003 |
| E221089 | P43596823 | 6759 nt deletion between GA20ox5_7090 and SAMT_304; 6 nt deletion at T161 | Homozygous | 1015; 1003 |
| E221089 | P43596801 | 6759 nt deletion between GA20ox5_7090 and SAMT_304; 6 nt deletion at T161 | Homozygous | 1015; 1003 |
| E221089 | P43596831 | 6759 nt deletion between GA20ox5_7090 and SAMT_304; 6 nt deletion at T161 | Homozygous | 1015; 1003 |
| E220938 | P43596469 | 6753 nt deletion between GA20ox5_7090 and SAMT_304; 8 nt deletion at T161 | Homozygous | 1016; 1001 |
| E220938 | P43596438 | 6753 nt deletion between GA20ox5_7090 and SAMT_304; 8 nt deletion at T161 | Homozygous | 1016; 1001 |
| E220938 | P43596489 | 6753 nt deletion between GA20ox5_7090 and SAMT_304; 8 nt deletion at T161 | Homozygous | 1016; 1001 |
| E220242 | P95046375 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046377 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046392 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046378 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046370 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046369 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046368 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046395 | 6344 nt deletion between GA20ox5_1654 and SAMT_304; 12 nt deletion at GA20ox5_7090; 3 nt deletion at SAMT_161 | Homozygous | 1008; 1017; 1002 |
| E220242 | P95046396 | 6344 nt deletion between GA20ox5_1654 and SAMT_304; 12 nt deletion at GA20ox5_7090; 3 nt deletion at SAMT_161 | Homozygous | 1008; 1017; 1002 |
| E220698 | P43596662 | 6518 nt deletion between GA20ox5_1654 and SAMT_161; 4 nt deletion at T7090 | Homozygous | 1005; 1018 |
| E220698 | P43596671 | 6518 nt deletion between GA20ox5_1654 and SAMT_161; 4 nt deletion at T7090 | Heterozygous | 1005; 1018 |
| E220698 | P43596694 | 6518 nt deletion between GA20ox5_1654 and SAMT_161; 4 nt deletion at T7090 | Homozygous | 1005; 1018 |
| E220698 | P43596679 | 6518 nt deletion between GA20ox5_1654 and SAMT_161; 4 nt deletion at T7090 | Homozygous | 1005; 1018 |
| E220698 | P43596701 | 6518 nt deletion between GA20ox5_1654 and SAMT_161; 4 nt deletion at T7090 | Heterozygous | 1005; 1018 |
| E220698 | P43596654 | 6518 nt deletion between GA20ox5_1654 and SAMT_161; 4 nt deletion at T7090 | Homozygous | 1005; 1018 |
| E220698 | P43596690 | 6518 nt deletion between GA20ox5_1654 and SAMT_161; 4 nt deletion at T7090 | Heterozygous | 1005; 1018 |
| E220698 | P43596703 | 6518 nt deletion between GA20ox5_1654 and SAMT_161; 4 nt deletion at T7090 | Homozygous | 1005; 1018 |
| E220698 | P43596711 | 6518 nt deletion between GA20ox5_1654 and SAMT_161; 4 nt deletion at T7090 | Homozygous | 1005; 1018 |
| E220055 | P95046321 | 6348 nt deletion between GA20ox5_1654 and SAMT_304; 39 nt deletion at T7090 | Homozygous | 1007; 1019 |
| E220055 | P95046342 | 6348 nt deletion between GA20ox5_1654 and SAMT_304; 39 nt deletion at T7090 | Homozygous | 1007; 1019 |
| E220055 | P95046314 | 6348 nt deletion between GA20ox5_1654 and SAMT_304; 39 nt deletion at T7090 | Homozygous | 1007; 1019 |
| E220055 | P95046297 | 6348 nt deletion between GA20ox5_1654 and SAMT_304; 39 nt deletion at T7090 | Homozygous | 1007; 1019 |
| E220228 | P43596770 | 6357 nt deletion between GA20ox5_1654 and SAMT_304 | Homozygous | 1004 |
| E220141 | P43596991 | 6342 nt deletion between GA20ox5_1654 and SAMT_304 | Homozygous | 1006 |

TABLE 5-continued

Deletion edits and genotype of R0 ad R1 plants.

| R0 Edit ID | R1 Plant ID | Editing Deletion Type | R1 zygosity call for deletion mutant | Deletion Junction Number(s) (Table 4) |
|---|---|---|---|---|
| E220141 | P43597019 | 6342 nt deletion between GA20ox5__1654 and SAMT__304 | Homozygous | 1006 |
| E220141 | P43596954 | 6342 nt deletion between GA20ox5__1654 and SAMT__304 | Homozygous | 1006 |
| E220141 | P43596970 | 6342 nt deletion between GA20ox5__1654 and SAMT__304 | Homozygous | 1006 |
| E220141 | P43596980 | 6342 nt deletion between GA20ox5__1654 and SAMT__304 | Homozygous | 1006 |
| E187994 | P43597077 | 6160 nt deletion between GA20ox5__6531 and SAMT__408 | Homozygous | 1010 |
| E187994 | P43597052 | 6160 nt deletion between GA20ox5__6531 and SAMT__408 | Heterozygous | 1010 |
| E187994 | P43597049 | 6160 nt deletion between GA20ox5__6531 and SAMT__408 | Heterozygous | 1010 |
| E187994 | P43597037 | 6160 nt deletion between GA20ox5__6531 and SAMT__408 | Homozygous | 1010 |
| E188579 | P43596586 | 6133 nt deletion between GA20ox5__6531 and SAMT__408 | Heterozygous | 1011 |
| E188579 | P43596582 | 6133 nt deletion between GA20ox5__6531 and SAMT__408 | Heterozygous | 1011 |
| E188579 | P43596603 | 6133 nt deletion between GA20ox5__6531 and SAMT__408 | Heterozygous | 1011 |
| E188579 | P43596594 | 6133 nt deletion between GA20ox5__6531 and SAMT__408 | Homozygous | 1011 |
| E188790 | P09617231 | 6130 nt deletion between GA20ox5__6531 and SAMT__408 | Homozygous | 1012 |
| E188790 | P09617182 | 6130 nt deletion between GA20ox5__6531 and SAMT__408 | Heterozygous | 1012 |
| E188790 | P09617144 | 6130 nt deletion between GA20ox5__6531 and SAMT__408 | Heterozygous | 1012 |
| E188790 | P09617191 | 6130 nt deletion between GA20ox5__6531 and SAMT__408 | Heterozygous | 1012 |
| E188790 | P09617225 | 6130 nt deletion between GA20ox5__6531 and SAMT__408 | Homozygous | 1012 |
| E188790 | P09617216 | 6130 nt deletion between GA20ox5__6531 and SAMT__408 | Homozygous | 1012 |
| E188790 | P09617192 | 6130 nt deletion between GA20ox5__6531 and SAMT__408 | Homozygous | 1012 |
| E188790 | P09617208 | 6130 nt deletion between GA20ox5__6531 and SAMT__408 | Homozygous | 1012 |
| E188569 | P43596926 | 6130 nt deletion between GA20ox5__6531 and SAMT__408 | Homozygous | 1013 |
| E188569 | P43596908 | 6130 nt deletion between GA20ox5__6531 and SAMT__408 | Homozygous | 1013 |
| E188569 | P43596931 | 6130 nt deletion between GA20ox5__6531 and SAMT__408 | Homozygous | 1013 |
| E188569 | P43596895 | 6130 nt deletion between GA20ox5__6531 and SAMT__408 | Heterozygous | 1013 |
| E188569 | P43596896 | 6130 nt deletion between GA20ox5__6531 and SAMT__408 | Heterozygous | 1013 |
| E188569 | P43596911 | 6130 nt deletion between GA20ox5__6531 and SAMT__408 | Heterozygous | 1013 |
| E189115 | P43596944 | 6131 nt deletion between GA20ox5__6531 and SAMT__408 | Homozygous | 1014 |
| E180294 | P43596566 | 6478 nt deletion between GA20ox5__1695 and SAMT__8165 | Homozygous | 1009 |
| E180294 | P43596550 | 6478 nt deletion between GA20ox5__1695 and SAMT__8165 | Homozygous | 1009 |
| E180294 | P43596542 | 6478 nt deletion between GA20ox5__1695 and SAMT__8165 | Homozygous | 1009 |
| E180294 | P43596530 | 6478 nt deletion between GA20ox5__1695 and SAMT__8165 | Homozygous | 1009 |
| E180294 | P43596524 | 6478 nt deletion between GA20ox5__1695 and SAMT__8165 | Homozygous | 1009 |
| E180294 | P43596534 | 6478 nt deletion between GA20ox5__1695 and SAMT__8165 | Homozygous | 1009 |
| E180294 | P43596558 | 6478 nt deletion between GA20ox5__1695 and SAMT__8165 | Homozygous | 1009 |
| E180294 | P43596538 | 6478 nt deletion between GA20ox5__1695 and SAMT__8165 | Homozygous | 1009 |

Example 29. Reduced Plant Height of Corn Plants with Edited Allele

R1 corn plants homozygous or heterozygous for an edited allele of the GA20 oxidase 5 gene (as identified in Example 28) were grown to maturity to measure their plant heights along with wild type control plants. R1 seeds were planted in soil and grown to maturity in the greenhouse under day/night temperatures of 85°/70° and 16/8 hours of photoperiod using standard nutrient and light conditions for corn plant growth and development. Plant heights (PHT) of R1 plants were measured at R2 growth stage from the soil level to the base of the uppermost fully expanded leaf.

Figure 22:
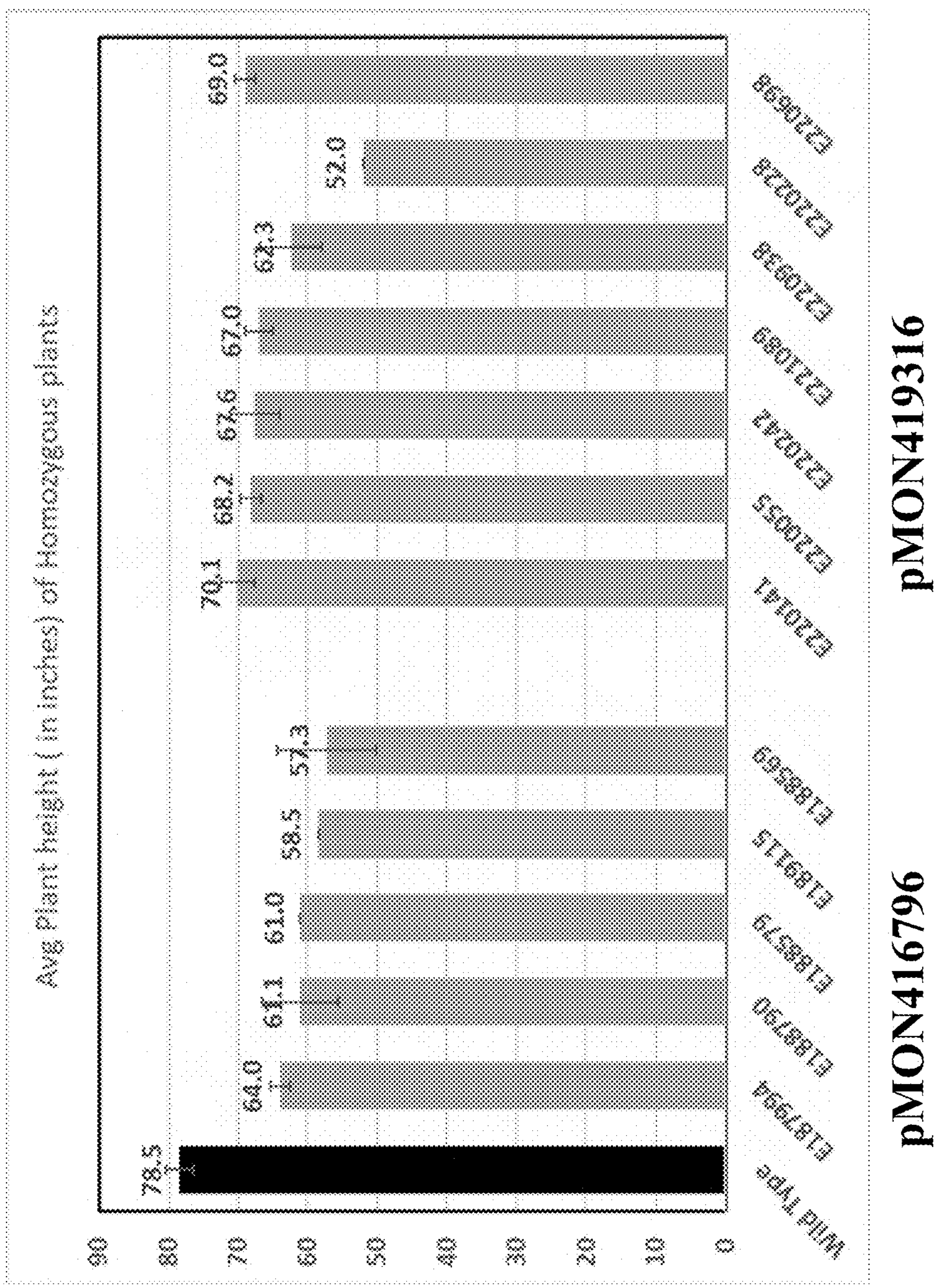
FIG. 22 depicts the average height of wild type plants and homozygous edited plants in inches (Y-axis).

Table 6 provides the plant heights of individual R1 plants homozygous for deletion edits between the GA20ox5 and SAMT genes made using the Vector-2 or Vector-1 construct described in Example 27, along with wild type (WT) control plants. Average plant heights for WT and each homozygous deletion edit are also provided in Table 6 (see also FIG. 22 showing the average plant heights with error bars). These plant heights demonstrate that plants homozygous for an edited GA20 oxidase 5 allele comprising a deletion between the GA20ox5 and SAMT genes have significantly reduced plant heights averaging between 57.3 inches and 70.1 inches for plants having the edited alleles, versus an average plant height of 78.5 inches for the WT control.

Figure 23:
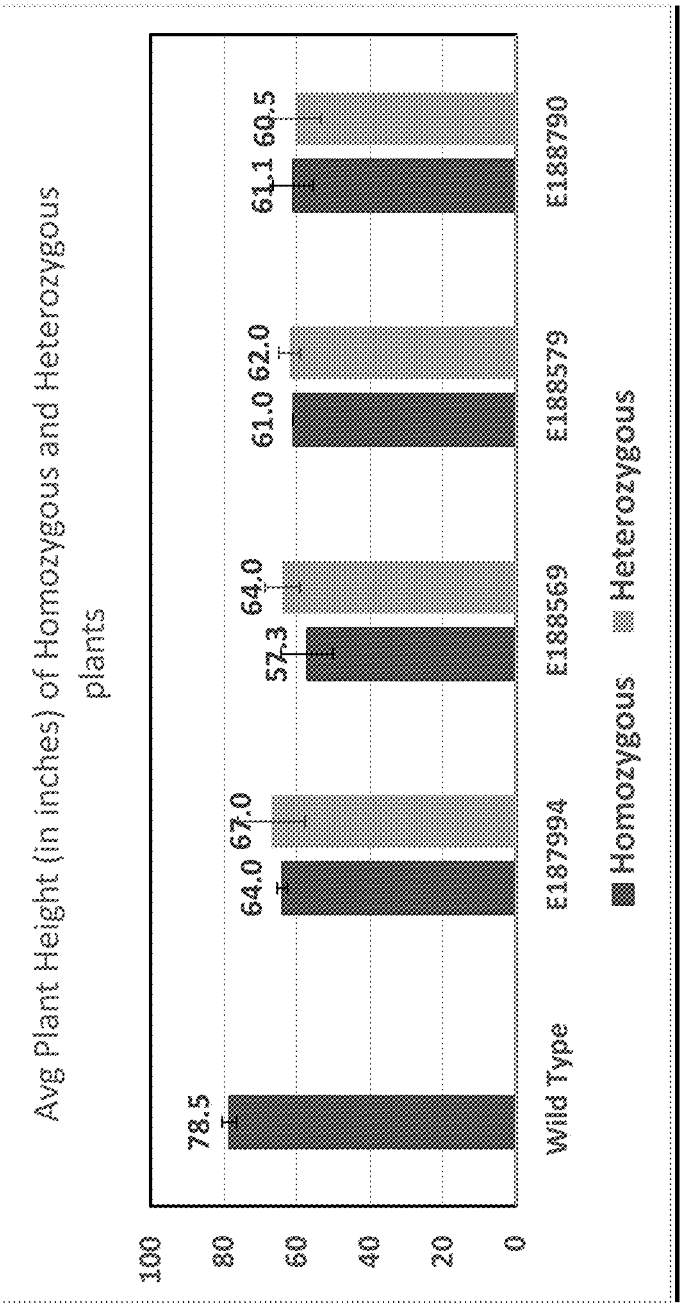
FIG. 23 depicts the average height of wild type plants and homozygous or heterozygous edited plants in inches (Y-axis).

Table 7 provides the plant heights of individual R1 plants homozygous or heterozygous for deletion edits between the GA20ox5 and SAMT genes made using the Vector-2 construct described in Example 27, along with wild type (WT) control plants (see also FIG. 23 showing average plant heights with error bars). The data in Table 7 overlaps with Table 6 since R1 plants homozygous for the deletion edits made using the Vector-2 construct and the wild type control plants are the same as in Table 6. These plant heights demonstrate that plants heterozygous or homozygous for the edited GA20 oxidase 5 alleles comprising a deletion between the GA20ox5 and SAMT genes and made using the Vector-2 construct have significantly reduced plant heights averaging between 57.3 inches and 64 inches for plants homozygous these edited alleles, and between 60.5 inches and 67 inches for plants heterozygous for these edited alleles, relative to an average plant height of 78.5 inches for the WT control plants. The reductions in plant height are similar between plants homozygous and heterozygous for the deletion edit alleles, but plant heights overall for plants comprising the deletion edit alleles regardless of zygosity are significantly lower than those of wild type control plants.

The plant height data described in this example demonstrate that deletion of the region between GA20ox5 and SAMT genes leads to reduced plant heights as compared to wild type control plants, for plants homozygous or heterozygous for the edited deletion alleles, suggesting that these deletion alleles of the GA20 oxidase 5 gene act in a dominant or semi-dominant manner to produce a reduced plant height phenotype (semi-dwarf or short stature corn plants), especially since edited loss-of-function alleles of the GA20 oxidase 3 or GA20 oxidase 5 genes alone without an antisense or inversion sequence have been shown to not produce short stature corn plants. See, e.g., Published PCT Application Nos. WO/2019/161149, WO12019/161147 and WO/2019/161144, the entire contents and disclosures of which are incorporated herein by reference. Further plant height measurements will be made in subsequent generations to confirm the shorter plant height phenotype.

TABLE 6

Plant Heights of homozygous R1 plants using Vector-2 and Vector-1.

| Editing Construct ID | Edit ID | R1 Plant ID | Plant height (inches) |
|---|---|---|---|
| Vector-2 | E187994 | P43597037 | 65 |
| Vector-2 | E187994 | P43597077 | 63 |
| | E187994 Average | | 64.0 |
| Vector-2 | E188569 | P43596931 | 65 |
| Vector-2 | E188569 | P43596908 | 55.75 |
| Vector-2 | E188569 | P43596926 | 51 |
| | E188569 Average | | 57.3 |
| Vector-2 | E188579 | P43596594 | 61 |
| Vector-2 | E188790 | P09617225 | 70 |
| Vector-2 | E188790 | P09617231 | 60.75 |
| Vector-2 | E188790 | P09617208 | 60.25 |
| Vector-2 | E188790 | P09617216 | 59.5 |
| Vector-2 | E188790 | P09617192 | 55 |
| | E188790 Average | | 61.1 |
| Vector-2 | E189115 | P43596944 | 58.5 |
| Vector-1 | E220055 | P95046314 | 69.5 |
| Vector-1 | E220055 | P95046342 | 69 |
| Vector-1 | E220055 | P95046321 | 68 |
| Vector-1 | E220055 | P95046297 | 66.25 |
| | E220055 Average | | 68.2 |
| Vector-1 | E220141 | P43596991 | 72 |
| Vector-1 | E220141 | P43596954 | 72 |
| Vector-1 | E220141 | P43596970 | 71.5 |
| Vector-1 | E220141 | P43596980 | 68 |
| Vector-1 | E220141 | P43597019 | 67 |
| | E220141 Average | | 70.1 |
| Vector-1 | E220228 | P43596770 | 52 |
| Vector-1 | E220242 | P95046370 | 74 |
| Vector-1 | E220242 | P95046369 | 71.5 |
| Vector-1 | E220242 | P95046392 | 69.5 |
| Vector-1 | E220242 | P95046395 | 69 |
| Vector-1 | E220242 | P95046378 | 69 |
| Vector-1 | E220242 | P95046368 | 66 |
| Vector-1 | E220242 | P95046396 | 65 |
| Vector-1 | E220242 | P95046377 | 64.75 |
| Vector-1 | E220242 | P95046399 | 64 |
| Vector-1 | E220242 | P95046375 | 63.5 |
| | E220242 Average | | 67.6 |
| Vector-1 | E220698 | P43596694 | 70 |
| Vector-1 | E220698 | P43596662 | 68 |
| | E220698 Average | | 69.0 |
| Vector-1 | E220938 | P43596438 | 68.5 |
| Vector-1 | E220938 | P43596469 | 60.5 |
| Vector-1 | E220938 | P43596489 | 58 |
| | E220938 Average | | 62.3 |
| Vector-1 | E221089 | P43596831 | 69 |
| Vector-1 | E221089 | P43596820 | 67 |
| Vector-1 | E221089 | P43596823 | 65 |
| | E221089 Average | | 67 |
| Wild type | WT1 | | 80 |
| Wild type | WT2 | | 79.5 |
| Wild type | WT3 | | 79 |
| Wild type | WT4 | | 79 |
| Wild type | WT5 | | 75 |
| | Wild type Average | | 78.5 |

TABLE 7

Plant Heights of homozygous and heterozygous R1 plants using Vector-2.

| Event ID | R1 Plant ID | R1 zygosity for deletion mutant | Plant height (inches) |
|---|---|---|---|
| E187994 | P43597052 | Heterozygous | 60.5 |
| E187994 | P43597049 | Heterozygous | 73.5 |
| | E187994 Heterozygous Average | | 67.0 |
| E187994 | P43597037 | Homozygous | 65 |
| E187994 | P43597077 | Homozygous | 63 |
| | E187994 Homozygous Average | | 64.0 |
| E188569 | P43596895 | Heterozygous | 63.5 |
| E188569 | P43596911 | Heterozygous | 59.5 |
| E188569 | P43596896 | Heterozygous | 69 |
| | E188569 Heterozygous Average | | 64.0 |
| E188569 | P43596908 | Homozygous | 55.75 |
| E188569 | P43596926 | Homozygous | 51 |
| E188569 | P43596931 | Homozygous | 65 |
| | E188569 Homozygous Average | | 57.3 |
| E188579 | P43596582 | Heterozygous | 62 |
| E188579 | P43596603 | Heterozygous | 59 |
| E188579 | P43596586 | Heterozygous | 65 |
| | E188579 Heterozygous Average | | 62.0 |
| E188579 | P43596594 | Homozygous | 61 |
| E188790 | P09617182 | Heterozygous | 65.75 |
| E188790 | P09617238 | Heterozygous | 65 |
| E188790 | P09617144 | Heterozygous | 61 |
| E188790 | P09617191 | Heterozygous | 50.25 |
| | E188790 Heterozygous Average | | 60.5 |
| E188790 | P09617192 | Homozygous | 55 |
| E188790 | P09617208 | Homozygous | 60.25 |
| E188790 | P09617225 | Homozygous | 70 |
| E188790 | P09617231 | Homozygous | 60.75 |
| E188790 | P09617216 | Homozygous | 59.5 |
| | E188790 Homozygous Average | | 61.1 |
| Wild type | WT1 | | 80 |
| Wild type | WT2 | | 79.5 |
| Wild type | WT3 | | 79 |
| Wild type | WT4 | | 79 |
| Wild type | WT5 | | 75 |
| | Wild type Average | | 78.5 |

Example 30. Collection of Samples from R2 Plants for Molecular Assays

For the E220141 and E221089 deletion edits from the Vector-1 construct, R1 plants homozygous for those deletion edits (P43596991 and P43596831, respectively) were selfed to produce homozygous inbred R2 plants. The R2 inbred plants containing one of the E220141 and E221089 edits, and wild type control plants of the same inbred line, were grown under standard conditions in the greenhouse and sampled at V2 growth stage for the molecular assays described below. The plants were cut just above the soil level and the entire above-ground portion of the plants were placed in 50 ml conical tubes and immediately frozen in liquid nitrogen. Each sample contained one or two sibling plants of the same genotype. The number of samples for each assay and genotype are provided in Table 8. The frozen samples were milled and used for the small RNA and GA hormone assays described in Examples 31 and 32 below.

TABLE 8

Description of samples for small RNA and GA hormones assays.

| Editing Construct ID | Edit ID (R2 Inbreds) | Number of samples for small RNA assay | Number of samples for GA hormone assay |
|---|---|---|---|
| Inbred Wild type | | 2 | |
| Vector-1 | E220141 | 2 | 7 |
| Vector-1 | E221089 | 1 | 10 |

Example 31. Detection of Small RNAs in Plants Having an Edited Deletion Allele To generate small RNA libraries for sequencing, Illumina's TruSeq small RNA Library Preparation Kit was used according to the manufacturer's protocol (Document #15004197v02) with a modification at the library purification step. Samples of each genotype for this small RNA assay experiment are identified in Example 30 above. After amplification of cDNA, individual libraries were gel purified using a 6% Novex TBE PAGE Gel for size separation. The gel was stained with 1×SYBR Gold for 20 minutes. The final library product was sequenced on Illumina's NextSeq platform with a minimum depth of 3 million reads per sample. After sequencing, reads were processed through the following steps: the sequencing adapters were trimmed; reads matching housekeeping noncoding RNAs were removed and libraries normalized to reads per million. Between 1 and 9 samples per genotype were assayed.

The mutated GA20 oxidase 5 (GA20ox5) gene containing the E220141 and E221089 deletion edits were predicted to produce antisense RNA transcripts spanning all or part of the coding sequence of the GA20ox5 gene under the control of the downstream native SAMT promoter in the reverse orientation that could hybridize to mRNA transcripts expressed from the wild type and/or mutant GA20 oxidase 5 alleles and/or the GA20 oxidase 3 gene or allele(s). Since antisense RNA sequences can trigger RNA interference (RNAi) and suppression of genes encoding identical or homologous RNA sequences, plants containing the deletion edits were assayed for the presence of small RNAs. Processing of the double stranded RNA would be expected to produce small RNAs of about 21, 22 or 24 nucleotides in length corresponding to the coding sequence of the GA20ox5 gene. In this experiment, the edited R2 plants, as well as wild type control plants, did not show a noticeable accumulation of small RNAs corresponding to the GA20ox5 gene in the 21, 22 or 24-nucleotide small RNA range, which was measured to be 0 or 1 read per million total sequencing reads (data not shown). These data indicate that the edited plants either do not produce small RNAs at the V2 growth stage sampled in this example or act through a different dominant negative mechanism. However, the pattern of expression of antisense RNA transcripts complementary to all or part of the coding sequence of the GA20 oxidase 5 gene is also dependent on the SAMT gene promoter, which may not drive expression (or expression at a sufficiently high level) at the V2 growth stage to produce a measurable effect on the levels of small RNAs. Without being bound by theory, it is possible that expression of antisense transcripts from an edited deletion allele of the endogenous GA20ox5 gene may be more robust at later stages of development and thus have a greater or more measurable effect on the level of small RNAs and RNAi suppression at those later stages.

Future experiments will also seek to determine whether the levels of GA20ox3 and/or GA20ox5 mRNA transcripts are reduced in plants homozygous or heterozygous for an edited GA20ox5 allele having a deletion between the GA20ox5 and SAMT genes, relative to controls.

Example 32. Detection of GA Hormones in Plants Having an Edited Deletion Allele Reduced expression of GA20 oxidase genes can alter the levels of GA hormones in corn plants, which can in turn affect plant height with lower levels of active GAs potentially reducing plant height. The levels of bioactive GA hormones and their precursors were measured in plants containing the edited GA20ox5 alleles. GA20 oxidase is active in the GA biosynthetic pathway and catalyzes the sequential oxidation of metabolic intermediates GA12 and GA53 into GA9 and GA20, respectively (the "early 13-hydroxylation pathway" and "non 13-hydroxylation pathway"). The primary bioactive forms of GA include GA1, GA3 and GA4, which are further downstream (3') of GA20 oxidase activity and the GA9 and GA20 intermediates in the biosynthetic pathway. A reduction or suppression of the expression level and/or enzymatic function of GA20 oxidase genes, as may be expected with the GA20ox5 deletion edits, may result in reduction of downstream metabolites (GA20 and GA9) and accumulation of upstream precursors (GA53 and GA12).

For this experiment, samples were collected as provided in Example 30 above. Freshly frozen plant sample tissues were extracted and cleaned using Waters solid phase extraction MAX cartridge plate. GA hormones and 2 internal standards were analyzed using UPLC coupled with an ABSciex 5500 Mass Spectrometry with MRM method. The final GA hormone values were calculated based on the calibration curve with ABSciex software Multi-Quan. Each GA hormone calibration curve was in good linear fit, the R2 linear regression>0.99. The 8 technical controls per 96-well plate for each hormone were also included and evaluated in analytical process for meeting the standard criterion. GA levels were measured in terms of pmol/gram of sample tissue.

Figure 24:
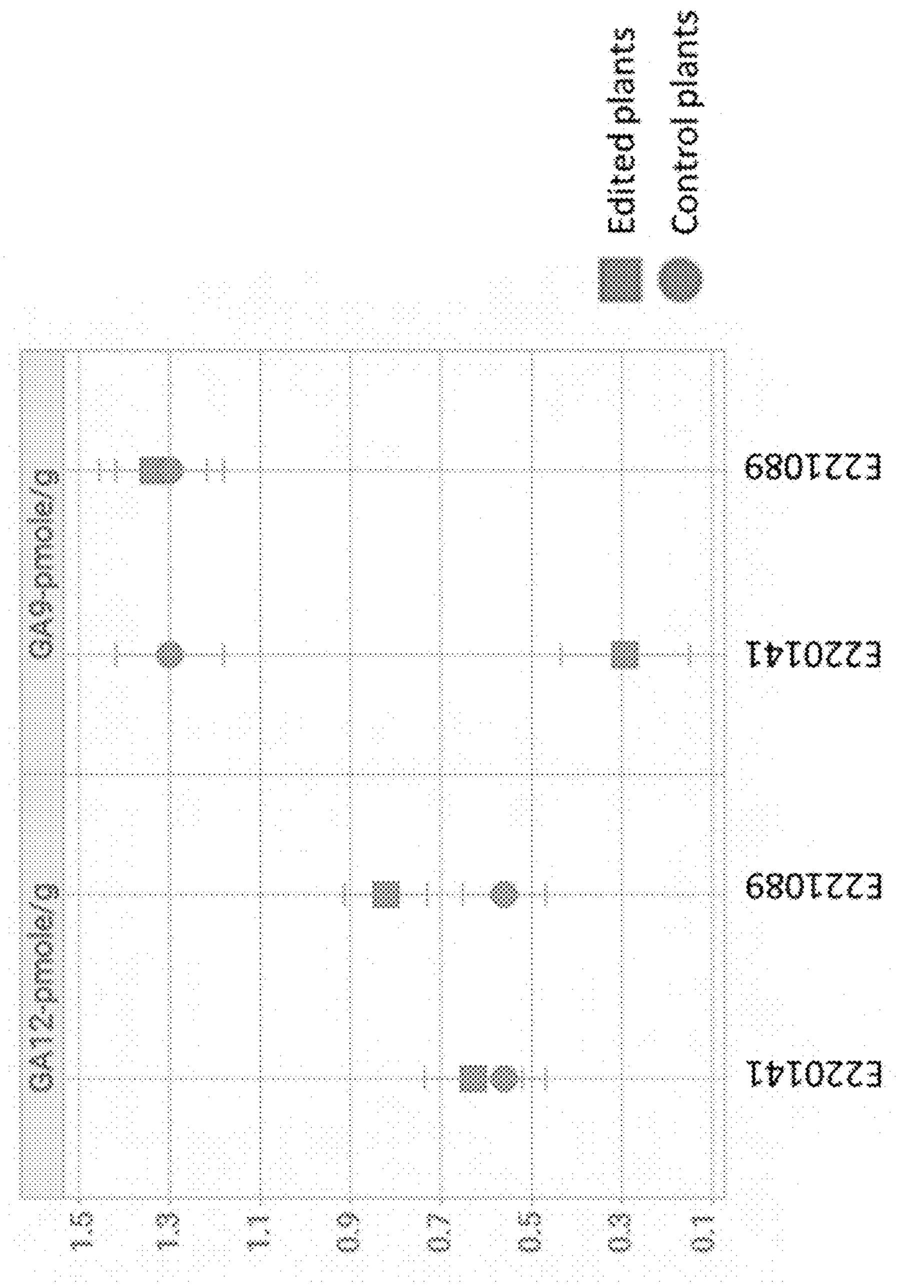
FIG. 24 depicts the concentration of GA12 and GA9 in pmol/g (Y-axis) in edited and control plants.

As shown in FIG. 24, the levels of GA12 were increased in inbred plants homozygous for the edited E221089 allele but were statistically neutral or unchanged in inbred plants homozygous for the edited E220141 allele, relative to wild type control plants. As further shown in FIG. 24, the levels of GA9 were decreased in inbred plants homozygous for the edited E220141 allele but neutral in inbred plants homozygous for the edited E221089 allele, relative to wild type control plants.

Figure 25:
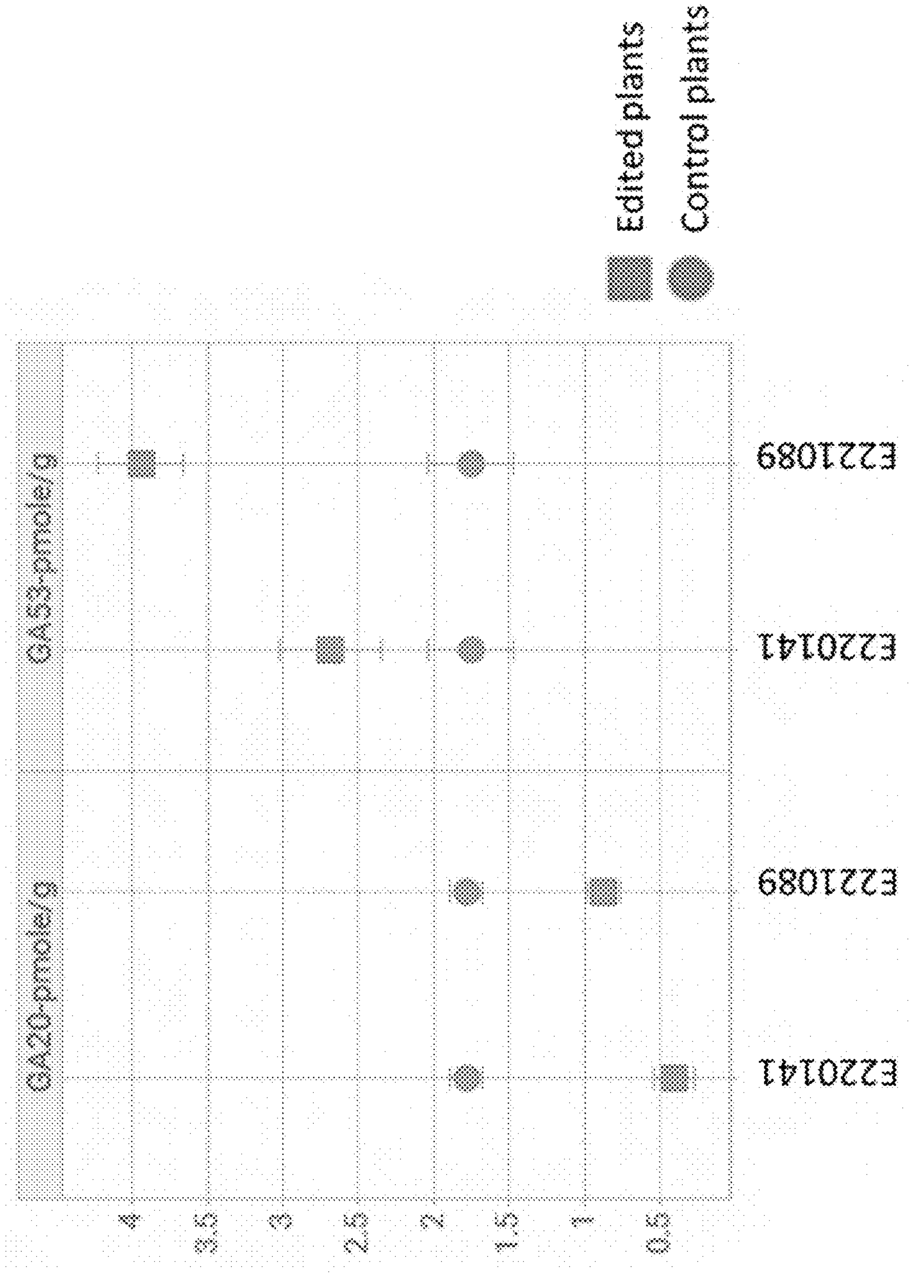
FIG. 25 depicts the concentration of GA20 and GA53 in pmol/g (Y-axis) in edited and control plants.

As shown in FIG. 25, the levels of GA20 were decreased in inbred plants homozygous for either of the edited alleles (E221089 or E220141), relative to wild type control plants. As further shown in FIG. 25, the levels of GA53 were increased in inbred plants homozygous for either of the edited alleles (E221089 or E220141), relative to wild type control plants.

Figure 26:
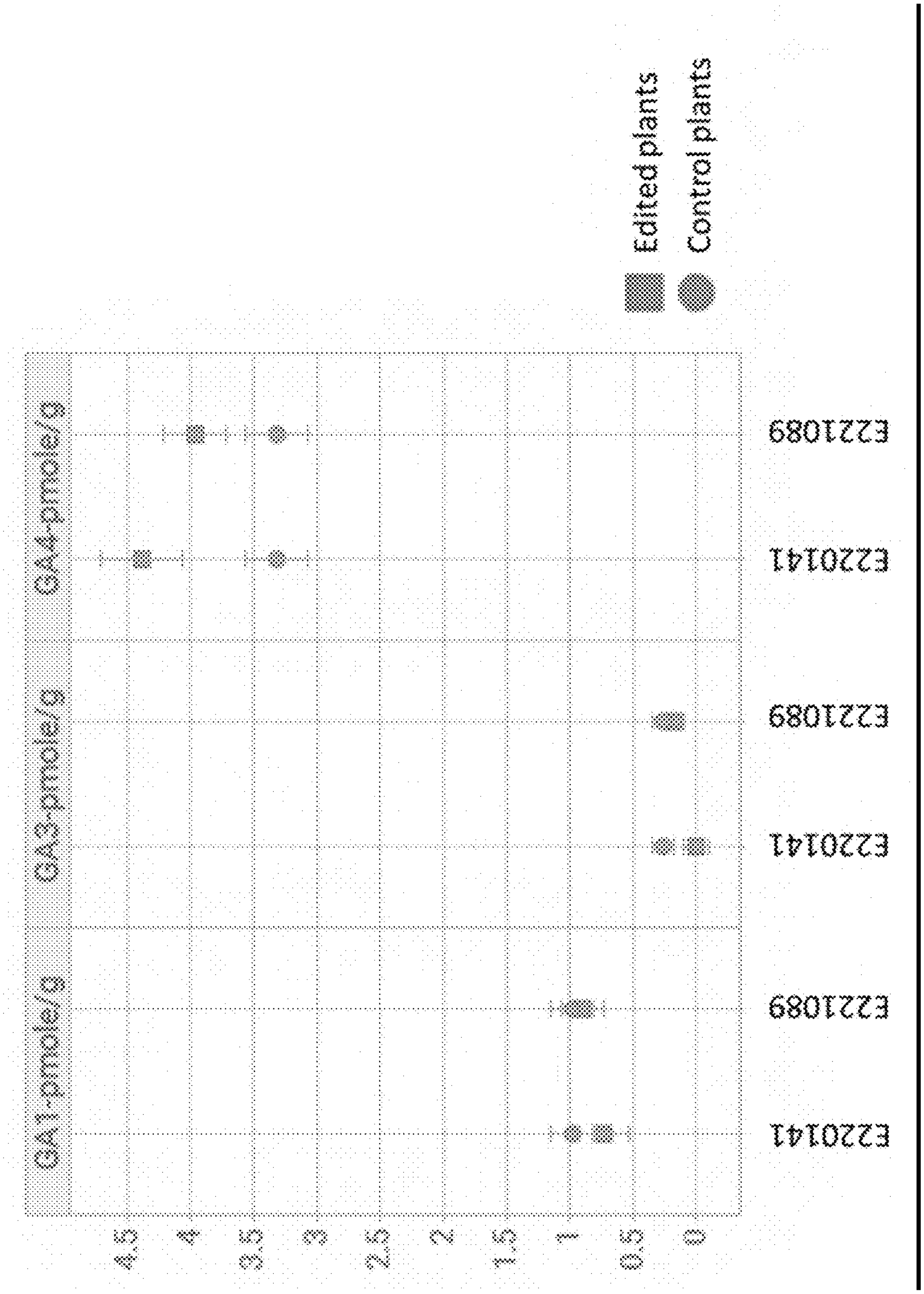
FIG. 26 depicts the concentration of the active gibberellic acids GA1, GA3, and GA4 in pmol/g (Y-axis) in edited and control plants.

FIG. 26 provides the results for levels of active GAs (GA1, GA3 and GA4) measured in samples collected at V2 growth stage of the edited inbred plants relative to wild type controls. As shown in FIG. 26, the levels of these active GAs were generally not statistically changed in the inbred plants homozygous for the edited alleles (E221089 or E220141), except for an increase in GA4 in inbred plants homozygous for either of the edited alleles (E221089 or E220141).

These data support the theory that an antisense transcript may be expressed from the edited GA20 oxidase 5 gene, allele or locus having a deletion between the neighboring GA20 oxidase 5 and SAMT genes, that may reduce the expression level(s) of the GA20 oxidase 5 and/or GA20 oxidase 3 gene(s) and thus affect the levels of GA hormones in plants containing the edited alleles. The data in this experiment show increased accumulation of the GA12 and GA53 precursors upstream (5') of GA20 oxidase activity and decreased levels of GA9 and GA20 products of GA20 oxidase activity in plants containing the edited GA20 oxidase 5 allele, although the levels of GA12 and GA9 were unchanged in the edited E220141 and E221089 inbred plants, respectively.

Although the levels of bioactive GAs were not shown to be reduced in this example, this may be due to the early V2 growth stage when the plant tissue samples were collected for this experiment. Indeed, the pattern of expression of an antisense RNA transcript complementary to all or part of the coding sequence of the GA20 oxidase 5 gene is dependent on the SAMT gene promoter, which may not drive expression (or expression at a sufficiently high level) at the early V2 growth stage to produce a measurable effect on the levels of active GAs. Without being bound by theory, it is possible that expression of antisense transcripts from the edited deletion alleles of the endogenous GA20ox5 gene under the control of the endogenous SAMT gene promoter may be more robust at later stages of development and thus have a greater or more measurable effect on the level(s) of active GAs at those later stages. The active GAs are also further downstream and not a direct product of GA20 oxidase enzyme activity. Future experiments will determine if lower active GA levels are observed at later stages of development in plants heterozygous or homozygous for an edited GA20 oxidase 5 locus comprising a deletion between the GA20ox5 and SAMT genes, which is supported by the altered levels of GA precursors observed in this example at the early V2 growth stage.

Figure 27:
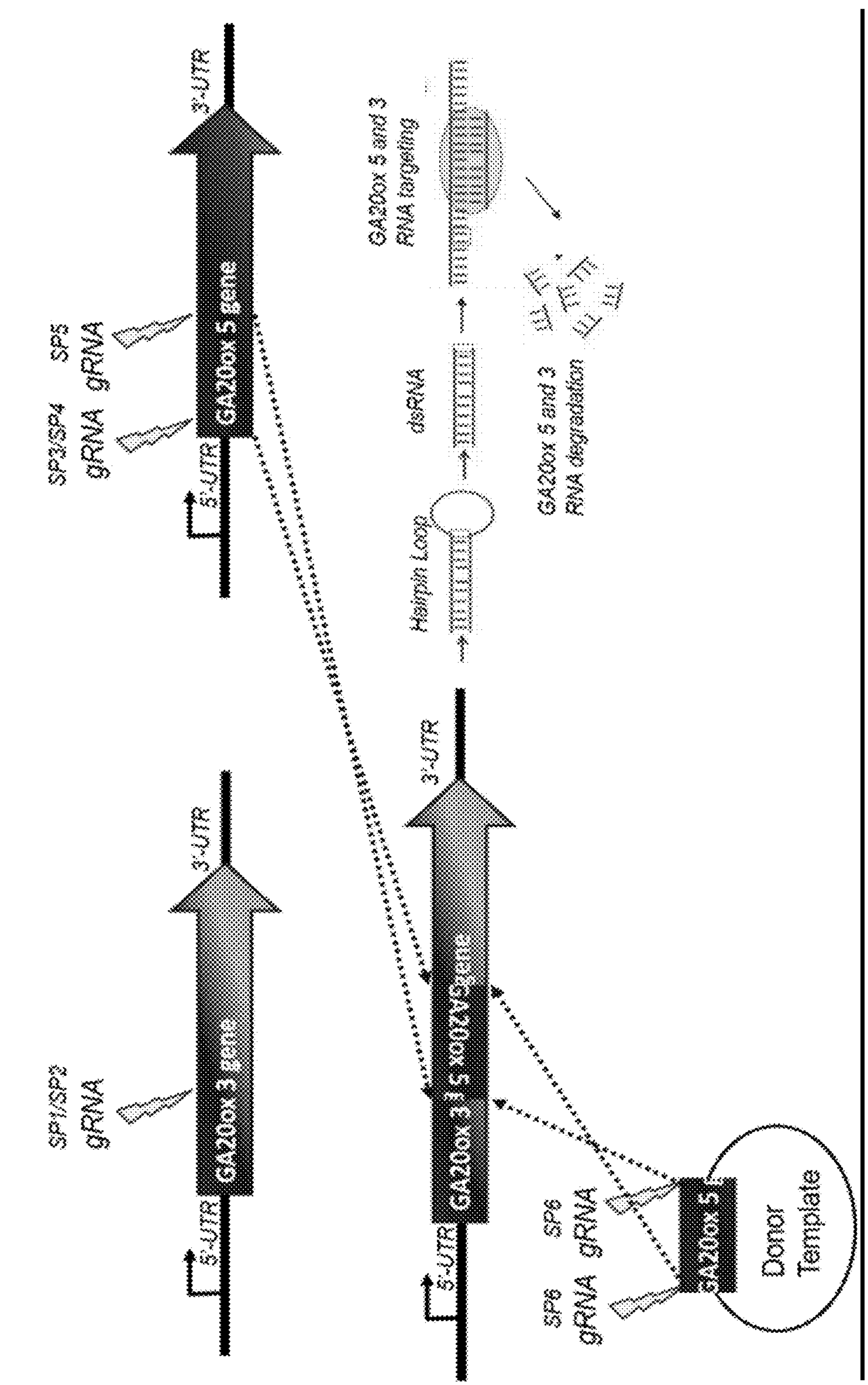
FIG. 27 provides illustrative examples for the production of a genomic modification of the Zm.GA20ox3 locus to encode a RNA transcript with an inverted sequence that can hybridize to a corresponding sequence of the RNA transcript to produce a stem-loop structure, to cause the suppression of one or both copies or alleles at the endogenous Zm.GA20ox3 and Zm.GA20ox5 loci.

Example 33. Creating Dominant Alleles by Genome Editing to Produce a Hairpin-Containing Transcript FIG. 27 provides illustrative examples for the production, through targeted gene editing, of a genomic modification of the Zm.GA20ox3 locus to encode a RNA transcript with an inverted sequence that can hybridize to a corresponding sequence of the RNA transcript to produce a stem-loop structure, to cause the suppression of one or both of the copies or alleles at the endogenous Zm.GA20ox3 and Zm.GA20ox5 loci. The Zm.GA20ox3 and Zm.GA20ox5 genes share a high level of nucleotide sequence similarity of their respective exon regions. Thus, a fragment of the Zm.GA20ox5 gene, sharing sufficient sequence identity or homology with a corresponding sequence of the Zm.GA20ox3 gene, inserted into a preselected site in the Zm.GA20ox3 gene in the reverse orientation near the corresponding Zm.GA20ox3 sequence, can hybridize to the corresponding sequence to form a stem-loop structure and trigger suppression of the Zm.GA20ox3 and Zm.GA20ox5 genes. The insertion site is determined by the design of the guide RNA directing a double-stranded genomic DNA cleavage. Without being bound to any particular theory, the edited Zm.GA20ox3 gene produces a transcript able to form a stem-loop structure which can induce suppression or gene silencing of the wild-type or other alleles of the Zm.GA20ox3 and Zm.GA20ox5 genes. In this example, the inserted Zm.GA20ox5 fragment can be excised from either copy or allele of the endogenous Zm.GA20ox5 gene. This type of editing is called trans-fragment targeting (TFT) editing since the fragment originates from the endogenous Zm.GA20ox5 gene. The boundaries of the excision fragment are defined by a pair of properly designed guide RNAs. According to this example, the inserted Zm.GA20ox5 fragment can also be excised from a donor template which is a double-stranded DNA molecule comprising the desired Zm.GA20ox5 fragment and flanked by target sites for guide RNA(s). The flanking gRNA target sites can be identical, utilizing the same gRNA, or different and according to some embodiments oriented to limit the amount of gRNA target site included in the DNA insertion fragment post cleavage. These target sites can match to the endogenous genome, be artificially-derived, or match to a non-endogenous genome, relative to the endogenous genome of the plant to be edited. According to some embodiments, the target sites flanking the insertion fragment of the donor template to be excised for insertion into the endogenous locus may be heterologous with respect to the native or endogenous genome, such that any off-target DNA cleavage within the endogenous genome can be minimized or eliminated. This method is referred to as "template assist" when performed in combination with guide RNAs targeted for excising a fragment from the endogenous Zm.GA20ox5 locus. Conversely, a Zm.GA20ox3 fragment may be excised via TFT from either copy or allele of the Zm.GA20ox3 gene and/or from a donor template (e.g., template assist method) and inserted into a pre-selected site of the endogenous Zm.GA20ox5 gene to produce an inverted-repeat sequence which can be transcribed into a RNA transcript comprising a stem-loop structure that triggers RNA-mediated suppression or silencing of the wild-type or other alleles of the Zm.GA20ox3 and/or Zm.GA20ox5 genes.

With either of these approaches, however, it is possible for other types of edits or mutations to be formed, such as deletion(s) and/or inversion(s) depending on which DNA cut(s) or break(s) are created at the gRNA or editing target site(s) and the fragment(s) inserted into or between those cut site(s). An inserted DNA fragment may originate from either copy or allele of the Zm.GA20ox3 or Zm.GA20ox5 gene, or from a DNA template molecule. Therefore, a deletion can be generated from cutting one or more target sites, and/or an inversion sequence can be generated by a DNA fragment being inserted in an opposite, reverse or antisense orientation relative to the coding sequence of the edited Zm.GA20 oxidase gene. The inversion may be present in the edited gene with or without a corresponding sequence that when expressed could hybridize to form a RNA hairpin or stem-loop structure with the encoded inversion sequence of the mRNA transcribed from the edited gene. The presence of an antisense inversion sequence without the corresponding sequence and resulting hairpin or stem-loop structure may be sufficient to trigger suppression of one or both of the Zm.GA20ox3 and Zm.GA20ox5 genes through canonical or non-canonical RNA mechanisms.

A plant transformation construct (Vector-4) was designed to create a double stranded break (DSB) in the Zm.GA20ox3 gene to allow for insertion of an antisense DNA fragment of the Zm.GA20ox5 gene either from the endogenous Zm.GA20ox5 locus or an exogenously provided donor template. In this example, the construct generally contains 4 functional regions or cassettes relevant to gene editing and creation of the insertion (e.g., inversion) in the edited gene: expression of a Cpf1 or Cas12a variant protein, expression of three guide RNAs for the Zm.GA20ox3 gene locus, expression of an additional three guide RNAs for the Zm.GA20ox5 gene locus, and a donor template region comprising a Zm.GA20ox5 gene fragment for the template assist method of inserting the Zm.GA20ox5 gene fragment (approximately 400 nucleotides in length) from the donor template. Each guide RNA unit contains a common scaffold compatible with the Cpf1 mutant, and a unique spacer/targeting sequence complementary to its intended target site.

The Cpf1 expression cassette comprises a maize ubiquitin promoter (SEQ ID NO: 37) operably linked to a sequence encoding a *Lachnospiraceae bacterium* G532R/K595R mutant Cpf1 RNA-guided endonuclease enzyme (SEQ ID NO: 39) fused to two nuclear localization signals (SEQ ID NOs: 42 and 43). See, e.g., Gao, L. et al., Nature Biotechnol. 35(8): 789-792 (2017), the entire contents and disclosure of which are incorporated herein by reference.

One expression cassette comprises a sequence encoding three guide RNAs (two guide RNAs having targeting/spacer sequences encoded by the SP1 and SP2 DNA sequences in Table 9 below (see also FIG. 27) that target two closely spaced-apart sites in exon 1 of the Zm.GA20ox3 gene; and another guide RNA having a targeting/spacer sequence encoded by the SP3 DNA sequence in Table 9 below (see also FIG. 27) targeting a site in exon 1 of the Zm.GA20ox5 gene), operably linked to a maize RNA polymerase III (Pol3) promoter (SEQ ID NO: 44). Spacer sequences SP1 and SP2 target two alternative breakage sites in exon-1 of Zm.GA20ox3 that are spaced apart by about 68 nucleotides, and either breakage site is able to receive a reverse complement insertion fragment, or the insertion fragment could replace the sequence between SP1 and SP2. It is also possible that the insertion fragment could integrate at both SP1 and SP2 target sites.

Another expression cassette comprises a sequence encoding an additional three guide RNAs (two guide RNAs having targeting/spacer sequences encoded by the SP4 and SP5 DNA sequences in Table 9 (see also FIG. 27) that target two closely spaced-apart target sites in exon 1 of the Zm.GA20ox5 gene; and another guide RNA having targeting/spacer sequences encoded by the SP6 DNA sequence in Table 9 (see also FIG. 27) targeting two identical engineered sites flanking the Zm.GA20ox5 gene fragment in the donor template region), operably linked to a synthetic promoter. Spacer sequences SP3 or SP4 target two alternative breakage sites in exon-1 of the endogenous Zm.GA20ox5 gene that are spaced apart by about 83 nucleotides, whereas the spacer sequence SP5 targets another breakage point in exon-1 of the endogenous Zm.GA20ox5 gene spaced apart from the cleavage site for the SP4 spacer by a greater distance of about 577 nucleotides. The targeting/spacer sequence SP6 is derived from a soybean PDS gene that has been separately demonstrated to work in combination with Cpf1 to direct cleavage of a target site in an endogenous PDS gene of a soybean plant.

Another nearly identical plant transformation construct (Vector-5) was designed to create a double stranded break (DSB) in the Zm.GA20ox3 gene to allow for insertion of an antisense DNA fragment of the Zm.GA20ox5 gene, but this second construct did not encode the guide RNA having the targeting/spacer sequence encoded by the SP6 DNA sequence for the template assist method, such that the fragment would originate from an endogenous copy of the Zm.GA20ox5 gene.

With the constructs described in this example, guide RNAs with spacers SP3 and SP4 may work in combination with a guide RNA with spacer SP5 would produce a fragment between about 500 and 700 bp from exon-1 of the endogenous Zm.GA20ox5 gene that could be inserted into a site within exon-1 of the endogenous Zm.GA20ox3 gene in the reverse complementary orientation, such that the RNA molecule transcribed from the endogenous Zm.GA20ox3 gene forms a stem-loop structure in the RNA transcript that can trigger suppression or silencing of the other copy/copies or allele(s) of the endogenous Zm.GA20ox3 and/or Zm.GA20ox5 gene(s). The resulting fragment could be referred to as a SP3-SP5 fragment (SEQ ID NO: 76) or a SP4-SP5 fragment (SEQ ID NO: 77), depending on whether spacer SP3 or SP4 was involved. In addition, a donor template containing a Zm.GA20ox5 gene fragment flanked by two SP6 spacer sequences can produce a Zm.GA20ox5 gene fragment (referred to as a SP6-SP6 fragment (e.g., SEQ ID NO: 88), if used in combination with the first transformation construct described above containing the SP6 sequence, for insertion into a site within the endogenous Zm.GA20ox3 gene in the reverse complementary orientation.

The DNA sequences encoding the guide RNA spacers and their intended target sites are listed in Table 9.

TABLE 9

Example guide RNAs used for editing the Zm.GA20ox3 locus

| Guide RNA Spacer | Target Site | Spacer Sequence | SEQ ID |
|---|---|---|---|
| SP1 | GA20ox3_2587 | CTGGAAGGAGACCCTGTCCTTCG | 78 |
| SP2 | GA20ox3_2655 | CCGGCACCCTCGGCCAAGATTTC | 79 |
| SP3 | GA20ox5_428 | CTCCCTGCCTTCGTCTTTGTCGT | 80 |
| SP4 | GA20ox5_511 | CTGCATACTTGCAGCTCGCACAT | 81 |
| SP5 | GA20ox5_1088 | CTGGAAGGAGACCCTGTCGTTCG | 82 |
| SP6 | Template Gm.PDS site | GTAAGAAGCTCTTCACCGTTCCA | 83 |

Zm.GA20ox5 gene fragment was inserted at the target site in the antisense orientation. In addition, whether the inserted Zm.GA20ox5 fragment originated from the endogenous Zm.GA20ox5 locus or the donor template region could also be determined and distinguished by PCR product size and/or sequencing the PCR products. This first PCR approach was used to determine which type of inverted insertion occurred in the endogenous Zm.GA20ox3 gene (see Tables 10 and 11).

According to a second PCR approach, a PCR primer pair including one primer (SEQ ID NO: 86) hybridizing to a sequence upstream (on the 5' side) of the two guide RNA target sites (SP1 and SP2) in the Zm.GA20ox3 gene and the other primer (SEQ ID NO: 87) hybridizing to a sequence downstream of the two SP1 and SP2 guide RNA target sites, such that a PCR product is generated spanning the possible insertion sites in the Zm.GA20ox3 gene. Thus, the presence and size of the PCR fragment using this approach would show whether an insertion occurred at the target sites, but independent of orientation. The PCR product can also be sequenced to determine the type and orientation of the insertion. According to this second approach, the size/sequence of the PCR product could also be used to determine whether the inserted GA20ox5 fragment originated from the endogenous GA20ox5 locus or the donor template

Example 34. Confirmation of Inversion Edits in Plants Using the Constructs in Example 33

An inbred corn plant line was transformed via *Agrobacterium*-mediated transformation with one of the transformation vectors described above in Example 33. The transformed plant tissues were grown to produce mature R0 plants. R0 plants having one or more unique genome edit(s) were self-crossed to produce R1 plants. To determine the edits and insertions in the endogenous Zm.GA20ox3 gene of the R0 and R1 plants, one or two PCR assay approaches were performed, with primers designed to identify the size or junctions of the intended insertions. One approach used a PCR primer pair including one primer (SEQ ID NO: 84) hybridizing to a sequence in the inserted Zm.GA20ox5 gene fragment and another primer (SEQ ID NO: 85) hybridizing to a sequence in the endogenous GA20ox3 gene, where the primers are oriented such that a PCR product is generated when the Zm.GA20ox5 gene fragment is inserted in the antisense orientation in the endogenous GA20ox3 gene (i.e., the PCR product was only generated across the 3' end of the inserted fragment when oriented in the inverted antisense direction). If a PCR fragment was generated, then a region, and the zygosity of the plant could be determined by whether the wild-type PCR fragment size/sequence was present.

Individual R1 plants produced by selfing R0 plants having one or more of the edits were assayed for the type of insertion and the zygosity of the insertion mutant or allele (see Tables 10 and 11). As used herein, "homo" means homozygous for the mutant allele, and "hetero" means heterozygous for the mutant allele. Tables 10 and 11 further provide the genomic DNA sequence of the coding sequence or region of the edited GA20 oxidase 3 gene from the start to stop codon and the sequence of the inversion or antisense sequence within such coding sequence or region of the edited GA20 oxidase 3 gene (each by SEQ ID NO). To avoid repetition, the inversion type and coding and inversion sequences are only provided in the first row of Tables 10 and 11 for each Edit ID. Edit IDs E270933 and E271059 in Table 10 were generated with the Vector-4 construct, and Edit IDs E376333 and E376314 in Table 11 (and Edit ID E376274) were created using the Vector-5 construct. Additional edits were generated with these constructs, but either were not recovered in R1 plants/seeds, had other T-DNA insertions and/or did not produce small RNAs, and were therefore discarded and not advanced for further testing. Edit ID E376274 created with the Vector-5 construct comprising an inverted GA20ox5 SP4-SP5 fragment inserted into the GA20ox3 SP1 target site was not recovered in R1 plants/seeds and was therefore not advanced. Edit ID E376274 for the GA20 oxidase 3 gene has a genomic coding sequence of SEQ ID NO: 97 and an inversion sequence of SEQ ID NO: 98.

Tables 10 and 11 also provide information about possible simple/small or larger edit(s) or deletion(s) that may be present in the GA20 oxidase 5 gene. Simple or small deletion(s) may also be present in the endogenous GA20 oxidase 5 (GA20ox5) gene at one or more of the individual SP3, SP4 and SP5 target sites, and large deletion(s) may be present in the endogenous GA20ox5 gene spanning between the SP3/SP5 or SP4/SP5 target sites. For the Vector-5 construct, Table 11 provides pooled information and numbers for the R1 plants grouped by Edit ID. As can be seen in Tables 10 and 11, R0 and R1 plants in many cases did contain one or more edits or deletions in the GA20ox5 locus, although some R1 plants (designated as "unknown" in the tables) were not determined to contain an edit or deletion in the GA20ox5 gene. In other cases, the zygosity of an edited GA20ox5 allele was not determined and is therefore designated as "homozygous or heterozygous". However, the edited GA20ox5 alleles present in R0 and R1 plants were removed and segregated away from the edited GA20ox3 alleles in subsequent generations.

TABLE 10

Editing Inversion and Zygosity in R0 and R1 plants for Vector-4

| Edit ID | R1 Plant ID | Editing inversion type | R1 zygosity call for GA20ox3 mutant | GA20ox5 Edit | Genomic Coding Sequence (SEQ ID NO) | Inversion Sequence (SEQ ID NO) |
|---|---|---|---|---|---|---|
| E270933 | P757870 | GA20ox5 SP4-SP5 fragment into GA20ox3 SP1 target site; 6 nucleotide deletion at SP2 | hetero | unknown | 89 | 90 |
| E270933 | P757885 | | hetero | unknown | | |
| E270933 | P758012 | | hetero | unknown | | |
| E270933 | P758049 | | hetero | unknown | | |
| E270933 | P758040 | | hetero | Heterozygous large deletion | | |
| E270933 | P758007 | | hetero | unknown | | |
| E270933 | P757888 | | hetero | Heterozygous large deletion | | |
| E270933 | P757932 | | hetero | Heterozygous large deletion | | |
| E270933 | P757965 | | hetero | unknown | | |
| E270933 | P758046 | | hetero | unknown | | |
| E270933 | P757857 | | hetero | unknown | | |
| E270933 | P757881 | | hetero | unknown | | |
| E270933 | P757925 | | hetero | unknown | | |
| E270933 | P757982 | | hetero | unknown | | |
| E270933 | P757985 | | hetero | Heterozygous large deletion | | |
| E270933 | P758051 | | hetero | unknown | | |
| E270933 | P757886 | | hetero | unknown | | |
| E270933 | P757853 | | hetero | unknown | | |
| E270933 | P757904 | | hetero | unknown | | |
| E270933 | P757956 | | hetero | unknown | | |
| E270933 | P757970 | | hetero | unknown | | |
| E270933 | P757987 | | hetero | unknown | | |
| E270933 | P757962 | | hetero | unknown | | |
| E270933 | P757949 | | hetero | unknown | | |
| E270933 | P758001 | | hetero | unknown | | |
| E270933 | P758004 | | hetero | unknown | | |
| E271059 | P758336 | donor template fragment into GA20ox3 SP1 target site; 9 nucleotide deletion at SP2 | hetero | Homozygous or heterozygous small deletion | 91 | 92 |
| E271059 | P758342 | | hetero | Homozygous or heterozygous small deletion | | |
| E271059 | P758343 | | hetero | Biallelic for small deletions; T-DNA insert | | |
| E271059 | P758349 | | hetero | Homozygous or heterozygous small deletion | | |
| E271059 | P758352 | | hetero | Homozygous small deletion | | |
| E271059 | P758354 | | hetero | Homozygous or heterozygous small deletion | | |
| E271059 | P758355 | | hetero | Homozygous small deletion | | |

TABLE 10-continued

Editing Inversion and Zygosity in R0 and R1 plants for Vector-4

| Edit ID | R1 Plant ID | Editing inversion type | R1 zygosity call for GA20ox3 mutant | GA20ox5 Edit | Genomic Coding Sequence (SEQ ID NO) | Inversion Sequence (SEQ ID NO) |
|---|---|---|---|---|---|---|
| E271059 | P758330 | | hetero | Homozygous or heterozygous small deletion | | |

TABLE 11

Editing Inversion and Zygosity in R0 and R1 plants for Vector-5

| Edit ID | Number of R1 Plants | Editing inversion type | R1 zygosity call for GA20ox3 mutant | GA20ox5 Deletion | Genomic Coding Sequence (SEQ ID NO) | Inversion Sequence (SEQ ID NO) |
|---|---|---|---|---|---|---|
| E376333 | 8 | GA20ox5 SP4-SP5 fragment to GA20ox3 SP2; 7 nucleotide deletion at SP1 | hetero | 4 with large GA20ox5 deletion; 1 with small GA20ox5 deletion; and 3 with both. | 93 | 94 |
| E376333 | 17 | | homo | 2 with large GA20ox5 deletion; 1 with small GA20ox5 deletion; 6 with both; and 8 unknown. | | |
| E376333 | 10 | | homo or hetero | unknown | | |
| E376314 | 8 | GA20ox5 SP4-SP5 fragment to GA20ox3 SP2; 6 nucleotide at SP1 | hetero | unknown | 95 | 96 |
| E376314 | 1 | | homo | unknown | | |
| E376314 | 1 | | homo or hetero | unknown | | |

Example 35. Reduced Plant Height of Corn Plants with Edited Allele

Figure 28:
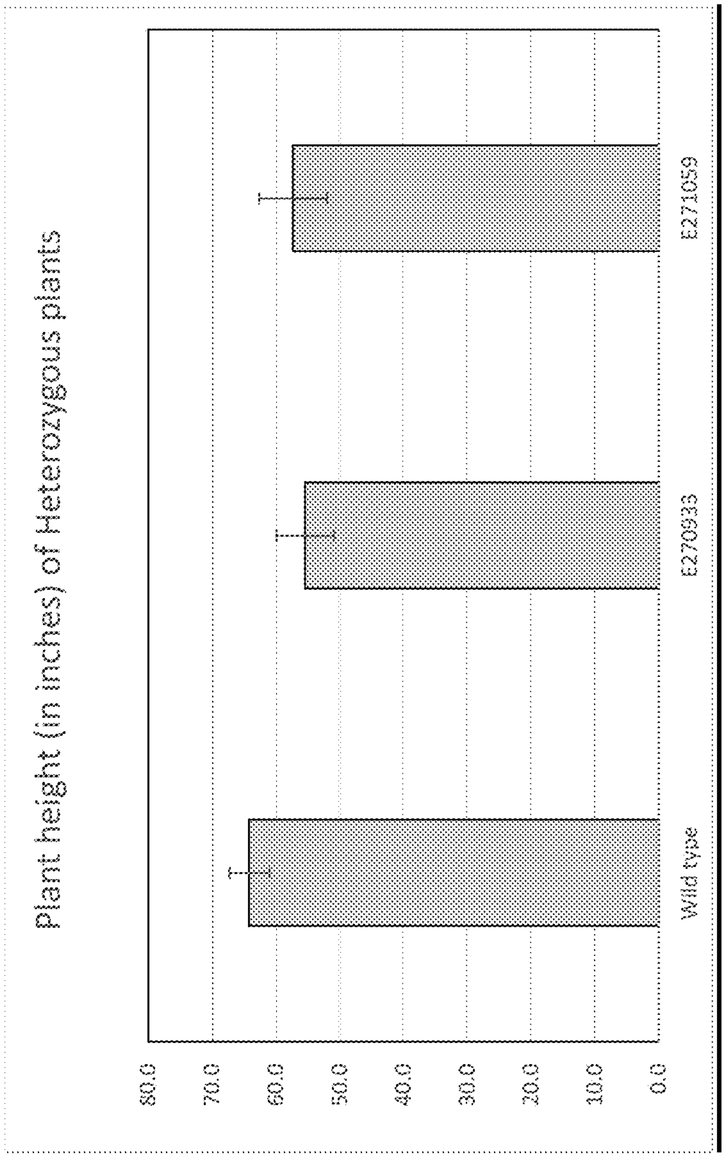
FIG. 28 depicts the average heights of wild type and heterozygous edited corn plants.

R1 corn plants heterozygous for an edited allele of the GA20 oxidase 3 gene with the corresponding inversion identified in Example 34 were grown to maturity to measure their plant heights along with wild type control plants. R1 seeds were planted in soil and grown to maturity in the greenhouse under day/night temperatures of 85° F./70° F. (29.4° C./21.1° C.) and a photoperiod of 16 hours light/8 hours dark using standard nutrient and light conditions for corn plant growth and development. Plant heights (PHT) of these R1 plants were measured at R2 growth stage from the soil level to the base of the uppermost fully expanded leaf. Table 12 provides the plant heights of individual R1 plants heterozygous for one of two hairpin inversion edits, along with wild type control plants. Average plant heights for WT and each edit are also provided (see also FIG. 28 showing the average plant heights with error bars).

These plant heights demonstrate that plants heterozygous for an edited GA20 oxidase 3 allele comprising an inversion sequence have reduced plant heights averaging 54.0 inches or 57.3 inches for the two edited alleles, versus an average plant height of 64.2 inches for the WT control.

The plant height data shown in this example demonstrate that plants heterozygous for an edited allele of the GA20 oxidase 3 gene comprising an antisense inversion sequence have significantly reduced plant heights in comparison to wild type control plants, suggesting that these edited hairpin inversion alleles of the GA20 oxidase 3 gene act in a dominant or semi-dominant manner to produce a reduced plant height phenotype (i.e., semi-dwarf or short stature corn plants), especially since edited loss-of-function alleles of the GA20 oxidase 3 or GA20 oxidase 5 genes alone without an antisense or inversion sequence have been shown to not produce short stature corn plants. See, e.g., Published PCT Application Nos. WO/2019/161149, WO/2019/161147 and WO/2019/161144, the entire contents and disclosures of which are incorporated herein by reference. However, many of these R1 plants may also be homozygous or heterozygous for edited GA20ox5 allele(s) (see Table 10). The presence and zygosity of edited GA20ox5 alleles is unknown for many of the R1 plants, but R1 Plant IDs P758040, P757888, P757932 and P757985 for the E270933 Edit ID were heterozygous for a large deletion in the GA20ox5 gene, R1 Plant ID P758352 was homozygous for a small deletion in the GA20ox5 gene, R1 Plant ID P758343 contained small deletion(s) and a T-DNA insert in the GA20ox5 gene, and P758336 was homozygous or heterozygous for a small deletion in the GA20ox5 gene. Therefore, it is possible that additional mutation(s) in the GA20ox5 gene could also have an effect on R1 plant height. Further plant height measurements will be made in subsequent generations having the edited GA20ox5 alleles removed to confirm the shorter plant height phenotype.

TABLE 12

Plant Heights of R1 plants heterozygous for edited inversion alleles of Zm.GA20ox3

| Edit ID | R1 Plant ID | Plant height (inches) |
|---|---|---|
| E270933 | P757870 | 56.25 |
| E270933 | P757885 | 49.75 |
| E270933 | P758012 | 55 |
| E270933 | P758049 | 48.5 |
| E270933 | P758040 | 54.5 |
| E270933 | P758007 | 62 |
| E270933 | P757888 | 58 |
| E270933 | P757932 | 58 |
| E270933 | P757965 | 52.75 |
| E270933 | P758046 | 56.5 |
| E270933 | P757857 | 61.5 |
| E270933 | P757881 | 63.5 |
| E270933 | P757925 | 53.25 |
| E270933 | P757982 | 56.75 |
| E270933 | P757985 | 50.25 |
| E270933 | P758051 | 50.5 |
| | Edit ID E270933 Average | 55.4 |
| E271059 | P758352 | 54 |
| E271059 | P758343 | 54.5 |
| E271059 | P758336 | 63.5 |
| | Edit ID E271059 Average | 57.3 |
| Wild type | WT1 | 63.5 |
| Wild type | WT2 | 63.75 |
| Wild type | WT3 | 68.5 |
| Wild type | WT4 | 61 |
| | Wild type Average | 64.2 |

Example 36. Collection of Samples from R2 or R3 Plants for Molecular Assays

For the E270933 inversion edit from the Vector-4 construct, a R1 plant heterozygous for the E270933 edit (P757982) was selfed (self-pollinated) to obtain selected homozygous R2 plants, which were themselves either (i) self-pollinated to produce homozygous inbred R3 plants or (ii) crossed to another elite parental line to produce heterozygous hybrid R3 plants. For the E376333 inversion edit from the Vector-5 construct, a R1 plant homozygous for the E376333 edit (P127584) containing a large deletion in the GA20ox5 gene was either (i) self-pollinated to produce homozygous inbred R2 plants or (ii) crossed to another elite parental line to produce heterozygous hybrid R2 plants. Edited GA20ox5 alleles present in R1 plants were removed in R2 and R3 plants by segregation and selection. The R3 plants containing the E270933 edit, the R2 plants containing the E376333 edit, and wild type control plants of the same parental lines, were grown under standard conditions in the greenhouse and sampled at V2 growth stage for the molecular assays described below. The plants were cut just above the soil level and the entire above-ground portion of the plants were placed in 50 mL conical tubes and immediately frozen in liquid nitrogen. Each sample contained one or two sibling plants of the same genotype. The number of samples for each assay and genotype are provided in Table 13. The frozen samples were milled and used for the small RNA and GA hormone assays described in Examples 37 and 38 below.

TABLE 13

Description of samples for small RNA and GA hormones assays.

| Editing Construct ID | Edit ID | Parental elite line(s) | Number of samples for small RNA assay | Number of samples for GA hormone assay |
|---|---|---|---|---|
| Vector-4 | E270933 | Hybrid | 8 | 10 |
| Vector-5 | E376333 | Hybrid | 5 | 5 |
| Vector-4 | E270933 | Inbred | 9 | 10 |
| Vector-5 | E376333 | Inbred | 9 | 10 |
| Hybrid Wild type | | | 1 | |
| Inbred Wild type | | | 2 | |

Example 37. Detection of Small RNAs in Plants Having an Edited Inversion Allele To generate small RNA libraries for sequencing, Illumina's TruSeq small RNA Library Preparation Kit was used according to the manufacturer's protocol (Document #15004197v02) with a modification at the library purification step. Samples of each genotype for this small RNA assay experiment are identified in Example 36 above. After amplification of cDNA, individual libraries were gel purified using a 6% Novex TBE PAGE gel for size separation. The gel was stained with 1×SYBR Gold for 20 minutes. The final library product was sequenced on Illumina's NextSeq platform with a minimum depth of 3 million reads per sample. After sequencing, reads were processed through the following steps: the sequencing adapters were trimmed; reads matching housekeeping noncoding RNAs were removed; and libraries were normalized to reads per million. Between 1 and 9 samples per genotype were assayed.

mRNAs expressed from the edited GA20 oxidase 3 genes containing the E270933 and E376333 inversion edits were predicted to produce a hairpin or stem-loop RNA structure comprising the inversion sequence and the native sequence in the GA20 oxidase 3 gene that is complementary and could hybridize to the inversion sequence. Since double stranded RNA hairpins or stem-loop structures can trigger RNA interference (RNAi) and suppression of genes encoding identical or homologous RNA sequences, plants containing the inversion edits were assayed for the presence of small RNAs. RNAi would be expected to produce small RNAs of about 21 nucleotides in length (21-mers) from the stem of the stem-loop structure consisting in this example of the GA20ox5 inversion sequence and the GA20ox3 native sequence.

Figure 29:
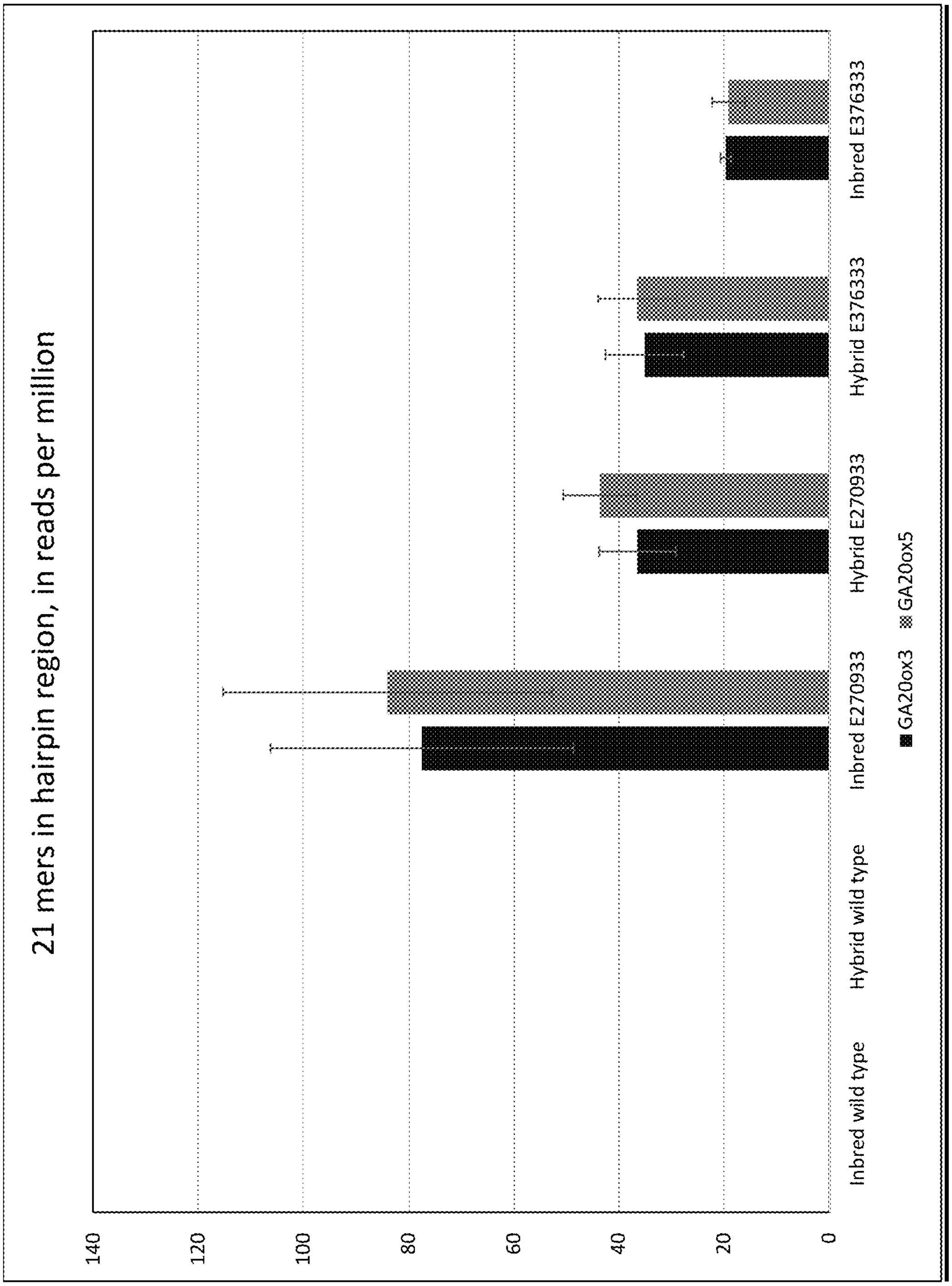
FIG. 29 depicts the number of 21-mer small RNAs (Y-axis) per million reads that mapped to the regions in the stem of the edited stem-loop comprising the inversion sequence from GA20ox5 and a corresponding sequence of the edited GA20ox3 gene that were detected in samples from plants containing edited GA20ox3 alleles.

As shown in FIG. 29, small 21-mer RNAs corresponding to the regions in the stem of the edited stem-loop comprising the inversion sequence from GA20ox5 and a corresponding sequence of the edited GA20ox3 gene were detected in samples from plants containing the edited GA20ox3 alleles indicating the presence of small RNAs in tissues from these edited plants, which were not present in wild type control plants. The abundance of these small RNAs was measured as the number of reads per million total sequencing reads. Small RNAs were present in inbred plants homozygous for the edited allele and hybrid plants heterozygous for the edited allele, with these small RNAs ranging between 19 and 84 reads per million. The abundance of small RNAs appeared consistent with the number of copies of the edited GA20ox3 allele given that heterozygous hybrid plants produced fewer small RNAs than the homozygous inbred plants.

The presence in these samples of small RNAs corresponding to the edited complementary stem region of the edited GA20ox3 gene is consistent with the edited GA20ox3 inversion allele triggering RNAi suppression of the GA20ox3 gene and possibly also the GA20ox5 gene. Additional experiments will determine whether the levels of GA20ox3 and/or GA20ox5 mRNA transcripts are reduced in plants homozygous or heterozygous for edited GA20ox3 or GA20ox5 alleles containing an inversion sequence, relative to controls.

Example 38. Detection of GA Hormones in Plants Having an Edited Inversion Allele Reduced expression of GA20 oxidase genes can alter the levels of GA hormones in corn plants, which can in turn affect plant height with lower levels of active GAs potentially reducing plant height. The levels of bioactive GA hormones and their precursors were measured in plants containing the edited GA20ox3 alleles. GA20 oxidase is active in the GA biosynthetic pathway and catalyzes the sequential oxidation of metabolic intermediates GA12 and GA53 into GA9 and GA20, respectively (the "early 13-hydroxylation pathway" and "non 13-hydroxylation pathway"). The primary bioactive forms of GA include GA1, GA3 and GA4, which are further downstream of GA20 oxidase activity and the GA9 and GA20 intermediates in the biosynthetic pathway. A reduction or suppression of the expression level and/or enzymatic function of GA20 oxidase genes, as may be expected with the GA20ox3 inversion edits, may result in reduction of downstream metabolites (GA20 and GA9) and accumulation of upstream precursors (GA53 and GA12).

For this experiment, samples were collected as provided in Example 36 above. Freshly frozen plant sample tissues were extracted and cleaned using Waters solid phase extraction MAX cartridge plate. GA hormones and two internal standards were analyzed using UPLC coupled with an ABSciex 5500 Mass Spectrometry with MRM method. The final GA hormone values were calculated based on the calibration curve with ABSciex software Multi-Quan. Each GA hormone calibration curve was in good linear fit, the R2 linear regression was >0.99. The eight technical controls per 96-well plate for each hormone were also included and evaluated in analytical process for meeting the standard criterion. GA levels were measured in terms of pmol/gram of sample tissue.

Figure 30:
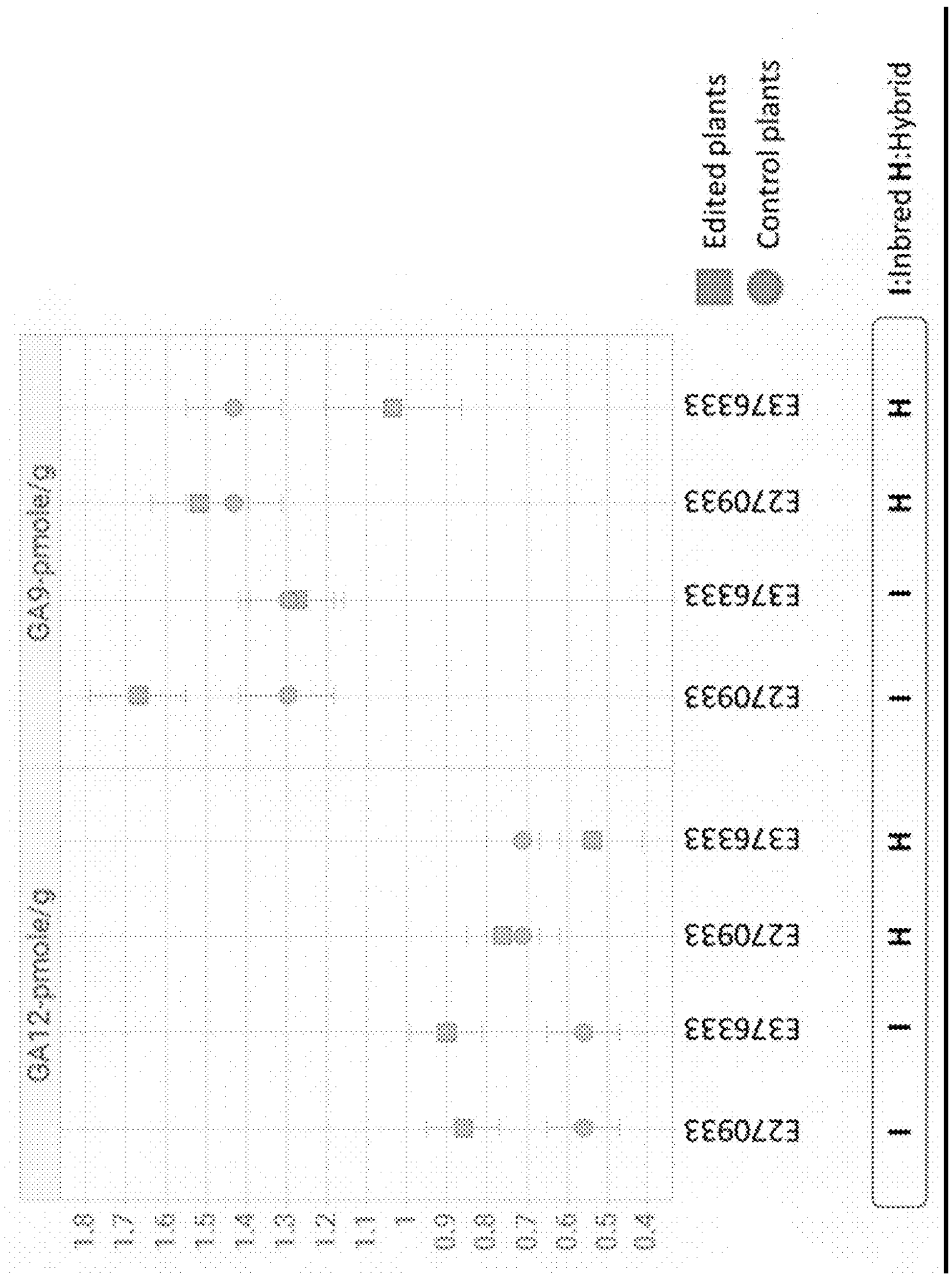
FIG. 30 depicts the concentrations of GA12 and GA9 in pmole/g (Y-axis) in edited and control corn plants.

As shown in FIG. 30, the levels of GA12 were increased in inbred plants homozygous for the edited allele (E270933 and E376333) but were statistically neutral or unchanged in hybrid plants heterozygous for the edited E270933 and E376333 alleles, relative to wild type control plants. As further shown in FIG. 30, the levels of GA9 were increased in inbred plants homozygous for one of the edited alleles (E270933) but neutral in inbred plants homozygous for the other edited allele (E376333), and the levels of GA9 were neutral (E270933) or decreased (E376333) in hybrid plants heterozygous for the edited allele, each relative to wild type control plants.

Figure 31:
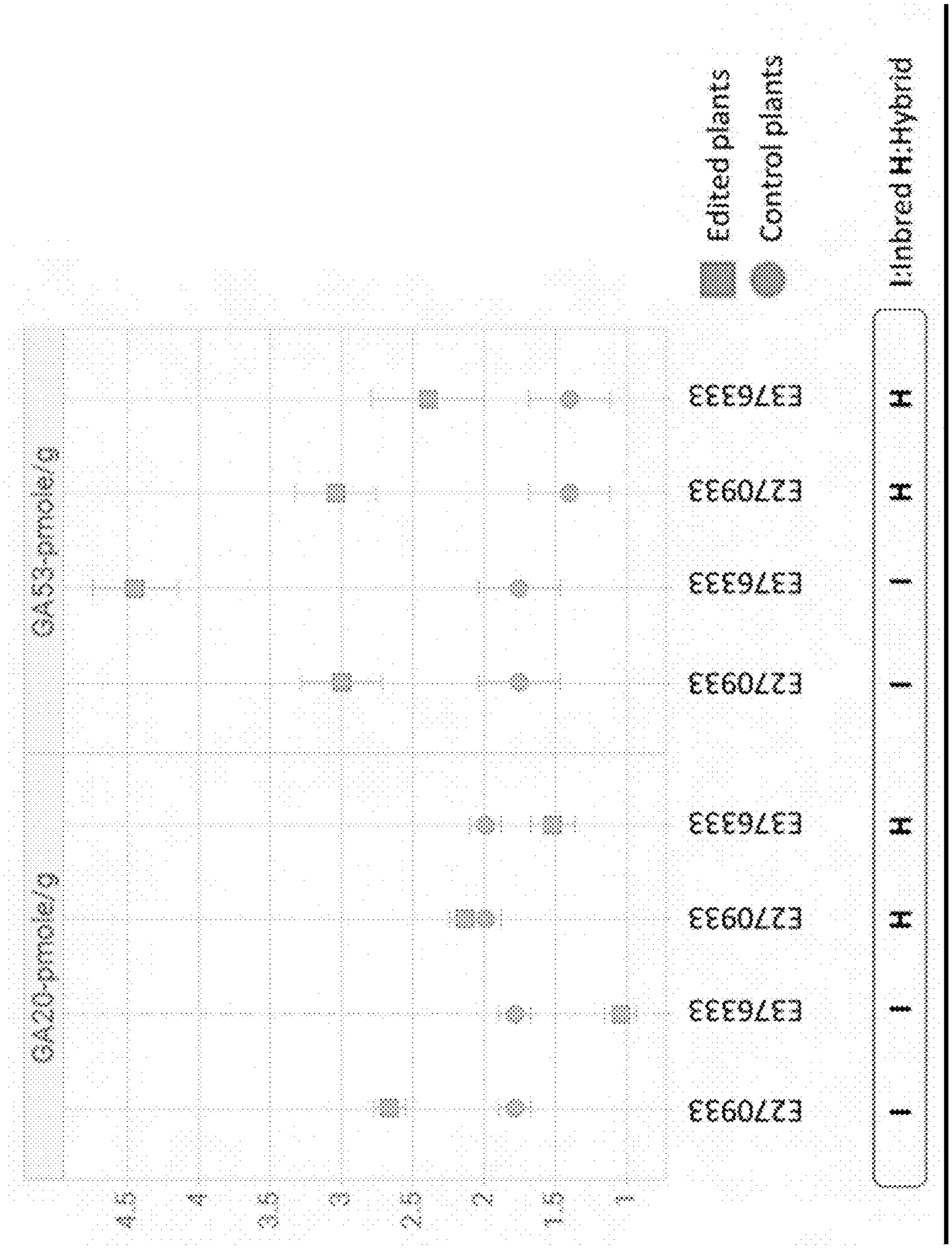
FIG. 31 depicts the concentrations of GA20 and GA53 in pmole/g (Y-axis) in edited and control corn plants.

As shown in FIG. 31, the levels of GA20 were decreased in inbred plants homozygous for one of the edited alleles (E376333) but were increased in inbred plants homozygous for the other edited allele (E270933), and the levels of GA20 were neutral (E270933) or decreased (E376333) in hybrid plants heterozygous for these edited alleles, each relative to wild type control plants. As further shown in FIG. 31, the levels of GA53 were increased in inbred plants homozygous for each edited allele (E270933 and E376333) and in hybrid plants heterozygous for each edited allele (E270933 and E376333), relative to wild type control plants.

Figure 32:
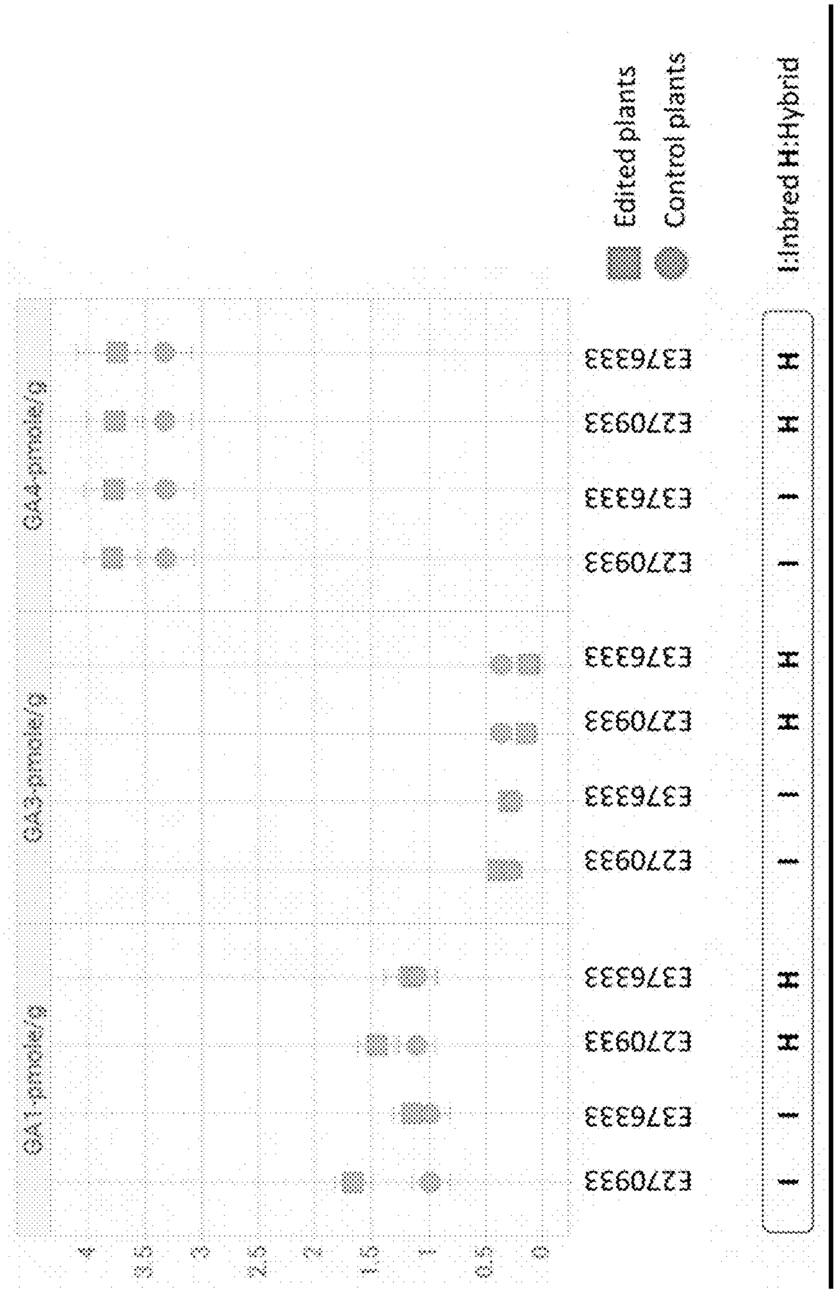
FIG. 32 depicts the concentrations of GA1 and GA3 and GA4 in pmole/g (Y-axis) in edited and control corn plants.

FIG. 32 provides the results for levels of active GAs (GA1, GA3 and GA4) measured in samples collected at V2 growth stage of the edited inbred and hybrid plants relative to wild type controls. As shown in FIG. 32, the levels of these active GAs were generally not statistically changed in the inbred and hybrid plants containing each of the edited alleles (E270933 and E376333), except for a small increase in GA4 in inbred plants homozygous for one of the edited alleles (E270933).

These data support the theory that the edited GA20 oxidase 3 gene containing an inversion sequence and encoding a transcript that may form a RNA stem-loop structure is able to affect the levels of GA hormones in inbred and hybrid plants containing the edited alleles. While the data in this experiment are mixed, there is support for increased accumulation of the GA12 and GA53 precursors upstream of GA20 oxidase activity and decreased levels of GA9 and GA20 products of GA20 oxidase activity in plants containing the edited GA20 oxidase 3 allele, although some samples had increased levels of the downstream GA9 and GA20 products. Greater support for decreased GA20 oxidase expression and/or activity with the edited GA20 oxidase 3 alleles is provided in this example by the accumulated levels of upstream GA12 and GA53 precursors. GA12 was neutral to increased in samples from plants with the edited GA20 oxidase 3 allele, and GA53 was increased across all samples from plants having the edited GA20 oxidase 3 allele.

Although the levels of bioactive GAs were not shown to be reduced in this example, this may be due to the early V2 growth stage when the plant tissue samples were collected. The pattern of expression from the endogenous GA20 oxidase 3 locus of transcripts containing the inversion, antisense or stem-loop sequence is also dependent on the endogenous GA20 oxidase 3 gene promoter, which may not drive expression (or expression at a sufficiently high level) at the V2 growth stage to produce a measurable effect on the levels of GA hormones. Without being bound by theory, it is possible that expression of an inversion/hairpin-containing transcript from an edited allele of an endogenous GA20ox3 or GA20ox5 gene under the control of the respective GA20ox3 or GA20ox5 endogenous promoter may be greater at later stages of development and thus have a greater effect on the level(s) of GA hormones at those later stages. The active GAs are also further downstream and not a direct product of GA20 oxidase activity. Future experiments will determine if lower active GA levels are observed at later stages of development in plants heterozygous or homozygous for an edited GA20 oxidase 3 or GA20 oxidase 5 allele. This is supported by the altered levels of GA precursors observed in this example at the early V2 growth stage.

Having described the present disclosure in detail, it will be apparent that modifications, variations, and equivalent aspects are possible without departing from the spirit and scope of the present disclosure as described herein and in the appended claims. Furthermore, it should be appreciated that all examples in the present disclosure are provided as non-limiting examples.

What is claimed is:

1. A method of generating a dominant negative allele of a gene in a cell comprising inverting a portion of the gene using a targeted editing technique, wherein the inversion results in the production of an antisense RNA transcript under the control of the native promoter of the gene, wherein the antisense RNA transcript is capable of triggering suppression of an unmodified allele of the gene, wherein the dominant negative allele is not exogenously introduced, wherein the gene is a GA20 oxidase gene, and wherein the GA20 oxidase gene is encoded by an mRNA that encodes a protein having at least 95% sequence identity to a sequence selected from the group consisting of SEQ ID NO: 30 and SEQ ID NO: 35.

2. A method of generating a dominant negative allele of a gene in a cell comprising inverting a portion of the gene using a targeted editing technique, wherein the inversion results in the production of an antisense RNA transcript under the control of the native promoter of the gene, wherein the antisense RNA transcript is capable of triggering suppression of an unmodified allele of the gene, wherein the dominant negative allele is not exogenously introduced, and wherein the unmodified allele comprises a polynucleotide sequence having at least 95% identity or complementarity to a sequence selected from the group consisting of SEQ ID NOs: 1, 12, 27, 28, 29, 31, 32 and 33.

3. A method of generating a dominant negative allele of a first gene in a cell comprising deleting a second gene with a native promoter that is positioned in the opposite orientation relative to the first gene using a targeted editing technique, wherein the deletion results in the production of an antisense RNA transcript of the first gene under the control of the native promoter of the second gene, wherein the dominant negative allele is not exogenously introduced, wherein the first gene is a GA20 oxidase gene, and wherein the GA20 oxidase gene is encoded by an mRNA that encodes a protein having at least 95% sequence identity to a sequence selected from the group consisting of SEQ ID NO: 30 and SEQ ID NO: 35.

4. A method of generating a dominant negative allele of a first gene in a cell comprising deleting a second gene with a native promoter that is positioned in the opposite orientation relative to the first gene using a targeted editing technique, wherein the deletion results in the production of an antisense RNA transcript of the first gene under the control of the native promoter of the second gene, wherein the dominant negative allele is not exogenously introduced, and wherein the unmodified allele comprises a polynucleotide sequence having at least 95% identity or complementarity to a sequence selected from the group consisting of SEQ ID NOs: 1, 12, 27, 28, 29, 31, 32 and 33.

5. A modified plant cell comprising a non-transposon mediated genome deletion or inversion of a gene, or a portion thereof, at the endogenous locus of the gene, wherein the deletion or inversion results in the production of an antisense RNA transcript of the gene, or portion thereof, wherein the RNA transcript is under the control of a native promoter and was not exogenously introduced, wherein the gene is a GA20 oxidase gene, and wherein the GA20 oxidase gene is encoded by an mRNA that encodes a protein having at least 95% sequence identity to a sequence selected from the group consisting of SEQ ID NO: 30 and SEQ ID NO: 35.

6. A modified plant cell comprising a non-transposon mediated genome deletion or inversion of a gene, or a portion thereof, at the endogenous locus of the gene, wherein the deletion or inversion results in the production of an antisense RNA transcript of the gene, or portion thereof, wherein the RNA transcript is under the control of a native promoter and was not exogenously introduced, and wherein the unmodified allele comprises a polynucleotide sequence having at least 95% identity or complementarity to a sequence selected from the group consisting of SEQ ID NOs: 1, 12, 27, 28, 29, 31, 32 and 33.

* * * * *

SEQUENCE LISTING

<160> NUMBER OF SEQ ID NOS: 101

<210> SEQ ID NO 1
<211> LENGTH: 7139
<212> TYPE: DNA
<213> ORGANISM: Zea mays

<400> SEQUENCE: 1
gctctgccac tctgctgagg tggggggaga ggagctcccc ctccctcctc tcccctcctc 60
gccatgtcta gcagcgaccc ggaggagatc agggcgcgcg tcgtcgttct cggttcgccc 120
catgccgacg gcggcgacga gtgggcccgg cccgagctcg aggccttcca tctgccgtct 180
cccgcccacc agcctcctgg cttcctagcc gggcaaccgg aagcagcaga gcaacccacg 240
ctccctgctc ctgctggccg cagcagcagc agcagcaaca cgcctactac atctgccggt 300
ggcggcgctg ctcctcctcc tccttcttcg cctccccctc cgccggcttc tctggagacc 360
gagcagccgc ccaatgccag gccagcctcc gccggcgcca atgacagcaa gaagcccacc 420
ccgcccgccg ccctgcgcga cctcttccgc ttcgccgacg gcctcgactg cgcgctcatg 480
ctcatcggca ccctcggcgc gctcgtccac gggtgctcgc tccccgtctt cctccgcttc 540
ttcgccgacc tcgtcgactc cttcggctcc cacgccgacg acccggacac catggtccgc 600
ctcgtcgtca agtacgcctt ctacttcctc gtcgtcggag cggcaatctg ggcatcctcg 660
tgggcaggta cgctatccct cctcctcctg ccgccccagc ttgtgtgcgt cgcgaattgg 720
cggtcaattt ggattggatg acaaatcacg tcggtcagcc aatcgccgtg gctacaaacg 780
agatgttcaa atcgttcgcc ccgctcgcaa gagatctctt gctggatgtg gaccggcgag 840
cggcagtcga cgcggatgcg gattcggtac ctggacgcgg cgctgcggca ggacgtgtcc 900
ttcttcgaca ccgacgtgcg ggcctcggac gtgatctacg ccatcaacgc ggacgccgtg 960
gtggtgcagg acgccatcag ccagaaactg ggcaacctca tccactacat ggccaccttc 1020
gtggccggct tcgtcgtggg gttcacggcc gcgtggcagc tggcgctggt cacgctggcc 1080
gtggtgccgc tcatcgccgt catcggcggg ctgagcgccg ccgcgctcgc caagctctcg 1140
tcccgcagcc aggacgcgct ctcgggcgcc agcggcatcg cggagcaggc gctcgcgcag 1200
atacggatcg tgcaggcgtt cgttggcgag gagcgcgaga tgcgggccta ctcggcggcg 1260
ctggccgtgg cgcagaggat cggctaccgc agcggcttcg ccaaggggct cggcctcggc 1320
ggcacctact tcaccgtctt ctgctgctac gggctcctgc tctggtacgg cggccacctc 1380
gtgcgcgccc agcacaccaa cggcgggctc gccatcgcca ccatgttctc cgtcatgatc 1440
ggcggactgt aaggcccacc acaccacgca ctctctcctt ctgctgtcct cggccgcccc 1500
cgtcgtcatt gctgctgacg gtatctgtgg atcgcgtgca ggcctcggca gtcggcgccg 1560
agcatggccg cgttcgccaa ggcgcgtgtg gcggctgcca agatcttccg catcatcgac 1620
cacaggccgg gcatctcctc gcgcgacggc gcggagccag agtcggtgac ggggcgggtg 1680
gagatgcggg gcgtggactt cgcgtacccg tcgcggccgg acgtccccat cctgcgcggc 1740
ttctcgctga gcgtgcccgc cgggaagacc atcgcgctgg tgggcagctc cggctccggg 1800
aagagcacgg tggtgtcgct catcgagaga ttctacgacc ccagcgcagg tatacctagt 1860
actgttacta cttttagcgc attaatctga ggatgtccag ttcgcttgct tgccaatcgc 1920
cattgccatc gcaacaacaa tacttcgcca actgccattg ctgggtagat tagtacagta 1980
gcagttagaa gaagcctcca ctgtacattg cattgccaaa caaaagtgaa ttgtgcagta 2040
actctgtacc accacattga catggaaatg aagtgaatgc ttggagcatg cagagctggc 2100

```
cggcctcatg ggctgctgct acctgctagc tagccaacca gaaccagcca tcctctttct   2160
tgcttttctt tttactttct ttggtcgtgg ctgtttgtgg tcatacatac attcacgcag   2220
agcagaagag ctagctaagc taggtgggtg tgcctgcaac gcgggacaaa gaaaactatt   2280
tgttgcctgg caagatgcta ctgttgccta gcacatgcct gccattgacc gactgctcag   2340
tgagaagtgg ttcagttgtg ctgttgacag tatagataga tatatatagt agccctgtag   2400
attttttttt cagacaaaaa aagaagaaga acgagatgaa gtctgcaatt cggttttggc   2460
agggcaaatc ctgctggacg ggcacgacct caggtcgctg gagctgcggt ggctgcggcg   2520
gcagatcggg ctggtgagcc aggagccggc gctgttcgcg acgagcatca gggagaacct   2580
gctgctgggg cgggacagcc agagcgcgac gctggcggag atggaggagg cggccagggt   2640
ggccaacgcc cactccttca tcatcaaact ccccgacggc tacgacacgc aggtccgtcc   2700
cgtatagcta gctcactagc tgcactgcca cttctctcgc ttgctccccc accgttgctg   2760
cctgttgctc tccaatccac ttgtcggtgt ctggaccaca cgtgctgctt gcctagctgc   2820
tccacatctg ctttccctgt ccaaccttat gcaactcact ctaatactat atcaaataca   2880
tttctagagt ttaaagctta tcttagaata aatgcatctt tagctacgag acaacctaac   2940
ttcagttgtt gttgttgttt tttttacttt ctctcttctc acaaatacta tgattacgtc   3000
tttacagcga tctttttttat tccaaaccta aaaatgcatg cactcactct aaaagcgcaa   3060
agggagcatc ttttttttccc ccatcatctg cacgcagcct tttcttttcc tcatgtcacg   3120
aagggactga aggtgtgtat gcagcgtcaa gtcatccatc cgttccactc cactcactca   3180
tgcgtcgcgc actctgcgct cgtgcctgcc cggggctaaa gctttagtag ctagcctcag   3240
atcagatact gttcgtgttt gttaggccgc ggcagctgca catgagctca tgacagccgg   3300
cagcaccacc accaacgcca tggaagaggg gtcggggtcc atcacataga cataatgcct   3360
gttgtagact aggacgggag ggcaattgtt aggcgcctgt tgccatcgca tttgctgctg   3420
tgggttgcca acaagtaaca tgccaggatg ctttgctatc acgcacagga caggagaggt   3480
ccttttttctc gacacaagct ctacagcctc tactaaacta gcacttgctg atgagtgcag   3540
aggatgaatg gacgatgaac atctagagtg agagagaaaa aaatgttaat aataataaaa   3600
agtagtagca ggattaagaa tcaacctggg gtacgtagga agaggtacaa tccctaggaa   3660
tctagagtat gagaagtatg ggaggagttg ggggagtgaa acggaacaaa ttccgagttg   3720
gtattttgtc gggaatgtca agttgatttt tgatcctagt gcaagcaaga attatcaatc   3780
actcagactc agcctgtctg tgtctgtcca ccccagctct tgctactcta cttactactg   3840
tgctactagt gggtagggta ggtatcttac ataaactgtt attataaact gtcatctgag   3900
aaagagagcc agtcaaaccc atgctgctgc ttattttaat cactgtcaaa tggcaggcag   3960
gcaggcagtc tggttagtta ataacatctg ggaagggttt aatcaaacca aatcaaatca   4020
gacgaaatct agaggccaca tgggatgggg ccatatgtac tgtactagca taactagcgg   4080
ctagatttta ttagaacacg gactcacact cccataacta taactgactt gatcatgatt   4140
ccttgccaag caatgctcgc atgcccatgc atgcatcatc cctggtcaaa ctcaaacact   4200
ctccaccgtc agggaataag acttattatt ttattaacaa ttcaattttt atttattaat   4260
tacgtctgga cgaggagtac tggtttattt gatgagagac atggcagtcc aagtcaaact   4320
cgtttgtctg accatggcgg tgatggccgg tgcaggttgg ggagcgcggc ctgcagctct   4380
ccggtgggca gaagcagcgc atcgccatcg cccgcgccat gctcaagaac cccgccatcc   4440
```

tgctgctgga cgaggccacc agcgcgctgg actccgagtc tgagaagctc gtgcaggagg 4500
cgctggaccg cttcatgatg gggcgcacca cccttggtga tcgcgcaaca ggctgtccac 4560
catccgcaaa ggccgacgtg gtggccgtgc tgcagggcgg cgccgtctcc gagatgagcg 4620
cgcacgacga gctgatggcc aagggcgaga acggcaccta cgccaagctc atccgcatgc 4680
aggagcaggc gcacgaggcg gcgctcgtca acgcccgccg cagcagcgcc aggccctcca 4740
gcgcccgcaa ctccgtcagc tcgcccatca tgacgcgcaa ctcctcctac ggccgctccc 4800
cctactcccg ccgcctctcc gacttctcca cctccgactt caccctctcc atccacgacc 4860
cgcaccacca ccaccggacc atggcggaca agcagctggc gttccgcgcc ggcgccagct 4920
ccttcctgcg cctcgccagg atgaactcgc ccgagtgggc ctacgcgctc gccggctcca 4980
tcggctccat ggtctgcggc tccttcagcg ccatcttcgc ctacatcctc agcgccgtgc 5040
tcagcgtcta ctacgcgccg gacccgcggt acatgaagcg cgagatcgca aaatactgtt 5100
acctgctcat cggcatgtcc tccgcggcgc tgctgttcaa cacggtgcag cacgtgttct 5160
gggacacggt gggcgagaac ttgaccaagc gggtgcgcga gaagatgttc gccgccgtgt 5220
tccgcaacga gatcgcctgg ttcgacgcgg acgagaacgc cagcgcgcgc gtgaccgcca 5280
ggctagcgct ggacgcccag aacgtgcgct ccgccatcgg ggaccgcatc tccgtcatcg 5340
tccagaactc ggcgctgatg ctggtggcct gcaccgcggg gttcgtcctc cagtggcgcc 5400
tcgcgctcgt gctcctcgcc gtgttcccgc tcgtcgtggg cgccaccgtg ctgcagaaga 5460
tgttcatgaa gggcttctcg gggacctgg aggccgcgca cgccagggcc acgcagatcg 5520
cgggcgaggc cgtggccaac ctgcgcaccg tggccgcgtt caacgcggag cgcaagatca 5580
cggggctgtt cgaggccaac ctgcgcggcc cgctccggcg ctgcttctgg aaggggcaga 5640
tcgccggcag cggctacggc gtggcgcagt tcctgctgta cgcgtcctac gcgctggggc 5700
tgtggtacgc ggcgtggctg gtgaagcacg gcgtgtccga cttctcgcgc accatccgcg 5760
tgttcatggt gctgatggtg tccgcgaacg gcgccgccga gacgctgacg ctggcgccgg 5820
acttcatcaa aggcgggcgc gcgatgcggt cggtgttcga gacaatcgac cgcaagacgg 5880
aggtggagcc ccacgacgtg gacgcggcgc cggtgccgga cggcccaggg gcgaaggtgg 5940
aacttaagca cgtggacttt ttgtacccgt cgcggccgga catccaagtg ttccgcgacc 6000
tgagcctccg tgcgcgcgcc ggaaaaacgt tggcgctggt ggggccgagc gggtccggca 6060
agagctcggt cctggctctg gtgcagcggt tctacaagcc cacgtccggg cgcgtgctct 6120
tggacggcaa ggacgtgcgc aagtacaacc tgcgggcgct gcggcgcgtg gtggcggtgg 6180
taccgcagga gccgttcctg ttcgcggcga gcatccacga gaacatcgcg tacgggcgcg 6240
agggcgcgac ggaggcggag gtggtggagg cggcggcgca ggcgaacgcg caccggttca 6300
tcgcggcgct gccggagggg taccggacgc aggtgggcga gcgcggggtg cagctgtcgg 6360
gggggcagcg gcagcggatc gcgatcgcgc gcgcgctggt gaagcaggcg gccatcgtgc 6420
tgctggacga ggcgaccagc gcgctggacg ccgagtcgga gcggtgcgtg caggaggcgc 6480
tggagcgcgc ggggtccggg cgcaccacca tcgtggtggc gcaccggctg gccacggtgc 6540
gcggcgcgca caccatcgcg gtcatcgacg acggcaaggt ggcggagcag gggtcgcact 6600
cgcacctgct caagcaccat cccgacgggt gctacgcgcg gatgctgcag cttgcagcgg 6660
ctgacgggcg cggcggccgg gcccgggccg tcgtcctcgt gcaacggggc cgcgtaggac 6720
ggaatggatg gatggatggg tttggttcct cgagagattg atgggtgagg aagctgaagc 6780
tccggatcaa atggtggtac tccatgatcg caacaatgag gggaaaaaag gaaaggagaa 6840
aatacggtgg ttcatatgat tgtacaattt gacgatctgt ttgagtcggg gttttaggat 6900
gatgtaaacc ttcactcgcc tttttttac tcttgtttct catccgcatc agtatcatct 6960
atctacatac agtgtcagag atgggaactg atcccgcatc atcatctacc tcccaaggca 7020
ccccagattg tattaatgta cttagttagc ctgttttata tatacttata agtaccaaat 7080
agcagaattt tactccttat ctgcagtagc acgaaagaaa aaaaaaaaaa gctaaacct 7139

<210> SEQ ID NO 2
<211> LENGTH: 5845
<212> TYPE: DNA
<213> ORGANISM: Zea mays
<220> FEATURE:
<221> NAME/KEY: misc_feature
<222> LOCATION: (4245)..(4344)
<223> OTHER INFORMATION: n is a, c, g, or t

<400> SEQUENCE: 2
gtcctcctct ggaaaaccac ctcttctcct agacttcttc cgttgcatct tctcttctgt 60
tctccacgac gcagttcggc tgccagacaa aaaccctaaa cgccgccgcc gccgccgctc 120
ttcctcgaga tgggaggcaa gtgcccgcac cgcaaggtaa agaagcgccg cctatcccac 180
aagacggctc gccgcggcaa gttcctcctg aaggccgacg atgccgtcta tgacgagctc 240
gtcaagctgg ccgaccaggg caaggacgct gaagccaagg agctccccgt cgatgaggac 300
ctcccaggcc tgggacagtt ctactgcctc cactgcgagt atgcgcttcc cctctcctct 360
ctttccctcc cttccattcc accggtatgc tatttcttat cctctgccaa tacaggtata 420
tgcccgtacg ttgctagttg taaaaaaaaa cgtttttctc aattcagcat tagtggagca 480
tgtgttttaa ttcattcgtg gtacaaaaaa cacctgacta gcgaatgata atcctgttta 540
tctttgcaaa aactaatttg aatttccatg tgtgcatgaa ttaaaactta ccgtactgtc 600
acacaataag atcttaaaat actggatact cttagtacac aaatgatcca aaagaaagca 660
caattccagc attccagtct ttcgctattt catcatcctc atgtgccaac aattattgtt 720
tgtttccctt cctggacaca cagaaaaatg caatgggatc cagcaccgta attaggccgc 780
aacaaagggt gaaattgtat agggaatttt caagcaccca ctctaggagt ctagggccat 840
caatttggtt tacttcgtca aagaacggat gaaattgaat aagtttcata tctatggtgt 900
aaacatctac tataccgata tgtagaaact gagaactatt cctgctgcac cgactgtaaa 960
gctggcatag ctgaatatgt agagcttctt gttgatgggg atgtctgcaa gagcttaccg 1020
tttggtattt gcattgagaa tggactgtga tttctttctt tgacgtgctt cacaatatcc 1080
aattctctaa ttgggtggtg atgtgtgtgt gtgggggggg gggaccccta ataaatctgc 1140
taaaacctcc ttgaagtctc tatttcaccc gccttttttt cctcccttat ttctaaactt 1200
ttagtactat tttaccttcc cttagttatg tacatctaat aaataccaca atagtggaag 1260
caattactgt ctgtttccac aaaaatagag cattgaggaa ccaatttgtc catcatttgt 1320
tgccacttct aggaagtcgg ttggcaggca catatatcta agctcttaat atatcatatc 1380
aaatagtaaa tatctctaat caacaaaaag ggaaacccca attataaaat ttatcccgta 1440
aatataattt atttttctag ctgtgctcag agagtaaaag caactccaaa agaagatgta 1500
aaccaacctt aaaacagata ttaggaagaa aatgattttc cttgctccaa tagctccctc 1560
atcgccccca aaaaaattgc atcccacatc cgcctcctcc cctcccgcat attttcgcgt 1620
gatccctttc tccccaatct gttcggcgtc tgcgtgcatg caggctcctg tgttttttat 1680
tttgccgcgc gctcatctgt ggccgtgcag accatcaatg agttggtaca gctttcctgc 1740
agcatgtggc gtcgtaggat catcatgctg gatcagcata aaggcccata tacccgccca 1800
tacccaggag caaagccagt tttcagtttt ttagttgttt aaggaaactg ttggagtaca 1860
cactataatt tactcttaat ttttttagaa tgcctccaat aatcattttt ttggggaaac 1920
tttttatcat tcttttggag ttagctggtg ggtcttacag gtctgagctt gctggccaat 1980
ggcagcattg atgaaggtaa tgttactgct aaataggcaa aatccaaatc taagagccca 2040
aagcactggc aattcaatga ccagacttga caaggggcag atcatgacat ggcgagatga 2100
tggacataag atgaactttg caggcttcat ctttagacca tgatatttat ctcatgttta 2160
tccacttata gataaaccct gtttgtggag ccagaagata cacctatatg aaatttgacc 2220
tgttggtatg agaaccagga aaaagcgacc gccctccatt ggtacaagaa tttcagaaca 2280
gagagtcaag agacatctga cagtttgcaa tcacaccatg caaccattgt agcatggaat 2340
ggccaaagac taattatgaa ccaaggaatg atggtgtcaa acttggtcca gtgcatacca 2400
tctaacaaaa cctggtgcag taatagccat tatcatctca caaggacctc ttttctctct 2460
ttacaaaatc taataaggat tctacaaatt ggatacattg taatattgaa taacgcaagc 2520
agaaaggtgt ctgtgtgtct ctgcaatttg tctgtcacaa tgatacaaca acaacaaagc 2580
ctttttgtcc caagcacgtt ggggtaggct agagatgaaa ccccgtatga aaacctcaga 2640
gctcaacccc caaagaacag aaaagggaaa caaaggcaaa ggagaaccga aaacaacgaa 2700
acggggaaac acataaaaga gataaaaccc acaaggacca gcaagatcta aaatggacac 2760
aagaaaaggt caaacgatta aggaggaaaa gcgaaactat caatcagggt tctggcacgt 2820
gaattgcaca cttccacccc ttcctatctg cggcgagctc tttatcaata ttccactcct 2880
tcaggtctct cttcacagcc tctgtccacg tcaaagttgg tcggcctcta cctctcttca 2940
cattttcggg acgcctaatt attccgatat gcactggtgc ctcttcaggt cttcgttgga 3000
tatgtccaaa ccatctcaag cgatgttgca taagcttctc ctcaattggc gccactccta 3060
ctctctctcg tatatcatca ttccggactc gatctctcct tgtgtggcca catatccagc 3120
gcaacatacg catctctgcc acacttagtt gttggacatg tcgtctttta gtgggccaac 3180
attctgctcc atacaacata gccggccgga ttgttgtcct gtagaatttg ccttttagtt 3240
tgcgtggcac ccggtggtcg cataagacac ccgcagcttg tcgccacttc aaccatccgg 3300
ctttaattct atgactgaca tcctcatcga tgtctccctc cttttgaagc attgatccta 3360
agtaacgaaa agtgtctttc ttgggtacca cttgcccatc aagactaaca tcgccatcct 3420
catacccccat ggcactgaaa tcacacttca tatactctgt tttagaccta ctaagcctaa 3480
aacctttttgc ttccagcgtc tgcctccaca attccaactt ttgagaaaca ccactcctac 3540
tctcctcaat aagtaccaca tcatcggcaa aaagcataca ccacggtaaa actccttgta 3600
tgtcccttgt gacctcatct atcaccaaag cgaaaagata agggctcaaa gccgaccctt 3660
gatgtagtcc tatgttaatt ggaaagtcat cggtgtctcc atcacttgtt cggacacttg 3720
tcacaacatt agtgtacata tctttaataa gattaatgta ctttgttgct actttgtgtt 3780
tttccaaggc ccaccacatt acactcctag gtactttgtc ataagccttc tccaagtcta 3840
tgaagaccat atgcaggtct ttcttttgtt ctctgaatct ctccataagt tgtcttagta 3900
agaaaatggc ctccatagtt gatctcccgg gcatgaaacc aaactgattt tgggtcacgc 3960
tcgtcatctt tcgcaggcgg tgttcaatga ctctctccca tagcttcatt gtatggctca 4020
tgagcttaat tccacggtaa ttagtacaac tttgaacatc tcctttgttc ttgaagattg 4080

```
gtactaatgt actccgccgc cactcgtcgg gcattctgtt tgcccgaaag atggtgttga   4140

aaagcttagt cagccatact atcgctatgt ctccaagaca tctccatacc tcgataggga   4200

taccatcagg gcccatcgcc tttcctacct tcatcctttt tagcnnnnnn nnnnnnnnnn   4260

nnnnnnnnnn nnnnnnnnnn nnnnnnnnnn nnnnnnnnnn nnnnnnnnnn nnnnnnnnnn   4320

nnnnnnnnnn nnnnnnnnnn nnnntctttt tagtggtaga agatcatacg agctgttcct   4380

gaactctctt gtattgtctt atcagcaaac gatagggcaa tttcagtgag ttacggttgg   4440

ttcatttgat gaattagttg tatggaagtg cacagtttat aagatgctgc tagtttttgt   4500

gttgatatta ataaactgag tgtttcagtt gagttgtctg gtatagagta aaatggtgaa   4560

atttggttga tgtttttgtg atttaatgct tcctggaatt tatgatagta gatgccttga   4620

attgatttag agggattagc aaaactgtgg ctacacttta aggtgtgatt gctggcgtta   4680

caatgcttgt gatgagaact gcacttatct tgtaaatgtg gtagctatat tctaatctcc   4740

tactgctaat cgatatatat ctggtattgg ctttggctgc agtcgctact ttgcaagtga   4800

aagcgtgaag gatgatcact accgctcaaa gcgccacaag aaaaggtgat ccattctgtt   4860

tgctctaagt ctaagtaata tcacggtaat catcattcat agataacatt aaagaaaaaa   4920

ctatcctgaa cacatttgat ttatgctacc agtttgattg gcaaacatgt aatgacctgc   4980

acttataagc tgtttggttt gaggaatgat ctagtccatc gtcttctcac tcctcacttt   5040

tttgtttggt ttgtggaatg gattgagttg atccatcatc gcctcattcc ttatagttat   5100

ttagttagta ctaatatgag gaatgaggtc atccaaccaa atttgaggaa tggatccatg   5160

atgcatcact acattttgga tgaaatgatt cctcaaacca aacacctcct tagagagcat   5220

ctccaacaag aagttctata tttgagtcct aaaaaattaa aataggacct gattttaagt   5280

gttcaggacc acaaaaacat ttgcagctcc aacggttgag tcctataacc agttgataaa   5340

acttggaggg accttgttgt gtggttctat atgacaccat aactaaatta gtgttgatca   5400

tgcgatagta actaaattag tgttggacct tgttgtgtgg ttcgataact aaattaccag   5460

tatgaccttt cccgtcggca gaccatgtga gaaatgtggt ataggacagg ttctggtaca   5520

cgtgagtgga ataattccga cctgctgtgg cgtgtgcctg tctctaatca caggcttcgg   5580

atgattgtag ggttaaggta atgtctggac cggccccgca cacgcagctt gatgcagaac   5640

tcgctgcagg gatgggaaag cctgacaacg gcctgaagct catgtccatg tgaaggaacc   5700

tcttgctggt actggtactt gttccgtgcc tttgttgctg ccgtacaatt gaagctgctt   5760

tgcgcagtaa gtaatagcaa gagttatagc agacggtttt tttttgttgt acgcaagact   5820

ttcgaagtgg gtgtaagttg tttta                                         5845
```

<210> SEQ ID NO 3
<211> LENGTH: 20
<212> TYPE: RNA
<213> ORGANISM: Zea mays

<400> SEQUENCE: 3

```
ggcaaucugg gcauccucgu                                                 20
```

<210> SEQ ID NO 4
<211> LENGTH: 20
<212> TYPE: RNA
<213> ORGANISM: Zea mays

<400> SEQUENCE: 4
aucucgagga agagcggcgg 20

<210> SEQ ID NO 5
<211> LENGTH: 30
<212> TYPE: DNA
<213> ORGANISM: Zea mays

<400> SEQUENCE: 5
agcagcctcg ccgttagacc cgtaggagca 30

<210> SEQ ID NO 6
<211> LENGTH: 50
<212> TYPE: DNA
<213> ORGANISM: Zea mays

<400> SEQUENCE: 6
ccctccgttc acgggcgtgg cgttccattt cttcgcggcg gatagggtgt 50

<210> SEQ ID NO 7
<211> LENGTH: 80
<212> TYPE: DNA
<213> ORGANISM: Artificial Sequence
<220> FEATURE:
<223> OTHER INFORMATION: Synthetic sequence

<400> SEQUENCE: 7
acgaggatgc ccagattgcc gctccgacga ccctccgttc acgggcgtgg cgttccattt 60
cttcgcggcg gatagggtgt 80

<210> SEQ ID NO 8
<211> LENGTH: 30
<212> TYPE: DNA
<213> ORGANISM: Zea mays

<400> SEQUENCE: 8
atctcgagga agagcggcgg cggcggcggc 30

<210> SEQ ID NO 9
<211> LENGTH: 50
<212> TYPE: DNA
<213> ORGANISM: Zea mays

<400> SEQUENCE: 9
gacgcacaca agctggggcg gcaggaggag gagggatagc gtacctgccc 50

<210> SEQ ID NO 10
<211> LENGTH: 80
<212> TYPE: DNA
<213> ORGANISM: Zea mays

<400> SEQUENCE: 10
gacgcacaca agctggggcg gcaggaggag gagggatagc gtacctgccc atctcgagga 60
agagcggcgg cggcggcggc 80

<210> SEQ ID NO 11
<211> LENGTH: 13308
<212> TYPE: DNA
<213> ORGANISM: Artificial Sequence
<220> FEATURE:
<223> OTHER INFORMATION: synthetic sequence
<220> FEATURE:
<221> NAME/KEY: misc_feature
<222> LOCATION: (4775)..(4874)
<223> OTHER INFORMATION: n is a, c, g, or t

```
<220> FEATURE:
<221> NAME/KEY: misc_feature
<222> LOCATION: (6376)..(6699)
<223> OTHER INFORMATION: n is a, c, g, or t

<400> SEQUENCE: 11

gctctgccac tctgctgagg tggggggaga ggagctcccc ctccctcctc tcccctcctc     60
gccatgtcta gcagcgaccc ggaggagatc agggcgcgcg tcgtcgttct cggttcgccc    120
catgccgacg gcggcgacga gtgggcccgg cccgagctcg aggccttcca tctgccgtct    180
cccgcccacc agcctcctgg cttcctagcc gggcaaccgg aagcagcaga gcaacccacg    240
ctccctgctc ctgctggccg cagcagcagc agcagcaaca cgcctactac atctgccggt    300
ggcggcgctg ctcctcctcc tccttcttcg cctccccctc cgccggcttc tctggagacc    360
gagcagccgc ccaatgccag gccagcctcc gccggcgcca atgacagcaa gaagcccacc    420
ccgcccgccg ccctgcgcga cctcttccgc ttcgccgacg gcctcgactg cgcgctcatg    480
ctcatcggca ccctcggcgc gctcgtccac gggtgctcgc tccccgtctt cctccgcttc    540
ttcgccgacc tcgtcgactc cttcggctcc cacgccgacg acccggacac catggtccgc    600
ctcgtcgtca agtacgcctt ctacttcctc gtcgtcggag cggcaatctg ggcatcctcg    660
tgggaggcaa gtgcccgcac cgcaaggtaa agaagcgccg cctatcccac aagacggctc    720
gccgcggcaa gttcctcctg aaggccgacg atgccgtcta tgacgagctc gtcaagctgg    780
ccgaccaggg caaggacgct gaagccaagg agctccccgt cgatgaggac ctcccaggcc    840
tgggacagtt ctactgcctc cactgcgagt atgcgcttcc cctctcctct ctttccctcc    900
cttccattcc accggtatgc tatttcttat cctctgccaa tacaggtata tgcccgtacg    960
ttgctagttg taaaaaaaaa cgtttttctc aattcagcat tagtggagca tgtgttttaa   1020
ttcattcgtg gtacaaaaaa cacctgacta gcgaatgata atcctgttta tctttgcaaa   1080
aactaatttg aatttccatg tgtgcatgaa ttaaaactta ccgtactgtc acacaataag   1140
atcttaaaat actggatact cttagtacac aaatgatcca aaagaaagca caattccagc   1200
attccagtct ttcgctattt catcatcctc atgtgccaac aattattgtt tgtttccctt   1260
cctggacaca cagaaaaatg caatgggatc cagcaccgta attaggccgc aacaaagggt   1320
gaaattgtat agggaatttt caagcaccca ctctaggagt ctagggccat caatttggtt   1380
tacttcgtca aagaacggat gaaattgaat aagtttcata tctatggtgt aaacatctac   1440
tataccgata tgtagaaact gagaactatt cctgctgcac cgactgtaaa gctggcatag   1500
ctgaatatgt agagcttctt gttgatgggg atgtctgcaa gagcttaccg tttggtattt   1560
gcattgagaa tggactgtga tttctttctt tgacgtgctt cacaatatcc aattctctaa   1620
ttgggtggtg atgtgtgtgt gtgggggggg gggacccota ataaatctgc taaaacctcc   1680
ttgaagtctc tatttcaccc gccttttttt cctcccttat ttctaaactt ttagtactat   1740
tttaccttcc cttagttatg tacatctaat aaataccaca atagtggaag caattactgt   1800
ctgtttccac aaaaatagag cattgaggaa ccaatttgtc catcatttgt tgccacttct   1860
aggaagtcgg ttggcaggca catatatcta agctcttaat atatcatatc aaatagtaaa   1920
tatctctaat caacaaaaag ggaaacccca attataaaat ttatcccgta aatataattt   1980
atttttctag ctgtgctcag agagtaaaag caactccaaa agaagatgta aaccaacctt   2040
aaaacagata ttaggaagaa aatgattttc cttgctccaa tagctccctc atcgccccca   2100
aaaaaattgc atcccacatc cgcctcctcc cctcccgcat attttcgcgt gatccctttc   2160
```

-continued

```
tccccaatct gttcggcgtc tgcgtgcatg caggctcctg tgttttttat tttgccgcgc   2220
gctcatctgt ggccgtgcag accatcaatg agttggtaca gctttcctgc agcatgtggc   2280
gtcgtaggat catcatgctg gatcagcata aaggcccata tacccgccca tacccaggag   2340
caaagccagt tttcagtttt ttagttgttt aaggaaactg ttggagtaca cactataatt   2400
tactcttaat ttttttagaa tgcctccaat aatcattttt ttggggaaac tttttatcat   2460
tcttttggag ttagctggtg ggtcttacag gtctgagctt gctggccaat ggcagcattg   2520
atgaaggtaa tgttactgct aaataggcaa aatccaaatc taagagccca aagcactggc   2580
aattcaatga ccagacttga caaggggcag atcatgacat ggcgagatga tggacataag   2640
atgaactttg caggcttcat ctttagacca tgatatttat ctcatgttta tccacttata   2700
gataaaccct gtttgtggag ccagaagata cacctatatg aaatttgacc tgttggtatg   2760
agaaccagga aaaagcgacc gccctccatt ggtacaagaa tttcagaaca gagagtcaag   2820
agacatctga cagtttgcaa tcacaccatg caaccattgt agcatggaat ggccaaagac   2880
taattatgaa ccaaggaatg atggtgtcaa acttggtcca gtgcatacca tctaacaaaa   2940
cctggtgcag taatagccat tatcatctca caaggacctc ttttctctct ttacaaaatc   3000
taataaggat tctacaaatt ggatacattg taatattgaa taacgcaagc agaaaggtgt   3060
ctgtgtgtct ctgcaatttg tctgtcacaa tgatacaaca acaacaaagc ctttttgtcc   3120
caagcacgtt ggggtaggct agagatgaaa ccccgtatga aaacctcaga gctcaacccc   3180
caaagaacag aaaagggaaa caaaggcaaa ggagaaccga aaacaacgaa acggggaaac   3240
acataaaaga gataaaaccc acaaggacca gcaagatcta aaatggacac aagaaaaggt   3300
caaacgatta aggaggaaaa gcgaaactat caatcagggt tctggcacgt gaattgcaca   3360
cttccacccc ttcctatctg cggcgagctc tttatcaata ttccactcct tcaggtctct   3420
cttcacagcc tctgtccacg tcaaagttgg tcggcctcta cctctcttca cattttcggg   3480
acgcctaatt attccgatat gcactggtgc ctcttcaggt cttcgttgga tatgtccaaa   3540
ccatctcaag cgatgttgca taagcttctc ctcaattggc gccactccta ctctctctcg   3600
tatatcatca ttccggactc gatctctcct tgtgtggcca catatccagc gcaacatacg   3660
catctctgcc acacttagtt gttggacatg tcgtctttta gtgggccaac attctgctcc   3720
atacaacata gccggccgga ttgttgtcct gtagaatttg ccttttagtt tgcgtggcac   3780
ccggtggtcg cataagacac ccgcagcttg tcgccacttc aaccatccgg ctttaattct   3840
atgactgaca tcctcatcga tgtctccctc cttttgaagc attgatccta agtaacgaaa   3900
agtgtctttc ttgggtacca cttgcccatc aagactaaca tcgccatcct catacccat    3960
ggcactgaaa tcacacttca tatactctgt tttagaccta ctaagcctaa aacctttgc    4020
ttccagcgtc tgcctccaca attccaactt ttgagaaaca ccactcctac tctcctcaat   4080
aagtaccaca tcatcggcaa aaagcataca ccacggtaaa actccttgta tgtcccttgt   4140
gacctcatct atcaccaaag cgaaaagata agggctcaaa gccgaccctt gatgtagtcc   4200
tatgttaatt ggaaagtcat cggtgtctcc atcacttgtt cggacacttg tcacaacatt   4260
agtgtacata tctttaataa gattaatgta ctttgttgct actttgtgtt tttccaaggc   4320
ccaccacatt acactcctag gtactttgtc ataagccttc tccaagtcta tgaagaccat   4380
atgcaggtct ttcttttgtt ctctgaatct ctccataagt tgtcttagta agaaaatggc   4440
ctccatagtt gatctcccgg gcatgaaacc aaactgattt tgggtcacgc tcgtcatctt   4500
tcgcaggcgg tgttcaatga ctctctccca tagcttcatt gtatggctca tgagcttaat   4560
```

```
tccacggtaa ttagtacaac tttgaacatc tcctttgttc ttgaagattg gtactaatgt   4620
actccgccgc cactcgtcgg gcattctgtt tgcccgaaag atggtgttga aaagcttagt   4680
cagccatact atcgctatgt ctccaagaca tctccatacc tcgataggga taccatcagg   4740
gcccatcgcc tttcctacct tcatcctttt tagcnnnnnn nnnnnnnnnn nnnnnnnnnn   4800
nnnnnnnnnn nnnnnnnnnn nnnnnnnnnn nnnnnnnnnn nnnnnnnnnn nnnnnnnnnn   4860
nnnnnnnnnn nnnntctttt tagtggtaga agatcatacg agctgttcct gaactctctt   4920
gtattgtctt atcagcaaac gatagggcaa tttcagtgag ttacggttgg ttcatttgat   4980
gaattagttg tatggaagtg cacagtttat aagatgctgc tagtttttgt gttgatatta   5040
ataaactgag tgtttcagtt gagttgtctg gtatagagta aaatggtgaa atttggttga   5100
tgtttttgtg atttaatgct tcctggaatt tatgatagta gatgccttga attgatttag   5160
agggattagc aaaactgtgg ctacacttta aggtgtgatt gctggcgtta caatgcttgt   5220
gatgagaact gcacttatct tgtaaatgtg gtagctatat tctaatctcc tactgctaat   5280
cgatatatat ctggtattgg ctttggctgc agtcgctact ttgcaagtga aagcgtgaag   5340
gatgatcact accgctcaaa gcgccacaag aaaaggtgat ccattctgtt tgctctaagt   5400
ctaagtaata tcacggtaat catcattcat agataacatt aaagaaaaaa ctatcctgaa   5460
cacatttgat ttatgctacc agtttgattg gcaaacatgt aatgacctgc acttataagc   5520
tgtttggttt gaggaatgat ctagtccatc gtcttctcac tcctcacttt tttgtttggt   5580
ttgtggaatg gattgagttg atccatcatc gcctcattcc ttatagttat ttagttagta   5640
ctaatatgag gaatgaggtc atccaaccaa atttgaggaa tggatccatg atgcatcact   5700
acattttgga tgaaatgatt cctcaaacca aacacctcct tagagagcat ctccaacaag   5760
aagttctata tttgagtcct aaaaaattaa aataggacct gattttaagt gttcaggacc   5820
acaaaaacat ttgcagctcc aacggttgag tcctataacc agttgataaa acttggaggg   5880
accttgttgt gtggttctat atgacaccat aactaaatta gtgttgatca tgcgatagta   5940
actaaattag tgttggacct tgttgtgtgg ttcgataact aaattaccag tatgaccttt   6000
cccgtcggca gaccatgtga gaaatgtggt ataggacagg ttctggtaca cgtgagtgga   6060
ataattccga cctgctgtgg cgtgtgcctg tctctaatca caggcttcgg atgattgtag   6120
ggttaaggta atgtctggac cggccccgca cacgcagctt gatgcagaac tcgctgcagg   6180
gatgggaaag cctgacaacg gcctgaagct catgtccatg tgaaggaacc tcttgctggt   6240
actggtactt gttccgtgcc tttgttgctg ccgtacaatt gaagctgctt tgcgcagtaa   6300
gtaatagcaa gagttatagc agacggtttt tttttgttgt acgcaagact ttcgaagtgg   6360
gtgtaagttg ttttannnnn nnnnnnnnnn nnnnnnnnnn nnnnnnnnnn nnnnnnnnnn   6420
nnnnnnnnnn nnnnnnnnnn nnnnnnnnnn nnnnnnnnnn nnnnnnnnnn nnnnnnnnnn   6480
nnnnnnnnnn nnnnnnnnnn nnnnnnnnnn nnnnnnnnnn nnnnnnnnnn nnnnnnnnnn   6540
nnnnnnnnnn nnnnnnnnnn nnnnnnnnnn nnnnnnnnnn nnnnnnnnnn nnnnnnnnnn   6600
nnnnnnnnnn nnnnnnnnnn nnnnnnnnnn nnnnnnnnnn nnnnnnnnnn nnnnnnnnnn   6660
nnnnnnnnnn nnnnnnnnnn nnnnnnnnnn nnnnnnnnna ggtttagctt tttttttttt   6720
tctttcgtgc tactgcagat aaggagtaaa attctgctat ttggtactta taagtatata   6780
taaaacaggc taactaagta cattaataca atctggggtg ccttgggagg tagatgatga   6840
tgcgggatca gttcccatct ctgacactgt atgtagatag atgatactga tgcggatgag   6900
```

```
aaacaagagt aaaaaaaagg cgagtgaagg tttacatcat cctaaaaccc cgactcaaac   6960
agatcgtcaa attgtacaat catatgaacc accgtatttt ctcctttcct tttttcccct   7020
cattgttgcg atcatggagt accaccattt gatccggagc ttcagcttcc tcacccatca   7080
atctctcgag gaaccaaacc catccatcca tccattccgt cctacgcggc cccgttgcac   7140
gaggacgacg gcccgggccc ggccgccgcg cccgtcagcc gctgcaagct gcagcatccg   7200
cgcgtagcac ccgtcgggat ggtgcttgag caggtgcgag tgcgacccct gctccgccac   7260
cttgccgtcg tcgatgaccg cgatggtgtg cgcgccgcgc accgtggcca gccggtgcgc   7320
caccacgatg gtggtgcgcc cggaccccgc gcgctccagc gcctcctgca cgcaccgctc   7380
cgactcggcg tccagcgcgc tggtcgcctc gtccagcagc acgatggccg cctgcttcac   7440
cagcgcgcgc gcgatcgcga tccgctgccg ctgcccccc gacagctgca ccccgcgctc   7500
gcccacctgc gtccggtacc cctccggcag cgccgcgatg aaccggtgcg cgttcgcctg   7560
cgccgccgcc tccaccacct ccgcctccgt cgcgccctcg cgcccgtacg cgatgttctc   7620
gtggatgctc gccgcgaaca ggaacggctc ctgcggtacc accgccacca cgcgccgcag   7680
cgcccgcagg ttgtacttgc gcacgtcctt gccgtccaag agcacgcgcc cggacgtggg   7740
cttgtagaac cgctgcacca gagccaggac cgagctcttg ccggacccgc tcggccccac   7800
cagcgccaac gtttttccgg cgcgcgcacg gaggctcagg tcgcggaaca cttggatgtc   7860
cggccgcgac gggtacaaaa agtccacgtg cttaagttcc accttcgccc ctgggccgtc   7920
cggcaccggc gccgcgtcca cgtcgtgggg ctccacctcc gtcttgcggt cgattgtctc   7980
gaacaccgac cgcatcgcgc gcccgccttt gatgaagtcc ggcgccagcg tcagcgtctc   8040
ggcggcgccg ttcgcggaca ccatcagcac catgaacacg cggatggtgc gcgagaagtc   8100
ggacacgccg tgcttcacca gccacgccgc gtaccacagc cccagcgcgt aggacgcgta   8160
cagcaggaac tgcgccacgc cgtagccgct gccggcgatc tgccccttcc agaagcagcg   8220
ccggagcggg ccgcgcaggt tggcctcgaa cagccccgtg atcttgcgct ccgcgttgaa   8280
cgcggccacg gtgcgcaggt tggccacggc ctcgcccgcg atctgcgtgg ccctggcgtg   8340
cgcggcctcc aggtcccccg agaagccctt catgaacatc ttctgcagca cggtggcgcc   8400
cacgacgagc gggaacacgg cgaggagcac gagcgcgagg cgccactgga ggacgaaccc   8460
cgcggtgcag gccaccagca tcagcgccga gttctggacg atgacggaga tgcggtcccc   8520
gatggcggag cgcacgttct gggcgtccag cgctagcctg gcggtcacgc gcgcgctggc   8580
gttctcgtcc gcgtcgaacc aggcgatctc gttgcggaac acggcggcga acatcttctc   8640
gcgcacccgc ttggtcaagt tctcgcccac cgtgtcccag aacacgtgct gcaccgtgtt   8700
gaacagcagc gccgcggagg acatgccgat gagcaggtaa cagtattttg cgatctcgcg   8760
cttcatgtac cgcgggtccg gcgcgtagta gacgctgagc acggcgctga ggatgtaggc   8820
gaagatggcg ctgaaggagc cgcagaccat ggagccgatg gagccggcga gcgcgtaggc   8880
ccactcgggc gagttcatcc tggcgaggcg caggaaggag ctggcgccgg cgcggaacgc   8940
cagctgcttg tccgccatgg tccggtggtg gtggtgcggg tcgtggatgg agagggtgaa   9000
gtcggaggtg gagaagtcgg agaggcggcg ggagtagggg gagcggccgt aggaggagtt   9060
gcgcgtcatg atgggcgagc tgacggagtt gcgggcgctg gagggcctgg cgctgctgcg   9120
gcgggcgttg acgagcgccg cctcgtgcgc ctgctcctgc atgcggatga gcttggcgta   9180
ggtgccgttc tcgcccttgg ccatcagctc gtcgtgcgcg ctcatctcgg agacggcgcc   9240
gccctgcagc acggccacca cgtcggcctt tgcggatggt ggacagcctg ttgcgcgatc   9300
```

```
accaagggtg gtgcgcccca tcatgaagcg gtccagcgcc tcctgcacga gcttctcaga   9360
ctcggagtcc agcgcgctgg tggcctcgtc cagcagcagg atggcggggt tcttgagcat   9420
ggcgcgggcg atggcgatgc gctgcttctg cccaccggag agctgcaggc cgcgctcccc   9480
aacctgcacc ggccatcacc gccatggtca gacaaacgag tttgacttgg actgccatgt   9540
ctctcatcaa ataaaccagt actcctcgtc cagacgtaat taataaataa aaattgaatt   9600
gttaataaaa taataagtct tattccctga cggtggagag tgtttgagtt tgaccaggga   9660
tgatgcatgc atgggcatgc gagcattgct tggcaaggaa tcatgatcaa gtcagttata   9720
gttatgggag tgtgagtccg tgttctaata aaatctagcc gctagttatg ctagtacagt   9780
acatatggcc ccatcccatg tggcctctag atttcgtctg atttgatttg gtttgattaa   9840
acccttccca gatgttatta actaaccaga ctgcctgcct gcctgccatt tgacagtgat   9900
taaaataagc agcagcatgg gtttgactgg ctctctttct cagatgacag tttataataa   9960
cagtttatgt aagataccta ccctacccac tagtagcaca gtagtaagta gagtagcaag  10020
agctggggtg gacagacaca gacaggctga gtctgagtga ttgataattc ttgcttgcac  10080
taggatcaaa aatcaacttg acattcccga caaaatacca actcggaatt tgttccgttt  10140
cactccccca actcctccca tacttctcat actctagatt cctagggatt gtacctcttc  10200
ctacgtaccc caggttgatt cttaatcctg ctactacttt ttattattat taacattttt  10260
ttctctctca ctctagatgt tcatcgtcca ttcatcctct gcactcatca gcaagtgcta  10320
gtttagtaga ggctgtagag cttgtgtcga gaaaaaggac ctctcctgtc ctgtgcgtga  10380
tagcaaagca tcctggcatg ttacttgttg gcaacccaca gcagcaaatg cgatggcaac  10440
aggcgcctaa caattgccct cccgtcctag tctacaacag gcattatgtc tatgtgatgg  10500
accccgaccc ctcttccatg gcgttggtgg tggtgctgcc ggctgtcatg agctcatgtg  10560
cagctgccgc ggcctaacaa acacgaacag tatctgatct gaggctagct actaaagctt  10620
tagccccggg caggcacgag cgcagagtgc gcgacgcatg agtgagtgga gtggaacgga  10680
tggatgactt gacgctgcat acacaccttc agtcccttcg tgacatgagg aaaagaaaag  10740
gctgcgtgca gatgatgggg gaaaaaaaga tgctcccttt gcgcttttag agtgagtgca  10800
tgcattttta ggtttggaat aaaaaagatc gctgtaaaga cgtaatcata gtatttgtga  10860
gaagagagaa agtaaaaaaa acaacaacaa caactgaagt taggttgtct cgtagctaaa  10920
gatgcattta ttctaagata agctttaaac tctagaaatg tatttgatat agtattagag  10980
tgagttgcat aaggttggac agggaaagca gatgtggagc agctaggcaa gcagcacgtg  11040
tggtccagac accgacaagt ggattggaga gcaacaggca gcaacggtgg gggagcaagc  11100
gagagaagtg gcagtgcagc tagtgagcta gctatacggg acggacctgc gtgtcgtagc  11160
cgtcggggag tttgatgatg aaggagtggg cgttggccac cctggccgcc tcctccatct  11220
ccgccagcgt cgcgctctgg ctgtcccgcc ccagcagcag gttctccctg atgctcgtcg  11280
cgaacagcgc cggctcctgg ctcaccagcc cgatctgccg ccgcagccac cgcagctcca  11340
gcgacctgag gtcgtgcccg tccagcagga tttgccctgc caaaaccgaa ttgcagactt  11400
catctcgttc ttcttctttt tttgtctgaa aaaaaaatct acagggctac tatatatatc  11460
tatctatact gtcaacagca caactgaacc acttctcact gagcagtcgg tcaatggcag  11520
gcatgtgcta ggcaacagta gcatcttgcc aggcaacaaa tagttttctt tgtcccgcgt  11580
tgcaggcaca cccacctagc ttagctagct cttctgctct gcgtgaatgt atgtatgacc  11640
```

```
acaaacagcc acgaccaaag aaagtaaaaa gaaaagcaag aaagaggatg gctggttctg  11700

gttggctagc tagcaggtag cagcagccca tgaggccggc cagctctgca tgctccaagc  11760

attcacttca tttccatgtc aatgtggtgg tacagagtta ctgcacaatt cacttttgtt  11820

tggcaatgca atgtacagtg gaggcttctt ctaactgcta ctgtactaat ctacccagca  11880

atggcagttg gcgaagtatt gttgttgcga tggcaatggc gattggcaag caagcgaact  11940

ggacatcctc agattaatgc gctaaaagta gtaacagtac taggtatacc tgcgctgggg  12000

tcgtagaatc tctcgatgag cgacaccacc gtgctcttcc cggagccgga gctgcccacc  12060

agcgcgatgg tcttcccggc gggcacgctc agcgagaagc cgcgcaggat ggggacgtcc  12120

ggccgcgacg ggtacgcgaa gtccacgccc cgcatctcca cccgccccgt caccgactct  12180

ggctccgcgc cgtcgcgcga ggagatgccc ggcctgtggt cgatgatgcg gaagatcttg  12240

gcagccgcca cacgcgcctt ggcgaacgcg gccatgctcg gcgccgactg ccgaggcctg  12300

cacgcgatcc acagataccg tcagcagcaa tgacgacggg ggcggccgag gacagcagaa  12360

ggagagagtg cgtggtgtgg tgggccttac agtccgccga tcatgacgga gaacatggtg  12420

gcgatggcga gcccgccgtt ggtgtgctgg gcgcgcacga ggtggccgcc gtaccagagc  12480

aggagcccgt agcagcagaa gacggtgaag taggtgccgc cgaggccgag ccccttggcg  12540

aagccgctgc ggtagccgat cctctgcgcc acggccagcg ccgccgagta ggcccgcatc  12600

tcgcgctcct cgccaacgaa cgcctgcacg atccgtatct gcgcgagcgc ctgctccgcg  12660

atgccgctgg cgcccgagag cgcgtcctgg ctgcgggacg agagcttggc gagcgcggcg  12720

gcgctcagcc cgccgatgac ggcgatgagc ggcaccacgg ccagcgtgac cagcgccagc  12780

tgccacgcgg ccgtgaaccc cacgacgaag ccggccacga aggtggccat gtagtggatg  12840

aggttgccca gtttctggct gatggcgtcc tgcaccacca cggcgtccgc gttgatggcg  12900

tagatcacgt ccgaggcccg cacgtcggtg tcgaagaagg acacgtcctg ccgcagcgcc  12960

gcgtccaggt accgaatccg catccgcgtc gactgccgct cgccggtcca catccagcaa  13020

gagatctctt gcgagcgggg cgaacgattt gaacatctcg tttgtagcca cggcgattgg  13080

ctgaccgacg tgatttgtca tccaatccaa attgaccgcc aattcgcgac gcacacaagc  13140

tggggcggca ggaggaggag ggatagcgta cctgcccatc tcgaggaaga gcggcggcgg  13200

cggcggcgtt tagggttttt gtctggcagc cgaactgcgt cgtggagaac agaagagaag  13260

atgcaacgga agaagtctag gagaagaggt ggttttccag aggaggac              13308
```

<210> SEQ ID NO 12
<211> LENGTH: 1982
<212> TYPE: DNA
<213> ORGANISM: Zea mays

<400> SEQUENCE: 12

```
tggtctatcc ttagttggtc cgacctttta agaaacaaaa ggtaactgta tgaccagcgc    60

agaagaaaat aggatctaga tgatgattga gagagaaacg tttcaggggg aaaaaatcca   120

atcaattaaa aattagacct gggaacattg gcagatcgat ctagagggtg gacaaggtgg   180

gctgattttg atcctgctaa attatataga tagttttgat ttatttgcta cttttgattc   240

tcatacgttg tagaacttaa aatgtgaact catttgttta ttgattctca taaggttgga   300

ccaccttaac tttaaatcct agatttgcca ctgggaagtg accgagagaa aactatctgt   360

gccacttagt ggtttgataa actatgttgt gataccaagt taccaacgtt ttgaaatcaa   420

taaatgttgt ggcagccatt cagggacatg attgaaggga tgaggagtga tcttaggaag   480
```

```
acaaggtata acaacttcga cgagctctac atgtactgct actatgttgc tggaactgtc    540
gggttaatga gcgtacctgt gatgggcatc gcaaccgagt ctaaagcaac aactgaaagc    600
gtatacagtg ctgccttggc tctgggaatt gcgaaccaac tcacgaacat actccgggat    660
gttggagagg agtaagtaac atatatattc ttcctgcgac aggcacgaac atgcatgtgt    720
tcaatagcac agatgtgatg atatgactgt caccatgtct tttagtgcta gaagaggaag    780
gatatattta ccacaagatg agcttgcaca ggcagggctc tctgatgagg acatcttcaa    840
aggggtcgtc acgaaccggt ggagaaactt catgaagagg cagatcaaga gggccaggat    900
gttttttgag gaggcagaga gaggggtaac tgagctctca caggctagca gatggccagt    960
aagtccactc aacttcacat ttcccaccca gtatagcaca gcatcctcac ttccttttct   1020
ttgttaccat tgcaggtatg ggcttccctg ttgttgtaca ggcagatcct ggatgagatc   1080
gaagccaacg actacaacaa cttcacgaag agggcgtatg ttggtaaagg gaagaagttg   1140
ctagcacttc ctgtggcata tggaaaatcg ctactgctcc catgttcatt gagaaatggc   1200
cagacctagc caccagagaa gctgcaatgc aaggttcagg ttaggctaga tagaaagtta   1260
aatggggcaa catcaggagg ccttgatgaa aaacagacaa cctggtgaat tgttgttggg   1320
atcaggcaca gaacagataa gagccgcgca gccaacctag ggcatgtttg gtttcaatta   1380
gttctaggac taaactttag tcctaggact aaactttagt ccctatatgt ttggttctag   1440
ggactaaata gattctaaag tcattaaata cattgtccaa agactcaaat acccttagaa   1500
tatactcatg atattagtta tctataaaaa ggtaagggca acatgataat tatgagcttt   1560
tagtctcttt tagcacctat gtgaaggact aaagactaaa tcattttagt ccatatttta   1620
gtcctagtgt ttggcaaaaa agggactaaa agggactaaa aactagagac taatctttag   1680
tccctctaac caaacacccc cctagatgga tacggaacat tcgcctctta ttcggagcaa   1740
tatatgtctc tcaaggaaag agcccaacat gtatactgcc ttctttttct catcccagat   1800
ttgggggaaa aacaatgtaa atgccaatgg tatcgtagga agattactag aagtaaatgc   1860
caatgtaaaa acagatgagt tggcatttac atgataggat ggtgggatca tcagactgaa   1920
aatgataggg gattgtgctc ccctgcgact ccaactatta aacaaggaat ccgtcagcag   1980
ta                                                                  1982
```

<210> SEQ ID NO 13
<211> LENGTH: 248
<212> TYPE: DNA
<213> ORGANISM: Zea mays

<400> SEQUENCE: 13

```
atgttgtggc agccattcag ggacatgatt gaagggatga ggagtgatct taggaagaca     60
aggtataaca acttcgacga gctctacatg tactgctact atgttgctgg aactgtcggg    120
ttaatgagcg tacctgtgat gggcatcgca accgagtcta aagcaacaac tgaaagcgta    180
tacagtgctg ccttggctct gggaattgcg aaccaactca cgaacatact ccgggatgtt    240
ggagagga                                                             248
```

<210> SEQ ID NO 14
<211> LENGTH: 248
<212> TYPE: DNA
<213> ORGANISM: Zea mays

<400> SEQUENCE: 14

```
tcctctccaa catcccggag tatgttcgtg agttggttcg caattcccag agccaaggca     60

gcactgtata cgctttcagt tgttgcttta gactcggttg cgatgcccat cacaggtacg    120

ctcattaacc cgacagttcc agcaacatag tagcagtaca tgtagagctc gtcgaagttg    180

ttataccttg tcttcctaag atcactcctc atcccttcaa tcatgtccct gaatggctgc    240

cacaacat                                                             248


<210> SEQ ID NO 15
<211> LENGTH: 20
<212> TYPE: RNA
<213> ORGANISM: Zea mays

<400> SEQUENCE: 15

aucuagaggg uggacaaggu                                                 20


<210> SEQ ID NO 16
<211> LENGTH: 20
<212> TYPE: RNA
<213> ORGANISM: Zea mays

<400> SEQUENCE: 16

aaaccaaaca ugcccuaggu                                                 20


<210> SEQ ID NO 17
<211> LENGTH: 308
<212> TYPE: DNA
<213> ORGANISM: Artificial Sequence
<220> FEATURE:
<223> OTHER INFORMATION: Synthetic sequence

<400> SEQUENCE: 17

tggcagatcg atctagaggg tggacaaggt tcctctccaa catcccggag tatgttcgtg     60

agttggttcg caattcccag agccaaggca gcactgtata cgctttcagt tgttgcttta    120

gactcggttg cgatgcccat cacaggtacg ctcattaacc cgacagttcc agcaacatag    180

tagcagtaca tgtagagctc gtcgaagttg ttataccttg tcttcctaag atcactcctc    240

atcccttcaa tcatgtccct gaatggctgc cacaacatac ctagggcatg tttggtttca    300

attagttc                                                             308


<210> SEQ ID NO 18
<211> LENGTH: 175
<212> TYPE: DNA
<213> ORGANISM: Artificial Sequence
<220> FEATURE:
<223> OTHER INFORMATION: Synthetic sequence

<400> SEQUENCE: 18

ttgctggaac tgtcgggtta atgagcgtac ctgtgatggg catcgcaacc gagtctaaag     60

caacaactga aagcgtatac agtgctgcct tggctctggg aattgcgaac caactcacga    120

acatactccg ggatgttgga gaggaacctt gtccaccctc tagatcgatc tgcca         175


<210> SEQ ID NO 19
<211> LENGTH: 175
<212> TYPE: DNA
<213> ORGANISM: Artificial Sequence
<220> FEATURE:
<223> OTHER INFORMATION: synthetic sequence

<400> SEQUENCE: 19

tgcccatcac aggtacgctc attaacccga cagttccagc aacatagtag cagtacatgt     60
```

agagctcgtc gaagttgtta taccttgtct tcctaagatc actcctcatc ccttcaatca 120
tgtccctgaa tggctgccac aacataccta gggcatgttt ggtttcaatt agttc 175

<210> SEQ ID NO 20
<211> LENGTH: 20
<212> TYPE: RNA
<213> ORGANISM: Zea mays

<400> SEQUENCE: 20
cugccacucu gcugaggugg 20

<210> SEQ ID NO 21
<211> LENGTH: 20
<212> TYPE: RNA
<213> ORGANISM: Zea mays

<400> SEQUENCE: 21
uccauccauu ccguccuacg 20

<210> SEQ ID NO 22
<211> LENGTH: 250
<212> TYPE: DNA
<213> ORGANISM: Zea mays

<400> SEQUENCE: 22
atgtctagca gcgacccgga ggagatcagg gcgcgcgtcg tcgttctcgg ttcgccccat 60
gccgacggcg gcgacgagtg ggcccggccc gagctcgagg ccttccatct gccgtctccc 120
gcccaccagc ctcctggctt cctagccggg caaccggaag cagcagagca acccacgctc 180
cctgctcctg ctggccgcag cagcagcagc agcaacacgc ctactacatc tgccggtggc 240
ggcgctgctc 250

<210> SEQ ID NO 23
<211> LENGTH: 250
<212> TYPE: DNA
<213> ORGANISM: Zea mays

<400> SEQUENCE: 23
gagcagcgcc gccaccggca gatgtagtag gcgtgttgct gctgctgctg ctgcggccag 60
caggagcagg gagcgtgggt tgctctgctg cttccggttg cccggctagg aagccaggag 120
gctggtgggc gggagacggc agatggaagg cctcgagctc gggccgggcc cactcgtcgc 180
cgccgtcggc atggggcgaa ccgagaacga cgacgcgcgc cctgatctcc tccgggtcgc 240
tgctagacat 250

<210> SEQ ID NO 24
<211> LENGTH: 303
<212> TYPE: DNA
<213> ORGANISM: Artificial Sequence
<220> FEATURE:
<223> OTHER INFORMATION: Synthetic sequence

<400> SEQUENCE: 24
gctctgccac tctgctgagg tgggagcagc gccgccaccg gcagatgtag taggcgtgtt 60
gctgctgctg ctgctgcggc cagcaggagc agggagcgtg ggttgctctg ctgcttccgg 120
ttgcccggct aggaagccag gaggctggtg ggcgggagac ggcagatgga aggcctcgag 180
ctcgggccgg gcccactcgt cgccgccgtc ggcatggggc gaaccgagaa cgacgacgcg 240
cgccctgatc tcctccgggt cgctgctaga catcgtagga cggaatggat ggatggatgg 300
gtt 303

<210> SEQ ID NO 25
<211> LENGTH: 175
<212> TYPE: DNA
<213> ORGANISM: Artificial Sequence
<220> FEATURE:
<223> OTHER INFORMATION: Synthetic sequence

<400> SEQUENCE: 25
ggccttccat ctgccgtctc ccgcccacca gcctcctggc ttcctagccg ggcaaccgga 60
agcagcagag caacccacgc tccctgctcc tgctggccgc agcagcagca gcagcaacac 120
gcctactaca tctgccggtg gcggcgctgc tcccacctca gcagagtggc agagc 175

<210> SEQ ID NO 26
<211> LENGTH: 175
<212> TYPE: DNA
<213> ORGANISM: Artificial Sequence
<220> FEATURE:
<223> OTHER INFORMATION: synthetic sequence

<400> SEQUENCE: 26
ctaggaagcc aggaggctgg tgggcgggag acggcagatg gaaggcctcg agctcgggcc 60
gggcccactc gtcgccgccg tcggcatggg gcgaaccgag aacgacgacg cgcgccctga 120
tctcctccgg gtcgctgcta gacatcgtag gacggaatgg atggatggat gggtt 175

<210> SEQ ID NO 27
<211> LENGTH: 8800
<212> TYPE: DNA
<213> ORGANISM: Zea mays

<400> SEQUENCE: 27
taaatttgtg atccttgtga agttgttata tcatgaattg tgaacttgtt gcatttgtga 60
tcttttgtca actttgttgt attgtgaagt ttgatatgtt taccgatcgt attttagatt 120
tcgatcgtta ccggtgtatt ttccgcacca aacttttgtt tccgatgttt tcgaaatacc 180
gatatcgttt ccgtttctat agttaccctt ttcaatttta tttccgatta aaaatatgaa 240
aacggtaatg gttttagtgt ttatcgaccg ttttcatctc taatcatccc tgccggtgaa 300
gtttaatttt tcccttggct aaagagatgc aagctgctgt aaaatacgtt aaaacaggca 360
aggcagcccc agcagccagc atcgcgtgcc cgtctatgta catcagtgga tacgtagcat 420
ctctagtgag taatataacg attgcatttg gctggaggac gtatgttata taagtatgtc 480
atttaccagt tgcattagta tcttccctaa ctcctataat aactctcttc gtggaatgga 540
cgtagacgta tgctatataa gtattaaaaa atagtttttt aagctggtgt cctcaatttt 600
gctattgttc tcgtttttat ctttagttgt gtcacaaatt taatccgtac aacaaatcaa 660
aaataccata cccttcttat attaattttc taacataaca tttgtttaga tattttcagt 720
cgtgaaaata caattctaat tctaacgtcg tagtatcaaa tcaaaccatc cagaatttga 780
ccaagcttaa ttataaaaaa tataaaattt atgatactga atagatagca ttagatttgt 840
tatataatat atttttataa aataccattt ttatggtata aatattggta ctcctttact 900
ttaaactata gatagttttg actaaggatg caactagaat tgcatcctct tttcactgca 960
ccttcattag ttttaatatt tatttagatg ggcccttgca aactgtagat atcatctctt 1020
gcaacattct ttctatagca ccacgaaaat gtattgcggc tttgaaatta taattgaatt 1080
agttgtatca tttctttcac cgatgcgtta aattcaaaat taagtgttat atttcttcat 1140
aatttgttaa atatatagac cctataatcc accattattt actataatag catacattaa 1200
cattggtttt agcctacact acgacactcg aggcattgaa ttttcctcta tcaaagaatt 1260
atatgtgtag tagtattgtt cttgacaaaa agggggatta aaattaaact accaatattg 1320
atacttatct tatcacatcc atgaatacaa tcaacactct tacaaaagat aagatacaag 1380
attaaaaagt accatgataa tacattaaga ttattagcaa tgcattaaat taaataaatg 1440
tgcaagtgaa tcatgatttt agttttatct attttacttt taaaatatga tattctctga 1500
ctacttctaa gcataaatgt gattctaagt catgaccgat cgtgcttatt cagaaaaatg 1560
aaggagacac agatttctat aaaaaaaggt tgtcatggga ctattgggtc aaccatctta 1620
ttcatttggg aaaataagtt tagaacacat caacccattt tagatgttga gtttggccct 1680
aatggtccat tgaccttact tttgtgggtt gacatagacc atctatccca agttattgtt 1740
gtgtcacatt ccctgatatc atgaatctat attttagctt tccgttttca tatttttagt 1800
cgttacatat tttttatccg cgtactagat taaaactcta gttgttgcaa tacattttgt 1860
tcattttttt ctatttcttc tttactaaca acatattcta gttcctagct acattcttaa 1920
gtaccatagt gctataaaca ttttttatcc tacattattc cacttaagaa attgaatttt 1980
ctgcataaaa aaattatatg tccagtagtg ttgtcttata aaagcataaa gtgattaaaa 2040
ttaaaaccat tattgatatc ttatttttca aaaaaaaata taagcttata gaaagtgaat 2100
taatttcatg gtaaattaat atagtttaaa ttgaattatt agtgttatta ctatgtttat 2160
tatcaatgaa acatttttca tggttgatat aacttagtgt tacttatttt agtatttttt 2220
atataattct agttaacttt tagtttttga tttaaaaaaa cgagaattgt gtccttttgt 2280
ggagtgagta taaagaaagt aatatctgtt catcataatt tggtttttta aggtacgtga 2340
aacttgcttt atatttggac tcaagctatg tctaaataca tagtaaaaaa gcaatatttc 2400
tagaaaagac aaaacatctt ataatttaga atcaaggaaa tatatagatt ttatgtgcag 2460
tgagaagcca tttacaatgg aacgttcaac gttgggccaa tagatatttt gcgatatgat 2520
gatgggcata tttttgcatg gttgtccctc cactagctat agtttgatga tacgatacgc 2580
tgcacacacc attgggttgt accatgttag tgtagcaaca gtagaaaccc aattgtggcc 2640
gtgaaccatg ataatactag gtagagtgct agctagaggt ttcaggctat tgatgcgtga 2700
attaaacttt ctgttgtgtt gcgaggaaac gagtattgtg aaatatttga aacggttttt 2760
tttgtgaaag atttgaaacg gtatttttgt tgtgaaataa agatcaaggc taaataaatt 2820
caaactaata aaacatatta attgacggcc tgaagccccc gcccccatgg ccccatgcca 2880
tagcatcagg tcccacatga catgaggccg cgcctccctc tatgttggct ccctgccttc 2940
gccgttgtcg tcgctcccga actccctctc ctcccctgtt acaaataccc ccacccgccc 3000
ggacagcttc cctgcacact cgcagctcgc acatctcatg gtgtcctaag aacggcaaga 3060
gccagctctg cctagcagca gcgcacagcc acatccatgg acgccagccc gaccccaccg 3120
ctccccctcc gcgccccaac tcccagcatt gacctccccg ctggcaagga cagggccgac 3180
gcggcggcta acaaggccgc ggctgtgttc gacctgcgcc gggagcccaa gatcccggag 3240
ccattcctgt ggccgcacga agaggcgcgg ccgacctcgg ccgcggagct ggaggtgccg 3300
gtggtggacg tgggcgtgct gcgcaatggc gacggcgcgg ggctccgccg cgccgcggcg 3360
caagtggcgg cggcgtgcgc gacgcacggg ttcttccagg tgtgcgggca cggcgtggac 3420
gcggcgctgg ggcgcgccgc gctggacggc gccagcgact tcttccggct gccgctggct 3480
gagaagcagc gggcccggcg cgtccccggc accgtgtccg ggtacacgag cgcgcacgcc 3540
gaccggttcg cgtccaagct cccctggaag gagaccctgt ccttcggctt ccacgacggc 3600
gccgcggcgc ccgtcgtcgt ggactacttc accggcaccc tcggccaaga tttcgagcca 3660
gtggggtgag taaagaagaa gatggcgccg aatttacatt tataagtagg accagcagaa 3720
gcccctgccc ctgggggcct tagcattgca ttcgactgat gaatacgcat ggcaggcggg 3780
tgtaccagag gtactgcgag gagatgaagg agctgtcgct gacgatcatg gagctgctgg 3840
agctgagcct gggcgtggag cgcggctact accgggagtt cttcgaggac agccgctcca 3900
tcatgcggtg caactactac ccgccgtgcc cggtgccgga gcgcacgctg ggcacgggcc 3960
cgcactgcga ccccacggcg ctgaccatcc tcctgcagga cgacgtcggc gggctggagg 4020
tcctggtgga cggcgagtgg cgccccgtcc ggcccgtccc aggcgccatg gtcatcaaca 4080
tcggcgacac cttcatggta acgaacgaaa gcgccggctc ctctgctttt cttggcctct 4140
ttgtccctgc cctgtgctgc tgtgcatatt cattcattca gttctctgtg gggttttttt 4200
tttgtttaat ttttttttgg gatcgtatcc agtgcacaag ggccacgccg tgcacaaatg 4260
cacaaaacga aatctggccg tccattttcc atccaacgac atgacggcgc ggggggtttt 4320
tcacaaaaca gactcggcaa gctacggagg ttgcgggagg gttcatctgc atatttacga 4380
cggccgttgg atggaaaatg gacggccaga tttcgttttg tgtatttgtg cacggcgtgg 4440
cccttgtgca ctggatacga tcccattttt ttttttgccc cgaatcctag tggacctaac 4500
tggacagatt acagcacgca cacgtaggca tgtcatgtag cagcactgca gtcgggtgca 4560
gtccagtcca gtcctgtcca gccgcgacac tgtagtacat agcgatgcaa cggagacacg 4620
cgttggagtt ggttccatct cttctcggcg gccgtgccga ggcttccgcg gggaagctgc 4680
gacaacagaa cggaccgccg ggggtgggca ggcagcaagc tccctgttgg cttgtgccgt 4740
tgcgcagcgg cgggtaccgg acaacgcttt cggcggcgcg cggcctcgtc ggcttcccct 4800
gtttttgatg ccgcctctcg gtgtccgggg accgggagga tcgatggggc ccgtgccgtc 4860
tgatccgcca cgcgagcggt cctatgcgat gcgccgcacg agcgcggggg ggccgtggaa 4920
cagtacacag ctgggtcact cactcactca tcccgctggt tgtggctgct tggttgcaac 4980
ttggctcggc tgtctgtctg ttgcccccgc cgcgttttct agccgtttcc gctttgctcg 5040
cggtttcgct ggcgatccgg cacgcggcgc ccacacccgg ggctggcccc ttggccgagt 5100
gggtggcagg cacttgcatg catccggccg gtttcccgcg accaagctgg cccgccgcaa 5160
caatgagagt gagacgagac tttgtgtcag tgtgtgtatg tacatgtatg tctgcgcgac 5220
agccctaccg tccgacacga tgattcttgt gcactgtact gtactgtact aactcccccc 5280 acccccctccg gtatgtaacg catgccatat gcaggcgctg tccaacgggc ggtacaagag 5340
ctgcctgcac cgcgcggtgg tgaaccggcg gcaggagcgg caatcgctgg ccttcttcct 5400
gtgcccgcgc gaggaccggg tggtgcgccc gccggccagc gccgcgccgc ggcagtaccc 5460
ggacttcacc tgggccgacc tcatgcgctt cacgcagcgc cactaccgcg ccgacacccg 5520
cacgctggac gccttcaccc gctggctctc ccacggcccg gcggcggcgg ctccctgcac 5580
ctaacgagcc ggccgtctct ttcgccgggg cccgcgcggg gttcgcccac gtggtgatca 5640
ggtggcagac atgtggccca cgggccccgc gccgccttcc ccatttttgg acgaccctac 5700
tgctactact actagtgtac atatgcaaaa aaatacatat atatataggt actttctcta 5760
atatttttat atataagcaa ggcggcctgg tgttcttttc tttgttttgt cgacaactgt 5820

```
ttgatcccat cctatggacg atggatagtt caatgtttgt acgtacgtaa ctactctcta   5880
tagactagaa tgggctcatg aaactggacc gatcgacacg gacgtcacgt gcgtctggta   5940
ccggtagtgc aacgggtgcc gaatgtttgc tgggcccgga cgagaatcgc ttctcctcgt   6000
cctcggtcct caccctgaac gaacgaataa ggaaaatgct gcaccgaaag ctccagacgt   6060
ttccgaattc caaattccaa aaccccaaat cttcttgctt cacatcagtc ttacccggtt   6120
catctgtgac aaaaaaaaaa tagtgctagt ttaggaactc aggtcgagat tgaaggcaat   6180
tgtggaggaa tttaccctat aatccttatg agaatttgag ttcccaaact aactgagttg   6240
gagcattcaa catttcccta aattttgtgc acatgtttct ttgctattta tctttggaca   6300
tgggacgatg ggagacgcag atttagggga cccttcaatt cagaacttca ggtgcacaaa   6360
ccgaggttgg cttgcctgca ttcttgtttc ggacatgccc aactaggcca ctactcacta   6420
ccttcatctg agataccaat tgctgaccta aatgacaagt atacacttac atttcagtga   6480
tagctgcaac aaaaaaaaaa atcttaccgc attttatctc tgcattctgc atgccgcatc   6540
ctgaacatta cgtatctttc ccggtgctct gttgcgttct cacgcagttg atggcatgca   6600
gtcttgcgcc accgaatcca gtgtactggt cgtggtgact tgtcgcacag acagcagccc   6660
ggcagcacca agcgtgtcac tgtaaactgt tgggcgttaa acaacaactt gcacaacagc   6720
tcaaatatgg catatgctat ccgacaaact gaacaaggtg cccaattgat ctgaatgtac   6780
ctgtgatttc cagcactatc gtacagcaac gttgtcaaaa caagtggggt ggggttgggg   6840
acagattttt tcgataaaga agcttttata aaaaataaca atgatacaaa tcctgggtta   6900
tagatgtaca gaaagcacga agcacgaaag tccagtccaa agcacgtttt tttgcctggt   6960
actagcccga tccggccggc acgaataagc gggtcgagct cggacgggaa gctaagcacg   7020
acggactagc ccgacacgac ccgtttacct ctaatcccgt taaacccgct tttttgcact   7080
aaaccgtgct taccgaaccg tttagcccgt tttttggcct gatttttcgt gcttaacggg   7140
ccaggctcgg acaaggaaac aagcccgcgg gcttagacga tccggcctgg ttttttaacc   7200
gtgcctagcg ggtcgagccc aaaataggtc gggcttcact gggcccgagc cgggcgaccc   7260
gtttggccat ctctaacctg agtacaactt ccgacttctg caaaatacat acagccaaat   7320
aaaagaaaag taaaaagatc taaaaaatct cagctagaaa caatcaatcc gaagactaga   7380
tcgcctccca taagtctgga aaaaagagac catggccact tgcaccaaga tgtgtgcatt   7440
attctacggt tacaccaaag atttttgttc tttaagggct agtttgggaa ccataatttt   7500
caaagggatt tctattttcc taaggaaaat tagttcattt ttccataaga aattagaaat   7560
ccattggaaa attgtggttc tcaaactagc cctaagcgtc gaaaagaacc atatgcatat   7620
ctagagacaa aattcctcta atttctattc aggcttcagc acatatactt cacgtgcttg   7680
cgtcaagttc cttgggccgc cacatggact tatggacttc tcgacgcagc gaaagccgtc   7740
gttgcccttg gtgtagctag gtcatccgca cctcccactg gccagtggcc actgcaggga   7800
cttggccatg ggcttgtttg gttcagcttt tttctgacca gcttttctga aaatctggct   7860
gtgtgaagaa tctggctgtg agagaatctg agtatcatta cgattacgtg tggatgaaga   7920
taaagttgtt catagggctc aggatctaga aagtgacgga ttcctactat tacaatgact   7980
caaccgatta tgtgtttatg ttgattttgg atgatttttg ccccaacaaa ttttatagaa   8040
gctggctgaa aagctgagcg tttggcagtc cacaacagtt tttggtggcc agaagctgcc   8100
agaagccgat acaaacaggg tccatgcttt ccatttcgtt taccgtgtac gcggtgtccc   8160
```

tcacaatcaa tcagtttacc ttgtggctcc aacacacatc aacctcggca caacaacact 8220
gtgaatcatt ttcggcggtc catattattt tcgacggttc atccctggcc gccgaaaatt 8280
gtctgttatt ttcggcggct tgacctagcc gtcgaaaata ggctgctatt ttcggcggcc 8340
aaatccgagc cgccgaaaat aaggctttta aaaaccgtcg gctccttctt cttctctgtt 8400
ctttctctcc tctcccaaag cccgccgccg ctcacccgcc gctcgctcgc cgggctgccc 8460
gccactccgc cgtcgtcgtc gagccaccgc atcgagaggt aaattttttt tgcgtgtttt 8520
attccttatt ttcggcggtt gatatttagg cgccgccaaa attagtgtat atttgtaatt 8580
gtgtttgttt aattactatt tgtaattagt attattgttt aattcgattt cattaatgta 8640
ttagtggtat atgtgattta gggattaggg gcatattgta tttaggcatt aatttcatat 8700
taatatgtgg tattattata ttattggttt taatagtaca ttatattggt acgtagaata 8760
gttgcattat tagtgtttgt ggtacttagt ttgacttgat 8800

<210> SEQ ID NO 28
<211> LENGTH: 1522
<212> TYPE: DNA
<213> ORGANISM: Zea mays

<400> SEQUENCE: 28
gcacactcgc agctcgcaca tctcatggtg tcctaagaac ggcaagagcc agctctgcct 60
agcagcagcg cacagccaca tccatggacg ccagcccgac cccaccgctc cccctccgcg 120
ccccaactcc cagcattgac ctcccccgctg gcaaggacag ggccgacgcg gcggctaaca 180
aggccgcggc tgtgttcgac ctgcgccggg agcccaagat cccggagcca ttcctgtggc 240
cgcacgaaga ggcgcggccg acctcggccg cggagctgga ggtgccggtg gtggacgtgg 300
gcgtgctgcg caatggcgac ggcgcggggc tccgccgcgc cgcggcgcaa gtggcggcgg 360
cgtgcgcgac gcacgggttc ttccaggtgt gcgggcacgg cgtggacgcg gcgctggggc 420
gcgccgcgct ggacggcgcc agcgacttct tccggctgcc gctggctgag aagcagcggg 480
cccggcgcgt ccccggcacc gtgtccgggt acacgagcgc gcacgccgac cggttcgcgt 540
ccaagctccc ctggaaggag accctgtcct tcggcttcca cgacggcgcc gcggcgcccg 600
tcgtcgtgga ctacttcacc ggcaccctcg gccaagattt cgagccagtg gggcgggtgt 660
accagaggta ctgcgaggag atgaaggagc tgtcgctgac gatcatggag ctgctggagc 720
tgagcctggg cgtggagcgc ggctactacc gggagttctt cgaggacagc cgctccatca 780
tgcggtgcaa ctactacccg ccgtgcccgg tgccggagcg cacgctgggc acgggcccgc 840
actgcgaccc cacggcgctg accatcctcc tgcaggacga cgtcggcggg ctggaggtcc 900
tggtggacgg cgagtggcgc cccgtccggc ccgtcccagg cgccatggtc atcaacatcg 960
gcgacacctt catggcgctg tccaacgggc ggtacaagag ctgcctgcac cgcgcggtgg 1020
tgaaccggcg gcaggagcgg caatcgctgg ccttcttcct gtgcccgcgc gaggaccggg 1080
tggtgcgccc gccggccagc gccgcgccgc ggcagtaccc ggacttcacc tgggccgacc 1140
tcatgcgctt cacgcagcgc cactaccgcg ccgacacccg cacgctggac gccttcaccc 1200
gctggctctc ccacggcccg gcggcggcgg ctccctgcac ctaacgagcc ggccgtctct 1260
ttcgccgggg cccgcgcggg gttcgcccac gtggtgatca ggtggcagac atgtggccca 1320
cgggccccgc gccgccttcc ccatttttgg acgaccctac tgctactact actagtgtac 1380
atatgcaaaa aaatacatat atatataggt actttctcta atatttttat atataagcaa 1440
ggcggcctgg tgttcttttc tttgttttgt cgacaactgt ttgatcccat cctatggacg 1500
atggatagtt caatgtttgt ac 1522

<210> SEQ ID NO 29
<211> LENGTH: 1161
<212> TYPE: DNA
<213> ORGANISM: Zea mays

<400> SEQUENCE: 29
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctgtccttcg gcttccacga cggcgccgcg gcgcccgtcg tcgtggacta cttcaccggc 540
accctcggcc aagatttcga gccagtgggg cgggtgtacc agaggtactg cgaggagatg 600
aaggagctgt cgctgacgat catggagctg ctggagctga gcctgggcgt ggagcgcggc 660
tactaccggg agttcttcga ggacagccgc tccatcatgc ggtgcaacta ctacccgccg 720
tgcccggtgc cggagcgcac gctgggcacg ggcccgcact gcgaccccac ggcgctgacc 780
atcctcctgc aggacgacgt cggcgggctg gaggtcctgg tggacggcga gtggcgcccc 840
gtccggcccg tcccaggcgc catggtcatc aacatcggcg acaccttcat ggcgctgtcc 900
aacgggcggt acaagagctg cctgcaccgc gcggtggtga accggcggca ggagcggcaa 960
tcgctggcct tcttcctgtg cccgcgcgag gaccgggtgg tgcgcccgcc ggccagcgcc 1020
gcgccgcggc agtacccgga cttcacctgg gccgacctca tgcgcttcac gcagcgccac 1080
taccgcgccg acacccgcac gctggacgcc ttcacccgct ggctctccca cggcccggcg 1140
gcggcggctc cctgcaccta a 1161

<210> SEQ ID NO 30
<211> LENGTH: 386
<212> TYPE: PRT
<213> ORGANISM: Zea mays

<400> SEQUENCE: 30

Met Asp Ala Ser Pro Thr Pro Pro Leu Pro Leu Arg Ala Pro Thr Pro
1               5                   10                  15

Ser Ile Asp Leu Pro Ala Gly Lys Asp Arg Ala Asp Ala Ala Ala Asn
            20                  25                  30

Lys Ala Ala Ala Val Phe Asp Leu Arg Arg Glu Pro Lys Ile Pro Glu
        35                  40                  45

Pro Phe Leu Trp Pro His Glu Glu Ala Arg Pro Thr Ser Ala Ala Glu
    50                  55                  60

Leu Glu Val Pro Val Val Asp Val Gly Val Leu Arg Asn Gly Asp Gly
65                  70                  75                  80

Ala Gly Leu Arg Arg Ala Ala Ala Gln Val Ala Ala Ala Cys Ala Thr
                85                  90                  95

His Gly Phe Phe Gln Val Cys Gly His Gly Val Asp Ala Ala Leu Gly
            100                 105                 110

```
Arg Ala Ala Leu Asp Gly Ala Ser Asp Phe Phe Arg Leu Pro Leu Ala
        115                 120                 125

Glu Lys Gln Arg Ala Arg Arg Val Pro Gly Thr Val Ser Gly Tyr Thr
    130                 135                 140

Ser Ala His Ala Asp Arg Phe Ala Ser Lys Leu Pro Trp Lys Glu Thr
145                 150                 155                 160

Leu Ser Phe Gly Phe His Asp Gly Ala Ala Ala Pro Val Val Val Asp
                165                 170                 175

Tyr Phe Thr Gly Thr Leu Gly Gln Asp Phe Glu Pro Val Gly Arg Val
            180                 185                 190

Tyr Gln Arg Tyr Cys Glu Glu Met Lys Glu Leu Ser Leu Thr Ile Met
        195                 200                 205

Glu Leu Leu Glu Leu Ser Leu Gly Val Glu Arg Gly Tyr Tyr Arg Glu
    210                 215                 220

Phe Phe Glu Asp Ser Arg Ser Ile Met Arg Cys Asn Tyr Tyr Pro Pro
225                 230                 235                 240

Cys Pro Val Pro Glu Arg Thr Leu Gly Thr Gly Pro His Cys Asp Pro
                245                 250                 255

Thr Ala Leu Thr Ile Leu Leu Gln Asp Asp Val Gly Gly Leu Glu Val
            260                 265                 270

Leu Val Asp Gly Glu Trp Arg Pro Val Arg Pro Val Pro Gly Ala Met
        275                 280                 285

Val Ile Asn Ile Gly Asp Thr Phe Met Ala Leu Ser Asn Gly Arg Tyr
    290                 295                 300

Lys Ser Cys Leu His Arg Ala Val Val Asn Arg Arg Gln Glu Arg Gln
305                 310                 315                 320

Ser Leu Ala Phe Phe Leu Cys Pro Arg Glu Asp Arg Val Val Arg Pro
                325                 330                 335

Pro Ala Ser Ala Ala Pro Arg Gln Tyr Pro Asp Phe Thr Trp Ala Asp
            340                 345                 350

Leu Met Arg Phe Thr Gln Arg His Tyr Arg Ala Asp Thr Arg Thr Leu
        355                 360                 365

Asp Ala Phe Thr Arg Trp Leu Ser His Gly Pro Ala Ala Ala Ala Pro
    370                 375                 380

Cys Thr
385
```

<210> SEQ ID NO 31
<211> LENGTH: 8859
<212> TYPE: DNA
<213> ORGANISM: Zea mays

<400> SEQUENCE: 31

```
cctattttgt gtctaatact cttcttatat taattgtttg gtcaaacttt agataaattt      60

gactaatgat gcaattaaaa ctgcatcacc tttactaagg tactgcttta tatgtttcga     120

caaaattttc aattattctc tatgtgtttt aatctttgcg ctacacctcc attgatttaa     180

atactcattt attttaaacc ataacttaaa ttatatcgga tctttgcatc ctttctatgg     240

caccatacat gaatcgatat tttggctgca aatttttaat catgttagtt ttagcatttt     300

ttcatatcca tgtgttaagt ttgaatcatg tgttgttttt atataattta ttgaaaatat     360

agatcctaaa cttcactaat acttacaaca atagcatcat catgtgtttt aatccacgcc     420

acaacactca aggcattgaa ttttcttcta ccaaagagtt gtatgtgtgt attgttcttt     480
```

```
aaaaaataga gtgattataa ttaaactacc agtattcata tgtaaaatgt atagacatct    540
aaaataaaat ttgcaaaaaa cattgttgca gactttcaat ataattaaga atgggtttta    600
gggtcatgat atatggtttg ttaaagaaac ttgttttttt ttgcaattga taaactataa    660
aatacatttt cactattgtg tgcatatgta cttggtatac atagtggcat atatcatttt    720
tgtttacttt gaggtttgaa ttatctatgt taaaattgga taacatagat acattggtgt    780
gcgtcctttg gcccatttac ttgactgagg agcaatacta taaagtaaaa catatttgga    840
tattttatct taaactccta gcataatatt gatttaatta tgaacaaata tatgtttagg    900
tgatagtttc atgggtggta aactatataa gaaggcttac catgatcttt gcaaactcta    960
ggctatgaaa gagttccatg atttgtctta gaagcataga caaaacagtg ataatgatct   1020
aaatcacact tatggcactg atgaccatat atgcaaagct aaatgcatgt taagttgtat   1080
tatatcatat gtttacaatg actatcgcat ataacgagga atacattgtc tatatagata   1140
gctattactg tagtagtgcc aaatgttgga caacatgaat cataatcttc aaacctagag   1200
aaattgtagt cagtcgtaca catatcgtct agtaagttgt ctatactttt tatttattgt   1260
atcaaatttt attgttatct tgcttgcttg tttgtttgta ccatagacac aatatggtca   1320
aaaagtggtc aatcgattcg aagaagattg caattgacga gtgctaacag ttgatccttt   1380
tgttgtgcac gctagcggag tagcatgaaa agagtaaaat atgaaattag cgttctaaac   1440
tgtttgtgct ataggtactt cgtatttaat ggagtgacta actataggaa ggtgagagct   1500
cagaagtcag caccctcaca cagagttcta gagttagtgg tcatcgaacc acgacaaact   1560
acatgatgag cagaagaggc aacatcaaga ctatgatcaa tagtttcggg tcaatgaatg   1620
acatcgtgat gagtatttat ctaactatat agaacaacaa cacatgatgt tttaagtaag   1680
ttcaactgat cttctattgc tatctttaag tatttaacgt agcgaataat gttttatcta   1740
tttcattcat aaataatgtt gtgacaaaag ggataaccca tcacttttac catgttctag   1800
ataccacaac catctccacc atcataatgg gttcttcatt ggtgcttgga cctcaaataa   1860
tcatatctat agccaactta gctcaattct aataaaatta ggcaacttgg cttcattgta   1920
gcaaaaatag ccaacttagc tcaattttat ctaaacttag ctaatctagc acaacttaga   1980
tcaatattag gaaaaactaa tcaatctaat ctagctcaac tatagcgaaa gatagatatt   2040
gtagcataac ttagtagatc tatctcaaat tttagcaaaa actaatcaat ttagataaac   2100
tctataaaat tttaatcatt atgacttatt tccaactaat tgtaacttgc atgattttta   2160
tgttccttct ttataattag caacacctaa agacacgaat gatgaggggt ctaacgcatt   2220
cattaaccag ttgttaaata atactctagg tagatgataa gaactctaat tattctatga   2280
atctaagcta aaagatgttt aatatttaag tattggtgtt tattatgtta tttagaacga   2340
ttcatgttac ttaaagattt gttatgattt ttaaatatga ttatgataat ttatgtggtg   2400
tggattaact tgtgaacata tgtgatgtag atgaatatgt atgttgtgga tggaaccata   2460
tgaatatata tacacactca tatactattc gttggtgtag gtaaagcttc atccatcggt   2520
aattactaaa tggtcttcag tcattaccac taggtgaagc ttcacacgac cgataattat   2580
tgaagaacgc tcattaattt ccggtaatgg cttattggcc ttcactagtc ggtgaaaatt   2640
agctattttt ataccaataa aaattagcta atatatgtaa accaggtcta atttttatgg   2700
gcctcttacc gaccaaaatt gattagatta ttgttacaat agttttagtc aaaagctagc   2760
tatgctataa aaattttgaa ttaaagtgag tttcgtaata aaaattgcat acttttaaaa   2820
taaaataatt aaaaaacagt ttttagaaat acaatcaaac accttatgct ataaaaaaat   2880
```

tgtaatgtac ctacaaatat ataatacttt actttaaaat aggcctgtgc cttctcggct 2940
ctatatgggc tgcctccaac gaagcgccat ggccatgggc tccactgtgt cgggtcccac 3000
atgaggccgc gcctccctcc aaatgttccc tccctgcctt cgtctttgtc gttgctcgca 3060
aactccctgt cctcccctgt tacaaatacc cccacccgcc cggacagctt ccctgcatac 3120
ttgcagctcg cacatctcat ggtgtcgcag gaacgacaag agccagctgt gcctagcagc 3180
agcagcagca gcgccaagcg cgcagccacg tccatggacg ccagcccggc cccgccgctc 3240
ctcctccgcg cccccactcc cagccccagc attgacctcc ccgctggcaa ggacaaggcc 3300
gacgcggcgg ccagcaaggc cggcgcggcc gtgttcgacc tgcgccggga gcccaagatc 3360
cccgcgccat tcctgtggcc gcaggaagag gcgcggccgt cctcggccgc ggagctggag 3420
gtgccgatgg tggacgtggg cgtgctgcgc aatggcgacc gcgcggggct gcggcgcgcc 3480
gcggcgcagg tggccgcggc gtgcgcgacg cacgggttct tccaggtgtg cgggcacggc 3540
gtggacgcgg cgctggggcg cgccgcgctg gacggcgcca gcgacttctt ccggctgccg 3600
ctcgccgaga agcagcgcgc ccggcgcgtc cccggcaccg tgtccgggta cacgagcgcg 3660
cacgccgacc ggttcgcggc caagctcccc tggaaggaga ccctgtcgtt cggctaccac 3720
gacggcgccg cgtcgcctgt cgtcgtggac tacttcgtcg gcaccctcgg ccaggatttc 3780
gagccaatgg ggtaagtaag gtagtaagaa ggagcgccgg tttacattta ccgcacgtcg 3840
gcgtgcggtc gagtcgggac tcgggagacg tatgaacccc cgtcccgtcc catgcatgtg 3900
tggcaggtgg gtgtaccaga ggtactgcga ggagatgaag gagctgtcgc tgacgatcat 3960
ggagctgctg gagctgagcc tgggcgtgga gctgcgcggc tactaccggg agttcttcga 4020
ggacagccgg tccatcatgc ggtgcaacta ctacccgccg tgcccggagc cggagcgcac 4080
gctgggcacg ggcccgcact gcgaccccac ggcgctcacc atcctcctgc aggacgacgt 4140
gggcgggctg gaggtgctgg tggacggtga gtggcgcccc gtccggcccg tcccgggcgc 4200
catggtcatc aacatcggcg acaccttcat ggtaacgaaa cgaaagcgct cgctcctctg 4260
ttttccttgg ccgctcttgt cctgtgtgta tattcagttg agctctctct gtgctgttat 4320
ttcccgaatc ctagtggacc taaacgggca ggttattaca gcacgcacac gtaggcatgt 4380
catgtagcta gtacatacat agcgatgccg atgcaaatgc aatagagaca tgcgttcgag 4440
ttggttccta tctcggcggg ctacggcagg tacacgcggc cgcggcgcgc tctctctagt 4500
ctatccgcgg ccgcgcccag gccgatcgag gcttccgggg gagagttgcg acaagagaac 4560
ggaccgaggg ggtcggctag cggtagcaag ttccctgttg gtttgtggcg ttggagcgtt 4620
gcggagaggc ttgcgcggcg gcggggacgt cgacggggac gtggcgggga gacgatacga 4680
tgggtgccgg gcagggcaac gctttcggcg ggtggccgtg tccaggtgcg cgcggccttg 4740
tcggtttccc cctctcggtg tccatggccg agaaatgggt cgacgaccga gaccgacgct 4800
cggtgcggcg cccatcccgt ctgatccgcc gcgccacgcg agcggcccta tgcgatgccg 4860
cacgggcgcg gagggccgtc gcgcggagta taatgtatag tatatagtac aaggttggtt 4920
ggagtcgggt tgggttggat cgggtcaccg gtacgtggtg gctgctgttg cccccgccgt 4980
ttccgcttgc acttttgtcg cggtttcgct ggcgatccgg cacgcggcgc ccacaccacg 5040
ccggggctcc aaacagctcg ggcccttggc cgtgtgggtg gcaggcactt gcacgcgtcc 5100
ggttgtcgcg gcctggcccg ccgccgggcg caccgcaaca atgagacagc ccgacacgat 5160
gattcttgtg cactgtgcta acccgcatgc catgcaggcg ctgtcgaacg ggaggtacaa 5220

```
gagctgcctg caccgcgcgg tggtgaacca gcggcgggcg cggcggtcgc tggccttctt   5280
cctgtgcccg cgcgaggacc gggtggtgcg cccgccggcc agtgctgcgc cgcggcgcta   5340
cccggacttc acctgggccg acctcatgcg cttcacgcag cgccactacc gcgccgacac   5400
ccgcacgctg gacgccttca cccgctggct ctcccacggc ccggcccagg cggcggcgcc   5460
tccctgcacc tagcgagccg ggccaaggcc gtctctttcg ccccacgtgc gcgcccagct   5520
gggcaggtgg ccagacacgc ggcccgcggg ccccgcgccg ccttgccatt ttttgacgct   5580
ggccctactg ctgtgctact agtgtacata tgcaagagta catatatata tatatatata   5640
cgtattttct atatattata tataaaagca aggcggcccg gtgcccttct cttgttttgt   5700
ccacaactgt ttgatcccat tattctatgg accatggata cttcaatgtt tgtactaaga   5760
ccgtgaacgt gggattcttt tccttcctct gtgtttttc tgagaaaaat taaactgatt   5820
tctgtgaaat ttctttgttt taacaagaaa acagaaaaat tacatgagga aaacgctcca   5880
tttatttcaa caagaaaaaa atacatgaaa cagaaggaga aaaaacgtgt tcgttctatc   5940
attttcacac gagaaaaaaa aacatagaaa acagaaaaac tccccgcgtt cagatgagct   6000
caagaaaatg gaacgacacg gacgtcaccc gcgtcttgta gcagtgggcg cacgggtgcc   6060
gaatgtttgc tgggccccca agagaatcgc ttctcctcac gctgaatgaa tgaatcaacg   6120
agggaaacgc tgcaccctga gttccagacg tttccgaatt ccaaacgttt ttgtggcgtg   6180
cgtccatggg gcgcccccaa acttcggacg tttccggcgc tccaacaaat cttctcgctt   6240
cacacgtcac cgtcgtcccg gattcatttg cctcgtcgct ccaccattcg ctgctctcct   6300
ctccacgtac tcttaccctg acctttggga aagaactgaa cattcgagat gcacaacagt   6360
tcaaatataa catatgcagc acaagatcgt tcgactgcta tccgacaagc caacaacgtg   6420
cccagtagaa ctgaatgtac ctgtgatttc cagcactaac ttacagcaac gttgtgaaaa   6480
aacaaaaacg aaaacaaacg gcagaaaaaa cagatgtatt gttctacagt tacaccaaat   6540
attttctggt cctttcagca ccaacaagag ccatacgcat atctagaaga caaaattcct   6600
ctaatttcac ccctacgtgg tagcagttcc tcctcaacac agttcacgtg ctagcgtcga   6660
gttctttggg ccgccacatc gacttctcga cgcagagcag gccctcgctg cccttggtgt   6720
aggtcatccg cacctcccac tgcacggact tggccatgct ctccagctca tttatcgtgt   6780
ccgcggtgtc cctcacgatc agcttgccct gtggcctcag tacacggtcg acctcggcga   6840
aaactgcagc cagtttgcat ctgtaaacag gcaacacaga tttttagtat ctaaaacact   6900
gcaggcaaac gccacaggtt ttagtcgcaa gaagcaataa aagcatgcaa acaatgctac   6960
gtgtacgtat caaaggaaca tgtcaaaact cgttgcatga acgatcattg atgtttcctt   7020
gctgaactag tcacatcagt ctgcttcaac ttctgggttt cactagtaga tataccagaa   7080
gggtagaata atgtgaagag caagaaatac agacctcttt ctgagctttg agaacagatg   7140
gtccgcgtgc agaaggtcat acgttcttgg gtaagtgctg aaagactcgc accagtcatg   7200
gtacatgcca aacaaaccgc gctcgtagat gatgggcagc gtgtctggtg aatcgatcgg   7260
cacgatattc atgacccaga ccttttggtc cctcagagct gcagcaaaac tgccatgcaa   7320
caatgtaaag cattagtcaa gaagaaggtg tacagtgcat ttctccttgt caacagtctt   7380
cagtaacaaa aaaaaagtgt tatgcttgac tgaatctttc aaagaaatat gcttgatgac   7440
ttatggtgga caagttgcct gttatagtgt tatgttttaa ttaactatgt gccagcttgg   7500
gtaactagta gttatgtagt gtgatctgaa ttaccaaaat ataaataaat aaataaacat   7560
gcccaagaaa ctacgaaaac catttactta ccctccatag acagctctca tgtccatgac   7620
```

```
atttctcact ttggaccagt caattcccat gccattcaca tacgatttac ttacaacccg   7680
tttccagtgg gcattatctg cctcaaaatc ttcatttgca ggctttccat agacaccaac   7740
cttggaacca tcaatccaga aaggggtctt ctcaagcctt tgcggccata actctggcca   7800
ttttgatcct cggacttttg agccaccagg cagtttgtgc atgcatgctt ccaacggtac   7860
attcctgcaa atcaaaaggc tgtgtaagca aagcagagaa gcacttttct ccattgaaaa   7920
tatactcttc tcaaagaacc gaaaccatac caagcagcat ctgcatcatc agattccttg   7980
cacaatggcg ggctgttttc agatcttttc tcatagcaaa tattgtccat tggtttctga   8040
tatatgacca taccaacttg gtttaactta tccttagtct tgttgaccat cttccagcac   8100
atggactttg tcaaagtaga catggctgaa aagggtatgt ggccacatgt tatgttagaa   8160
ataaaattca attttgaaca gttggtccat agcatgtatt ttgaacaaat gcaatccttc   8220
tccatccatg aaagaagttg acccttcata cttaggatta ttcagtactt tcactcatgt   8280
ctgctgaatt tgttctcttg gtagttgcta tacaagaaag ggggaagtac agagtagcta   8340
aacttataca agctatagtc tgatatttgt atgaaacata aattttggta tggatgtctt   8400
attaaaatgg gaggttgtat aatatttttc tagcctacct caacttgctt gagactaaaa   8460
ggctttgttg ttgttgttga ggctgtatgg tgctttgact ttacaaatca agttatcagc   8520
taccctactt atggatatac acctctcata aaatgatggt aagaagtttc gatatgtcac   8580
attaacataa gaacttcatt cagttagggt acaacgaagt taagtagtta cggaaatacc   8640
attccaaatc tcaacatcct ctgggagctt ttggtaaaca ggagtggcag accagacaaa   8700
gtaaccacca gggcgtaaca agcggttcaa ttccagcaaa agcatgccac ctaaaagtag   8760
cgagccagca ataagattca gttctatagc aaatcaataa atgaaaggag gacatgtcaa   8820
tatgtaacca gcaggacaaa ccttcgatgt gccaaggga                          8859
```

<210> SEQ ID NO 32
<211> LENGTH: 1733
<212> TYPE: DNA
<213> ORGANISM: Zea mays

<400> SEQUENCE: 32

```
atgaggccgc gcctccctcc aaatgttccc tccctgcctt cgtctttgtc gttgctcgca     60
aactccctgt cctcccctgt tacaaatacc cccacccgcc cggacagctt ccctgcatac    120
ttgcagctcg cacatctcat ggtgtcgcag gaacgacaag agccagctgt gcctagcagc    180
agcagcagca gcgccaagcg cgcagccacg tccatggacg ccagcccggc cccgccgctc    240
ctcctccgcg cccccactcc cagccccagc attgacctcc ccgctggcaa ggacaaggcc    300
gacgcggcgg ccagcaaggc cggcgcggcc gtgttcgacc tgcgccggga gcccaagatc    360
cccgcgccat tcctgtggcc gcaggaagag gcgcggccgt cctcggccgc ggagctggag    420
gtgccgatgg tggacgtggg cgtgctgcgc aatggcgacc gcgcggggct gcggcgcgcc    480
gcggcgcagg tggccgcggc gtgcgcgacg cacgggttct tccaggtgtg cgggcacggc    540
gtggacgcgg cgctggggcg cgccgcgctg gacggcgcca gcgacttctt ccggctgccg    600
ctcgccgaga agcagcgcgc ccggcgcgtc cccggcaccg tgtccgggta cacgagcgcg    660
cacgccgacc ggttcgcggc caagctcccc tggaaggaga ccctgtcgtt cggctaccac    720
gacggcgccg cgtcgcctgt cgtcgtggac tacttcgtcg gcaccctcgg ccaggatttc    780
gagccaatgg ggtgggtgta ccagaggtac tgcgaggaga tgaaggagct gtcgctgacg    840
```

```
atcatggagc tgctggagct gagcctgggc gtggagctgc gcggctacta ccgggagttc    900

ttcgaggaca gccggtccat catgcggtgc aactactacc cgccgtgccc ggagccggag    960

cgcacgctgg gcacgggccc gcactgcgac cccacggcgc tcaccatcct cctgcaggac   1020

gacgtgggcg ggctggaggt gctggtggac ggtgagtggc gccccgtccg gcccgtcccg   1080

ggcgccatgg tcatcaacat cggcgacacc ttcatggcgc tgtcgaacgg gaggtacaag   1140

agctgcctgc accgcgcggt ggtgaaccag cggcgggcgc ggcggtcgct ggccttcttc   1200

ctgtgcccgc gcgaggaccg ggtggtgcgc ccgccggcca gtgctgcgcc gcggcgctac   1260

ccggacttca cctgggccga cctcatgcgc ttcacgcagc gccactaccg cgccgacacc   1320

cgcacgctgg acgccttcac ccgctggctc tcccacggcc cggcccaggc ggcggcgcct   1380

ccctgcacct agcgagccgg gccaaggccg tctctttcgc cccacgtgcg cgcccagctg   1440

ggcaggtggc cagacacgcg gcccgcgggc cccgcgccgc cttgccattt tttgacgctg   1500

gccctactgc tgtgctacta gtgtacatat gcaagagtac atatatatat atatatatac   1560

gtattttcta tatattatat ataaaagcaa ggcggcccgg tgcccttctc ttgttttgtc   1620

cacaactgtt tgatcccatt attctatgga ccatggatac ttcaatgttt gtactaagac   1680

cgtgaacgtg ggattctttt ccttcctctg tgttttttct gagaaaaatt aaa          1733


<210> SEQ ID NO 33
<211> LENGTH: 1392
<212> TYPE: DNA
<213> ORGANISM: Zea mays

<400> SEQUENCE: 33

atgaggccgc gcctccctcc aaatgttccc tccctgcctt cgtctttgtc gttgctcgca     60

aactccctgt cctcccctgt tacaaatacc cccacccgcc cggacagctt ccctgcatac    120

ttgcagctcg cacatctcat ggtgtcgcag gaacgacaag agccagctgt gcctagcagc    180

agcagcagca gcgccaagcg cgcagccacg tccatggacg ccagcccggc cccgccgctc    240

ctcctccgcg cccccactcc cagccccagc attgacctcc ccgctggcaa ggacaaggcc    300

gacgcggcgg ccagcaaggc cggcgcggcc gtgttcgacc tgcgccggga gcccaagatc    360

cccgcgccat tcctgtggcc gcaggaagag gcgcggccgt cctcggccgc ggagctggag    420

gtgccgatgg tggacgtggg cgtgctgcgc aatggcgacc gcgcggggct gcggcgcgcc    480

gcggcgcagg tggccgcggc gtgcgcgacg cacgggttct tccaggtgtg cgggcacggc    540

gtggacgcgg cgctggggcg cgccgcgctg gacggcgcca gcgacttctt ccggctgccg    600

ctcgccgaga agcagcgcgc ccggcgcgtc cccggcaccg tgtccgggta cacgagcgcg    660

cacgccgacc ggttcgcggc caagctcccc tggaaggaga ccctgtcgtt cggctaccac    720

gacggcgccg cgtcgcctgt cgtcgtggac tacttcgtcg gcaccctcgg ccaggatttc    780

gagccaatgg ggtgggtgta ccagaggtac tgcgaggaga tgaaggagct gtcgctgacg    840

atcatggagc tgctggagct gagcctgggc gtggagctgc gcggctacta ccgggagttc    900

ttcgaggaca gccggtccat catgcggtgc aactactacc cgccgtgccc ggagccggag    960

cgcacgctgg gcacgggccc gcactgcgac cccacggcgc tcaccatcct cctgcaggac   1020

gacgtgggcg ggctggaggt gctggtggac ggtgagtggc gccccgtccg gcccgtcccg   1080

ggcgccatgg tcatcaacat cggcgacacc ttcatggcgc tgtcgaacgg gaggtacaag   1140

agctgcctgc accgcgcggt ggtgaaccag cggcgggcgc ggcggtcgct ggccttcttc   1200

ctgtgcccgc gcgaggaccg ggtggtgcgc ccgccggcca gtgctgcgcc gcggcgctac   1260
```

```
ccggacttca cctgggccga cctcatgcgc ttcacgcagc gccactaccg cgccgacacc   1320

cgcacgctgg acgccttcac ccgctggctc tcccacggcc cggcccaggc ggcggcgcct   1380

ccctgcacct ag                                                       1392


<210> SEQ ID NO 34
<211> LENGTH: 463
<212> TYPE: PRT
<213> ORGANISM: Zea mays

<400> SEQUENCE: 34

Met Arg Pro Arg Leu Pro Pro Asn Val Pro Ser Leu Pro Ser Ser Leu
1               5                   10                  15

Ser Leu Leu Ala Asn Ser Leu Ser Ser Pro Val Thr Asn Thr Pro Thr
            20                  25                  30

Arg Pro Asp Ser Phe Pro Ala Tyr Leu Gln Leu Ala His Leu Met Val
        35                  40                  45

Ser Gln Glu Arg Gln Glu Pro Ala Val Pro Ser Ser Ser Ser Ser Ser
    50                  55                  60

Ala Lys Arg Ala Ala Thr Ser Met Asp Ala Ser Pro Ala Pro Pro Leu
65                  70                  75                  80

Leu Leu Arg Ala Pro Thr Pro Ser Pro Ser Ile Asp Leu Pro Ala Gly
                85                  90                  95

Lys Asp Lys Ala Asp Ala Ala Ala Ser Lys Ala Gly Ala Ala Val Phe
            100                 105                 110

Asp Leu Arg Arg Glu Pro Lys Ile Pro Ala Pro Phe Leu Trp Pro Gln
        115                 120                 125

Glu Glu Ala Arg Pro Ser Ser Ala Ala Glu Leu Glu Val Pro Met Val
    130                 135                 140

Asp Val Gly Val Leu Arg Asn Gly Asp Arg Ala Gly Leu Arg Arg Ala
145                 150                 155                 160

Ala Ala Gln Val Ala Ala Ala Cys Ala Thr His Gly Phe Phe Gln Val
                165                 170                 175

Cys Gly His Gly Val Asp Ala Ala Leu Gly Arg Ala Ala Leu Asp Gly
            180                 185                 190

Ala Ser Asp Phe Phe Arg Leu Pro Leu Ala Glu Lys Gln Arg Ala Arg
        195                 200                 205

Arg Val Pro Gly Thr Val Ser Gly Tyr Thr Ser Ala His Ala Asp Arg
    210                 215                 220

Phe Ala Ala Lys Leu Pro Trp Lys Glu Thr Leu Ser Phe Gly Tyr His
225                 230                 235                 240

Asp Gly Ala Ala Ser Pro Val Val Val Asp Tyr Phe Val Gly Thr Leu
                245                 250                 255

Gly Gln Asp Phe Glu Pro Met Gly Trp Val Tyr Gln Arg Tyr Cys Glu
            260                 265                 270

Glu Met Lys Glu Leu Ser Leu Thr Ile Met Glu Leu Leu Glu Leu Ser
        275                 280                 285

Leu Gly Val Glu Leu Arg Gly Tyr Tyr Arg Glu Phe Phe Glu Asp Ser
    290                 295                 300

Arg Ser Ile Met Arg Cys Asn Tyr Tyr Pro Pro Cys Pro Glu Pro Glu
305                 310                 315                 320

Arg Thr Leu Gly Thr Gly Pro His Cys Asp Pro Thr Ala Leu Thr Ile
                325                 330                 335

Leu Leu Gln Asp Asp Val Gly Gly Leu Glu Val Leu Val Asp Gly Glu
```

```
            340                 345                 350

Trp Arg Pro Val Arg Pro Val Pro Gly Ala Met Val Ile Asn Ile Gly
        355                 360                 365

Asp Thr Phe Met Ala Leu Ser Asn Gly Arg Tyr Lys Ser Cys Leu His
    370                 375                 380

Arg Ala Val Val Asn Gln Arg Arg Ala Arg Arg Ser Leu Ala Phe Phe
385                 390                 395                 400

Leu Cys Pro Arg Glu Asp Arg Val Val Arg Pro Pro Ala Ser Ala Ala
                405                 410                 415

Pro Arg Arg Tyr Pro Asp Phe Thr Trp Ala Asp Leu Met Arg Phe Thr
            420                 425                 430

Gln Arg His Tyr Arg Ala Asp Thr Arg Thr Leu Asp Ala Phe Thr Arg
        435                 440                 445

Trp Leu Ser His Gly Pro Ala Gln Ala Ala Ala Pro Pro Cys Thr
    450                 455                 460


<210> SEQ ID NO 35
<211> LENGTH: 9067
<212> TYPE: DNA
<213> ORGANISM: Zea mays

<400> SEQUENCE: 35

ggtaatggct tattggcctt cactagtcgg tgaaaattag ctatttttat accaataaaa     60

attagctaat atatgtaaac caggtctaat ttttatgggc ctcttaccga ccaaaattga    120

ttagattatt gttacaatag ttttagtcaa aagctagcta tgctataaaa attttgaatt    180

aaagtgagtt tcgtaataaa aattgcatac ttttaaaata aaataattaa aaaacagttt    240

ttagaaatac aatcaaacac cttatgctat aaaaaaattg taatgtacct acaaatatat    300

aatactttac tttaaaatag gcctgtgcct tctcggctct atatgggctg cctccaacga    360

agcgccatgg ccatgggctc cactgtgtcg ggtcccacat gaggccgcgc ctccctccaa    420

atgttccctc cctgccttcg tctttgtcgt tgctcgcaaa ctccctgtcc tcccctgtta    480

caaatacccc cacccgcccg gacagcttcc ctgcatactt gcagctcgca catctcatgg    540

tgtcgcagga acgacaagag ccagctgtgc ctagcagcag cagcagcagc gccaagcgcg    600

cagccacgtc catggacgcc agcccggccc cgccgctcct cctccgcgcc cccactccca    660

gccccagcat tgacctcccc gctggcaagg acaaggccga cgcggcggcc agcaaggccg    720

gcgcggccgt gttcgacctg cgccgggagc ccaagatccc cgcgccattc ctgtggccgc    780

aggaagaggc gcggccgtcc tcggccgcgg agctggaggt gccgatggtg gacgtgggcg    840

tgctgcgcaa tggcgaccgc gcggggctgc ggcgcgccgc ggcgcaggtg gccgcggcgt    900

gcgcgacgca cgggttcttc caggtgtgcg ggcacggcgt ggacgcggcg ctggggcgcg    960

ccgcgctgga cggcgccagc gacttcttcc ggctgccgct cgccgagaag cagcgcgccc   1020

ggcgcgtccc cggcaccgtg tccgggtaca cgagcgcgca cgccgaccgg ttcgcggcca   1080

agctcccctg gaaggagacc ctgtcgttcg gctaccacga cggcgccgcg tcgcctgtcg   1140

tcgtggacta cttcgtcggc accctcggcc aggatttcga gccaatgggg taagtaaggt   1200

agtaagaagg agcgccggtt tacatttacc gcacgtcggc gtgcggtcga gtcgggactc   1260

gggagacgta tgaacccccg tcccgtccca tgcatgtgtg gcaggtgggt gtaccagagg   1320

tactgcgagg agatgaagga gctgtcgctg acgatcatgg agctgctgga gctgagcctg   1380

ggcgtggagc tgcgcggcta ctaccgggag ttcttcgagg acagccggtc catcatgcgg   1440
```

```
tgcaactact acccgccgtg cccggagccg gagcgcacgc tgggcacggg cccgcactgc   1500
gaccccacgg cgctcaccat cctcctgcag gacgacgtgg gcgggctgga ggtgctggtg   1560
gacggtgagt ggcgccccgt ccggcccgtc ccgggcgcca tggtcatcaa catcggcgac   1620
accttcatgg taacgaaacg aaagcgctcg ctcctctgtt ttccttggcc gctcttgtcc   1680
tgtgtgtata ttcagttgag ctctctctgt gctgttattt cccgaatcct agtggaccta   1740
aacgggcagg ttattacagc acgcacacgt aggcatgtca tgtagctagt acatacatag   1800
cgatgccgat gcaaatgcaa tagagacatg cgttcgagtt ggttcctatc tcggcgggct   1860
acggcaggta cacgcggccg cggcgcgctc tctctagtct atccgcggcc gcgcccaggc   1920
cgatcgaggc ttccggggga gagttgcgac aagagaacgg accgaggggg tcggctagcg   1980
gtagcaagtt ccctgttggt ttgtggcgtt ggagcgttgc ggagaggctt gcgcggcggc   2040
ggggacgtcg acggggacgt ggcggggaga cgatacgatg ggtgccgggc agggcaacgc   2100
tttcggcggg tggccgtgtc caggtgcgcg cggccttgtc ggtttccccc tctcggtgtc   2160
catggccgag aaatgggtcg acgaccgaga ccgacgctcg gtgcggcgcc catcccgtct   2220
gatccgccgc gccacgcgag cggccctatg cgatgccgca cgggcgcgga gggccgtcgc   2280
gcggagtata atgtatagta tatagtacaa ggttggttgg agtcgggttg ggttggatcg   2340
ggtcaccggt acgtggtggc tgctgttgcc cccgccgttt ccgcttgcac ttttgtcgcg   2400
gtttcgctgg cgatccggca cgcggcgccc acaccacgcc ggggctccaa acagctcggg   2460
cccttggccg tgtgggtggc aggcacttgc acgcgtccgg ttgtcgcggc ctggcccgcc   2520
gccgggcgca ccgcaacaat gagacagccc gacacgatga ttcttgtgca ctgtgctaac   2580
ccgcatgcca tgcaggcgct gtcgaacggg aggtacaaga gctgcctgca ccgcgcggtg   2640
gtgaaccagc ggcgggcgcg gcggtcgctg gccttcttcc tgtgcccgcg cgaggaccgg   2700
gtggtgcgcc cgccggccag tgctgcgccg cggcgctacc cggacttcac ctgggccgac   2760
ctcatgcgct tcacgcagcg ccactaccgc gccgacaccc gcacgctgga cgccttcacc   2820
cgctggctct cccacggccc ggcccaggcg gcggcgcctc cctgcaccta gcgagccggg   2880
ccaaggccgt ctctttcgcc ccacgtgcgc gcccagctgg gcaggtggcc agacacgcgg   2940
cccgcgggcc ccgcgccgcc ttgccatttt ttgacgctgg ccctactgct gtgctactag   3000
tgtacatatg caagagtaca tatatatata tatatatacg tattttctat atattatata   3060
taaaagcaag gcggcccggt gcccttctct tgttttgtcc acaactgttt gatcccatta   3120
ttctatggac catggatact tcaatgtttg tactaagacc gtgaacgtgg gattcttttc   3180
cttcctctgt gttttttctg agaaaaatta aactgatttc tgtgaaattt ctttgtttta   3240
acaagaaaac agaaaaatta catgaggaaa acgctccatt tatttcaaca agaaaaaaat   3300
acatgaaaca gaaggagaaa aaacgtgttc gttctatcat tttcacacga gaaaaaaaaa   3360
catagaaaac agaaaaactc cccgcgttca gatgagctca agaaaatgga acgacacgga   3420
cgtcacccgc gtcttgtagc agtgggcgca cgggtgccga atgtttgctg ggcccccaag   3480
agaatcgctt ctcctcacgc tgaatgaatg aatcaacgag ggaaacgctg caccctgagt   3540
tccagacgtt tccgaattcc aaacgttttt gtggcgtgcg tccatggggc gcccccaaac   3600
ttcggacgtt tccggcgctc caacaaatct tctcgcttca cacgtcaccg tcgtcccgga   3660
ttcatttgcc tcgtcgctcc accattcgct gctctcctct ccacgtactc ttaccctgac   3720
ctttgggaaa gaactgaaca ttcgagatgc acaacagttc aaatataaca tatgcagcac   3780
aagatcgttc gactgctatc cgacaagcca acaacgtgcc cagtagaact gaatgtacct   3840
```

```
gtgatttcca gcactaactt acagcaacgt tgtgaaaaaa caaaaacgaa aacaaacggc   3900
agaaaaaaca gatgtattgt tctacagtta caccaaatat tttctggtcc tttcagcacc   3960
aacaagagcc atacgcatat ctagaagaca aaattcctct aatttcaccc ctacgtggta   4020
gcagttcctc ctcaacacag ttcacgtgct agcgtcgagt tctttgggcc gccacatcga   4080
cttctcgacg cagagcaggc cctcgctgcc cttggtgtag gtcatccgca cctcccactg   4140
cacggacttg gccatgctct ccagctcatt tatcgtgtcc gcggtgtccc tcacgatcag   4200
cttgccctgt ggcctcagta cacggtcgac ctcggcgaaa actgcagcca gtttgcatct   4260
gtaaacaggc aacacagatt tttagtatct aaaacactgc aggcaaacgc cacaggtttt   4320
agtcgcaaga agcaataaaa gcatgcaaac aatgctacgt gtacgtatca aaggaacatg   4380
tcaaaactcg ttgcatgaac gatcattgat gtttccttgc tgaactagtc acatcagtct   4440
gcttcaactt ctgggtttca ctagtagata taccagaagg gtagaataat gtgaagagca   4500
agaaatacag acctctttct gagctttgag aacagatggt ccgcgtgcag aaggtcatac   4560
gttcttgggt aagtgctgaa agactcgcac cagtcatggt acatgccaaa caaaccgcgc   4620
tcgtagatga tgggcagcgt gtctggtgaa tcgatcggca cgatattcat gacccagacc   4680
ttttggtccc tcagagctgc agcaaaactg ccatgcaaca atgtaaagca ttagtcaaga   4740
agaaggtgta cagtgcattt ctccttgtca acagtcttca gtaacaaaaa aaaagtgtta   4800
tgcttgactg aatctttcaa agaaatatgc ttgatgactt atggtggaca agttgcctgt   4860
tatagtgtta tgttttaatt aactatgtgc cagcttgggt aactagtagt tatgtagtgt   4920
gatctgaatt accaaaatat aaataaataa ataaacatgc ccaagaaact acgaaaacca   4980
tttacttacc ctccatagac agctctcatg tccatgacat ttctcacttt ggaccagtca   5040
attcccatgc cattcacata cgatttactt acaacccgtt tccagtgggc attatctgcc   5100
tcaaaatctt catttgcagg ctttccatag acaccaacct tggaaccatc aatccagaaa   5160
ggggtcttct caagcctttg cggccataac tctggccatt ttgatcctcg gacttttgag   5220
ccaccaggca gtttgtgcat gcatgcttcc aacggtacat tcctgcaaat caaaaggctg   5280
tgtaagcaaa gcagagaagc acttttctcc attgaaaata tactcttctc aaagaaccga   5340
aaccatacca agcagcatct gcatcatcag attccttgca caatggcggg ctgttttcag   5400
atcttttctc atagcaaata ttgtccattg gtttctgata tatgaccata ccaacttggt   5460
ttaacttatc cttagtcttg ttgaccatct tccagcacat ggactttgtc aaagtagaca   5520
tggctgaaaa gggtatgtgg ccacatgtta tgttagaaat aaaattcaat tttgaacagt   5580
tggtccatag catgtatttt gaacaaatgc aatccttctc catccatgaa agaagttgac   5640
ccttcatact taggattatt cagtactttc actcatgtct gctgaatttg ttctcttggt   5700
agttgctata caagaaaggg ggaagtacag agtagctaaa cttatacaag ctatagtctg   5760
atatttgtat gaaacataaa ttttggtatg gatgtcttat taaaatggga ggttgtataa   5820
tatttttcta gcctacctca acttgcttga gactaaaagg ctttgttgtt gttgttgagg   5880
ctgtatggtg ctttgacttt acaaatcaag ttatcagcta ccctacttat ggatatacac   5940
ctctcataaa atgatggtaa gaagtttcga tatgtcacat taacataaga acttcattca   6000
gttagggtac aacgaagtta agtagttacg gaaataccat tccaaatctc aacatcctct   6060
gggagctttt ggtaaacagg agtggcagac cagacaaagt aaccaccagg gcgtaacaag   6120
cggttcaatt ccagcaaaag catgccacct aaaagtagcg agccagcaat aagattcagt   6180
```

```
tctatagcaa atcaataaat gaaaggagga catgtcaata tgtaaccagc aggacaaacc   6240
ttcgatgtgc caagggaccc tgcagcgagc gcaatgaatg acatcaaaga ctctgctggg   6300
gtacggaagt ctcttggtgc ccatcacagc tgatattgct ggaattcccc tttctaatgc   6360
aaattgtact tgagcttcat gctcatcttt tggagcaaaa gacatggtaa gcgcatctct   6420
atcaaacatg tagcctccaa agctggcaac tccacaacca acatccaata tgacacggct   6480
tcgtttgccc catgcaatat caggtagtgc ctgtgaatgg cagtttaatc agcatagggt   6540
gaaagcaagt gtgataacat taagttcaaa gacgcaacat gaaacctcaa tatcatggta   6600
cagtactcag cttatttgct atattaatgt agggatgaga ctaaaaaaaa ggaaagtttt   6660
atccgccaga atgagaggct gaaaatacag ggatgactaa tgttgcttag tctagcacat   6720
acaaagttac aaactgtcct caacacctgc agatttctat atggtgctat ttgacaaatt   6780
atgtttgtgg aatagtataa caataaatca atcactgatg ctcaaaagtg tgaggcagac   6840
aagtacaagt ctaaggagtg actaatatga gatgctggga tgattataat atacctgctg   6900
aatagtatca atatagtgga gggcaccatt cttgaactga gtcccacccc cagggaacaa   6960
gagatagtca cctgagacct taacccaatt ttgatgcccc ttgtactctg caagcctagt   7020
gtgaggaaca ttgctgtacc atacctgcaa aaaacagcac agcgtggtaa taagcaaaca   7080
cgcatcttgg tcagctaaag atgattcggt gttgtacaat tcagaataaa cagaatcacc   7140
ttgtccctgc tctttggcca ctcaattggc cgtttatatc cttctgggag tggaacaagg   7200
caggtaggag gctcctcagg gcaatgcctc tcacgatgtt cataatgttt ggtagttcga   7260
agcttcttga tagccttctc gttgtcaagg caaggtatgt aatctgttga ggcactacta   7320
ttacataatt tccaggtata gctggttgca tcgcctgaag acttcggtaa cgcttggact   7380
tccttttcat tctttgactc tgcagcctgt gtggggaatg aaccgttctg ggtatttgac   7440
tccttcagaa gctctgattg ggccccatca ggaaatacct cgttggagtt tgagctctga   7500
tccttctctc cattttcttc cacgttctct tctattttag gttgctcctc ctgagcggca   7560
tcgccatcag gcttctcttc ttgaccgtcc ttactctcac catcagtttt ttcatcacca   7620
ctctcatttg tgatttcatt gtctttcttc tccacactct tctccccatc atcattcttc   7680
gtttcatctg acagcccttc tgattttcca tttgcgtcat caaacatatc cttggtctcc   7740
gctttctcta ccggcacttc cagctctttc tcttcaggct tctcattgaa attctcttgc   7800
tcagaagcat cctgtttatt cggttcctct gggactgtgg catcattgtt gtcggtgtcc   7860
tcaaatttct cggacccttc accagcaatg ccaggtgatg cctcctgcga cgccccgaaa   7920
ttgacaggcg caggctgttg cttcaccacc ggcttcttat tggacgaaat ctccagcggg   7980
aagacagtgg acgaggtcat catccacgcg ccgactaggc agagcgccac aaagagcacg   8040
accgtggtgg ttgtgcagaa cgacgacgac gacgacgatg aggacggccg gcggccgtcc   8100
atctttccac ctcggccaaa tgccatcagt gcctggcgaa catgtaccag agcaccagcc   8160
ttcacgtggt ttatctccac caacaaccac ggctggacca acagcccccc caaaatcgca   8220
gctttgtctg ccctgtgtat gctgttacga cttacgaccg cgcggcaccg aagcaaacca   8280
caaaaaagaa actaaatcgc tgcgggttta aatcaagctg ctggatctag agaaggaaac   8340
ggagatctac tcaagcgaca ccgaaaggac ggtcccggat tggtgctatt agcatcttgt   8400
ttcctactac agcgtctctt tgaagaaaag aacgcggaga aatcaccccg taaggccaag   8460
catggaaaga aattcagtaa agcgcgggca ttaaaacccc cccgtcctgc tccttccgcg   8520
gagagctacg gcaccttcca attgagctac tagctctcag ctgggcgcag aacccgcact   8580
```

aataaatggc ggattccatc cagaaaaaag aagaagaaga aacagctaaa taatccagca 8640
cctcgctcgc ctcctcgttc gctagctcat cggcggggaa ggacgggacc agctccgctg 8700
gatccacgcc agcaagcggg tgcaaggaga gagggaacgg agcagcaatg cggaggcggt 8760
aggctggtac ctcgccggaa ccgaccggag cggtcgcggt ggccctccga gtggatctcg 8820
aggcgaggcg cgtccttggg ttctctgcct ccccgcactg ggctcgccgc gttataaagg 8880
caggcgggca gcgcagtgga ggtgggagag tggagtgcaa cctgtttgtg ttagtgtgcc 8940
cagagcggaa gcggaggaga tgggtccgcg ttataaaggg cctgtttggt tcagcttttt 9000
tctgaccagc ttttttaaga atctggctgt gaggagaatc tggctgtggg gagaaactga 9060
gtattat 9067

<210> SEQ ID NO 36
<211> LENGTH: 9067
<212> TYPE: DNA
<213> ORGANISM: Zea mays

<400> SEQUENCE: 36
ataatactca gtttctcccc acagccagat tctcctcaca gccagattct taaaaaagct 60
ggtcagaaaa aagctgaacc aaacaggccc tttataacgc ggacccatct cctccgcttc 120
cgctctgggc acactaacac aaacaggttg cactccactc tcccacctcc actgcgctgc 180
ccgcctgcct ttataacgcg gcgagcccag tgcggggagg cagagaaccc aaggacgcgc 240
ctcgcctcga gatccactcg gagggccacc gcgaccgctc cggtcggttc cggcgaggta 300
ccagcctacc gcctccgcat tgctgctccg ttccctctct ccttgcaccc gcttgctggc 360
gtggatccag cggagctggt cccgtccttc cccgccgatg agctagcgaa cgaggaggcg 420
agcgaggtgc tggattattt agctgtttct tcttcttctt ttttctggat ggaatccgcc 480
atttattagt gcgggttctg cgcccagctg agagctagta gctcaattgg aaggtgccgt 540
agctctccgc ggaaggagca ggacgggggg gttttaatgc ccgcgcttta ctgaatttct 600
ttccatgctt ggccttacgg ggtgatttct ccgcgttctt ttcttcaaag agacgctgta 660
gtaggaaaca agatgctaat agcaccaatc cgggaccgtc ctttcggtgt cgcttgagta 720
gatctccgtt tccttctcta gatccagcag cttgatttaa acccgcagcg atttagtttc 780
ttttttgtgg tttgcttcgg tgccgcgcgg tcgtaagtcg taacagcata cacagggcag 840
acaaagctgc gattttgggg gggctgttgg tccagccgtg gttgttggtg gagataaacc 900
acgtgaaggc tggtgctctg gtacatgttc gccaggcact gatggcattt ggccgaggtg 960
gaaagatgga cggccgccgg ccgtcctcat cgtcgtcgtc gtcgtcgttc tgcacaacca 1020
ccacggtcgt gctctttgtg gcgctctgcc tagtcggcgc gtggatgatg acctcgtcca 1080
ctgtcttccc gctggagatt tcgtccaata agaagccggt ggtgaagcaa cagcctgcgc 1140
ctgtcaattt cggggcgtcg caggaggcat cacctggcat tgctggtgaa gggtccgaga 1200
aatttgagga caccgacaac aatgatgcca cagtcccaga ggaaccgaat aaacaggatg 1260
cttctgagca agagaatttc aatgagaagc ctgaagagaa agagctggaa gtgccggtag 1320
agaaagcgga gaccaaggat atgtttgatg acgcaaatgg aaaatcagaa gggctgtcag 1380
atgaaacgaa gaatgatgat ggggagaaga gtgtggagaa gaaagacaat gaaatcacaa 1440
atgagagtgg tgatgaaaaa actgatggtg agagtaagga cggtcaagaa gagaagcctg 1500
atggcgatgc cgctcaggag gagcaaccta aaatagaaga gaacgtggaa gaaaatggag 1560

```
agaaggatca gagctcaaac tccaacgagg tatttcctga tggggcccaa tcagagcttc   1620
tgaaggagtc aaatacccag aacggttcat tccccacaca ggctgcagag tcaaagaatg   1680
aaaaggaagt ccaagcgtta ccgaagtctt caggcgatgc aaccagctat acctggaaat   1740
tatgtaatag tagtgcctca acagattaca taccttgcct tgacaacgag aaggctatca   1800
agaagcttcg aactaccaaa cattatgaac atcgtgagag gcattgccct gaggagcctc   1860
ctacctgcct tgttccactc ccagaaggat ataaacggcc aattgagtgg ccaaagagca   1920
gggacaaggt gattctgttt attctgaatt gtacaacacc gaatcatctt tagctgacca   1980
agatgcgtgt ttgcttatta ccacgctgtg ctgtttttg caggtatggt acagcaatgt    2040
tcctcacact aggcttgcag agtacaaggg gcatcaaaat tgggttaagg tctcaggtga   2100
ctatctcttg ttccctgggg gtgggactca gttcaagaat ggtgccctcc actatattga   2160
tactattcag caggtatatt ataatcatcc cagcatctca tattagtcac tccttagact   2220
tgtacttgtc tgcctcacac ttttgagcat cagtgattga tttattgtta tactattcca   2280
caaacataat ttgtcaaata gcaccatata gaaatctgca ggtgttgagg acagtttgta   2340
actttgtatg tgctagacta agcaacatta gtcatccctg tattttcagc ctctcattct   2400
ggcggataaa actttccttt tttttagtct catccctaca ttaatatagc aaataagctg   2460
agtactgtac catgatattg aggtttcatg ttgcgtcttt gaacttaatg ttatcacact   2520
tgctttcacc ctatgctgat taaactgcca ttcacaggca ctacctgata ttgcatgggg   2580
caaacgaagc cgtgtcatat tggatgttgg ttgtggagtt gccagctttg gaggctacat   2640
gtttgataga gatgcgctta ccatgtcttt tgctccaaaa gatgagcatg aagctcaagt   2700
acaatttgca ttagaaaggg gaattccagc aatatcagct gtgatgggca ccaagagact   2760
tccgtacccc agcagagtct ttgatgtcat tcattgcgct cgctgcaggg tcccttggca   2820
catcgaaggt ttgtcctgct ggttacatat tgacatgtcc tcctttcatt tattgatttg   2880
ctatagaact gaatcttatt gctggctcgc tacttttagg tggcatgctt ttgctggaat   2940
tgaaccgctt gttacgccct ggtggttact ttgtctggtc tgccactcct gtttaccaaa   3000
agctcccaga ggatgttgag atttggaatg gtatttccgt aactacttaa cttcgttgta   3060
ccctaactga atgaagttct tatgttaatg tgacatatcg aaacttctta ccatcatttt   3120
atgagaggtg tatatccata agtagggtag ctgataactt gatttgtaaa gtcaaagcac   3180
catacagcct caacaacaac aacaaagcct tttagtctca agcaagttga ggtaggctag   3240
aaaaatatta tacaacctcc cattttaata agacatccat accaaaattt atgtttcata   3300
caaatatcag actatagctt gtataagttt agctactctg tacttccccc tttcttgtat   3360
agcaactacc aagagaacaa attcagcaga catgagtgaa agtactgaat aatcctaagt   3420
atgaagggtc aacttctttc atggatggag aaggattgca tttgttcaaa atacatgcta   3480
tggaccaact gttcaaaatt gaattttatt tctaacataa catgtggcca catacccttt   3540
tcagccatgt ctactttgac aaagtccatg tgctggaaga tggtcaacaa gactaaggat   3600
aagttaaacc aagttggtat ggtcatatat cagaaaccaa tggacaatat ttgctatgag   3660
aaaagatctg aaaacagccc gccattgtgc aaggaatctg atgatgcaga tgctgcttgg   3720
tatggtttcg gttctttgag aagagtatat tttcaatgga gaaaagtgct tctctgcttt   3780
gcttacacag ccttttgatt tgcaggaatg taccgttgga agcatgcatg cacaaactgc   3840
ctggtggctc aaaagtccga ggatcaaaat ggccagagtt atggccgcaa aggcttgaga   3900
agaccccttt ctggattgat ggttccaagg ttggtgtcta tggaaagcct gcaaatgaag   3960
```

attttgaggc agataatgcc cactggaaac gggttgtaag taaatcgtat gtgaatggca 4020
tgggaattga ctggtccaaa gtgagaaatg tcatggacat gagagctgtc tatggagggt 4080
aagtaaatgg ttttcgtagt ttcttgggca tgtttattta tttatttata ttttggtaat 4140
tcagatcaca ctacataact actagttacc caagctggca catagttaat taaaacataa 4200
cactataaca ggcaacttgt ccaccataag tcatcaagca tatttctttg aaagattcag 4260
tcaagcataa cacttttttt ttgttactga agactgttga caaggagaaa tgcactgtac 4320
accttcttct tgactaatgc tttacattgt tgcatggcag ttttgctgca gctctgaggg 4380
accaaaaggt ctgggtcatg aatatcgtgc cgatcgattc accagacacg ctgcccatca 4440
tctacgagcg cggtttgttt ggcatgtacc atgactggtg cgagtctttc agcacttacc 4500
caagaacgta tgaccttctg cacgcggacc atctgttctc aaagctcaga aagaggtctg 4560
tatttcttgc tcttcacatt attctaccct tctggtatat ctactagtga aacccagaag 4620
ttgaagcaga ctgatgtgac tagttcagca aggaaacatc aatgatcgtt catgcaacga 4680
gttttgacat gttcctttga tacgtacacg tagcattgtt tgcatgcttt tattgcttct 4740
tgcgactaaa acctgtggcg tttgcctgca gtgttttaga tactaaaaat ctgtgttgcc 4800
tgtttacaga tgcaaactgg ctgcagtttt cgccgaggtc gaccgtgtac tgaggccaca 4860
gggcaagctg atcgtgaggg acaccgcgga cacgataaat gagctggaga gcatggccaa 4920
gtccgtgcag tgggaggtgc ggatgaccta caccaagggc agcgagggcc tgctctgcgt 4980
cgagaagtcg atgtggcggc ccaaagaact cgacgctagc acgtgaactg tgttgaggag 5040
gaactgctac cacgtagggg tgaaattaga ggaattttgt cttctagata tgcgtatggc 5100
tcttgttggt gctgaaagga ccagaaaata tttggtgtaa ctgtagaaca atacatctgt 5160
tttttctgcc gtttgttttc gtttttgttt tttcacaacg ttgctgtaag ttagtgctgg 5220
aaatcacagg tacattcagt tctactgggc acgttgttgg cttgtcggat agcagtcgaa 5280
cgatcttgtg ctgcatatgt tatatttgaa ctgttgtgca tctcgaatgt tcagttcttt 5340
cccaaaggtc agggtaagag tacgtggaga ggagagcagc gaatggtgga gcgacgaggc 5400
aaatgaatcc gggacgacgg tgacgtgtga agcgagaaga tttgttggag cgccggaaac 5460
gtccgaagtt tgggggcgcc ccatggacgc acgccacaaa aacgtttgga attcggaaac 5520
gtctggaact cagggtgcag cgtttccctc gttgattcat tcattcagcg tgaggagaag 5580
cgattctctt gggggcccag caaacattcg gcacccgtgc gcccactgct acaagacgcg 5640
ggtgacgtcc gtgtcgttcc attttcttga gctcatctga acgcggggag tttttctgtt 5700
ttctatgttt ttttttctcg tgtgaaaatg atagaacgaa cacgtttttt ctccttctgt 5760
ttcatgtatt tttttcttgt tgaaataaat ggagcgtttt cctcatgtaa tttttctgtt 5820
ttcttgttaa aacaaagaaa tttcacagaa atcagtttaa tttttctcag aaaaaacaca 5880
gaggaaggaa aagaatccca cgttcacggt cttagtacaa acattgaagt atccatggtc 5940
catagaataa tgggatcaaa cagttgtgga caaaacaaga gaagggcacc gggccgcctt 6000
gcttttatat ataatatata gaaaatacgt atatatatat atatatatgt actcttgcat 6060
atgtacacta gtagcacagc agtagggcca gcgtcaaaaa atggcaaggc ggcgcggggc 6120
ccgcgggccg cgtgtctggc cacctgccca gctgggcgcg cacgtggggc gaaagagacg 6180
gccttggccc ggctcgctag gtgcagggag gcgccgccgc ctgggccggg ccgtgggaga 6240
gccagcgggt gaaggcgtcc agcgtgcggg tgtcggcgcg gtagtggcgc tgcgtgaagc 6300
gcatgaggtc ggcccaggtg aagtccgggt agcgccgcgg cgcagcactg gccggcgggc 6360
gcaccacccg gtcctcgcgc gggcacagga agaaggccag cgaccgccgc gcccgccgct 6420
ggttcaccac cgcgcggtgc aggcagctct tgtacctccc gttcgacagc gcctgcatgg 6480
catgcgggtt agcacagtgc acaagaatca tcgtgtcggg ctgtctcatt gttgcggtgc 6540
gcccggcggc gggccaggcc gcgacaaccg gacgcgtgca agtgcctgcc acccacacgg 6600
ccaagggccc gagctgtttg gagccccggc gtggtgtggg cgccgcgtgc cggatcgcca 6660
gcgaaaccgc gacaaaagtg caagcggaaa cggcgggggc aacagcagcc accacgtacc 6720
ggtgacccga tccaacccaa cccgactcca accaaccttg tactatatac tatacattat 6780
actccgcgcg acggccctcc gcgcccgtgc ggcatcgcat agggccgctc gcgtggcgcg 6840
gcggatcaga cgggatgggc gccgcaccga gcgtcggtct cggtcgtcga cccatttctc 6900
ggccatggac accgagaggg ggaaaccgac aaggccgcgc gcacctggac acggccaccc 6960
gccgaaagcg ttgccctgcc cggcacccat cgtatcgtct ccccgccacg tccccgtcga 7020
cgtccccgcc gccgcgcaag cctctccgca acgctccaac gccacaaacc aacagggaac 7080
ttgctaccgc tagccgaccc cctcggtccg ttctcttgtc gcaactctcc cccggaagcc 7140
tcgatcggcc tgggcgcggc cgcggataga ctagagagag cgcgccgcgg ccgcgtgtac 7200
ctgccgtagc ccgccgagat aggaaccaac tcgaacgcat gtctctattg catttgcatc 7260
ggcatcgcta tgtatgtact agctacatga catgcctacg tgtgcgtgct gtaataacct 7320
gcccgtttag gtccactagg attcgggaaa taacagcaca gagagagctc aactgaatat 7380
acacacagga caagagcggc caaggaaaac agaggagcga gcgctttcgt ttcgttacca 7440
tgaaggtgtc gccgatgttg atgaccatgg cgcccgggac gggccggacg gggcgccact 7500
caccgtccac cagcacctcc agcccgccca cgtcgtcctg caggaggatg gtgagcgccg 7560
tggggtcgca gtgcgggccc gtgcccagcg tgcgctccgg ctccgggcac ggcgggtagt 7620
agttgcaccg catgatggac cggctgtcct cgaagaactc ccggtagtag ccgcgcagct 7680
ccacgcccag gctcagctcc agcagctcca tgatcgtcag cgacagctcc ttcatctcct 7740
cgcagtacct ctggtacacc cacctgccac acatgcatgg gacgggacgg gggttcatac 7800
gtctcccgag tcccgactcg accgcacgcc gacgtgcggt aaatgtaaac cggcgctcct 7860
tcttactacc ttacttaccc cattggctcg aaatcctggc cgagggtgcc gacgaagtag 7920
tccacgacga caggcgacgc ggcgccgtcg tggtagccga acgacagggt ctccttccag 7980
gggagcttgg ccgcgaaccg gtcggcgtgc gcgctcgtgt acccggacac ggtgccgggg 8040
acgcgccggg cgcgctgctt ctcggcgagc ggcagccgga agaagtcgct ggcgccgtcc 8100
agcgcggcgc gccccagcgc cgcgtccacg ccgtgcccgc acacctggaa gaacccgtgc 8160
gtcgcgcacg ccgcggccac ctgcgccgcg gcgcgccgca gccccgcgcg gtcgccattg 8220
cgcagcacgc ccacgtccac catcggcacc tccagctccg cggccgagga cggccgcgcc 8280
tcttcctgcg gccacaggaa tggcgcgggg atcttgggct cccggcgcag gtcgaacacg 8340
gccgcgccgg ccttgctggc cgccgcgtcg gccttgtcct tgccagcggg gaggtcaatg 8400
ctggggctgg gagtgggggc gcggaggagg agcggcgggg ccgggctggc gtccatggac 8460
gtggctgcgc gcttggcgct gctgctgctg ctgctaggca cagctggctc ttgtcgttcc 8520
tgcgacacca tgagatgtgc gagctgcaag tatgcaggga agctgtccgg gcgggtgggg 8580
gtatttgtaa caggggagga cagggagttt gcgagcaacg acaaagacga aggcagggag 8640
ggaacatttg gagggaggcg cggcctcatg tgggacccga cacagtggag cccatggcca 8700
tggcgcttcg ttggaggcag cccatataga gccgagaagg cacaggccta ttttaaagta 8760
aagtattata tatttgtagg tacattacaa tttttttata gcataaggtg tttgattgta 8820
tttctaaaaa ctgtttttta attattttat tttaaaagta tgcaattttt attacgaaac 8880
tcactttaat tcaaaatttt tatagcatag ctagcttttg actaaaacta ttgtaacaat 8940
aatctaatca attttggtcg gtaagaggcc cataaaaatt agacctggtt tacatatatt 9000
agctaatttt tattggtata aaaatagcta attttcaccg actagtgaag gccaataagc 9060
cattacc 9067

<210> SEQ ID NO 37
<211> LENGTH: 877
<212> TYPE: DNA
<213> ORGANISM: Zea mays

<400> SEQUENCE: 37
gtcgtgcccc tctctagaga taaagagcat tgcatgtcta aagtataaaa aattaccaca 60
tatttttttg tcacacttat ttgaagtgta gtttatctat ctctatacat atatttaaac 120
ttcactctac aaataatata gtctataata ctaaaataat attagtgttt tagaggatca 180
tataaataaa ctgctagaca tggtctaaag gataattgaa tattttgaca atctacagtt 240
ttatcttttt agtgtgcatg tgatctctct gttttttttg caaatagctt gacctatata 300
atacttcatc cattttatta gtacatccat ttaggattta gggttgatgg tttctataga 360
ctaattttta gtacatccat tttattcttt ttagtctcta aatttttttaa aactaaaact 420 ctattttagt tttttattta ataatttaga tataaaatga aataaaataa attgactaca 480
aataaaacaa ataccctta agaaataaaa aaactaagca aacatttttc ttgtttcgag 540
tagataatga caggctgttc aacgccgtcg acgagtctaa cggacaccaa ccagcgaacc 600
agcagcgtcg cgtcgggcca agcgaagcag acggcacggc atctctgtag ctgcctctgg 660
acccctctcg agagttccgc tccaccgttg gacttgctcc gctgtcggca tccagaaatt 720
gcgtggcgga gcggcagacg tgaggcggca cggcaggcgg cctcttcctc ctctcacggc 780
accggcagct acgggggatt cctttcccac cgctccttcg ctttcccttc ctcgcccgcc 840
gtaataaata gacaccccct ccacaccctc tttcccc 877

<210> SEQ ID NO 38
<211> LENGTH: 1227
<212> TYPE: PRT
<213> ORGANISM: Lachnospiraceae bacterium ND2006

<400> SEQUENCE: 38

Ser Lys Leu Glu Lys Phe Thr Asn Cys Tyr Ser Leu Ser Lys Thr Leu
1 5 10 15

Arg Phe Lys Ala Ile Pro Val Gly Lys Thr Gln Glu Asn Ile Asp Asn
20 25 30

Lys Arg Leu Leu Val Glu Asp Glu Lys Arg Ala Glu Asp Tyr Lys Gly
35 40 45

Val Lys Lys Leu Leu Asp Arg Tyr Tyr Leu Ser Phe Ile Asn Asp Val
50 55 60

Leu His Ser Ile Lys Leu Lys Asn Leu Asn Asn Tyr Ile Ser Leu Phe
65 70 75 80

Arg Lys Lys Thr Arg Thr Glu Lys Glu Asn Lys Glu Leu Glu Asn Leu
85 90 95

```
Glu Ile Asn Leu Arg Lys Glu Ile Ala Lys Ala Phe Lys Gly Asn Glu
            100                 105                 110

Gly Tyr Lys Ser Leu Phe Lys Lys Asp Ile Ile Glu Thr Ile Leu Pro
        115                 120                 125

Glu Phe Leu Asp Asp Lys Asp Glu Ile Ala Leu Val Asn Ser Phe Asn
    130                 135                 140

Gly Phe Thr Thr Ala Phe Thr Gly Phe Phe Asp Asn Arg Glu Asn Met
145                 150                 155                 160

Phe Ser Glu Glu Ala Lys Ser Thr Ser Ile Ala Phe Arg Cys Ile Asn
                165                 170                 175

Glu Asn Leu Thr Arg Tyr Ile Ser Asn Met Asp Ile Phe Glu Lys Val
            180                 185                 190

Asp Ala Ile Phe Asp Lys His Glu Val Gln Glu Ile Lys Glu Lys Ile
        195                 200                 205

Leu Asn Ser Asp Tyr Asp Val Glu Asp Phe Phe Glu Gly Glu Phe Phe
    210                 215                 220

Asn Phe Val Leu Thr Gln Glu Gly Ile Asp Val Tyr Asn Ala Ile Ile
225                 230                 235                 240

Gly Gly Phe Val Thr Glu Ser Gly Glu Lys Ile Lys Gly Leu Asn Glu
                245                 250                 255

Tyr Ile Asn Leu Tyr Asn Gln Lys Thr Lys Gln Lys Leu Pro Lys Phe
            260                 265                 270

Lys Pro Leu Tyr Lys Gln Val Leu Ser Asp Arg Glu Ser Leu Ser Phe
        275                 280                 285

Tyr Gly Glu Gly Tyr Thr Ser Asp Glu Glu Val Leu Glu Val Phe Arg
    290                 295                 300

Asn Thr Leu Asn Lys Asn Ser Glu Ile Phe Ser Ser Ile Lys Lys Leu
305                 310                 315                 320

Glu Lys Leu Phe Lys Asn Phe Asp Glu Tyr Ser Ser Ala Gly Ile Phe
                325                 330                 335

Val Lys Asn Gly Pro Ala Ile Ser Thr Ile Ser Lys Asp Ile Phe Gly
            340                 345                 350

Glu Trp Asn Val Ile Arg Asp Lys Trp Asn Ala Glu Tyr Asp Asp Ile
        355                 360                 365

His Leu Lys Lys Lys Ala Val Val Thr Glu Lys Tyr Glu Asp Asp Arg
    370                 375                 380

Arg Lys Ser Phe Lys Lys Ile Gly Ser Phe Ser Leu Glu Gln Leu Gln
385                 390                 395                 400

Glu Tyr Ala Asp Ala Asp Leu Ser Val Val Glu Lys Leu Lys Glu Ile
                405                 410                 415

Ile Ile Gln Lys Val Asp Glu Ile Tyr Lys Val Tyr Gly Ser Ser Glu
            420                 425                 430

Lys Leu Phe Asp Ala Asp Phe Val Leu Glu Lys Ser Leu Lys Lys Asn
        435                 440                 445

Asp Ala Val Val Ala Ile Met Lys Asp Leu Leu Asp Ser Val Lys Ser
    450                 455                 460

Phe Glu Asn Tyr Ile Lys Ala Phe Phe Gly Glu Gly Lys Glu Thr Asn
465                 470                 475                 480

Arg Asp Glu Ser Phe Tyr Gly Asp Phe Val Leu Ala Tyr Asp Ile Leu
                485                 490                 495

Leu Lys Val Asp His Ile Tyr Asp Ala Ile Arg Asn Tyr Val Thr Gln
            500                 505                 510

Lys Pro Tyr Ser Lys Asp Lys Phe Lys Leu Tyr Phe Gln Asn Pro Gln
```

```
        515                 520                 525

Phe Met Gly Gly Trp Asp Lys Asp Lys Glu Thr Asp Tyr Arg Ala Thr
    530                 535                 540

Ile Leu Arg Tyr Gly Ser Lys Tyr Tyr Leu Ala Ile Met Asp Lys Lys
545                 550                 555                 560

Tyr Ala Lys Cys Leu Gln Lys Ile Asp Lys Asp Asp Val Asn Gly Asn
                565                 570                 575

Tyr Glu Lys Ile Asn Tyr Lys Leu Leu Pro Gly Pro Asn Lys Met Leu
            580                 585                 590

Pro Lys Val Phe Phe Ser Lys Lys Trp Met Ala Tyr Tyr Asn Pro Ser
        595                 600                 605

Glu Asp Ile Gln Lys Ile Tyr Lys Asn Gly Thr Phe Lys Lys Gly Asp
    610                 615                 620

Met Phe Asn Leu Asn Asp Cys His Lys Leu Ile Asp Phe Phe Lys Asp
625                 630                 635                 640

Ser Ile Ser Arg Tyr Pro Lys Trp Ser Asn Ala Tyr Asp Phe Asn Phe
                645                 650                 655

Ser Glu Thr Glu Lys Tyr Lys Asp Ile Ala Gly Phe Tyr Arg Glu Val
            660                 665                 670

Glu Glu Gln Gly Tyr Lys Val Ser Phe Glu Ser Ala Ser Lys Lys Glu
        675                 680                 685

Val Asp Lys Leu Val Glu Glu Gly Lys Leu Tyr Met Phe Gln Ile Tyr
    690                 695                 700

Asn Lys Asp Phe Ser Asp Lys Ser His Gly Thr Pro Asn Leu His Thr
705                 710                 715                 720

Met Tyr Phe Lys Leu Leu Phe Asp Glu Asn Asn His Gly Gln Ile Arg
                725                 730                 735

Leu Ser Gly Gly Ala Glu Leu Phe Met Arg Arg Ala Ser Leu Lys Lys
            740                 745                 750

Glu Glu Leu Val Val His Pro Ala Asn Ser Pro Ile Ala Asn Lys Asn
        755                 760                 765

Pro Asp Asn Pro Lys Lys Thr Thr Thr Leu Ser Tyr Asp Val Tyr Lys
    770                 775                 780

Asp Lys Arg Phe Ser Glu Asp Gln Tyr Glu Leu His Ile Pro Ile Ala
785                 790                 795                 800

Ile Asn Lys Cys Pro Lys Asn Ile Phe Lys Ile Asn Thr Glu Val Arg
                805                 810                 815

Val Leu Leu Lys His Asp Asp Asn Pro Tyr Val Ile Gly Ile Asp Arg
            820                 825                 830

Gly Glu Arg Asn Leu Leu Tyr Ile Val Val Val Asp Gly Lys Gly Asn
        835                 840                 845

Ile Val Glu Gln Tyr Ser Leu Asn Glu Ile Ile Asn Asn Phe Asn Gly
    850                 855                 860

Ile Arg Ile Lys Thr Asp Tyr His Ser Leu Leu Asp Lys Lys Glu Lys
865                 870                 875                 880

Glu Arg Phe Glu Ala Arg Gln Asn Trp Thr Ser Ile Glu Asn Ile Lys
                885                 890                 895

Glu Leu Lys Ala Gly Tyr Ile Ser Gln Val Val His Lys Ile Cys Glu
            900                 905                 910

Leu Val Glu Lys Tyr Asp Ala Val Ile Ala Leu Glu Asp Leu Asn Ser
        915                 920                 925

Gly Phe Lys Asn Ser Arg Val Lys Val Glu Lys Gln Val Tyr Gln Lys
    930                 935                 940
```

```
Phe Glu Lys Met Leu Ile Asp Lys Leu Asn Tyr Met Val Asp Lys Lys
945                 950                 955                 960

Ser Asn Pro Cys Ala Thr Gly Gly Ala Leu Lys Gly Tyr Gln Ile Thr
                965                 970                 975

Asn Lys Phe Glu Ser Phe Lys Ser Met Ser Thr Gln Asn Gly Phe Ile
            980                 985                 990

Phe Tyr Ile Pro Ala Trp Leu Thr  Ser Lys Ile Asp Pro  Ser Thr Gly
        995                 1000                 1005

Phe Val  Asn Leu Leu Lys Thr  Lys Tyr Thr Ser Ile  Ala Asp Ser
    1010                 1015                 1020

Lys Lys  Phe Ile Ser Ser Phe  Asp Arg Ile Met Tyr  Val Pro Glu
    1025                 1030                 1035

Glu Asp  Leu Phe Glu Phe Ala  Leu Asp Tyr Lys Asn  Phe Ser Arg
    1040                 1045                 1050

Thr Asp  Ala Asp Tyr Ile Lys  Lys Trp Lys Leu Tyr  Ser Tyr Gly
    1055                 1060                 1065

Asn Arg  Ile Arg Ile Phe Arg  Asn Pro Lys Lys Asn  Asn Val Phe
    1070                 1075                 1080

Asp Trp  Glu Glu Val Cys Leu  Thr Ser Ala Tyr Lys  Glu Leu Phe
    1085                 1090                 1095

Asn Lys  Tyr Gly Ile Asn Tyr  Gln Gln Gly Asp Ile  Arg Ala Leu
    1100                 1105                 1110

Leu Cys  Glu Gln Ser Asp Lys  Ala Phe Tyr Ser Ser  Phe Met Ala
    1115                 1120                 1125

Leu Met  Ser Leu Met Leu Gln  Met Arg Asn Ser Ile  Thr Gly Arg
    1130                 1135                 1140

Thr Asp  Val Asp Phe Leu Ile  Ser Pro Val Lys Asn  Ser Asp Gly
    1145                 1150                 1155

Ile Phe  Tyr Asp Ser Arg Asn  Tyr Glu Ala Gln Glu  Asn Ala Ile
    1160                 1165                 1170

Leu Pro  Lys Asn Ala Asp Ala  Asn Gly Ala Tyr Asn  Ile Ala Arg
    1175                 1180                 1185

Lys Val  Leu Trp Ala Ile Gly  Gln Phe Lys Lys Ala  Glu Asp Glu
    1190                 1195                 1200

Lys Leu  Asp Lys Val Lys Ile  Ala Ile Ser Asn Lys  Glu Trp Leu
    1205                 1210                 1215

Glu Tyr  Ala Gln Thr Ser Val  Lys His
    1220                 1225


<210> SEQ ID NO 39
<211> LENGTH: 1229
<212> TYPE: PRT
<213> ORGANISM: Lachnospiraceae bacterium ND2006

<400> SEQUENCE: 39

Ala Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
        35                  40                  45

Gly Val Lys Lys Leu Leu Asp Arg Tyr Tyr Leu Ser Phe Ile Asn Asp
    50                  55                  60

Val Leu His Ser Ile Lys Leu Lys Asn Leu Asn Asn Tyr Ile Ser Leu
```

-continued

```
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
        115                 120                 125

Pro Glu Phe Leu Asp Asp Lys Asp Glu Ile Ala Leu Val Asn Ser Phe
    130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
        195                 200                 205

Ile Leu Asn Ser Asp Tyr Asp Val Glu Asp Phe Phe Glu Gly Glu Phe
    210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
        275                 280                 285

Phe Tyr Gly Glu Gly Tyr Thr Ser Asp Glu Glu Val Leu Glu Val Phe
    290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
                325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
        355                 360                 365

Ile His Leu Lys Lys Lys Ala Val Val Thr Glu Lys Tyr Glu Asp Asp
    370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
                405                 410                 415

Ile Ile Ile Gln Lys Val Asp Glu Ile Tyr Lys Val Tyr Gly Ser Ser
            420                 425                 430

Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
    450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495
```

```
Leu Leu Lys Val Asp His Ile Tyr Asp Ala Ile Arg Asn Tyr Val Thr
            500                 505                 510

Gln Lys Pro Tyr Ser Lys Asp Lys Phe Lys Leu Tyr Phe Gln Asn Pro
        515                 520                 525

Gln Phe Met Arg Gly Trp Asp Lys Asp Lys Glu Thr Asp Tyr Arg Ala
    530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
            580                 585                 590

Leu Pro Arg Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
    610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
            660                 665                 670

Val Glu Glu Gln Gly Tyr Lys Val Ser Phe Glu Ser Ala Ser Lys Lys
        675                 680                 685

Glu Val Asp Lys Leu Val Glu Glu Gly Lys Leu Tyr Met Phe Gln Ile
    690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
            740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
    770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
            820                 825                 830

Arg Gly Glu Arg Asn Leu Leu Tyr Ile Val Val Val Asp Gly Lys Gly
        835                 840                 845

Asn Ile Val Glu Gln Tyr Ser Leu Asn Glu Ile Ile Asn Asn Phe Asn
    850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
            900                 905                 910
```

Glu Leu Val Glu Lys Tyr Asp Ala Val Ile Ala Leu Glu Asp Leu Asn
915 920 925

Ser Gly Phe Lys Asn Ser Arg Val Lys Val Glu Lys Gln Val Tyr Gln
930 935 940

Lys Phe Glu Lys Met Leu Ile Asp Lys Leu Asn Tyr Met Val Asp Lys
945 950 955 960

Lys Ser Asn Pro Cys Ala Thr Gly Gly Ala Leu Lys Gly Tyr Gln Ile
965 970 975

Thr Asn Lys Phe Glu Ser Phe Lys Ser Met Ser Thr Gln Asn Gly Phe
980 985 990

Ile Phe Tyr Ile Pro Ala Trp Leu Thr Ser Lys Ile Asp Pro Ser Thr
995 1000 1005

Gly Phe Val Asn Leu Leu Lys Thr Lys Tyr Thr Ser Ile Ala Asp
1010 1015 1020

Ser Lys Lys Phe Ile Ser Ser Phe Asp Arg Ile Met Tyr Val Pro
1025 1030 1035

Glu Glu Asp Leu Phe Glu Phe Ala Leu Asp Tyr Lys Asn Phe Ser
1040 1045 1050

Arg Thr Asp Ala Asp Tyr Ile Lys Lys Trp Lys Leu Tyr Ser Tyr
1055 1060 1065

Gly Asn Arg Ile Arg Ile Phe Arg Asn Pro Lys Lys Asn Asn Val
1070 1075 1080

Phe Asp Trp Glu Glu Val Cys Leu Thr Ser Ala Tyr Lys Glu Leu
1085 1090 1095

Phe Asn Lys Tyr Gly Ile Asn Tyr Gln Gln Gly Asp Ile Arg Ala
1100 1105 1110

Leu Leu Cys Glu Gln Ser Asp Lys Ala Phe Tyr Ser Ser Phe Met
1115 1120 1125

Ala Leu Met Ser Leu Met Leu Gln Met Arg Asn Ser Ile Thr Gly
1130 1135 1140

Arg Thr Asp Val Asp Phe Leu Ile Ser Pro Val Lys Asn Ser Asp
1145 1150 1155

Gly Ile Phe Tyr Asp Ser Arg Asn Tyr Glu Ala Gln Glu Asn Ala
1160 1165 1170

Ile Leu Pro Lys Asn Ala Asp Ala Asn Gly Ala Tyr Asn Ile Ala
1175 1180 1185

Arg Lys Val Leu Trp Ala Ile Gly Gln Phe Lys Lys Ala Glu Asp
1190 1195 1200

Glu Lys Leu Asp Lys Val Lys Ile Ala Ile Ser Asn Lys Glu Trp
1205 1210 1215

Leu Glu Tyr Ala Gln Thr Ser Val Lys His Ala
1220 1225

<210> SEQ ID NO 40
<211> LENGTH: 30
<212> TYPE: DNA
<213> ORGANISM: Lycopersicon esculentum

<400> SEQUENCE: 40
ggatctaaga agagaagaat taaacaagat 30

<210> SEQ ID NO 41
<211> LENGTH: 30
<212> TYPE: DNA
<213> ORGANISM: Lycopersicon esculentum

<400> SEQUENCE: 41
ggatctaaga agagaagaat taaacaagat 30

<210> SEQ ID NO 42
<211> LENGTH: 33
<212> TYPE: DNA
<213> ORGANISM: Solanum tuberosum

<400> SEQUENCE: 42
atgggtagca aaaagaggcg tatcaagcag gac 33

<210> SEQ ID NO 43
<211> LENGTH: 30
<212> TYPE: DNA
<213> ORGANISM: Solanum tuberosum

<400> SEQUENCE: 43
ggatctaaga agcgtaggat caagcaagat 30

<210> SEQ ID NO 44
<211> LENGTH: 200
<212> TYPE: DNA
<213> ORGANISM: Zea mays

<400> SEQUENCE: 44
cggcgtatgt gccaaaaact tcgtcacaga gagggccata agaaacatgg cccacggccc 60
aatacgaagc accgcgacga agcccaaaca gcagtccgta ggtggagcaa agcgctgggt 120
aatacgcaaa cgttttgtcc caccttgact aatcacaaga gtggagcgta ccttataaac 180
cgagccgcaa gcaccgaatt 200

<210> SEQ ID NO 45
<211> LENGTH: 23
<212> TYPE: DNA
<213> ORGANISM: Zea mays

<400> SEQUENCE: 45
aggacaccga caacaatgat gcc 23

<210> SEQ ID NO 46
<211> LENGTH: 23
<212> TYPE: DNA
<213> ORGANISM: Zea mays

<400> SEQUENCE: 46
ggtccactag gattcgggaa ata 23

<210> SEQ ID NO 47
<211> LENGTH: 23
<212> TYPE: DNA
<213> ORGANISM: Zea mays

<400> SEQUENCE: 47
gagccaatgg ggtaagtaag gta 23

<210> SEQ ID NO 48
<211> LENGTH: 23
<212> TYPE: DNA
<213> ORGANISM: Zea mays

<400> SEQUENCE: 48
gttaccatga aggtgtcgcc gat 23

<210> SEQ ID NO 49
<211> LENGTH: 23
<212> TYPE: DNA
<213> ORGANISM: Zea mays

<400> SEQUENCE: 49
gtccaataag aagccggtgg tga 23

<210> SEQ ID NO 50
<211> LENGTH: 23
<212> TYPE: DNA
<213> ORGANISM: Zea mays

<400> SEQUENCE: 50
cacctcggcc aaatgccatc agt 23

<210> SEQ ID NO 51
<211> LENGTH: 23
<212> TYPE: DNA
<213> ORGANISM: Zea mays

<400> SEQUENCE: 51
gttgagctct ctctgtgctg tta 23

<210> SEQ ID NO 52
<211> LENGTH: 23
<212> TYPE: DNA
<213> ORGANISM: Zea mays

<400> SEQUENCE: 52
ctaggattcg ggaaataaca gca 23

<210> SEQ ID NO 53
<211> LENGTH: 23
<212> TYPE: DNA
<213> ORGANISM: Zea mays

<400> SEQUENCE: 53
cctcggccaa atgccatcag tgc 23

<210> SEQ ID NO 54
<211> LENGTH: 23
<212> TYPE: DNA
<213> ORGANISM: Zea mays

<400> SEQUENCE: 54
cgtggtttat ctccaccaac aac 23

<210> SEQ ID NO 55
<211> LENGTH: 19
<212> TYPE: DNA
<213> ORGANISM: Artificial Sequence
<220> FEATURE:
<223> OTHER INFORMATION: PCR primer1

<400> SEQUENCE: 55
aggtgccgat ggtggacgt 19

<210> SEQ ID NO 56
<211> LENGTH: 19
<212> TYPE: DNA
<213> ORGANISM: Artificial Sequence
<220> FEATURE:

<223> OTHER INFORMATION: PCR primer2

<400> SEQUENCE: 56
agcctaccgc ctccgcatt 19

<210> SEQ ID NO 57
<211> LENGTH: 60
<212> TYPE: DNA
<213> ORGANISM: Zea mays

<400> SEQUENCE: 57
gcggccgtcc atctttccac ctcggccaaa gtgcctggcg aacatgtacc agagcaccag 60

<210> SEQ ID NO 58
<211> LENGTH: 60
<212> TYPE: DNA
<213> ORGANISM: Zea mays

<400> SEQUENCE: 58
ggccgtccat ctttccacct cggccaaatg tcagtgcctg gcgaacatgt accagagcac 60

<210> SEQ ID NO 59
<211> LENGTH: 60
<212> TYPE: DNA
<213> ORGANISM: Zea mays

<400> SEQUENCE: 59
ggccgtccat ctttccacct cggccaaatg gtgcctggcg aacatgtacc agagcaccag 60

<210> SEQ ID NO 60
<211> LENGTH: 60
<212> TYPE: DNA
<213> ORGANISM: Zea mays

<400> SEQUENCE: 60
gagtggcgcc ccgtccggcc cgtcccgggc ttcttattgg acgaaatctc cagcgggaag 60

<210> SEQ ID NO 61
<211> LENGTH: 60
<212> TYPE: DNA
<213> ORGANISM: Zea mays

<400> SEQUENCE: 61
ccggcccgtc ccgggcgcca tggtcatcaa gtgcctggcg aacatgtacc agagcaccag 60

<210> SEQ ID NO 62
<211> LENGTH: 60
<212> TYPE: DNA
<213> ORGANISM: Zea mays

<400> SEQUENCE: 62
gtccggcccg tcccgggcgc catggtcatc ggcttcttat tggacgaaat ctccagcggg 60

<210> SEQ ID NO 63
<211> LENGTH: 60
<212> TYPE: DNA
<213> ORGANISM: Zea mays

<400> SEQUENCE: 63
gtccggcccg tcccgggcgc catggtcatc ttattggacg aaatctccag cgggaagaca 60

<210> SEQ ID NO 64
<211> LENGTH: 60

<212> TYPE: DNA
<213> ORGANISM: Zea mays

<400> SEQUENCE: 64
cgtccggccc gtcccgggcg ccatggtcat gcttcttatt ggacgaaatc tccagcggga 60

<210> SEQ ID NO 65
<211> LENGTH: 60
<212> TYPE: DNA
<213> ORGANISM: Zea mays

<400> SEQUENCE: 65
ctgtgtgtat attcagttga gctctctctg cacggctgga ccaacagccc ccccaaaatc 60

<210> SEQ ID NO 66
<211> LENGTH: 60
<212> TYPE: DNA
<213> ORGANISM: Zea mays

<400> SEQUENCE: 66
cttggccgct cttgtcctgt gtgtatattc ggtgtcctca aatttctcgg acccttcacc 60

<210> SEQ ID NO 67
<211> LENGTH: 60
<212> TYPE: DNA
<213> ORGANISM: Zea mays

<400> SEQUENCE: 67
tgtatattca gttgagctct ctctgtgctg gttgtcggtg tcctcaaatt tctcggaccc 60

<210> SEQ ID NO 68
<211> LENGTH: 60
<212> TYPE: DNA
<213> ORGANISM: Lachnospiraceae bacterium ND2006

<400> SEQUENCE: 68
tatattcagt tgagctctct ctgtgctgtt tgttgtcggt gtcctcaaat ttctcggacc 60

<210> SEQ ID NO 69
<211> LENGTH: 60
<212> TYPE: DNA
<213> ORGANISM: Zea mays

<400> SEQUENCE: 69
atattcagtt gagctctctc tgtgctgtta gttgtcggtg tcctcaaatt tctcggaccc 60

<210> SEQ ID NO 70
<211> LENGTH: 60
<212> TYPE: DNA
<213> ORGANISM: Zea mays

<400> SEQUENCE: 70
attcagttga gctctctctg tgctgttatt gtcggtgtcc tcaaatttct cggacccttc 60

<210> SEQ ID NO 71
<211> LENGTH: 60
<212> TYPE: DNA
<213> ORGANISM: Zea mays

<400> SEQUENCE: 71
ctcggccagg atttcgagcc aatggggtaa cttcttattg gacgaaatct ccagcgggaa 60

<210> SEQ ID NO 72

<211> LENGTH: 60
<212> TYPE: DNA
<213> ORGANISM: Zea mays

<400> SEQUENCE: 72
cggccaggat ttcgagccaa tggggtaagt ccggcttctt attggacgaa atctccagcg 60

<210> SEQ ID NO 73
<211> LENGTH: 60
<212> TYPE: DNA
<213> ORGANISM: Zea mays

<400> SEQUENCE: 73
tcggccagga tttcgagcca atggggtaag aaggagcgcc ggtttacatt taccgcacgt 60

<210> SEQ ID NO 74
<211> LENGTH: 60
<212> TYPE: DNA
<213> ORGANISM: Zea mays

<400> SEQUENCE: 74
tcggccagga tttcgagcca atggggtaag gtagtaagaa ggagcgccgg tttacattta 60

<210> SEQ ID NO 75
<211> LENGTH: 60
<212> TYPE: DNA
<213> ORGANISM: Zea mays

<400> SEQUENCE: 75
ggactacttc gtcggcaccc tcggccagga gccggtttac atttaccgca cgtcggcgtg 60

<210> SEQ ID NO 76
<211> LENGTH: 665
<212> TYPE: DNA
<213> ORGANISM: Zea mays

<400> SEQUENCE: 76
gtcgttgctc gcaaactccc tgtcctcccc tgttacaaat acccccaccc gcccggacag 60
cttccctgca tacttgcagc tcgcacatct catggtgtcg caggaacgac aagagccagc 120
tgtgcctagc agcagcagca gcagcgccaa gcgcgcagcc acgtccatgg acgccagccc 180
ggccccgccg ctcctcctcc gcgcccccac tcccagcccc agcattgacc tccccgctgg 240
caaggacaag gccgacgcgg cggccagcaa ggccggcgcg gccgtgttcg acctgcgccg 300
ggagcccaag atccccgcgc cattcctgtg gccgcaggaa gaggcgcggc cgtcctcggc 360
cgcggagctg gaggtgccga tggtggacgt gggcgtgctg cgcaatggcg accgcgcggg 420
gctgcggcgc gccgcggcgc aggtggccgc ggcgtgcgcg acgcacgggt tcttccaggt 480
gtgcgggcac ggcgtggacg cggcgctggg gcgcgccgcg ctggacggcg ccagcgactt 540
cttccggctg ccgctcgccg agaagcagcg cgcccggcgc gtccccggca ccgtgtccgg 600
gtacacgagc gcgcacgccg accggttcgc ggccaagctc ccctggaagg agaccctgtc 660
gttcg 665

<210> SEQ ID NO 77
<211> LENGTH: 582
<212> TYPE: DNA
<213> ORGANISM: Zea mays

<400> SEQUENCE: 77
cacatctcat ggtgtcgcag gaacgacaag agccagctgt gcctagcagc agcagcagca 60
gcgccaagcg cgcagccacg tccatggacg ccagcccggc cccgccgctc ctcctccgcg 120
cccccactcc cagccccagc attgacctcc ccgctggcaa ggacaaggcc gacgcggcgg 180
ccagcaaggc cggcgcggcc gtgttcgacc tgcgccggga gcccaagatc cccgcgccat 240
tcctgtggcc gcaggaagag gcgcggccgt cctcggccgc ggagctggag gtgccgatgg 300
tggacgtggg cgtgctgcgc aatggcgacc gcgcggggct gcggcgcgcc gcggcgcagg 360
tggccgcggc gtgcgcgacg cacgggttct tccaggtgtg cgggcacggc gtggacgcgg 420
cgctggggcg cgccgcgctg gacggcgcca gcgacttctt ccggctgccg ctcgccgaga 480
agcagcgcgc ccggcgcgtc cccggcaccg tgtccgggta cacgagcgcg cacgccgacc 540
ggttcgcggc caagctcccc tggaaggaga ccctgtcgtt cg 582

<210> SEQ ID NO 78
<211> LENGTH: 23
<212> TYPE: DNA
<213> ORGANISM: Zea mays

<400> SEQUENCE: 78
ctggaaggag accctgtcct tcg 23

<210> SEQ ID NO 79
<211> LENGTH: 23
<212> TYPE: DNA
<213> ORGANISM: Zea mays

<400> SEQUENCE: 79
ccggcaccct cggccaagat ttc 23

<210> SEQ ID NO 80
<211> LENGTH: 23
<212> TYPE: DNA
<213> ORGANISM: Zea mays

<400> SEQUENCE: 80
ctccctgcct tcgtctttgt cgt 23

<210> SEQ ID NO 81
<211> LENGTH: 23
<212> TYPE: DNA
<213> ORGANISM: Zea mays

<400> SEQUENCE: 81
ctgcatactt gcagctcgca cat 23

<210> SEQ ID NO 82
<211> LENGTH: 23
<212> TYPE: DNA
<213> ORGANISM: Zea mays

<400> SEQUENCE: 82
ctggaaggag accctgtcgt tcg 23

<210> SEQ ID NO 83
<211> LENGTH: 23
<212> TYPE: DNA
<213> ORGANISM: Glycine max

<400> SEQUENCE: 83
gtaagaagct cttcaccgtt cca 23

<210> SEQ ID NO 84
<211> LENGTH: 18
<212> TYPE: DNA
<213> ORGANISM: Artificial Sequence
<220> FEATURE:
<223> OTHER INFORMATION: PCR primer MD2611

<400> SEQUENCE: 84
cacgcccacg tccaccat 18

<210> SEQ ID NO 85
<211> LENGTH: 27
<212> TYPE: DNA
<213> ORGANISM: Artificial Sequence
<220> FEATURE:
<223> OTHER INFORMATION: PCR primer MD2615

<400> SEQUENCE: 85
agaactgaat gaatgaatat gcacagc 27

<210> SEQ ID NO 86
<211> LENGTH: 19
<212> TYPE: DNA
<213> ORGANISM: Artificial Sequence
<220> FEATURE:
<223> OTHER INFORMATION: PCR primer LR1151

<400> SEQUENCE: 86
acgggttctt ccaggtgtg 19

<210> SEQ ID NO 87
<211> LENGTH: 21
<212> TYPE: DNA
<213> ORGANISM: Artificial Sequence
<220> FEATURE:
<223> OTHER INFORMATION: PCR primer LR1148

<400> SEQUENCE: 87
ttcatctcct cgcagtacct c 21

<210> SEQ ID NO 88
<211> LENGTH: 400
<212> TYPE: DNA
<213> ORGANISM: Zea mays

<400> SEQUENCE: 88
tcccagcccc agcattgacc tccccgctgg caaggacaag gccgacgcgg cggccagcaa 60
ggccggcgcg gccgtgttcg acctgcgccg ggagcccaag atccccgcgc cattcctgtg 120
gccgcaggaa gaggcgcggc cgtcctcggc cgcggagctg gaggtgccga tggtggacgt 180
gggcgtgctg cgcaatggcg accgcgcggg gctgcggcgc gccgcggcgc aggtggccgc 240
ggcgtgcgcg acgcacgggt tcttccaggt gtgcgggcac ggcgtggacg cggcgctggg 300
gcgcgccgcg ctggacggcg ccagcgactt cttccggctg ccgctcgccg agaagcagcg 360
cgcccggcgc gtccccggca ccgtgtccgg gtacacgagc 400

<210> SEQ ID NO 89
<211> LENGTH: 3042
<212> TYPE: DNA
<213> ORGANISM: Artificial Sequence
<220> FEATURE:
<223> OTHER INFORMATION: genome edited sequence

<400> SEQUENCE: 89

-continued

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctcccctg gaaggagacc    480
caaggtctcc ttccagggga gcttggccgc gaaccggtcg gcgtgcgcgc tcgtgtaccc    540
ggacacggtg ccggggacgc gccgggcgcg ctgcttctcg gcgagcggca gccggaagaa    600
gtcgctggcg ccgtccagcg cggcgcgccc cagcgccgcg tccacgccgt gcccgcacac    660
ctggaagaac ccgtgcgtcg cgcacgccgc ggccacctgc gccgcggcgc gccgcagccc    720
cgcgcggtcg ccattgcgca gcacgcccac gtccaccatc ggcacctcca gctccgcggc    780
cgaggacggc cgcgcctctt cctgcggcca caggaatggc gcggggatct tgggctcccg    840
gcgcaggtcg aacacggccg cgccggcctt gctggccgcc gcgtcggcct tgtccttgcc    900
agcggggagg tcaatgctgg ggctgggagt gggggcgcgg aggaggagcg gcggggccgg    960
gctggcgtcc atggacgtgg ctgcgcgctt ggcgctgctg ctgctgctgc taggcacagc   1020
tggctcttgt cgttcctgcg acaccatgag gcttccacga cggcgccgcg gcgcccgtcg   1080
tcgtggacta cttcaccggc accctcggcc acgagccagt ggggtgagta aagaagaaga   1140
tggcgccgaa tttacattta taagtaggac cagcagaagc ccctgcccct gggggcctta   1200
gcattgcatt cgactgatga atacgcatgg caggcgggtg taccagaggt actgcgagga   1260
gatgaaggag ctgtcgctga cgatcatgga gctgctggag ctgagcctgg gcgtggagcg   1320
cggctactac cgggagttct tcgaggacag ccgctccatc atgcggtgca actactaccc   1380
gccgtgcccg gtgccggagc gcacgctggg cacgggcccg cactgcgacc ccacggcgct   1440
gaccatcctc ctgcaggacg acgtcggcgg gctggaggtc ctggtggacg gcgagtggcg   1500
ccccgtccgg cccgtcccag gcgccatggt catcaacatc ggcgacacct tcatggtaac   1560
gaacgaaagc gccggctcct ctgcttttct tggcctcttt gtccctgccc tgtgctgctg   1620
tgcatattca ttcattcagt tctctgtggg gttttttttt tgtttaattt tttttggga    1680
tcgtatccag tgcacaaggg ccacgccgtg cacaaatgca caaaacgaaa tctggccgtc   1740
cattttccat ccaacgacat gacggcgcgg ggggtttttc acaaaacaga ctcggcaagc   1800
tacggaggtt gcgggagggt tcatctgcat atttacgacg gccgttggat ggaaaatgga   1860
cggccagatt tcgttttgtg tatttgtgca cggcgtggcc cttgtgcact ggatacgatc   1920
ccattttttt ttttgccccg aatcctagtg gacctaactg gacagattac agcacgcaca   1980
cgtaggcatg tcatgtagca gcactgcagt cgggtgcagt ccagtccagt cctgtccagc   2040
cgcgacactg tagtacatag cgatgcaacg gagacacgcg ttggagttgg ttccatctct   2100
tctcggcggc cgtgccgagg cttccgcggg gaagctgcga caacagaacg gaccgccggg   2160
ggtgggcagg cagcaagctc cctgttggct tgtgccgttg cgcagcggcg ggtaccggac   2220
aacgctttcg gcggcgcgcg gcctcgtcgg cttcccctgt ttttgatgcc gcctctcggt   2280
gtccggggac cgggaggatc gatggggccc gtgccgtctg atccgccacg cgagcggtcc   2340
```

tatgcgatgc gccgcacgag cgcggggggg ccgtggaaca gtacacagct gggtcactca 2400
ctcactcatc ccgctggttg tggctgcttg gttgcaactt ggctcggctg tctgtctgtt 2460
gcccccgccg cgttttctag ccgtttccgc tttgctcgcg gtttcgctgg cgatccggca 2520
cgcggcgccc acacccgggg ctggcccctt ggccgagtgg gtggcaggca cttgcatgca 2580
tccggccggt ttcccgcgac caagctggcc cgccgcaaca atgagagtga gacgagactt 2640
tgtgtcagtg tgtgtatgta catgtatgtc tgcgcgacag ccctaccgtc cgacacgatg 2700
attcttgtgc actgtactgt actgtactaa ctccccccac cccctccggt atgtaacgca 2760
tgccatatgc aggcgctgtc caacgggcgg tacaagagct gcctgcaccg cgcggtggtg 2820
aaccggcggc aggagcggca atcgctggcc ttcttcctgt gcccgcgcga ggaccgggtg 2880
gtgcgcccgc cggccagcgc cgcgccgcgg cagtacccgg acttcacctg ggccgacctc 2940
atgcgcttca cgcagcgcca ctaccgcgcc gacacccgca cgctggacgc cttcacccgc 3000
tggctctccc acggcccggc ggcggcggct ccctgcacct aa 3042

<210> SEQ ID NO 90
<211> LENGTH: 569
<212> TYPE: DNA
<213> ORGANISM: Artificial Sequence
<220> FEATURE:
<223> OTHER INFORMATION: genome edited sequence

<400> SEQUENCE: 90
aaggtctcct tccaggggag cttggccgcg aaccggtcgg cgtgcgcgct cgtgtacccg 60
gacacggtgc cggggacgcg ccgggcgcgc tgcttctcgg cgagcggcag ccggaagaag 120
tcgctggcgc cgtccagcgc ggcgcgcccc agcgccgcgt ccacgccgtg cccgcacacc 180
tggaagaacc cgtgcgtcgc gcacgccgcg gccacctgcg ccgcggcgcg ccgcagcccc 240
gcgcggtcgc cattgcgcag cacgcccacg tccaccatcg gcacctccag ctccgcggcc 300
gaggacggcc gcgcctcttc ctgcggccac aggaatggcg cggggatctt gggctcccgg 360
cgcaggtcga acacggccgc gccggccttg ctggccgccg cgtcggcctt gtccttgcca 420
gcggggaggt caatgctggg gctgggagtg ggggcgcgga ggaggagcgg cggggccggg 480
ctggcgtcca tggacgtggc tgcgcgcttg gcgctgctgc tgctgctgct aggcacagct 540
ggctcttgtc gttcctgcga caccatgag 569

<210> SEQ ID NO 91
<211> LENGTH: 2850
<212> TYPE: DNA
<213> ORGANISM: Artificial Sequence
<220> FEATURE:
<223> OTHER INFORMATION: genome edited sequence

<400> SEQUENCE: 91
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacg 480

```
acacggtgcc ggggacgcgc cgggcgcgct gcttctcggc gagcggcagc cggaagaagt    540
cgctggcgcc gtccagcgcg gcgcgcccca gcgccgcgtc cacgccgtgc ccgcacacct    600
ggaagaaccc gtgcgtcgcg cacgccgcgg ccacctgcgc cgcggcgcgc cgcagccccg    660
cgcggtcgcc attgcgcagc acgcccacgt ccaccatcgg cacctccagc tccgcggccg    720
aggacggccg cgcctcttcc tgcggccaca ggaatggcgc ggggatcttg ggctcccggc    780
gcaggtcgaa cacggccgcg ccggccttgc tggccgccgc gtcggccttg tccttgccag    840
cggggaggtc aatgctgggg ctgggatttc cacgacggcg ccgcggcgcc cgtcgtcgtg    900
gactacttca ccggcaccct cggccagcca gtggggtgag taaagaagaa gatggcgccg    960
aatttacatt tataagtagg accagcagaa gcccctgccc ctgggggcct tagcattgca   1020
ttcgactgat gaatacgcat ggcaggcggg tgtaccagag gtactgcgag gagatgaagg   1080
agctgtcgct gacgatcatg gagctgctgg agctgagcct gggcgtggag cgcggctact   1140
accgggagtt cttcgaggac agccgctcca tcatgcggtg caactactac ccgccgtgcc   1200
cggtgccgga gcgcacgctg ggcacgggcc cgcactgcga ccccacggcg ctgaccatcc   1260
tcctgcagga cgacgtcggc gggctggagg tcctggtgga cggcgagtgg cgccccgtcc   1320
ggcccgtccc aggcgccatg gtcatcaaca tcggcgacac cttcatggta acgaacgaaa   1380
gcgccggctc ctctgctttt cttggcctct ttgtccctgc cctgtgctgc tgtgcatatt   1440
cattcattca gttctctgtg gggttttttt tttgtttaat ttttttttgg gatcgtatcc   1500
agtgcacaag ggccacgccg tgcacaaatg cacaaaacga aatctggccg tccattttcc   1560
atccaacgac atgacggcgc gggggttttt cacaaaacag actcggcaag ctacggaggt   1620
tgcgggaggg ttcatctgca tatttacgac ggccgttgga tggaaaatgg acggccagat   1680
ttcgttttgt gtatttgtgc acggcgtggc ccttgtgcac tggatacgat cccatttttt   1740
tttttgcccc gaatcctagt ggacctaact ggacagatta cagcacgcac acgtaggcat   1800
gtcatgtagc agcactgcag tcgggtgcag tccagtccag tcctgtccag ccgcgacact   1860
gtagtacata gcgatgcaac ggagacacgc gttggagttg gttccatctc ttctcggcgg   1920
ccgtgccgag gcttccgcgg ggaagctgcg acaacagaac ggaccgccgg gggtgggcag   1980
gcagcaagct ccctgttggc ttgtgccgtt gcgcagcggc gggtaccgga caacgctttc   2040
ggcggcgcgc ggcctcgtcg gcttcccctg tttttgatgc cgcctctcgg tgtccgggga   2100
ccgggaggat cgatggggcc cgtgccgtct gatccgccac gcgagcggtc ctatgcgatg   2160
cgccgcacga gcgcgggggg gccgtggaac agtacacagc tgggtcactc actcactcat   2220
cccgctggtt gtggctgctt ggttgcaact tggctcggct gtctgtctgt tgccccgccg   2280
cgttttctag ccgtttccgc tttgctcgcg gtttcgctgg cgatccggca cgcggcgccc   2340
acacccgggg ctggcccctt ggccgagtgg gtggcaggca cttgcatgca tccggccggt   2400
ttcccgcgac caagctggcc cgccgcaaca atgagagtga gacgagactt tgtgtcagtg   2460
tgtgtatgta catgtatgtc tgcgcgacag ccctaccgtc cgacacgatg attcttgtgc   2520
actgtactgt actgtactaa ctcccccccc cctccggtat gtaacgcatg ccatatgcag   2580
gcgctgtcca acgggcggta caagagctgc ctgcaccgcg cggtggtgaa ccggcggcag   2640
gagcggcaat cgctggcctt cttcctgtgc ccgcgcgagg accgggtggt gcgcccgccg   2700
gccagcgccg cgccgcggca gtacccggac ttcacctggg ccgacctcat gcgcttcacg   2760
cagcgccact accgcgccga cacccgcacg ctggacgcct tcacccgctg gctctcccac   2820
```

ggcccggcgg cggcggctcc ctgcacctaa 2850

<210> SEQ ID NO 92
<211> LENGTH: 387
<212> TYPE: DNA
<213> ORGANISM: Artificial Sequence
<220> FEATURE:
<223> OTHER INFORMATION: genome edited sequence

<400> SEQUENCE: 92
tcccagcccc agcattgacc tccccgctgg caaggacaag gccgacgcgg cggccagcaa 60
ggccggcgcg gccgtgttcg acctgcgccg ggagcccaag atccccgcgc cattcctgtg 120
gccgcaggaa gaggcgcggc cgtcctcggc cgcggagctg gaggtgccga tggtggacgt 180
gggcgtgctg cgcaatggcg accgcgcggg gctgcggcgc gccgcggcgc aggtggccgc 240
ggcgtgcgcg acgcacgggt tcttccaggt gtgcgggcac ggcgtggacg cggcgctggg 300
gcgcgccgcg ctggacggcg ccagcgactt cttccggctg ccgctcgccg agaagcagcg 360
cgcccggcgc gtccccggca ccgtgtc 387

<210> SEQ ID NO 93
<211> LENGTH: 3010
<212> TYPE: DNA
<213> ORGANISM: Artificial Sequence
<220> FEATURE:
<223> OTHER INFORMATION: genome edited sequence

<400> SEQUENCE: 93
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctggcttcca cgacggcgcc gcggcgcccg tcgtcgtgga ctacttcacc ggcacgcgaa 540
ccggtcggcg tgcgcgctcg tgtacccgga cacggtgccg gggacgcgcc gggcgcgctg 600
cttctcggcg agcggcagcc ggaagaagtc gctggcgccg tccagcgcgg cgcgccccag 660
cgccgcgtcc acgccgtgcc cgcacacctg gaagaacccg tgcgtcgcgc acgccgcggc 720
cacctgcgcc gcggcgcgcc gcagccccgc gcggtcgcca ttgcgcagca cgcccacgtc 780
caccatcggc acctccagct ccgcggccga ggacggccgc gcctcttcct gcggccacag 840
gaatggcgcg gggatcttgg gctcccggcg caggtcgaac acggccgcgc cggccttgct 900
ggccgccgcg tcggccttgt ccttgccagc ggggaggtca atgctggggc tgggagtggg 960
ggcgcggagg aggagcggcg gggccgggct ggcgtccatg gacgtggctg cgcgcttggc 1020
gctgctgctg ctgctgctag gcacagctgg ctcttgtcgt tcctgcgaca ccatgagttc 1080
gagccagtgg ggtgagtaaa gaagaagatg gcgccgaatt tacatttata agtaggacca 1140
gcagaagccc ctgcccctgg gggccttagc attgcattcg actgatgaat acgcatggca 1200
ggcgggtgta ccagaggtac tgcgaggaga tgaaggagct gtcgctgacg atcatggagc 1260
tgctggagct gagcctgggc gtggagcgcg gctactaccg ggagttcttc gaggacagcc 1320
gctccatcat gcggtgcaac tactacccgc cgtgcccggt gccggagcgc acgctgggca 1380
cgggcccgca ctgcgacccc acggcgctga ccatcctcct gcaggacgac gtcggcgggc 1440
tggaggtcct ggtggacggc gagtggcgcc ccgtccggcc cgtcccaggc gccatggtca 1500
tcaacatcgg cgacaccttc atggtaacga acgaaagcgc cggctcctct gcttttcttg 1560
gcctctttgt ccctgccctg tgctgctgtg catattcatt cattcagttc tctgtggggt 1620 ttttttttg tttaattttt ttttgggatc gtatccagtg cacaagggcc acgccgtgca 1680
caaatgcaca aaacgaaatc tggccgtcca ttttccatcc aacgacatga cggcgcgggg 1740
ggtttttcac aaaacagact cggcaagcta cggaggttgc gggagggttc atctgcatat 1800
ttacgacggc cgttggatgg aaaatggacg gccagatttc gttttgtgta tttgtgcacg 1860
gcgtggccct tgtgcactgg atacgatccc attttttttt ttgccccgaa tcctagtgga 1920
cctaactgga cagattacag cacgcacacg taggcatgtc atgtagcagc actgcagtcg 1980
ggtgcagtcc agtccagtcc tgtccagccg cgacactgta gtacatagcg atgcaacgga 2040
gacacgcgtt ggagttggtt ccatctcttc tcggcggccg tgccgaggct tccgcgggga 2100
agctgcgaca acagaacgga ccgccggggg tgggcaggca gcaagctccc tgttggcttg 2160
tgccgttgcg cagcggcggg taccggacaa cgctttcggc ggcgcgcggc ctcgtcggct 2220
tcccctgttt ttgatgccgc ctctcggtgt ccggggaccg ggaggatcga tggggcccgt 2280
gccgtctgat ccgccacgcg agcggtccta tgcgatgcgc cgcacgagcg cgggggggcc 2340
gtggaacagt acacagctgg gtcactcact cactcatccc gctggttgtg gctgcttggt 2400
tgcaacttgg ctcggctgtc tgtctgttgc ccccgccgcg ttttctagcc gtttccgctt 2460
tgctcgcggt ttcgctggcg atccggcacg cggcgcccac acccggggct ggccccttgg 2520
ccgagtgggt ggcaggcact tgcatgcatc cggccggttt cccgcgacca agctggcccg 2580
ccgcaacaat gagagtgaga cgagactttg tgtcagtgtg tgtatgtaca tgtatgtctg 2640
cgcgacagcc ctaccgtccg acacgatgat tcttgtgcac tgtactgtac tgtactaact 2700
ccccccaccc cctccggtat gtaacgcatg ccatatgcag gcgctgtcca acgggcggta 2760
caagagctgc ctgcaccgcg cggtggtgaa ccggcggcag gagcggcaat cgctggcctt 2820
cttcctgtgc ccgcgcgagg accgggtggt gcgcccgccg gccagcgccg cgccgcggca 2880
gtacccggac ttcacctggg ccgacctcat gcgcttcacg cagcgccact accgcgccga 2940
cacccgcacg ctggacgcct tcacccgctg gctctcccac ggcccggcgg cggcggctcc 3000
ctgcacctaa 3010

<210> SEQ ID NO 94
<211> LENGTH: 542
<212> TYPE: DNA
<213> ORGANISM: Artificial Sequence
<220> FEATURE:
<223> OTHER INFORMATION: genome edited sequence

<400> SEQUENCE: 94
ctcatggtgt cgcaggaacg acaagagcca gctgtgccta gcagcagcag cagcagcgcc 60
aagcgcgcag ccacgtccat ggacgccagc ccggccccgc cgctcctcct ccgcgccccc 120
actcccagcc ccagcattga cctccccgct ggcaaggaca aggccgacgc ggcggccagc 180
aaggccggcg cggccgtgtt cgacctgcgc cgggagccca agatccccgc gccattcctg 240
tggccgcagg aagaggcgcg gccgtcctcg gccgcggagc tggaggtgcc gatggtggac 300
gtgggcgtgc tgcgcaatgg cgaccgcgcg gggctgcggc gcgccgcggc gcaggtggcc 360
gcggcgtgcg cgacgcacgg gttcttccag gtgtgcgggc acggcgtgga cgcggcgctg 420
gggcgcgccg cgctggacgg cgccagcgac ttcttccggc tgccgctcgc cgagaagcag 480
cgcgcccggc gcgtccccgg caccgtgtcc gggtacacga gcgcgcacgc cgaccggttc 540
gc 542

<210> SEQ ID NO 95
<211> LENGTH: 3037
<212> TYPE: DNA
<213> ORGANISM: Artificial Sequence
<220> FEATURE:
<223> OTHER INFORMATION: genome edited sequence

<400> SEQUENCE: 95
atggacgcca gcccgacccc accgctcccc ctccgcgccc caactcccag cattgacctc 60
cccgctggca aggacagggc cgacgcggcg gctaacaagg ccgcggctgt gttcgacctg 120
cgccgggagc ccaagatccc ggagccattc ctgtggccgc acgaagaggc gcggccgacc 180
tcggccgcgg agctggaggt gccggtggtg gacgtgggcg tgctgcgcaa tggcgacggc 240
gcggggctcc gccgcgccgc ggcgcaagtg gcggcggcgt gcgcgacgca cgggttcttc 300
caggtgtgcg ggcacggcgt ggacgcggcg ctggggcgcg ccgcgctgga cggcgccagc 360
gacttcttcc ggctgccgct ggctgagaag cagcgggccc ggcgcgtccc cggcaccgtg 420
tccgggtaca cgagcgcgca cgccgaccgg ttcgcgtcca agctcccctg gaaggagacc 480
ctcggcttcc acgacggcgc cgcggcgccc gtcgtcgtgg actacttcac cggcaccctc 540
ggccgagggt ctccttccag gggagcttgg ccgcgaaccg gtcggcgtgc gcgctcgtgt 600
acccggacac ggtgccgggg acgcgccggg cgcgctgctt ctcggcgagc ggcagccgga 660
agaagtcgct ggcgccgtcc agcgcggcgc gccccagcgc cgcgtccacg ccgtgcccgc 720
acacctggaa gaacccgtgc gtcgcgcacg ccgcggccac ctgcgccgcg gcgcgccgca 780
gccccgcgcg gtcgccattg cgcagcacgc ccacgtccac catcggcacc tccagctccg 840
cggccgagga cggccgcgcc tcttcctgcg gccacaggaa tggcgcgggg atcttgggct 900
cccggcgcag gtcgaacacg gccgcgccgg ccttgctggc cgccgcgtcg gccttgtcct 960
tgccagcggg gaggtcaatg ctggggctgg gagtgggggc gcggaggagg agcggcgggg 1020
ccgggctggc gtccatggac gtggctgcgc gcttggcgct gctgctgctg ctgctaggca 1080
cagctggctc ttgtcgttcc tgcgaccgag ccagtggggt gagtaaagaa gaagatggcg 1140
ccgaatttac atttataagt aggaccagca gaagcccctg cccctggggg ccttagcatt 1200
gcattcgact gatgaatacg catggcaggc gggtgtacca gaggtactgc gaggagatga 1260
aggagctgtc gctgacgatc atggagctgc tggagctgag cctgggcgtg gagcgcggct 1320
actaccggga gttcttcgag gacagccgct ccatcatgcg gtgcaactac tacccgccgt 1380
gcccggtgcc ggagcgcacg ctgggcacgg gcccgcactg cgaccccacg gcgctgacca 1440
tcctcctgca ggacgacgtc ggcgggctgg aggtcctggt ggacggcgag tggcgccccg 1500
tccggcccgt cccaggcgcc atggtcatca acatcggcga caccttcatg gtaacgaacg 1560
aaagcgccgg ctcctctgct tttcttggcc tctttgtccc tgccctgtgc tgctgtgcat 1620
attcattcat tcagttctct gtggggtttt ttttttgttt aattttttttt tgggatcgta 1680 tccagtgcac aagggccacg ccgtgcacaa atgcacaaaa cgaaatctgg ccgtccattt 1740
tccatccaac gacatgacgg cgcggggggt ttttcacaaa acagactcgg caagctacgg 1800
aggttgcggg agggttcatc tgcatattta cgacggccgt tggatggaaa atggacggcc 1860
agatttcgtt ttgtgtattt gtgcacggcg tggcccttgt gcactggata cgatcccatt 1920 ttttttttg ccccgaatcc tagtggacct aactggacag attacagcac gcacacgtag 1980
gcatgtcatg tagcagcact gcagtcgggt gcagtccagt ccagtcctgt ccagccgcga 2040
cactgtagta catagcgatg caacggagac acgcgttgga gttggttcca tctcttctcg 2100
gcggccgtgc cgaggcttcc gcggggaagc tgcgacaaca gaacggaccg ccgggggtgg 2160
gcaggcagca agctccctgt tggcttgtgc cgttgcgcag cggcgggtac cggacaacgc 2220
tttcggcggc gcgcggcctc gtcggcttcc cctgtttttg atgccgcctc tcggtgtccg 2280
gggaccggga ggatcgatgg ggcccgtgcc gtctgatccg ccacgcgagc ggtcctatgc 2340
gatgcgccgc acgagcgcgg gggggccgtg gaacagtaca cagctgggtc actcactcac 2400
tcatcccgct ggttgtggct gcttggttgc aacttggctc ggctgtctgt ctgttgcccc 2460
cgccgcgttt tctagccgtt tccgctttgc tcgcggtttc gctggcgatc cggcacgcgg 2520
cgcccacacc cggggctggc cccttggccg agtgggtggc aggcacttgc atgcatccgg 2580
ccggtttccc gcgaccaagc tggcccgccg caacaatgag agtgagacga gactttgtgt 2640
cagtgtgtgt atgtacatgt atgtctgcgc gacagcccta ccgtccgaca cgatgattct 2700
tgtgcactgt actgtactgt actaactccc cccacccct ccggtatgta acgcatgcca 2760
tatgcaggcg ctgtccaacg ggcggtacaa gagctgcctg caccgcgcgg tggtgaaccg 2820
gcggcaggag cggcaatcgc tggccttctt cctgtgcccg cgcgaggacc gggtggtgcg 2880
cccgccggcc agcgccgcgc cgcggcagta cccggacttc acctgggccg acctcatgcg 2940
cttcacgcag cgccactacc gcgccgacac ccgcacgctg gacgccttca cccgctggct 3000
ctcccacggc ccggcggcgg cggctccctg cacctaa 3037

<210> SEQ ID NO 96
<211> LENGTH: 562
<212> TYPE: DNA
<213> ORGANISM: Artificial Sequence
<220> FEATURE:
<223> OTHER INFORMATION: genome edited sequence

<400> SEQUENCE: 96
gtcgcaggaa cgacaagagc cagctgtgcc tagcagcagc agcagcagcg ccaagcgcgc 60
agccacgtcc atggacgcca gcccggcccc gccgctcctc ctccgcgccc ccactcccag 120
ccccagcatt gacctccccg ctggcaagga caaggccgac gcggcggcca gcaaggccgg 180
cgcggccgtg ttcgacctgc gccgggagcc caagatcccc gcgccattcc tgtggccgca 240
ggaagaggcg cggccgtcct cggccgcgga gctggaggtg ccgatggtgg acgtgggcgt 300
gctgcgcaat ggcgaccgcg cggggctgcg gcgcgccgcg gcgcaggtgg ccgcggcgtg 360
cgcgacgcac gggttcttcc aggtgtgcgg gcacggcgtg gacgcggcgc tggggcgcgc 420
cgcgctggac ggcgccagcg acttcttccg gctgccgctc gccgagaagc agcgcgcccg 480
gcgcgtcccc ggcaccgtgt ccgggtacac gagcgcgcac gccgaccggt tcgcggccaa 540
gctcccctgg aaggagaccc tc 562

<210> SEQ ID NO 97
<211> LENGTH: 3044
<212> TYPE: DNA
<213> ORGANISM: Artificial Sequence
<220> FEATURE:

<223> OTHER INFORMATION: genome edited sequence

<400> SEQUENCE: 97

```
atggacgcca gcccgacccc accgctcccc ctccgcgccc caactcccag cattgacctc     60
cccgctggca aggacagggc cgacgcggcg gctaacaagg ccgcggctgt gttcgacctg    120
cgccgggagc ccaagatccc ggagccattc ctgtggccgc acgaagaggc gcggccgacc    180
tcggccgcgg agctggaggt gccggtggtg gacgtgggcg tgctgcgcaa tggcgacggc    240
gcggggctcc gccgcgccgc ggcgcaagtg gcggcggcgt gcgcgacgca cgggttcttc    300
caggtgtgcg ggcacggcgt ggacgcggcg ctggggcgcg ccgcgctgga cggcgccagc    360
gacttcttcc ggctgccgct ggctgagaag cagcgggccc ggcgcgtccc cggcaccgtg    420
tccgggtaca cgagcgcgca cgccgaccgg ttcgcgtcca agctccccctg gaaggagacc   480
cgtctccttc caggggagct tggccgcgaa ccggtcggcg tgcgcgctcg tgtacccgga    540
cacggtgccg gggacgcgcc gggcgcgctg cttctcggcg agcggcagcc ggaagaagtc    600
gctggcgccg tccagcgcgg cgcgccccag cgccgcgtcc acgccgtgcc cgcacacctg    660
gaagaacccg tgcgtcgcgc acgccgcggc cacctgcgcc gcggcgcgcc gcagccccgc    720
gcggtcgcca ttgcgcagca cgcccacgtc caccatcggc acctccagct ccgcggccga    780
ggacggccgc gcctcttcct gcggccacag gaatggcgcg gggatcttgg gctcccggcg    840
caggtcgaac acggccgcgc cggccttgct ggccgccgcg tcggccttgt ccttgccagc    900
ggggaggtca atgctggggc tgggagtggg ggcgcggagg aggagcggcg gggccgggct    960
ggcgtccatg gacgtggctg cgcgcttggc gctgctgctg ctgctgctag gcacagctgg   1020
ctcttgtcgt tcctgcgaca ccttcggctt ccacgacggc gccgcggcgc ccgtcgtcgt   1080
ggactacttc accggcaccc tcggccaaga tttcgagcca gtggggtgag taaagaagaa   1140
gatggcgccg aatttacatt tataagtagg accagcagaa gcccctgccc ctgggggcct   1200
tagcattgca ttcgactgat gaatacgcat ggcaggcggg tgtaccagag gtactgcgag   1260
gagatgaagg agctgtcgct gacgatcatg gagctgctgg agctgagcct gggcgtggag   1320
cgcggctact accgggagtt cttcgaggac agccgctcca tcatgcggtg caactactac   1380
ccgccgtgcc cggtgccgga gcgcacgctg ggcacgggcc cgcactgcga ccccacggcg   1440
ctgaccatcc tcctgcagga cgacgtcggc gggctggagg tcctggtgga cggcgagtgg   1500
cgccccgtcc ggcccgtccc aggcgccatg gtcatcaaca tcggcgacac cttcatggta   1560
acgaacgaaa gcgccggctc ctctgctttt cttggcctct ttgtccctgc cctgtgctgc   1620
tgtgcatatt cattcattca gttctctgtg gggttttttt tttgtttaat ttttttttgg   1680
gatcgtatcc agtgcacaag ggccacgccg tgcacaaatg cacaaaacga aatctggccg   1740
tccattttcc atccaacgac atgacggcgc ggggggtttt tcacaaaaca gactcggcaa   1800
gctacggagg ttgcgggagg gttcatctgc atatttacga cggccgttgg atggaaaatg   1860
gacggccaga tttcgttttg tgtatttgtg cacggcgtgg cccttgtgca ctggatacga   1920
tcccattttt ttttttgccc cgaatcctag tggacctaac tggacagatt acagcacgca   1980
cacgtaggca tgtcatgtag cagcactgca gtcgggtgca gtccagtcca gtcctgtcca   2040
gccgcgacac tgtagtacat agcgatgcaa cggagacacg cgttggagtt ggttccatct   2100
cttctcggcg gccgtgccga ggcttccgcg gggaagctgc gacaacagaa cggaccgccg   2160
ggggtgggca ggcagcaagc tccctgttgg cttgtgccgt tgcgcagcgg cgggtaccgg   2220
acaacgcttt cggcggcgcg cggcctcgtc ggcttcccct gtttttgatg ccgcctctcg   2280
```

gtgtccgggg accgggagga tcgatggggc ccgtgccgtc tgatccgcca cgcgagcggt 2340
cctatgcgat gcgccgcacg agcgcggggg ggccgtggaa cagtacacag ctgggtcact 2400
cactcactca tcccgctggt tgtggctgct tggttgcaac ttggctcggc tgtctgtctg 2460
ttgcccccgc cgcgttttct agccgtttcc gctttgctcg cggtttcgct ggcgatccgg 2520
cacgcggcgc ccacacccgg ggctggcccc ttggccgagt gggtggcagg cacttgcatg 2580
catccggccg gtttcccgcg accaagctgg cccgccgcaa caatgagagt gagacgagac 2640
tttgtgtcag tgtgtgtatg tacatgtatg tctgcgcgac agccctaccg tccgacacga 2700
tgattcttgt gcactgtact gtactgtact aactcccccc accccctccg gtatgtaacg 2760
catgccatat gcaggcgctg tccaacgggc ggtacaagag ctgcctgcac cgcgcggtgg 2820
tgaaccggcg gcaggagcgg caatcgctgg ccttcttcct gtgcccgcgc gaggaccggg 2880
tggtgcgccc gccggccagc gccgcgccgc ggcagtaccc ggacttcacc tgggccgacc 2940
tcatgcgctt cacgcagcgc cactaccgcg ccgacacccg cacgctggac gccttcaccc 3000
gctggctctc ccacggcccg gcggcggcgg ctccctgcac ctaa 3044

<210> SEQ ID NO 98
<211> LENGTH: 559
<212> TYPE: DNA
<213> ORGANISM: Artificial Sequence
<220> FEATURE:
<223> OTHER INFORMATION: genome edited sequence

<400> SEQUENCE: 98
gtctccttcc aggggagctt ggccgcgaac cggtcggcgt gcgcgctcgt gtacccggac 60
acggtgccgg ggacgcgccg ggcgcgctgc ttctcggcga gcggcagccg gaagaagtcg 120
ctggcgccgt ccagcgcggc gcgccccagc gccgcgtcca cgccgtgccc gcacacctgg 180
aagaacccgt gcgtcgcgca cgccgcggcc acctgcgccg cggcgcgccg cagccccgcg 240
cggtcgccat tgcgcagcac gcccacgtcc accatcggca cctccagctc cgcggccgag 300
gacggccgcg cctcttcctg cggccacagg aatggcgcgg ggatcttggg ctcccggcgc 360
aggtcgaaca cggccgcgcc ggccttgctg gccgccgcgt cggccttgtc cttgccagcg 420
gggaggtcaa tgctggggct gggagtgggg gcgcggagga ggagcggcgg ggccgggctg 480
gcgtccatgg acgtggctgc gcgcttggcg ctgctgctgc tgctgctagg cacagctggc 540
tcttgtcgtt cctgcgaca 559

<210> SEQ ID NO 99
<211> LENGTH: 1516
<212> TYPE: DNA
<213> ORGANISM: Zea mays

<400> SEQUENCE: 99
atggcagctg cggagctgcc atctttgcac gaagacacac acacacagca gctgagcagc 60
agcaacacgc tcccatcatc tctcgccatg cgcccaacac gctcccctgt gccggctacg 120
gcgctgctcc tgcttgccgt ggcactggca ctggccgcca cggcggcggc ccgccacttc 180
tacaccacca ccaccaccac ccgcgtcccg gcgccagcgg agcgggcgga cgaggaggta 240
aggcgcatgt acgaggcgtg gaagtcgaag cacgggcgcg gcggcagcag caacgacgac 300
tgcgacatgg cgcccggcga tgatgagcag gaggaggacc gccggctgcg gctggaggtg 360
ttccgcgaca accttcggta catcgacaag cacaacgcgg aggcggacgc tgggctccac 420

```
accttccgcc tcggcctcac ccccttcgcc gacctcaccc tggacgagta ccgcggccgc    480

gtcctcggat tccgcgcccg cgcccgccgc agcggcgccc gctacggcca cggccacggc    540

taccgcgccc gtccccgcgg cggcgacctc ctccccgacg ccatcgactg gcgccagctt    600

ggcgccgtca ccgaggtcaa ggaccagcaa cagtgcggtg ggtgctgggc gttctcggcg    660

gtggcggcca tcgaggggat caacgcgatc gcgacgggta acctggtgtc gctgtcggag    720

caggagatca tcgactgcga cgcccaggac agcggctgcg acggcgggca gatggagaac    780

gcgttccggt tcgtcatcgg caacggcggg atcgacaccg aggccgacta ccccttcatc    840

ggaaccgacg gcacttgtga cgccagcaag gagaacaacg agaaggtcgc caccatagat    900

gggttggtgg aggtggcgag caacaacgag acggcgctgc aggaggcggt ggcgatccag    960

cccgtcagtg tcgccatcga cgcaagcggg cgtgcgttcc agcactacag ttcgggcatc   1020

ttcaacgggc catgcgggac gagcctggac cacggcgtca cggcggtggg ctacggcagc   1080

gagagcggca aggactactg gatcgtgaag aactcgtgga gcgccagctg gggcgaggcc   1140

ggctacatcc gcatgaggcg caacgtgccc cggcccacgg gcaagtgcgg catcgccatg   1200

gacgcgtcct accctgtgaa ggacacctac cacgaccccg gcaccggcac cggcaccgcc   1260

acggctacgg cagctgccat ggatgtgatc aagatggttc ttgcttagga gggagcgagc   1320

ggagcaggca gcagagagcc gatggtcttg tcgtgttgaa ctttacatat ggtagctagg   1380

taccactggg gataattaag ttaatccgtt atggtgtggc aagttaatta atatgtgcgt   1440

atctcttttg atgagtgcca tatatgatgt aatgaagtta cataaactca aataaagtcg   1500

taatcgtaat ggtaaa                                                   1516
```

<210> SEQ ID NO 100
<211> LENGTH: 435
<212> TYPE: PRT
<213> ORGANISM: Zea mays

<400> SEQUENCE: 100

```
Met Ala Ala Ala Glu Leu Pro Ser Leu His Glu Asp Thr His Thr Gln
1               5                   10                  15

Gln Leu Ser Ser Ser Asn Thr Leu Pro Ser Ser Leu Ala Met Arg Pro
            20                  25                  30

Thr Arg Ser Pro Val Pro Ala Thr Ala Leu Leu Leu Leu Ala Val Ala
        35                  40                  45

Leu Ala Leu Ala Ala Thr Ala Ala Ala Arg His Phe Tyr Thr Thr Thr
    50                  55                  60

Thr Thr Thr Arg Val Pro Ala Pro Ala Glu Arg Ala Asp Glu Glu Val
65                  70                  75                  80

Arg Arg Met Tyr Glu Ala Trp Lys Ser Lys His Gly Arg Gly Gly Ser
                85                  90                  95

Ser Asn Asp Asp Cys Asp Met Ala Pro Gly Asp Asp Glu Gln Glu Glu
            100                 105                 110

Asp Arg Arg Leu Arg Leu Glu Val Phe Arg Asp Asn Leu Arg Tyr Ile
        115                 120                 125

Asp Lys His Asn Ala Glu Ala Asp Ala Gly Leu His Thr Phe Arg Leu
    130                 135                 140

Gly Leu Thr Pro Phe Ala Asp Leu Thr Leu Asp Glu Tyr Arg Gly Arg
145                 150                 155                 160

Val Leu Gly Phe Arg Ala Arg Ala Arg Arg Ser Gly Ala Arg Tyr Gly
                165                 170                 175
```

```
His Gly His Gly Tyr Arg Ala Arg Pro Arg Gly Gly Asp Leu Leu Pro
            180                 185                 190

Asp Ala Ile Asp Trp Arg Gln Leu Gly Ala Val Thr Glu Val Lys Asp
        195                 200                 205

Gln Gln Gln Cys Gly Gly Cys Trp Ala Phe Ser Ala Val Ala Ala Ile
    210                 215                 220

Glu Gly Ile Asn Ala Ile Ala Thr Gly Asn Leu Val Ser Leu Ser Glu
225                 230                 235                 240

Gln Glu Ile Ile Asp Cys Asp Ala Gln Asp Ser Gly Cys Asp Gly Gly
                245                 250                 255

Gln Met Glu Asn Ala Phe Arg Phe Val Ile Gly Asn Gly Gly Ile Asp
            260                 265                 270

Thr Glu Ala Asp Tyr Pro Phe Ile Gly Thr Asp Gly Thr Cys Asp Ala
        275                 280                 285

Ser Lys Glu Asn Asn Glu Lys Val Ala Thr Ile Asp Gly Leu Val Glu
    290                 295                 300

Val Ala Ser Asn Asn Glu Thr Ala Leu Gln Glu Ala Val Ala Ile Gln
305                 310                 315                 320

Pro Val Ser Val Ala Ile Asp Ala Ser Gly Arg Ala Phe Gln His Tyr
                325                 330                 335

Ser Ser Gly Ile Phe Asn Gly Pro Cys Gly Thr Ser Leu Asp His Gly
            340                 345                 350

Val Thr Ala Val Gly Tyr Gly Ser Glu Ser Gly Lys Asp Tyr Trp Ile
        355                 360                 365

Val Lys Asn Ser Trp Ser Ala Ser Trp Gly Glu Ala Gly Tyr Ile Arg
    370                 375                 380

Met Arg Arg Asn Val Pro Arg Pro Thr Gly Lys Cys Gly Ile Ala Met
385                 390                 395                 400

Asp Ala Ser Tyr Pro Val Lys Asp Thr Tyr His Asp Pro Gly Thr Gly
                405                 410                 415

Thr Gly Thr Ala Thr Ala Thr Ala Ala Ala Met Asp Val Ile Lys Met
            420                 425                 430

Val Leu Ala
        435


<210> SEQ ID NO 101
<211> LENGTH: 2871
<212> TYPE: DNA
<213> ORGANISM: Zea mays

<400> SEQUENCE: 101

ttaccacgaa ttaattgaac ttgagtgggg ttaaggaaaa tgagtgatct aagaataacc      60

ttaaccacct cgtggtcatc ccacttcttg ctcccgaggt tgcgcacttg gttcaccaaa     120

gtcttgagcc ggttgtacat gtcttgtggc tcttcccctt ggcgaagtcg aaagcgaccg     180

agctccccct cgatcgtttc ccgcttggtg atctttgtta gttcatcacc ctcgtgcgcg     240

gtcttgagga ggtcccaaat ttcctttgca ttcttcaacc cttgcacctt gttgtattcc     300

tctctattta gagaggccaa gagtatggtt gtggcttggg agttgaagtg ctcgatttgg     360

gccacctcgt cctcatcata atcctcatcc cctacggatg gtacctgtgc tccaaactca     420

acaacattcc atatactttt gtggagtgag gttagatgaa atttcattaa atcactccac     480

ctagcataat cttcaccgtc aaaggttggc ggtttgccta atggaacgga aagtaatgga     540

gtatgtctag atgtacgagg atagtgtaag gggatcttac taaacttctt acgctcttgg     600
```

-continued

```
cgtttagaag ttacggaggg tgcatcggag ccggaggtcg atgttgatga agtgtcggtc    660
tcgtagtaga ccacttttct catcctcttg tgcttgtccc cactccgatg tggcttgtga    720
gaggaagatc tctccttctt ctctttgtgg tgagaagagg atttcttctc cttccctttg    780
ttggaggagc tcttcttctt ctccttcctc ttggtgcgtg actcttccga tgaagtgctc    840
ccgtggcttg tagtgggctt ttcgccggtc tccatctcct tcttggcgtg atctcccgac    900
atcacttcga gcggttaggc tctaatgaag caccgggctt tgataccaat tgatagtcgc    960
ctagaggggg ggtgaatagg gcgaaactga aatttacaaa tataaacaca acttcaagcc   1020
gggttagcgt tagaaatgta aacgagtccg cgagagaggg cgcaaaacaa atcgcaagca   1080
aatgaagagt gtgacacgcg gatttgtttt accgaggttc ggttctcgca aacctactcc   1140
ccgttgagga ggccacaaag gccgggtctc tttcaaccct tccctctctc aaacggtccc   1200
tcggaccgag tgagcttctc ttctcaaatc aaagccggga ataaaacttc cccgcaaggg   1260
ccaccacaca attggtgcct cttgccttga ttacaattga gtgttgatca caagagcaag   1320
tgagaaagaa aagaagcaat ccaagcgcaa gagctcaaaa gaacacggca aatctctctc   1380
gctaatcact aaagcctttt gtggaattgg agaggatttg atctctttgg tgtgtctaga   1440
attgaatgcc tagctcttgt aagtggttga gaagtggaaa acttggtttc catgaatgtg   1500
ggggtggttg gggtatttat agccccaacc accaaaagtg gccgttggga ggctgtctgt   1560
ttgatggcgc accggacagt ccggtgcaca ccggacatgt ccggtgcccc cgccacgtca   1620
tcactaccgt tggattctga ccgttggagc tcctgactcg tgggcccgcc tggatgtccg   1680
gtgcacaccg gacatgcact gttccttgtc cggtgcgcca gtatgggcgc gcctgtcttc   1740
tgcgcgcgca gagcgcgcaa taaatgcgtc gcaggtagcc gttggcgccg aatagccgtt   1800
gctccggagt tgcaccggac agtccggtgc acaccggaca tgtccggtga attatagcgg   1860
actagccgtt ggagatttcc gaagccggcg agttcctgag gccgctcttc cttggcgcac   1920
cggacactgt ccggtgtaca ccggacagtc cggtgaatta tagcgcgctg gcctgagaaa   1980
ttcccgaagg tagcgagttc gagttggagt cctctggtgc accggacact gtccggtggt   2040
gcaccggaca ctgtccggtg gtgcaccgga cactgtccgg tgcctccaga ccagaggtgc   2100
cttcggttga ctctttgctc ctttgttgaa tccaaaactt gatcttttta ttggctgagt   2160
gtgaaccttt tatacctgta taatctatac acttgagcaa actagttagt ccaattattt   2220
gtgttgggca attcaaccac caaaattaat tagggactag gtgtaagcct aattcccttt   2280
caacgcttac agctaatgac tgcttacata ttagttattg actttataga tataaataac   2340
acaatgacga ctatagatgg ccaataagca cgaggcccac gagcccggca cgaagcccgc   2400
tgtatgggcc cggtccgagc ccggtacgac acggttctat gcgggctcgg gtcggtccgg   2460
cacgaataag cgggccgatc tcggacagga aactaggcac ggtgggctag cctgacacgg   2520
cccgtttacc cataaacccg tttttttata ctaaaacgtg cttatcagcc cgcttagccc   2580
tcttttcggc ccgcttagcc cgctttttgg cccaattttt ttgtgctaaa ctgtccgggc   2640
cgtttaggcc cgctgtgggc cgggctcggc cagaaaattg agtccgcgga cttatacggc   2700
ccgacacggt tttctaatcg tgtctagcgg gccaagcttc accgggctcg ggccggaccg   2760
ggccgagcgg ctcgtttggc catctctgac gacacaagac acggcgaccc gacgtcaccg   2820
aacgcacaag tgtcgccggc gaccgagccg cggcctggtc tagtacagta g            2871
```